United States Patent [19]
Basu et al.

[11] Patent Number: 6,127,381
[45] Date of Patent: Oct. 3, 2000

[54] ISOQUINOLINE COMPOUND MELANOCORTIN RECEPTOR LIGANDS AND METHODS OF USING SAME

[76] Inventors: Amaresh Basu, 15213 Calle Juanito, San Diego, Calif. 92129; Timothy C. Gahman, 262 Chapalita, Encinitas, Calif. 92024; Beverly E. Girten, 5225 Fiore Ter., #111, San Diego, Calif. 92122; Michael C. Griffith, 5676 Greenshade Rd., San Diego, Calif. 92121; Curtis C. Hecht, 627 Law St., San Diego, Calif. 92109; John S. Kiely, 4230 Conte Facil, San Diego, Calif. 92130; Sandra R. Slivka, 5021 Maynard St., San Diego, Calif. 92122

[21] Appl. No.: 09/301,391

[22] Filed: Apr. 28, 1999

Related U.S. Application Data

[60] Provisional application No. 60/083,368, Apr. 29, 1998.

[51] Int. Cl.$^7$ .................................................. C07D 217/14
[52] U.S. Cl. .......................... 514/307; 546/144; 546/150; 546/139; 514/310
[58] Field of Search ................................... 546/139, 144, 546/150; 514/307, 310

[56] References Cited

U.S. PATENT DOCUMENTS

| | | | |
|---|---|---|---|
| 5,010,175 | 4/1991 | Rutter et al. | 530/334 |
| 5,182,366 | 1/1993 | Huebner et al. | 530/334 |
| 5,288,514 | 2/1994 | Ellman | 427/2 |
| 5,324,483 | 6/1994 | Cody et al. | 422/131 |
| 5,420,109 | 5/1995 | Suto et al. | 514/8 |
| 5,618,791 | 4/1997 | Du | 514/17 |
| 5,726,156 | 3/1998 | Girten et al. | 514/16 |
| 5,874,443 | 2/1999 | Kiely et al. | 514/309 |
| 5,916,899 | 6/1999 | Kiely et al. | 514/309 |

FOREIGN PATENT DOCUMENTS

| | | |
|---|---|---|
| 0 590 455 | 9/1993 | European Pat. Off. . |
| WO 91/19735 | 12/1991 | WIPO . |
| WO 94/01102 | 1/1994 | WIPO . |
| WO 95/02566 | 1/1995 | WIPO . |
| WO 95/04277 | 2/1995 | WIPO . |
| WO 95/13086 | 5/1995 | WIPO . |
| WO 96/27386 | 9/1996 | WIPO . |
| WO 97/22356 | 6/1997 | WIPO . |

OTHER PUBLICATIONS

Abou–Mohamed et al., "HP–228, a novel synthetic peptide, inhibits the induction of nitric oxide synthase in vivo but not in vitro," *J. Pharmacology Experimental Therapeutics,* 275:584–591 (1995).

Berge et al., "Pharmaceutical salts," *J. Pharm. Sci.,* 66:1–19 (1977).

Castagnoli, "The condensation of succinic anhydride with benzylidinemethylamine. A stereoselective synthesis of trans– and cis–1–Methyl–4–carboxy–5–phenyl–2–pyrrolidinone." *J. of Org. Chem.,* 34(10):3187–3189 (1969).

Catania and Lipton, "α–Melanocyte–Stimulating Hormone Peptides in Host Responese, From Basic Evidence to Human Research," *Annals N.Y. Acad.Sci.,* 680:412–423 (1993).

Catania et al., "The Neuropeptide α–MSH Has Specific Receptros on Neutrophils and Reduces Chemotaxis In Vitro," *Peptides,* 17(4):675–679 (1996).

Chowdhary et al., "Localization of the human melanocortin–5 receptor gene (MC5R) to chromosome band 18p11.2 by fluorescence in situ hybridization," *Cytogenet Cell Genet* 68:79–81 (1995).

Coppola, Gary, "Novel heterocycles. 8. Fused isoquinolines derived from the reaction of homophthalic anhydride with cyclic imino ethers." *J. Heterocyclic Chem.,* 18:767–770 (1981).

Cushman and Castagnoli, "The synthesis of trans–3–methylnicotine." *J. Org. Chem.,* 37(8):1268–1271 (1972).

Cushman and Castagnoli, "Synthesis of pharmacologically active nitrogen analogs of the tetrahydrocannabinols." *J. Org. Chem.,* 39(11):1546–1550 (1974).

Cushman and Castagnoli, "The condensation of succinic anhydrides with schiff bases. Scope and mechanism." *J. Org. Chem.,* 36(22):3404–3406 (1971).

Cushman and Castagnoli, "A novel approach to the synthesis of nitrogen analogs of the tetrahydrocannabinols." *J. Org. Chem.,* 38(3):440–448 (1973).

Cushman and Madaj, "A study and mechanistic interpretation of the electronic and steric effects that determine the stereochemical outcome of the reaction of schiff bases with homophthalic anhydride and a 3–phenylsuccinic anhydride." *J. Org. Chem.,* 52(5):907–915 (1987).

Dooley et al., "Melanocortin receptor binding assay in rat brain homogenate: identification of tetrapeptide ligands from a combinatorial library," *Society for Neuroscience* 23:964 Abstract 383.18 (Aug. 21, 1997).

Dorr et al., "Evaluation of melanotan–II, a superpotent cyclic melanotropic peptide in a pilot phase–I clinical study," *Life Sci.,* 58(20):1777–1784 (1996).

Fan et al., "Role of melanocortinergic neurons in feeding and the agouti obesity syndrome," *Nature,* 385:165–168 (1997).

Frandberg et al., "Glutamine$^{235}$ and arginine$^{272}$ in human melanocortin 5 receptor determines its low affinity to MSH," *Biochem. Biophys. Res. Commun.* 236:489–492 (1997).

Friedman, "The alphabet of weight control," *Nature,* 385:119–120 (1997).

(List continued on next page.)

Primary Examiner—Joseph McKane
Assistant Examiner—Taofiq A. Solola
Attorney, Agent, or Firm—Campbell & Flores LLP

[57] ABSTRACT

The invention relates to melanocortin receptor ligands and methods of using the ligands to alter or regulate the activity of a melanocortin receptor. The invention further relates to tetrahydroisoquinoline aromatic amines that function as melanocortin receptor ligands and as agents for controlling cytokine-regulated physiologic processes and pathologies, and combinatorial libraries thereof.

69 Claims, 7 Drawing Sheets

OTHER PUBLICATIONS

Gallop et al., "Applications of Combinatorial Technologies to Drug Discovery. 1. Background and Peptide Combinatorial Libraries," *J. Med. Chem.,* 37:1233–1251 (1994).

Gantz et al., "Molecular cloning, expression, and gene localization of a fourth melanocortin receptor," *J. Biol. Chem.* 268:15174–15179 (1993).

Gantz et al., "Molecular cloning of a novel melanocortin receptor," *J. Biol. Chem.* 268:8246–8250 (1993).

Gantz et al., "Molecular cloning, expression, and characterization of a fifth melanocortin receptor," *Biochem. Biophys. Res. Commun.* 200:1214–1220 (1994).

Goff and Zuckermann, "Solid–phase synthesis of highly substituted peptide 1(2H)–Isoquinolinones." *J. Org. Chem.,* 60:5748–5749 (1995).

Gordon et al., "Application of combinatorial technologies to drug discovery. 2. Combinatorial organic synthesis, library screening strategies, and future directions." *J. of Med. Chem.,* 37(10):1385–1401 (1994).

Gura, "Obesity Sheds Its Secrets," *Science,* 275:751–753 (1997).

Haimova et al., "A highly stereoselective synthesis of 3,4–dihydro–1(2H)–isoquinolinones and 8–oxoberbines from homophthalic anhydrides and azomethines." *Tetrahedron,* 33:331–336 (1977).

Haskell–Luevano et al., "Binding and cAMP studies of melanotropin peptides with the cloned human peripheral melanocortin receptor, hMC1R," *Biochem. Biophys. Res. Commun.* 204:1137–1142 (1994).

Haskell–Luevano et al., "Discovery of prototype peptidomimetic agonists at the human melanocortin receptors MC1R and MC4R," *J. Med. Chem.* 40:2133–2139 (1997).

Hotamisligil and Spiegelman, "Tumor necrosis factor α: A key component of the obesity–diabetes link," *Diabetes,* 43:1271–1278 (1994).

Hotamisligil et al., "Reduced tyrosine kinase activity of the insulin receptor in obesity–diabetes. Central role of tumor necrosis factor–alpha," *J. Clin. Invest.,* 94:1543–1549 (1994).

Hotamisligil et al., "Increased adipose tissue expression of tumor necrosis factor–alpha in human obesity and insulin resistance," *J. Clin. Invest.,* 95:2409–2415 (1995).

Houghten et al., "Generation and use of synthetic peptide combinatorial libraries for basic research and drug discovery." *Nature,* 354:84–86 (1991).

Huszar et al., "Targeted disruption of the melanocortin–4 receptor results in obesity in mice," *Cell,* 88:131–141 (1997).

Lee et al., Cycloaddition of Homophthalic Anhydrides to Azodicarboxylate and Alkylidenecarbamates. *Chemical Abstracts,* 106(3):18331a (1987).

Ollman et al., "Antagonism of central melanocortin receptors in vitro and in vivo by agouti–related protein," *Science,* 278:135–138 (1997).

Omholt et al., "Oral Formulation of the Heptapeptide HP 228 Modulates Inflammation and Resting Oxygen Consumption in the Mouse and Rat," *The Pharmacologist,* 39(1):29, Abstract 53 (1997).

Ostresh et al., "Libraries from libraries: Chemical transformation of combinatorial libraries to extend the range and repertoire of chemical diversity." *Proc. Natl. Acad. Sci. USA,* 91:11138–11142 (1994).

Platzer et al., "Up–regulation of monocytic IL–10 by tumor necrosis factor–α and cAMP elevating drugs," *International Immunology,* 7(4)517–523 (1995).

Schiöth et al., "Characterization of the binding of MSH–B, HP–228, GHRP–6 and 153N–6 to the human melanocortin receptor subtypes," *Neuropeptides* 31:565–571 (1997).

Smith et al., "Synthetic approaches to hexahydropyrrolo[1,2–b]isoquinolones." *J. Heterocyclic Chem.,* 26:1815–1817 (1989).

Smith and Atigadda, "Condensation of homophthalic anhydrides with heterocyclic imines and DMAD under mild conditions." *J. Heterocyclic Chem.,* 28:1813–1815 (1991).

Star et al., "Evidence of autocrine modulation of macrophage nitric oxide synthase by α–melanocyte–stimulating hormone," *Proc. Natl. Acad. Sci. USA,* 92:8016–8020 (1995).

Tamura et al., "Strong base induced cycloaddition of homophthalic anhydrides leading to peri–hydroxy polycyclic compounds." *J. Org. Chem.,* 49:473–478 (1984).

Tamura et al., "Cycloaddition of homophthalic anhydride: A new and simple route to linearly condensed phenolic compounds." *Tetrahedron Letters,* 22(43):4283–4286 (1981).

Tatro, "Receptor biology of the melanocortins, a family of neuroimmunomodulatory peptides," *Neuroimmunomodulation,* 3:259–284 (1996).

Wenker, Henry, "Syntheses from ethanolamine. V. Synthesis of Δ–Oxazoline and of 2,2'–Δ$^2$–Di–oxazoline." *J. of Am. Chem. Society,* 60(8):2152–2153 (1938).

Xia et al., "Expression of melanocortin 1 receptor in periaqueductal gray matter," *Neuroreport,* 6:2193–2196 (1995).

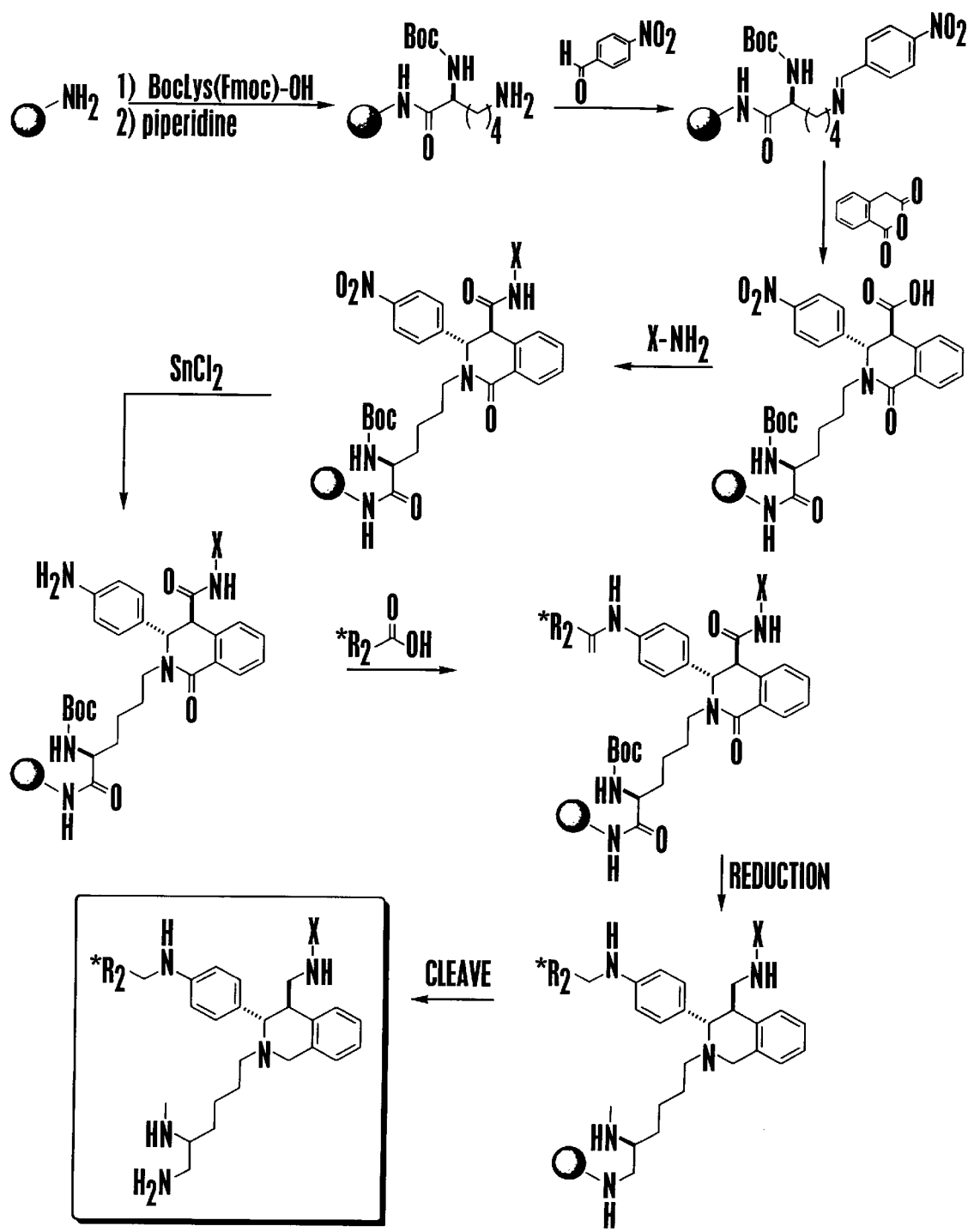
Fig. 1A  TRG 2409 Reaction Scheme
[$R_2$ = 4-NITROPHENYL: *$R_2$ INCREASES DIVERSITY OF $R_2$]

Fig. 1B  TRG 2411 Reaction Scheme
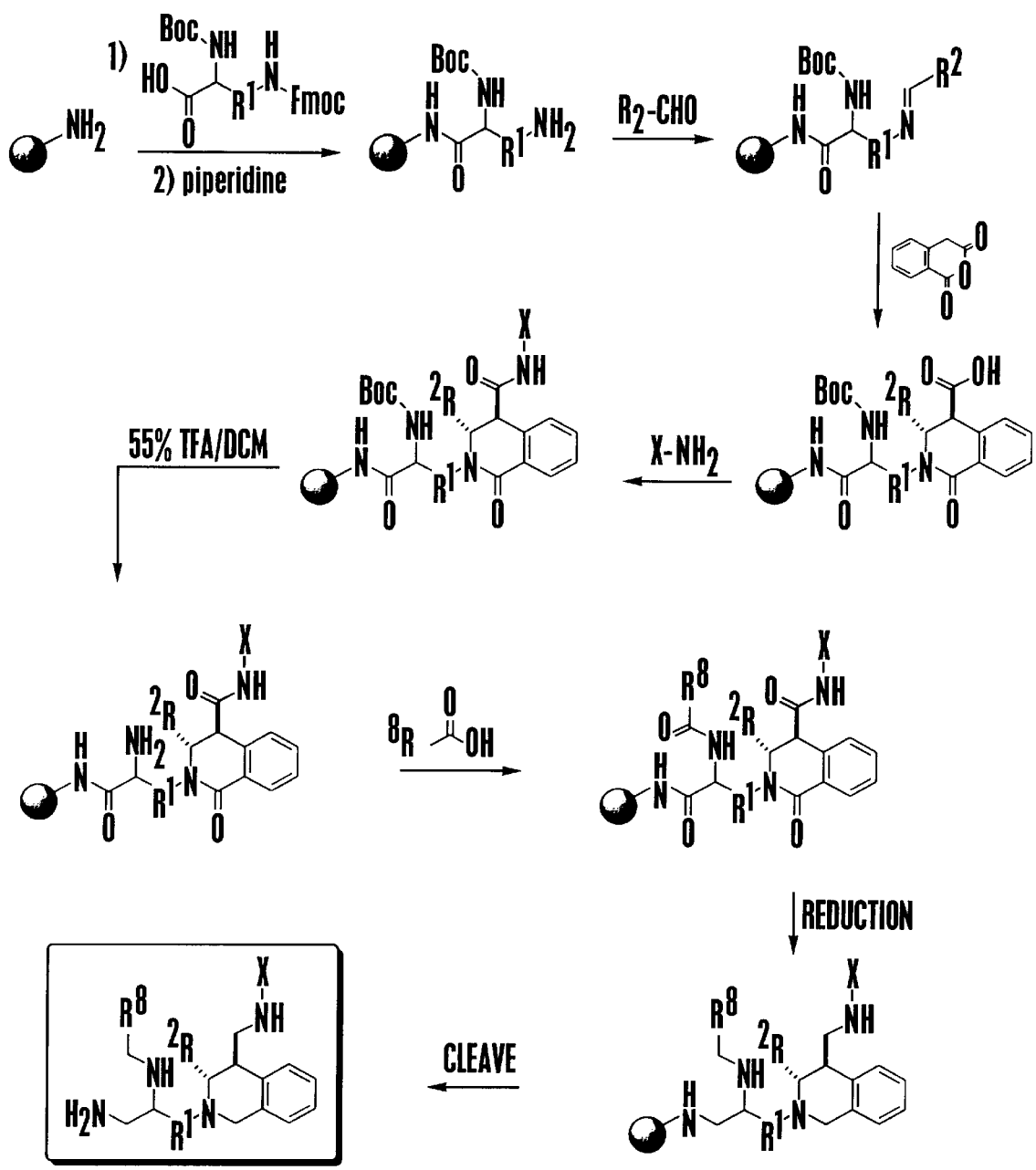

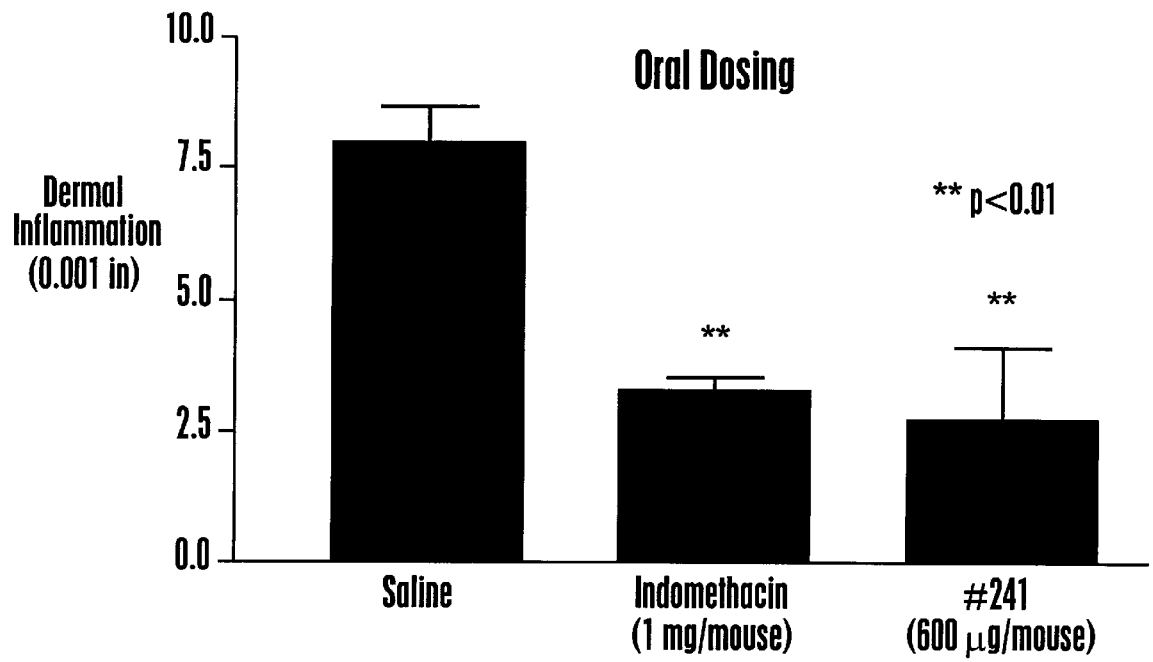
Fig. 2  Arachidonic Acid Induced Dermal Inflammaton
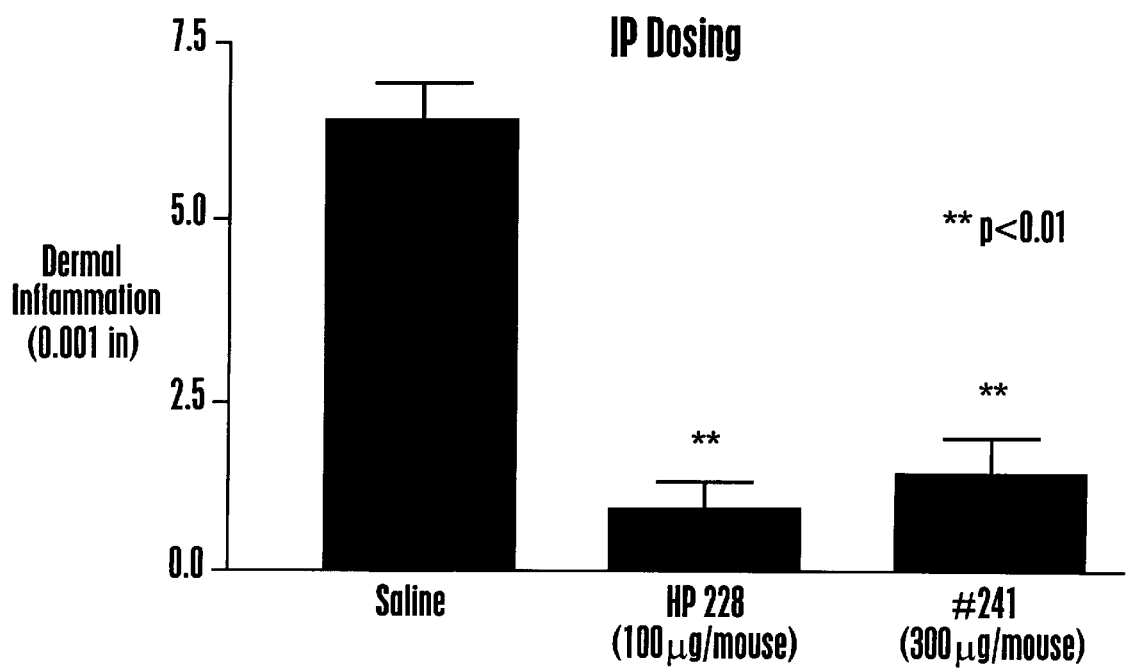
Fig. 3  Arachidonic Acid Induced Dermal Inflammaton

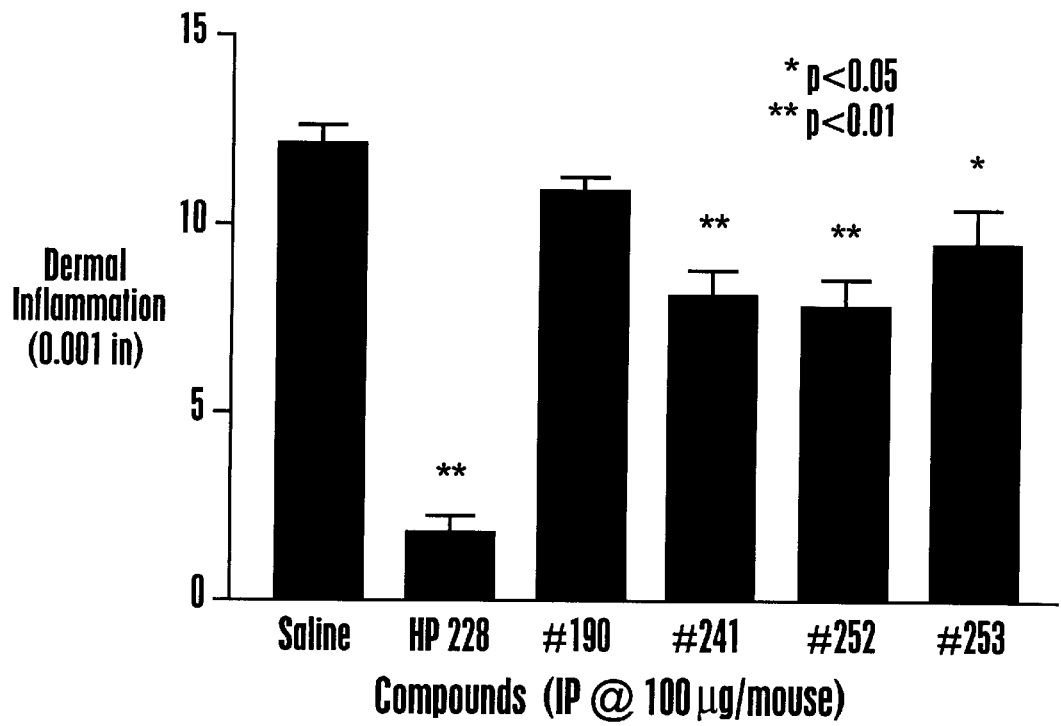
Fig. 4 Arachidonic Acid Induced Dermal Inflammation
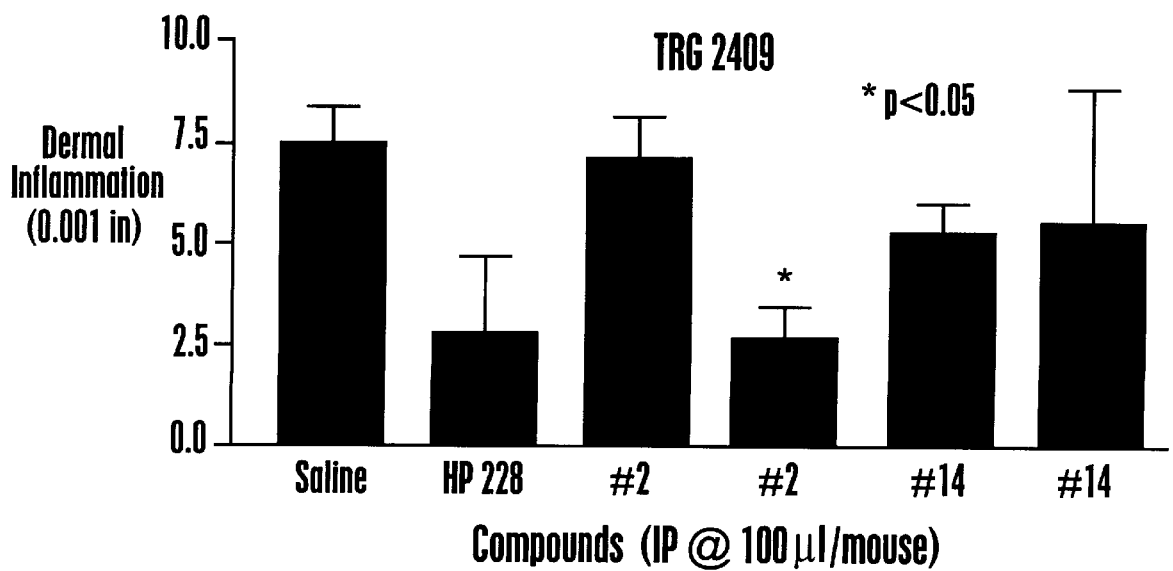
Fig. 5 Arachidonic Acid Induced Dermal Inflammation

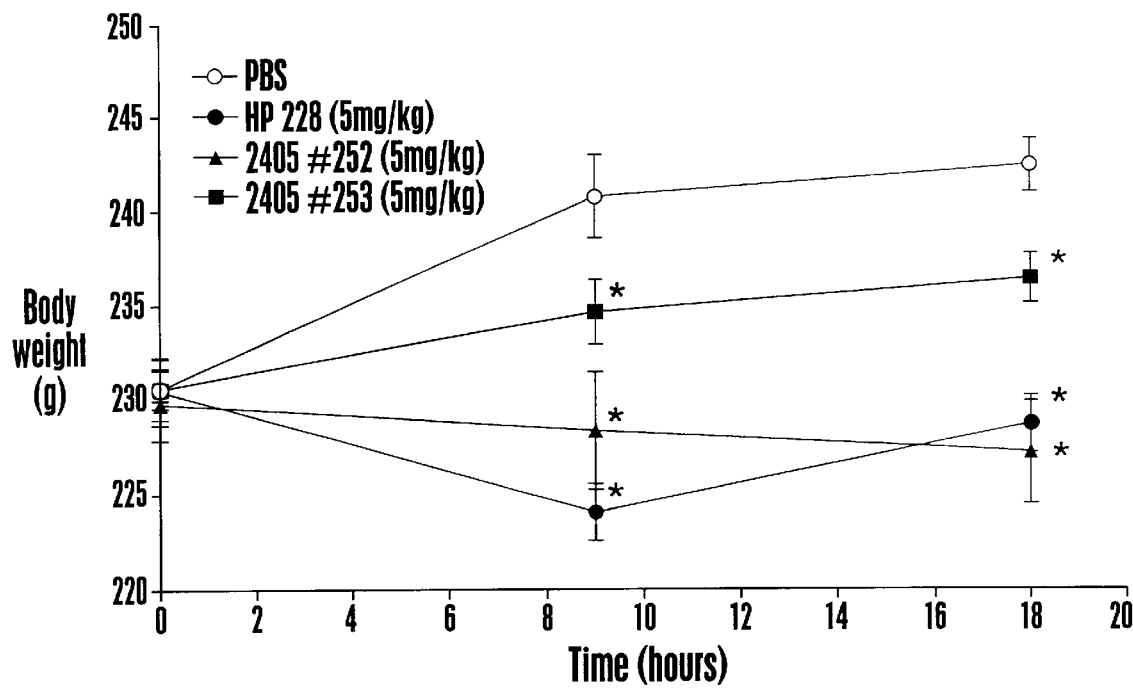
Fig. 7A  Effect of TRG 2405 #252 and #253 on Body Weight and Food Consumption
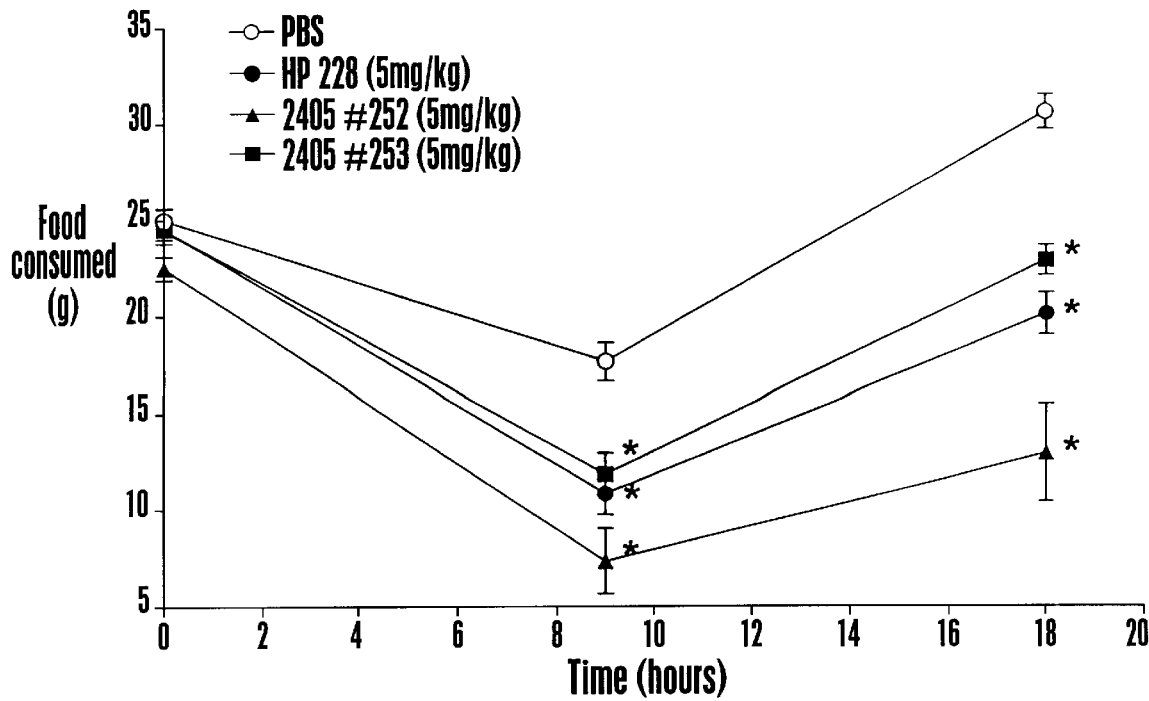
Fig. 7B Fig. 8 Effect of Novel Small Molecule Compound Compared to HP 228 on Penile Erections in Rats
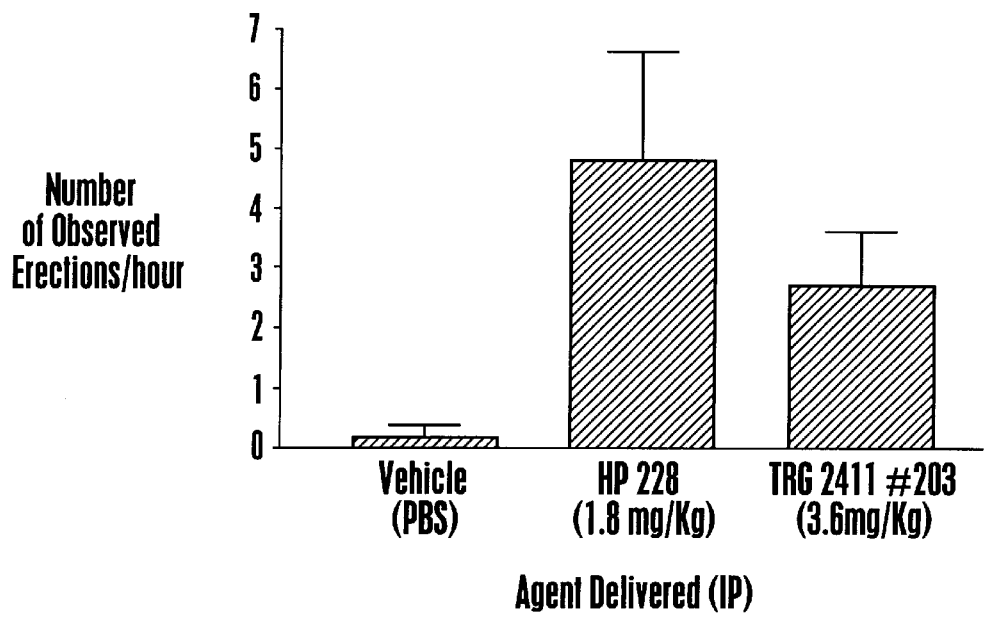
Fig. 9 Effect of Novel Small Molecule Compound Compared to HP 228 on Yawns & Stretches in Rats
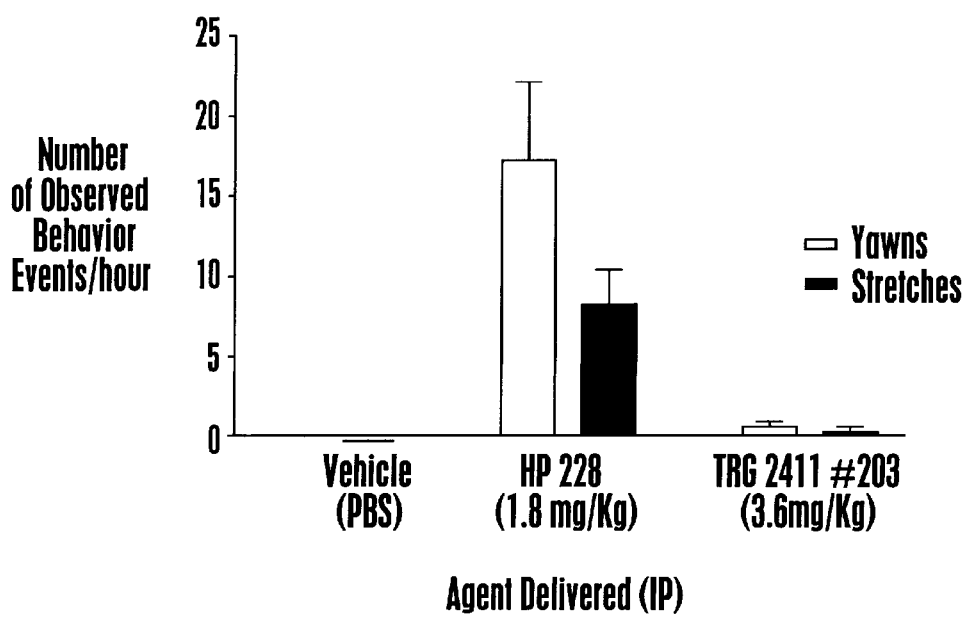

ISOQUINOLINE COMPOUND
MELANOCORTIN RECEPTOR LIGANDS
AND METHODS OF USING SAME

This application claims the benefit of U.S. Provisional Application No. 60/083,368, filed Apr. 28, 1998, and is incorporated herein by reference.

FIELD OF THE INVENTION

The present invention relates generally to the fields of medicinal chemistry and molecular pathology and, more specifically, to novel isoquinoline compounds and their use as melanocortin receptor ligands and as agents for controlling cytokine-regulated physiologic processes and pathologies, as well as combinatorial libraries comprising such compounds.

BACKGROUND INFORMATION

The melanocortin (MC) receptors are a group of cell surface proteins that mediate a variety of physiological effects, including regulation of adrenal gland function such as production of the glucocorticoids cortisol and aldosterone; control of melanocyte growth and pigment production; thermoregulation; immunomodulation; and analgesia. Five distinct MC receptors have been cloned and are expressed in a variety of tissues, including melanocytes, adrenal cortex, brain, gut, placenta, skeletal muscle, lung, spleen, thymus, bone marrow, pituitary, gonads and adipose tissue (Tatro, *Neuroimmunomodulation* 3:259–284 (1996)). Three MC receptors, MCR-1, MCR-3 and MCR-4, are expressed in brain tissue (Xia et al., *Neuroreport* 6:2193–2196 (1995)).

A variety of ligands termed melanocortins function as agonists that stimulate the activity of MC receptors. The melanocortins include melanocyte-stimulating hormones (MSH) such as α-MSH, β-MSH and γ-MSH, as well as adrenocorticotropic hormone (ACTH). Individual ligands can bind to multiple MC receptors with differing relative affinities. The variety of ligands and MC receptors with differential tissue-specific expression likely provides the molecular basis for the diverse physiological effects of melanocortins and MC receptors. For example, α-MSH antagonizes the actions of immunological substances such as cytokines and acts to modulate fever, inflammation and immune responses (Catania and Lipton, *Annals N.Y. Acad. Sci.* 680:412–423 (1993)).

More recently, the role of specific MC receptors in some of the physiological effects described above for MC receptors has been elucidated. For example, MCR-1 is involved in pain and inflammation. MCR-1 mRNA is expressed in neutrophils (Catania et al., *Peptides* 17:675–679 (1996)). The anti-inflammatory agent α-MSH was found to inhibit migration of neutrophils. Thus, the presence of MCR-1 in neutrophils correlates with the anti-inflammatory activity of α-MSH.

An interesting link of MC receptors to regulation of food intake and obesity has recently been described. The brain MC receptor MCR-4 has been shown to function in the regulation of body weight and food intake. Mice in which MCR-4 has been knocked out exhibit weight gain (Huszar et al., *Cell* 88:131–141 (1997)). In addition, injection into brain of synthetic peptides that mimic melanocortins and bind to MCR-4 caused suppressed feeding in normal and mutant obese mice (Fan et al., *Nature* 385:165–168 (1997)). These results indicate that the brain MC receptor MCR-4 functions in regulating food intake and body weight.

Due to the varied physiological activities of MC receptors, high affinity ligands of MC receptors could be used to exploit the varied physiological responses of MC receptors by functioning as potential therapeutic agents or as lead compounds for the development of therapeutic agents. Furthermore, due to the effect of MC receptors on the activity of various cytokines, high affinity MC receptor ligands could also be used to regulate cytokine activity.

Thus, there exists a need for ligands that bind to MC receptors with high affinity for use in altering MC receptor activity. The present invention satisfies this need and provides related advantages as well.

SUMMARY OF THE INVENTION

The invention provides melanocortin receptor ligands and methods of using the ligands to alter or regulate the activity of a melanocortin receptor. The invention further relates to tetrahydroisoquinoline aromatic amines that function as melanocortin receptor ligands.

BRIEF DESCRIPTION OF THE DRAWINGS

FIG. 1A and 1B shows a reaction scheme for synthesis of tetrahydroisoquinoline aromatic amines.

FIG. 2 shows inhibition of arachidonic acid induced dermal inflammation with indomethacin (1 mg/mouse) or TRG 2405–241 (600 μg/mouse) administered orally.

FIG. 3 shows inhibition of arachidonic acid induced dermal inflammation with HP 228 (100 μg/mouse) or TRG 2405–241 (300 μg/mouse) administered intraperitoneally.

FIG. 4 shows inhibition of arachidonic acid induced dermal inflammation with HP 228, TRG 2405–190, TRG 2405–241, TRG 2405–252 or TRG 2405–253 (100 μg/mouse) administered intraperitoneally.

FIG. 5 shows inhibition of arachidonic acid induced dermal inflammation with HP 228 (100 μg/mouse) or with TRG 2409-2 or TRG 2409-14 (100 or 300 μg/mouse) administered intraperitoneally.

FIG. 7 shows the effect of HP 228 (5 mg/kg), TRG 2405-252 and TRG 2405-253 (5 mg/kg) on body weight and food consumption in mouse at 9 and 18 hr.

FIG. 8 shows the effect of TRG 2411-203 (3.6 mg/kg) compared to HP 228 (1.8 mg/kg) on penile erections in rats.

FIG. 9 shows the effect of TRG 2411-203 (3.6 mg/kg) compared to HP 228 (1.8 mg/kg) on yawns and stretches in rats.

DETAILED DESCRIPTION OF THE INVENTION

Figure 6A:
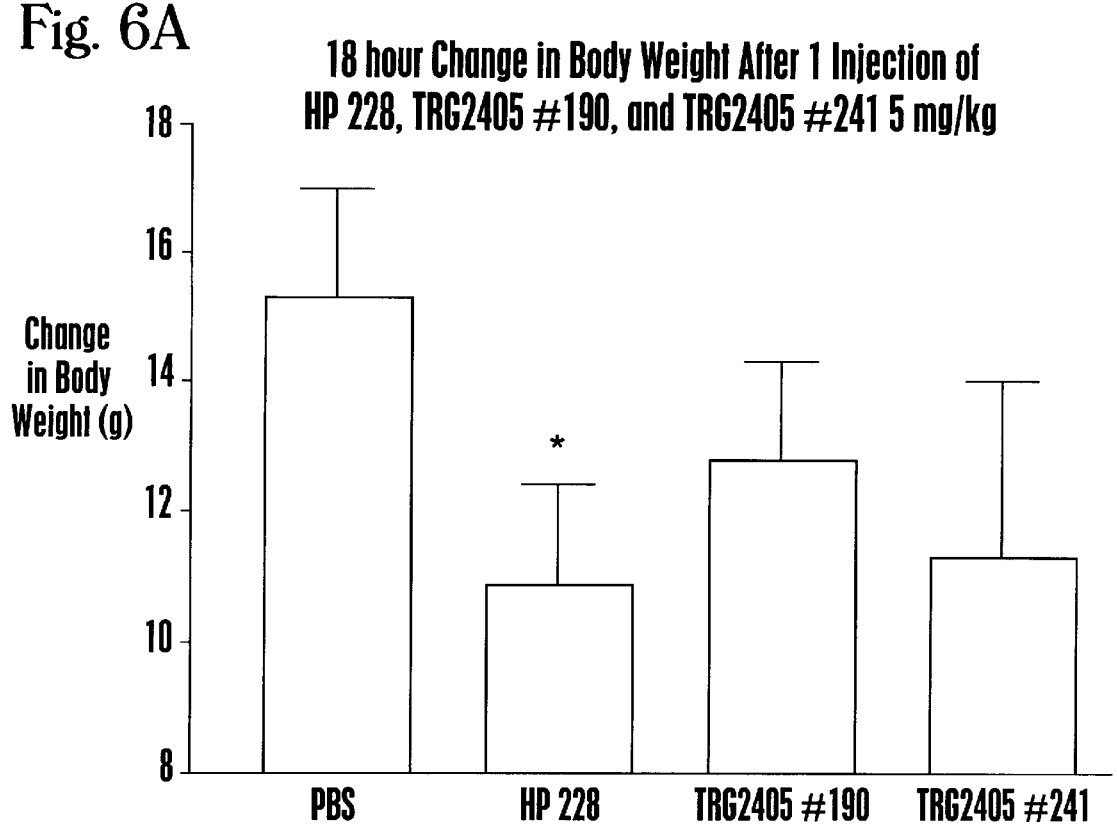
FIG. 6 shows the effect of HP 228 (5 mg/kg), TRG 2405-190 and TRG 2405-241 (5 mg/kg) on body weight and food consumption in mouse at 18 hr.

The invention provides ligands for MC receptors and methods for altering the activity of a MC receptor. The invention also provides MC receptor ligands that are useful for regulating cytokine activity and body weight in an individual. The invention further provides isoquinoline compounds which are MC receptor ligands, as well as combinatorial libraries of such compounds. Isoquinoline compounds of the present invention are more specifically tetrahydroisoquinoline aromatic amines, although other isoquinoline compounds or derivatives thereof can similarly be used as MC receptor ligands.

The invention provides isoquinoline compound MC receptor ligands and combinatorial libraries having the structure:

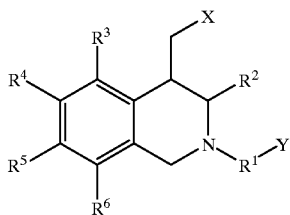

wherein:
R¹ is a $C_1$ to $C_9$ alkylene, $C_1$ to $C_9$ substituted alkylene, $C_2$ to $C_9$ alkenylene, $C_2$ to $C_9$ substituted alkenylene, $C_2$ to $C_9$ alkynylene, $C_2$ to $C_9$ substituted alkynylene, $C_7$ to $C_{12}$ phenylalkylene, $C_7$ to $C_{12}$ substituted phenylalkylene or a group of the formula:

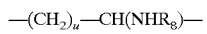
—(CH₂)ᵤ—CH(NHR₈)— wherein u is selected from a number 1 to 8; and $R^8$ is hydrogen atom, $C_1$ to $C_9$ alkyl, $C_1$ to $C_9$ substituted alkyl, $C_7$ to $C_{12}$ phenylalkyl or a $C_7$ to $C_{12}$ substituted phenylalkyl;

$R^2$ is phenyl, substituted phenyl, naphthyl, substituted naphthyl, $C_7$ to $C_{12}$ phenylalkyl, $C_7$ to $C_{12}$ substituted phenylalkyl, a heterocyclic ring or a substituted heterocyclic ring;

$R^3$, $R^4$, $R^5$ and $R^6$ are, independently, a hydrogen atom, halo, hydroxy, protected hydroxy, cyano, nitro, $C_1$ to $C_6$ alkyl, $C_2$ to $C_7$ alkenyl, $C_2$ to $C_7$ alkynyl, $C_1$ to $C_6$ substituted alkyl, $C_2$ to $C_7$ substituted alkenyl, $C_2$ to $C_7$ substituted alkynyl, $C_1$ to $C_7$ alkoxy, $C_1$ to $C_7$ acyloxy, $C_1$ to $C_7$ acyl, $C_3$ to $C_7$ cycloalkyl, $C_3$ to $C_7$ substituted cycloalkyl, $C_5$ to $C_7$ cycloalkenyl, $C_5$ to $C_7$ substituted cycloalkenyl, a heterocyclic ring, $C_7$ to $C_{12}$ phenylalkyl, $C_7$ to $C_{12}$ substituted phenylalkyl, phenyl, substituted phenyl, naphthyl, substituted naphthyl, cyclic $C_2$ to $C_7$ alkylene, substituted cyclic $C_2$ to $C_7$ alkylene, cyclic $C_2$ to $C_7$ heteroalkylene, substituted cyclic $C_2$ to $C_7$ heteroalkylene, carboxy, protected carboxy, hydroxymethyl, protected hydroxymethyl, amino, protected amino, (monosubstituted)amino, protected (monosubstituted) amino, (disubstituted) amino, carboxamide, protected carboxamide, $C_1$ to $C_4$ alkylthio, $C_1$ to $C_4$ alkylsulfonyl, $C_1$ to $C_4$ alkylsulfoxide, phenylthio, substituted phenylthio, phenylsulfoxide, substituted phenylsulfoxide, phenylsulfonyl or substituted phenylsulfonyl;

X is hydroxy, amino, protected amino, an amino acid, (monosubstituted)amino,(disubstituted)amino, aniline, substituted aniline, a heterocyclic ring, a substituted heterocyclic ring, an aminosubstituted heterocyclic ring, or a substituted aminosubstituted heterocyclic ring; and Y is $CH_2NHR^7$ or $C(O)NHR^7$, wherein $R^7$ is a hydrogen atom, $C_1$ to $C_6$ alkyl or $C_1$ to $C_6$ substituted alkyl.

The invention also provides the above identified substituents with the exception that $R^1$ is preferably formula —(CH₂)ᵤ—CH(NHR⁸)— with the above given u variables and $R^8$ substituents.

The invention also provides isoquinoline compounds and combinatorial libraries having the above formula, wherein:
R¹ is $C_1$ to $C_9$ alkylene or $C_1$ to $C_9$ substituted alkylene, or a group of the formula:

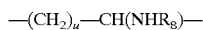
—(CH₂)ᵤ—CH(NHR₈)— wherein u is selected from a number 1 to 8; and $R^8$ is hydrogen atom, $C_1$ to $C_9$ alkyl, $C_1$ to $C_9$ substituted alkyl, $C_7$ to $C_{12}$ phenylalkyl or $C_7$ to $C_{12}$ substituted phenylalkyl;

$R^2$ is phenyl, a substituted phenyl, a heterocyclic ring or a substituted heterocyclic ring;

$R^3$, $R^4$, $R^5$ and $R^6$ are, independently, a hydrogen atom;

X is hydroxy, amino, protected amino, (monosubstituted) amino, (disubstituted)amino, aniline, a substituted aniline, a heterocyclic ring, a substituted heterocyclic ring, an aminosubstituted heterocyclic ring, or a substituted aminosubstituted heterocyclic ring; and Y is selected from the group consisting of $CH_2NHR^7$ or $C(O)NHR^7$, wherein $R^7$ is a hydrogen atom, $C_1$ to $C_6$ alkyl or $C_1$ to $C_6$ substituted alkyl.

The invention also provides compounds and combinatorial libraries having the substituents identified directly above, with the exception that $R^1$ is preferably formula —(CH₂)ᵤ—CH(NHR⁸)— with the above given u variables and $R^8$ substituents.

The invention also provides isoquinoline compounds and combinatorial libraries having the above formula, wherein:
$R^1$ is methylene or the formula:

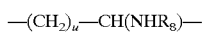
—(CH₂)ᵤ—CH(NHR₈)— wherein u is selected from a number 1 to 6; and $R^8$ is methyl, ethyl, phenethyl, 2-(N-methylamino)ethyl, 2-aminoethyl, hydroxyethyl, 2-(N-methyl)propyl, 2-(N-methyl)-2-phenyl ethyl, a reduced and/or modified form of succinic anhydride, methoxyethyl, butyl, cyclohexanemethyl, benzyl, 4-bromophenethyl, 4-methoxyphenethyl, 4-chlorobenzyl, 4-methoxybenzyl, 2-naphthylethyl, or cyclohexylethyl;

$R^2$ is phenyl, 2-hydroxyphenyl, 1,4-benzodioxan-6-yl, 1-methyl-2-pyrrolyl, 1-naphthyl, 2,3,4-trifluorophenyl, 2,3,5-trichlorophenyl, 2,3-(methylenedioxy)phenyl, 2,3-difluorophenyl, 2,4-dichlorophenyl, 2,6-difluorophenyl, 2-bromophenyl, 2-chloro-5-nitrophenyl, 2-chloro-6-fluorophenyl, 2-aminomethylphenyl, 2-fluorophenyl, 2-imidazolyl, 2-methoxybenzyl, 2-naphthyl, 2-thiophene-yl, 3,4-(methylenedioxy)phenyl, 3,4-dihydroxyphenyl, 3,4-dichlorophenyl, 3,4-difluorophenyl, 3,5-bis(trifluoromethyl)phenyl, 3,5-dihydroxyphenyl, 3,5-dichlorophenyl, 3,5-dimethoxyphenyl, 3,5-dimethyl-4-hydroxyphenyl, 3-(3,4-dichlorophenoxy)phenyl, 3-(4-methoxyphenoxy)phenyl, 3-(trifluoromethyl)phenyl, 3-bromo-4-fluorophenyl, 3-bromophenyl, 3-hydroxymethylphenyl, 3-aminomethylphenyl, 3-fluoro-4-methoxyphenyl, 3-fluorophenyl, 3-hydroxyphenyl, 3-methoxy-4-hydroxy-5-nitrophenyl, 3-methoxyphenyl, 3-methyl-4-methoxyphenyl, 3-methylphenyl, 3-nitro-4-chlorophenyl, 3-nitrophenyl, 3-phenoxyphenyl, 3-pyridinyl, 3-thiophene-yl, 4-(3-dimethylaminopropoxy)phenyl, 4-(dimethylamino) phenyl, 4-hydroxymethylphenyl, 4-(methylthio) phenyl, 4-(trifluoromethyl)phenyl, 4-ethylaminophenyl, 4-methoxyphenyl (p-anisaldehyde), 4-biphenylcarboxaldehyde, 4-bromophenyl, 4-aminomethylphenyl, 4-fluorophenyl, 4-hydroxyphenyl, 4-isopropylphenyl, 4-methoxy-1-naphthyl, 4-methylphenyl, 3-hydroxy-4-nitrophenyl, 4-nitrophenyl, 4-phenoxyphenyl, 4-propoxyphenyl, 4-pyridinyl, 3-methoxy-4-hydroxy-5-bromophenyl, 5-methyl-2-thiophene-yl, 5-methyl-2-furyl, 8-hydroxyquinoline-2-yl, 9-ethyl-3-carbazole-yl, 9-formyl-8-hydroxyjulolidin-yl, pyrrole-2-yl, 3-hydroxy-4-methoxyphenyl, 4-methylsulphonylphenyl, 4-methoxy-3-(sulfonic acid, Na)phenyl, 5-bromo-2-furyl, 4-ethoxyphenyl, 4-propoxyphenyl, 4-butoxyphenyl, 4-amylphenyl, 4-propylaminophenyl, 4-butylaminophenyl, 4-pentylaminophenyl, 4-cyclohexylmethylaminophenyl, 4-isobutylaminophenyl, 4-(2-methoxy)-ethylaminophenyl, 4-methoxybenzylaminophenyl, phenethylaminophenyl, 4-methoxyphenethylaminophenyl, 2-(2-norbornyl)-ethylaminophenyl, 3,4-dichlorphenethylaminophenyl, 4-benzylaminophenyl, or 4-p-chlorobenzylaminophenyl;

$R^3$, $R^4$, $R^5$, $R^6$ are independently a hydrogen atom;

X is anilinyl, N-methylanilinyl, 2-chloroanilinyl, 2-methoxyanilinyl, 3-chloroanilinyl, 3-ethoxyanilinyl, 3-aminophenol, 4-chloroanilinyl, 4-methoxyanilinyl, benzylamino, N-benzylmethylamino, 2-chlorobenzylamino, 2-(trifluoromethyl)benzylamino, 2-hydroxybenzylamino, 3-methoxybenzylamino, 3-(trifluoromethyl)benzylamino, 4-chlorobenzylamino, 4-methoxybenzylamino, 4-(trifluoromethyl) benzylamino, phenethylamino, 2-chlorophenethylamino, 2-methoxyphenethylamino, 3-chlorophenethylamino, 4-methoxyphenthylamino, 3-phenyl-1-propylamino, cyclopentylamino, isopropylamino, cycloheptylamino, N-methylcyclohexylamino, (aminomethyl) cyclohexane, piperidinyl, morpholinyl, 1-aminopiperidinyl, diethylamino, 3-hydroxypropyl, isopropylamino, 2-trimethylaminoethyl chloride, ammonia, or hydroxy; and Y is $CH_2NH_2$.

The invention also provides compounds and combinatorial libraries having the substituents identified directly above with the exception that $R^1$ is preferably formula —$(CH_2)_u$—$CH(NHR^8)$— with the above given u variables and $R^8$ substituents.

The invention further provides isoquinoline compounds and combinatorial libraries having the above formula, wherein:

$R^1$ is methylene or the formula:

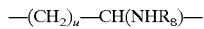
—$(CH_2)_u$—$CH(NHR_8)$— wherein u is 1, 2 or 4;

$R^2$ is phenyl, 2-hydroxyphenyl, 1,4-benzodioxan-6-yl, 1-methyl-2-pyrrolyl, 1-naphthyl, 2,3,4-trifluorophenyl, 2,3,5-trichlorophenyl, 2,3-(methylenedioxy)phenyl, 2,3-difluorophenyl, 2,4-dichlorophenyl, 2,6-difluorophenyl, 2-bromophenyl, 2-chloro-5-nitrophenyl, 2-chloro-6-fluorophenyl, 2-cyanophenyl, 2-fluorophenyl, 2-imidazolyl, 2-methoxybenzyl, 2-naphthyl, 2-thiophene-yl, 3,4-(methylenedioxy) phenyl, 3,4-dihydroxyphenyl, 3,4-dichlorophenyl, 3,4-difluorophenyl, 3,5-bis(trifluoromethyl)phenyl, 3,5-dihydroxyphenyl, 3,5-dichlorophenyl, 3,5-dimethoxyphenyl, 3,5-dimethyl-4-hydroxyphenyl, 3-(3,4-dichlorophenoxy)phenyl, 3-(4-methoxyphenoxy)phenyl, 3-(trifluoromethyl)phenyl, 3-bromo-4-fluorophenyl, 3-bromophenyl, 3-hydroxymethylphenyl, 3-aminomethylphenyl, 3-fluoro-4-methoxyphenyl, 3-fluorophenyl, 3-hydroxyphenyl, 3-methoxy-4-hydroxy-5-nitrophenyl, 3-methoxyphenyl, 3-methyl-4-methoxyphenyl, 3-methylphenyl, 3-nitro-4-chlorophenyl, 3-nitrophenyl, 3-phenoxyphenyl, 3-pyridinyl, 3-thiophene-yl, 4-(3-dimethylaminopropoxy)phenyl, 4-(dimethylamino) phenyl, 4-hydroxymethylphenyl, 4-(methylthio) phenyl, 4-(trifluoromethyl)phenyl, 4-ethylaminophenyl, 4-methoxyphenyl, 4-biphenyl, 4-bromophenyl, 4-aminomethylphenyl, 4-fluorophenyl, 4-hydroxyphenyl, 4-isopropylphenyl, 4-methoxy-1-naphthyl, 4-methylphenyl, 3-hydroxy-4-nitrophenyl, 4-nitrophenyl, 4-phenoxyphenyl, 4-propoxyphenyl, 4-pyridinyl, 3-methoxy-4-hydroxy-5-bromophenyl, 5-methyl-2-thiophene-yl, 5-methyl-2-furyl, 8-hydroxyquinoline-2-yl, 9-ethyl-3-carbazole-yl, 9-formyl-8-hydroxyjulolidin-yl, pyrrole-2-yl, 3-hydroxy-4-methoxyphenyl, 4-methylsulphonylphenyl, 4-methoxy-3-(sulfonic acid, Na)phenyl or 5-bromo-2-furyl;

$R^3$, $R^4$, $R^5$, $R^6$ are independently a hydrogen atom;

x is cyclohexylamino;

$R^8$ is methyl; and is $CH_2NH_2$.

The invention also provides isoquinoline compounds and combinatorial libraries having the above formula, wherein:

$R^1$ is methylene or the formula:

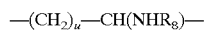
—$(CH_2)_u$—$CH(NHR_8)$— wherein u is 1, 2 or 4;

$R^2$ is 3-(3,4-dichlorophenoxy)phenyl, 1-methyl-2-pyrrolyl, 3-phenoxyphenyl, 4-phenoxyphenyl, 4-propoxyphenyl, 3-methoxy-4-hydroxy-5-bromophenyl, or 9-ethyl-3-carbazolyl;

$R^3$, $R^4$, $R^5$, $R^6$ are independently a hydrogen atom;

$R^8$ is methyl;

X is 2-hydroxybenzyl; and

Y is $CH_2NH_2$.

The invention additionally provides isoquinoline compounds and combinatorial libraries having the above formula, wherein:

$R^1$ is methylene or the formula:

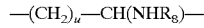
—$(CH_2)_u$—$CH(NHR_8)$— wherein u is 1, 2 or 4;

$R^2$ is 2,4-dichlorophenyl, 4-biphenyl or 4-ethylaminophenyl;

$R^3$, $R^4$, $R^5$, $R^6$ are independently a hydrogen atom;

X is anilinyl, N-methylanilinyl, 2-chloroanilinyl, 2-methoxyanilinyl, 3-chloroanilinyl, 3-ethoxyanilinyl, 3-aminophenol, 4-chloroanilinyl, 4-methoxyanilinyl, benzylamino, N-benzylmethylamino, 2-chlorobenzylamino, 2-(trifluoromethyl)benzylamino, 2-hydroxybenzylamino, 3-methoxybenzylamino, 3-(trifluoromethyl)benzylamino, 4-chlorobenzylamino, 4-methoxybenzylamino, 4-(trifluoromethyl) benzylamino, phenethylamino, 2-chlorophenethylamino, 2-methoxyphenethylamino, 3-chlorophenethylamino, 4-methoxyphenthylamino, 3-phenyl-1-propylamino, cyclopentylamino, isopropylamino, cycloheptylamino, N-methylcyclohexylamino, cyclohexylmethylamino, piperidinyl, morpholinyl, 1-aminopiperidinyl, diethylamino, allylamino, isopropylamino, (2-aminoethyl)-trimethylammonium, ammonium, or hydroxy;

$R^8$ is methyl; and

Y is $CH_2NH_2$.

Also provided are isoquinoline compounds and combinatorial libraries having the above formula, wherein:

$R^1$ is the formula:

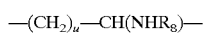
—$(CH_2)_u$—$CH(NHR_8)$— wherein u is 1, 2 or 4;

$R^2$ is 2,4-dichlorophenyl, 4-biphenyl or 4-ethylaminophenyl;

$R^3$, $R^4$, $R^5$, $R^6$ are independently a hydrogen atom;

X is cyclohexylamino or 2-hydroxybenzylamino;

$R^8$ is a hydrogen atom, methyl, phenylethyl, 2-(N-methyl)aminoethyl or 2-aminoethyl; and Y is $CH_2NH_2$.

The invention further provides isoquinoline compounds and combinatorial libraries having the above formula, wherein:

$R^1$ is the formula:

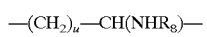
—$(CH_2)_u$—$CH(NHR_8)$— herein u is 4;

$R^2$ is 4-propylaminophenyl, 4-butylaminophenyl, 4-cyclohexylmethylaminophenyl, 4-isobutylaminophenyl, 4-(2-methoxy)-ethylaminophenyl, 4-(4-methoxybenzyl)aminophenyl, 4-phenethylaminophenyl, 4-(4-methoxyphenethyl)aminophenyl, 2-(2-norboranyl)-ethylaminophenyl, 3,4-dichlorophenethylaminophenyl, 4-benzylaminophenyl or 4-p-chlorobenzylaminophenyl;

$R^3$, $R^4$, $R^5$, $R^6$ are independently a hydrogen atom;

X is cyclohexylamino or 2-hydroxybenzylamino;

$R^8$ is methyl; and

Y is $CH_2NH_2$.

The invention also provides isoquinoline compounds and combinatorial libraries having the above formula, wherein:

$R^1$ is the formula:

—$(CH_2)_u$—$CH(NHR_8)$— wherein u is 3 or 4;

$R^2$ is -biphenyl, 4-ethylaminophenyl or 4-butylaminophenyl;

$R^3$, $R^4$, $R^5$, $R^6$ are independently a hydrogen atom;

X is cyclohexylamino, ammonia or phenethylamino;

$R^8$ is hidrogen atom, methyl, ethyl, phenylethyl, 2-(N-methyl)aminoethyl, 2aminoethyl, 2-(N-methyl)aminopropyl, hydroxyethyl, 2-(N-methyl)amino2-phenyl, ethyl, a reduced form of succinic anhydride, methoxyethyl, butyl, cyclohexylmethyl, benzyl, 4-bromophenylethyl, 4-methoxybenzyl, 2-naphthylethyl or cyclohexylethyl; and Y is $CH_2NH_2$.

The invention additionally provides isoquinoline compounds and combinatorial libraries having the above formula, wherein:

$R^1$ is the formula:

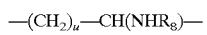
—$(CH_2)_u$—$CH(NHR_8)$— wherein u is 3 or 4;

$R^2$ is 4-pentylaminophenyl, 4-ethoxyphenyl, 4-propoxyphenyl 4, butoxyphenyl or 4-amylphenyl;

$R^3$, $R^4$, $R^5$, $R^6$ are independently a hydrogen atom;

X is phenethylamino;

$R^8$ is methyl, phenethyl or benzyl; and

Y is $CH_2NH_2$.

The invention further provides isoquinoline compounds and combinatorial libraries having the above formula, wherein:

$R^1$ is the formula:

—$(CH_2)_u$—$CH(NHR_8)$— wherein u is 3 or 4;

$R^2$ is 4-biphenyl, 4-ethylaminophenyl or 4-nitrophenyl;

$R^3$, $R^4$, $R^5$, $R^6$ are independently a hydrogen atom;

X is phenethyl, ammonia or cyclohexylamino;

$R^8$ is methyl, 2-(N-methyl)aminoethyl or 2-aminoethyl, phenethyl; and

Y is $CH_2NH_2$.

The invention further provides isoquinoline compounds and combinatorial libraries having the above formula, wherein:

$R^1$ is of the formula:

—$(CH_2)_u$—$CH(NHR_8)$— wherein u is 3 and $R^8$ is a hydrogen atom, phenylethyl, benzyl or 4-isobutyl-α-methylphenylethyl;

$R^2$ is 2,4-dichlorophenyl, 2-bromophenyl, 3,5-bis(trifluoromethyl)phenyl, 3-phenoxyphenyl, 4-phenoxyphenyl or 4-propoxyphenyl;

$R^3$, $R^4$, $R^5$, $R^6$ are, independently, a hydrogen atom;

X is 2-(trifluoromethyl)benzylamino, 2-ethoxybenzylamino, 2-methoxyphenethylamino, 3-chlorophenethylamino, 3-methoxybenzylamino, 4-methoxybenzylamino, 4-methoxyphenethylamino, benzylamino, cycloheptylamino or cyclohexylamino; and Y is $CH_2NH_2$.

The invention further provides isoquinoline compounds and combinatorial libraries having the above formula, wherein:

$R^1$ is of the formula:

—$(CH_2)_u$—$CH(NHR_8)$— wherein u is 3 or 4 and $R^8$ is ethyl or cyclohexylethyl;

$R^2$ is 4-amylphenyl, 4-butoxyphenyl, 4-butylaminophenyl, 4-ethoxyphenyl, 4-ethylphenyl or 4-n-propoxyphenyl;

$R^3$, $R^4$, $R^5$, $R^6$ are, independently, a hydrogen atom;

X is ammonia, hydroxy or phenethylamino; and

Y is $CH_2NH_2$.

In addition, the invention provides isoquinoline compounds and combinatorial libraries having the above formula, wherein:

$R^1$ is of the formula:

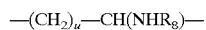
—$(CH_2)_u$—$CH(NHR_8)$— wherein u is 3 and $R^8$ is 4-aminobutyl, 4-aminobenzylbutyl, 4-diethylaminobutyl, 4-isopropylaminobutyl, 4-hydroxybutyl, 4-phenethylaminobutyl, 4-piperidinobutyl, 4-t-butylaminobutyl or 4-aminophenylbutyl;

$R^2$ is 4-ethylaminophenyl;

$R^3$, $R^4$, $R^5$, $R^6$ are, independently, a hydrogen atom;

X is ammonia or phenethylamino; and

Y is $CH_2NH_2$.

The invention also provides isoquinoline compounds and combinatorial libraries having the above formula, wherein:

$R^1$ is of the formula:

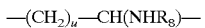

—(CH$_2$)$_u$—CH(NHR$_8$)— wherein u is 3 and $R^8$ is 4-(isopropylamino)-butyl, 4-(benzoamino)-butyl, 4-(diethylamino)-butyl, 4-(phenethylamino)-butyl, 5-(isopropylamino)-(3,4) cyclopropane-pentyl, 5-(benzoamino)-(3,4) cyclopropane-pentyl, 5-(diethylamino)-(3,4) cyclopropane-pentyl, 5-(phenethylamino)-(3,4) cyclopropane-pentyl, 2-amino-2-ethoxy-N-ethylisopropylamino-2-amino-2-ethoxy-N-ethylbenzyl, 2-amino-2-ethoxy-N-ethyldiethyl, 2-amino-2-ethoxy-N-ethylphenethyl, (2,3)benzyl-4-isopropylamino, (2,3)benzyl-4-benzylamino, (2,3) benzyl-4-diethylamino, (2,3)benzyl-4-phenethylamino, 3-(hydroxy)-5-(isopropylamino)-3-pentyl, 3-(hydroxy)-5-(benzylamino)-3-pentyl, 3-(hydroxy)-5-(diethylamino)-3-pentyl or 3-(hydroxy)-5-(phenethylamino)-3-pentyl;

$R^2$ is 4-ethylaminophenyl;

$R^3$, $R^4$, $R^5$, $R^6$ are, independently, a hydrogen atom;

X is phenethylamino or ammonia; and

Y is $CH_2NH_2$.

The invention further provides isoquinoline compounds and combinatorial libraries having the above formula, wherein:

$R^1$ is of the formula:

—(CH$_2$)$_u$—CH(NHR$_8$)— u is 4 and $R^8$ is benzyl, p-methylbenzyl, p-bromobenzyl, p-methoxybenzyl or 4-phenylbenzyl;

$R^2$ is 3,5-bis(trifluoromethyl)phenyl or 3-(trifluoromethyl)phenyl;

$R^3$, $R^4$, $R^5$, $R^6$ are, independently, a hydrogen atom;

X is phenethylamino, tyramino, 2-(4-methoxyphenyl) ethylamino, 3,4-dimethoxyphenylethylamino, 4-ethoxyphenethylamino, 4-phenoxyphenethylamino, 2-(4-chlorophenyl)ethylamino or 2-(3-methoxyphenyl) ethylamino; and Y is $CH_2NH_2$.

Additionally, the invention provides isoquinoline compounds and combinatorial libraries having the above formula, wherein:

$R^1$ is 5-(2-aminoethylamino)pentyl;

$R^2$ is p-(N-ethylamino)benzyl;

$R^3$, $R^4$, $R^5$, $R^6$ are, independently, a hydrogen atom;

X is 2-methoxybenzylamino, 4-methoxybenzylamino, cyclohexylamino, phenethylamino or ammonia; and Y is $CH_2NH_2$.

Moreover, the invention provides isoquinoline compounds and combinatorial libraries having the above formula, wherein:

$R^1$ is of the formula:

—(CH$_2$)$_u$—CH(NHR$_8$)— wherein u is 3 or 4 and $R^8$ is pentyl, 4-phenoxybutyl or 4-hydroxypentyl;

$R^2$ is p-(N-ethylamino)benzyl;

$R^3$, $R^4$, $R^5$, $R^6$ are, independently, a hydrogen atom;

X is phenethylamino or ammonia; and

Y is $CH_2NH_2$.

Furthermore, the invention provides isoquinoline compounds and combinatorial libraries having the above formula, wherein:

$R^1$ is of the formula:

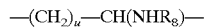

—(CH$_2$)$_u$—CH(NHR$_8$)— wherein u is 4 and $R^8$ is ($\alpha,\alpha,\alpha$-trifluoro-p-tolyl)ethyl, 3-(4-methoxyphenyl)propyl, 4-biphenylmethyl, 4-biphenylethyl, 4-chlorophenylethyl, 4-phenoxybutyl, butyl, glycolyl, a hydrogen atom, hydrocinnamylmethyl, isobutylmethyl, methyl, p-methoxybenzyl, 4-hydroxybutyl or 2-(trimethyl) ethyl;

$R^2$ is 4-propoxyphenyl, 4-amylphenyl or 3,5-bistrifluoromethylphenyl;

$R^3$, $R^4$, $R^5$, $R^6$ are, independently, a hydrogen atom;

X is ammonia or cycloheptylamino; and is $CH_2NH_2$.

The invention additionally provides isoquinoline compounds and combinatorial libraries having the above formula, wherein:

$R^1$ is of the formula:

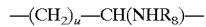

—(CH$_2$)$_u$—CH(NHR$_8$)— wherein u is 4 and $R^8$ is methyl or phenethyl;

$R^2$ is 4-propoxyphenyl, 4-amylphenyl or 3,5-bistrifluoromethylphenyl;

$R^3$, $R^4$, $R^5$, $R^6$ are, independently, a hydrogen atom;

X is 4-chlorobenzylamino, 4-methoxybenzylamino, 4-methoxyphenethylamino, phenylamino, benzylamino, cyclohexanemethylamino, cyclohexylamino, cyclooctylamino, cyclopentylamino, diethylamino, ethanolamino, isopropylamino, morpholino, n-methylanilino, n-methylcyclohexylamino, hydroxy, p-anisidino, phenethylamino, piperidino or t-butylamino; and Y is $CH_2NH_2$.

The invention also provides isoquinoline compounds and combinatorial libraries having the above formula, wherein:

$R^1$ is of the formula:

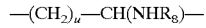

—(CH$_2$)$_u$—CH(NHR$_8$)— wherein u is 4 and $R^8$ is ($\alpha,\alpha,\alpha$-trifluoro-p-tolyl)ethyl, 1-adamantaneethyl, 3-(4-methoxyphenyl)propyl, 4-phenylbenzyl, 4-phenylphenethyl, 4-chlorophenethyl, 4-imidazolemethyl, 4-methoxyphenyethyl, 4-phenoxypentyl, $\alpha,\alpha,\alpha$-trifluoro-p-toluylethyl, ethyl, benzyl, butyl, glycolyl, hydrocinnamylmethyl, isobutylmethyl, p-methoxybenzyl, phenethyl, 4-hydroxybutyl or 2-(trimethyl)ethyl;

$R^2$ is 4-propoxyphenyl, 4-amylphenyl or 3,5-bistrifluoromethylphenyl;

$R^3$, $R^4$, $R^5$, $R^6$ are, independently, a hydrogen atom; X is ammonia or cycloheptylamino; and Y is $CH_2NH_2$.

The invention further provides an isoquinoline compound having the above formula, wherein $R^1$ is —$(CH_2)_u$—CH($NHR^8$)—; u is the number 4; and $R^8$ is methyl; $R^2$ is 2,4-dichlorophenyl; $R^3$, $R^4$, $R^5$, $R^6$ are independently a hydrogen atom; X is cyclohexylamino; and Y is $CH_2NH_2$. This isoquinoline compound is designated TRG 2405#190.

The invention also provides an isoquinoline compound having the above formula, wherein $R^1$ is —$(CH_2)_u$—CH($NHR^8$)—; u is the number 4; and $R^8$ is methyl; $R^2$ is 4-ethylaminophenyl; $R^3$, $R^4$, $R^5$, $R^6$ are independently a hydrogen atom; X is cyclohexylamino; and Y is $CH_2NH_2$. This isoquinoline compound is designated TRG 2405#239.

The invention additionally provides provides an isoquinoline compound having the above formula, wherein $R^1$ is —$(CH_2)_u$—CH($NHR^8$)—; u is the number 4; and $R^8$ is methyl; $R^2$ is 4-biphenyl; $R^3$, $R^4$, $R^5$, $R^6$ are independently a hydrogen atom; X is cyclohexylamino; and Y is $CH_2NH_2$. This isoquinoline compound is designated TRG 2405#241.

The invention further provides an isoquinoline compound having the above formula, wherein $R^1$ is —$(CH_2)_u$—CH($NHR^8$)—; u is the number 4; and $R^8$ is methyl; $R^2$ is 4-phenoxyphenyl; $R^3$, $R^4$, $R^5$, $R^6$ are independently a hydrogen atom; X is cyclohexylamino; and Y is $CH_2NH_2$. This isoquinoline compound is designated TRG 2405#252.

The invention also provides an isoquinoline compound having the above formula, wherein $R^1$ is —$(CH_2)_u$—CH($NHR^8$)—; u is the number 4; and $R^8$ is methyl; $R^2$ is 4-propoxyphenyl; $R^3$, $R^4$, $R^5$, $R^6$ are independently a hydrogen atom; X is cyclohexylamino; and Y is $CH_2NH_2$. This isoquinoline compound is designated TRG 2405#253.

The invention additionally provides an isoquinoline compound having the above formula, wherein $R^1$ is —$(CH_2)_u$—CH($NHR^8$)—; u is the number 4; and $R^8$ is methyl; $R^2$ is 4-ethylaminophenyl; $R^3$, $R^4$, $R^5$, $R^6$ are independently a hydrogen atom; X is cyclohexylamino; and Y is $CH_2NH_2$. This isoquinoline compound is designated TRG 2408#30.

Also provided is an isoquinoline compound having the above formula, wherein $R^1$ is —$(CH_2)_u$—CH($NHR^8$)—; u is the number 3; and $R^8$ is 2-phenylethyl; $R^2$ is 4-ethylaminophenyl; $R^3$, $R^4$, $R^5$, $R^6$ are independently a hydrogen atom; X is 2-hydroxybenzylamino; and Y is $CH_2NH_2$. This isoquinoline compound is designated TRG 2408#57.

Additionally provided is an isoquinoline compound having the above formula, wherein $R^1$ is —$(CH_2)_u$—CH($NHR^8$)—; u is the number 3; and $R^8$ is 2-phenylethyl; $R^2$ is 4-ethylaminophenyl; $R^3$, $R^4$, $R^5$, $R^6$ are independently a hydrogen atom; X is cyclohexylamino; and Y is $CH_2NH_2$. This isoquinoline compound is designated TRG 2408#62.

The invention further provides an isoquinoline compound having the above formula, wherein $R^1$ is —$(CH_2)_u$—CH($NHR^8$)—; u is the number 4; and $R^8$ is methyl; $R^2$ is 4-butylaminophenyl; $R^3$, $R^4$, $R^5$, $R^6$ are independently a hydrogen atom; X is 2-hydroxybenzylamino; and Y is $CH_2NH_2$. This isoquinoline compound is designated TRG 2409#2.

The invention also provides an isoquinoline compound having the above formula, wherein $R^1$ is —$(CH_2)_u$—CH($NHR^8$)—; u is the number 4; and $R^8$ is methyl; $R^2$ is 4-butylaminophenyl; $R^3$, $R^4$, $R^5$, $R^6$ are independently a hydrogen atom; X is cyclohexylamino; and Y is $CH_2NH_2$. This isoquinoline compound is designated TRG 2409#14.

The invention additionally provides an isoquinoline compound having the above formula, wherein $R^1$ is —$(CH_2)_u$—CH($NHR^8$)—; u is the number 4; and $R^8$ is 2-(N-methyl)aminoethyl; $R^2$ is 4-biphenyl; $R^3$, $R^4$, $R^5$, $R^6$ are independently a hydrogen atom; X is amino; and Y is $CH_2NH_2$. This isoquinoline compound is designated TRG 2411#26.

The invention further provides an isoquinoline compound having the above formula, wherein $R^1$ is —$(CH_2)_u$—CH($NHR^8$)—; u is the number 4; and $R^8$ is butyl; $R^2$ is 4-ethylaminophenyl; $R^3$, $R^4$, $R^5$, $R^6$ are independently a hydrogen atom; X is cyclohexylamino; and Y is $CH_2NH_2$. This isoquinoline compound is designated TRG 2411#50.

Further provided is an isoquinoline compound having the above formula, wherein $R^1$ is —$(CH_2)_u$—CH($NHR^8$)—; u is the number 4; and R8 is ethyl; $R^2$ is 4-ethylaminophenyl; $R^3$, $R^4$, $R^5$, $R^6$ are independently a hydrogen atom; X is amino; and Y is $CH_2NH_2$. This isoquinoline compound is designated TRG 2411#60.

The invention also provides an isoquinoline compound having the above formula, wherein $R^1$ is —$(CH_2)_u$—CH($NHR^8$)—; u is the number 4; and $R^8$ is 2-cyclohexylethyl; $R^2$ is 4-butylaminophenyl; $R^3$, $R^4$, $R^5$, $R^6$ are independently a hydrogen atom; X is amino; and Y is $CH_2NH_2$. This isoquinoline compound is designated TRG 2411#111.

The invention additionally provides an isoquinoline compound having the above formula, wherein $R^1$ is —$(CH_2)_u$—CH($NHR^8$)—; u is the number 3; and $R^8$ is 2-cyclohexylethyl; $R^2$ is 4-ethylaminophenyl; $R^3$, $R^4$, $R^5$, $R^6$ are independently a hydrogen atom; X is amino; and Y is $CH_2NH_2$. This isoquinoline compound is designated TRG 2411#186.

The invention additionally provides an isoquinoline compound having the above formula, wherein $R^1$ is —$(CH_2)_u$—CH($NHR^8$)—; u is 3; and $R^8$ is 4-hydroxybutyl; $R^2$ is 4-ethylaminophenyl; $R^3$, $R^4$, $R^5$, $R^6$ are, independently, a hydrogen atom; X is 2-phenethylamino; and Y is $CH_2NH_2$.

The invention additionally provides an isoquinoline compound having the above formula, wherein $R^1$ is —$(CH_2)_u$—CH($NHR^8$)—; u is 4; and $R^8$ is 2-phenethyl; $R^2$ is 4-propoxyphenyl; $R^3$, $R^4$, $R^5$, $R^6$ are, independently, a hydrogen atom; X is cycloheptylamino; and Y is $CH_2NH_2$.

The invention also provides an isoquinoline compound having the above formula, wherein $R^1$ is —$(CH_2)_u$—CH($NHR^8$)—; u is 4; and $R^8$ is ethyl; $R^2$ is 4-ethoxyphenyl; $R^3$, $R^4$, $R^5$, $R^6$ are, independently, a hydrogen atom; X is amino; and Y is $CH_2NH_2$.

The invention also provides an isoquinoline compound having the above formula, wherein $R^1$ is —$(CH_2)_u$—CH($NHR^8$)—; u is 4; and $R^8$ is ethyl; $R^2$ is 4-propoxyphenyl; $R^3$, $R^4$, $R^5$, $R^6$ are, independently, a hydrogen atom; X is amino; and Y is $CH_2NH_2$.

In addition, the invention also provides an isoquinoline compound having the above formula, wherein $R^1$ is —$(CH_2)_u$—CH($NHR^8$)—; u is 4; and $R^8$ is ethyl; $R^2$ is 4-n-butoxyphenyl; $R^3$, $R^4$, $R^5$, $R^6$ are, independently, a hydrogen atom; X is amino; and Y is $CH_2NH_2$.

Moreover, the invention also provides an isoquinoline compound having the above formula, wherein $R^1$ is —$(CH_2)_u$—CH($NHR^8$)—; u is 4; and $R^8$ is ethyl; $R^2$ is 4-n-pentylphenyl; $R^3$, $R^4$, $R^5$, $R^6$ are, independently, a hydrogen atom; X is amino; and Y is $CH_2NH_2$.

Furthermore, the invention also provides an isoquinoline compound having the above formula, wherein $R^1$ is —$(CH_2)_u$—CH($NHR^8$)—; u is 3; and $R^8$ is 4-hydroxybutyl; $R^2$ is 4-ethylaminophenyl; $R^3$, $R^4$, $R^5$, $R^6$ are, independently, a hydrogen atom; X is amino; and Y is $CH_2NH_2$.

The invention further provides an isoquinoline compound having the above formula, wherein $R^1$ is —$(CH_2)_u$—CH (NHR$^8$)—; u is 3; and R$^8$ is pentyl; R$^2$ is 4-ethylaminophenyl; R$^3$, R$^4$, R$^5$, R$^6$ are, independently, a hydrogen atom; X is 2-phenethylamino; and Y is CH$_2$NH$_2$.

The invention further provides an isoquinoline compound having the above formula, wherein R$^1$ is —(CH$_2$)$_u$—CH(NHR$^8$)—; u is 4; and R$^8$ is 4-hydroxybutyl; R$^2$ is 4-pentylphenyl; R$^3$, R$^4$, R$^5$, R$^6$ are, independently, a hydrogen atom; X is amino; and Y is CH$_2$NH$_2$.

In the above formula, the R$^1$-Y substituents are such that Y is always bonded to the 1-position of the R$^1$ radical. All naming hereinafter reflects this positioning between the two substituents.

Unless otherwise indicated, in the above formula the stereochemistry of chiral centers associated with the R$^1$ through R$^8$ groups can independently be in the R or S configuration, or a mixture of the two.

In the above formula, the term "ene" (such as alylene) denotes that the "ene" group connects together two separate additional groups.

In the above formula, the term "alkyl" (such as C$_1$ to C$_9$ alkyl or C$_1$ to C$_6$ alkyl) denotes such radicals as methyl, ethyl, n-propyl, isopropyl, n-butyl, sec-butyl, tert-butyl, pentyl, tert-amyl, hexyl and the like up to chains of nine carbon atoms. Preferably, the compounds have C$_1$ to C$_8$, more preferably C$_1$ to C$_6$ and even more preferably C$_1$ to C$_3$ carbon chains. Most preferred is methyl.

The term "alkenyl" (such as C$_2$ to C$_9$ alkenyl or C$_2$ to C$_7$ alkenyl) denotes such radicals as vinyl, allyl, 2-butenyl, 3-butenyl, 2-pentenyl, 3-pentenyl, 4-pentenyl, 2-hexenyl, 3-hexenyl, 4-hexenyl, 5-hexenyl, 2-heptenyl, 3-heptenyl, 4-heptenyl, 5-heptenyl, 6-heptenyl, as well as dienes and trienes of straight and branched chains.

The term "alkynyl" (such as C$_2$ to C$_9$ alkynyl or C$_2$ to C$_7$ alkynyl) denotes such radicals as ethynyl, propynyl, butynyl, pentynyl, hexynyl, heptynyl, as well as di- and tri-ynes of straight and branched chains.

The terms "substituted alkyl," "substituted alkenyl," and "substituted alkynyl," denote that the above alkyl, alkenyl and alkynyl groups are substituted by one or more, and preferably one or two, halogen, hydroxy, protected hydroxy, oxo, protected oxo, cyclohexyl, naphthyl, amino, protected amino, (monosubstituted)amino, protected (monosubstituted)amino, (disubstituted)amino, guanidino, heterocyclic ring, substituted heterocyclic ring, imidazolyl, indolyl, pyrrolidinyl, C$_1$ to C$_7$ alkoxy, C$_1$ to C$_7$ acyl, C$_1$ to C$_7$ acyloxy, nitro, C$_1$ to C$_7$ alkyl ester, carboxy, protected carboxy, carbamoyl, carboxamide, protected carboxamide, N-(C$_1$ to C$_6$ alkyl)carboxamide, protected N-(C$_1$ to C$_6$ alkyl)carboxamide, N,N-di (C$_1$ to C$_6$ alkyl)carboxamide, cyano, methylsulfonylamino, thio, C$_1$ to C$_4$ alkylthio or C$_1$ to C$_4$ alkyl sulfonyl groups. The substituted alkyl groups may be substituted once or more, and preferably once or twice, with the same or with different substituents.

Examples of the above substituted alkyl groups include the 2-oxo-prop-1-yl, 3-oxo-but-1-yl, cyanomethyl, nitromethyl, chloromethyl, hydroxymethyl, tetrahydropyranyloxymethyl, trityloxymethyl, propionyloxymethyl, amino, methylamino, aminomethyl, dimethylamino, carboxymethyl, allyloxycarbonylmethyl, allyloxycarbonylaminomethyl, methoxymethyl, ethoxymethyl, t-butoxymethyl, acetoxymethyl, chloromethyl, bromomethyl, iodomethyl, trifluoromethyl, 6-hydroxyhexyl, 2,4-dichloro(n-butyl), 2-aminopropyl, chloroethyl, bromoethyl, fluoroethyl, iodoethyl, chloropropyl, bromopropyl, fluoropropyl, iodopropyl and the like.

Examples of the above substituted alkenyl groups include styrenyl, 3-chloro-propen-1-yl, 3-chloro-buten-1-yl, 3-methoxy-propen-2-yl, 3-phenyl-buten-2-yl, 1-cyano-buten-3-yl and the like. The geometrical isomerism is not critical, and all geometrical isomers for a given substituted alkenyl can be used.

Examples of the above substituted alkynyl groups include phenylacetylen-1-yl, 1-phenyl-2-propyn-1-yl and the like.

The term "oxo" denotes a carbon atom bonded to two additional carbon atoms substituted with an oxygen atom doubly bonded to the carbon atom, thereby forming a ketone moiety.

The term "protected oxo" denotes a carbon atom bonded to two additional carbon atoms substituted with two alkoxy groups or twice bonded to a substituted diol moiety, thereby forming an acyclic or cyclic ketal moiety.

The term "C$_1$ to C$_7$ alkoxy" as used herein denotes groups such as methoxy, ethoxy, n-propoxy, isopropoxy, n-butoxy, t-butoxy and like groups. A preferred alkoxy is methoxy.

The term "C$_1$ to C$_7$ acyloxy" denotes herein groups such as formyloxy, acetoxy, propionyloxy, butyryloxy, pentanoyloxy, hexanoyloxy, heptanoyloxy and the like.

Similarly, the term "C$_1$ to C$_7$ acyl" encompasses groups such as formyl, acetyl, propionyl, butyryl, pentanoyl, pivaloyl, hexanoyl, heptanoyl, benzoyl and the like. Preferred acyl groups are acetyl and benzoyl.

The term "C$_3$ to C$_7$ cycloalkyl" includes the cyclopropyl, cyclobutyl, cyclopentyl, cyclohexyl or cycloheptyl rings. The substituent term "C$_3$ to C$_7$ substituted cycloalkyl" indicates the above cycloalkyl rings substituted by one or two halogen, hydroxy, protected hydroxy, C$_1$ to C$_6$ alkyl, C$_1$ to C$_7$ alkoxy, oxo, protected oxo, (monosubstituted)amino, (disubstituted)amino, trifluoromethyl, carboxy, protected carboxy, phenyl, substituted phenyl, amino, or protected amino groups.

The term "C$_5$ to C$_7$ cycloalkenyl" indicates a 1,2, or 3-cyclopentenyl ring, a 1,2,3 or 4-cyclohexenyl ring or a 1,2,3,4 or 5-cycloheptenyl ring, while the term "substituted C$_5$ to C$_7$ cycloalkenyl" denotes the above C$_5$ to C$_7$ cycloalkenyl rings substituted by a C$_1$ to C$_6$ alkyl radical, halogen, hydroxy, protected hydroxy, C$_1$ to C$_7$ alkoxy, trifluoromethyl, carboxy, protected carboxy, oxo, protected oxo, (monosubstituted)amino, protected (monosubstituted) amino (disubstituted)amino, phenyl, substituted phenyl, amino, or protected amino.

The term "heterocyclic ring" denotes optionally substituted five-membered or six-membered rings that have 1 to 4 heteroatoms, such as oxygen, sulfur and/or nitrogen, in particular nitrogen, either alone or in conjunction with sulfur or oxygen ring atoms. These five-membered or six-membered rings may be saturated, fully saturated or partially unsaturated, with fully saturated rings being preferred. An "amino-substituted heterocyclic ring" means any one of the above-described heterocyclic rings is substituted with at least one amino group. Preferred heterocyclic rings include morpholino, piperidinyl, piperazinyl, tetrahydrofurano, pyrrolo, and tetrahydrothiophen-yl.

The term "substituted heterocyclic ring" means the above-described heterocyclic ring is substituted with, for example, one or more, and preferably one or two, substituents which are the same or different which substituents can be halogen, hydroxy, protected hydroxy, cyano, nitro, C$_1$ to C$_6$ alkyl, C$_1$ to C$_7$ alkoxy, C$_1$ to C$_7$ acyl, C$_1$ to C$_7$ acyloxy, carboxy, protected carboxy, carboxymethyl, protected carboxymethyl, hydroxymethyl, protected hydroxymethyl, amino, protected amino, (monosubstituted) amino, protected (monosubstituted) amino, (disubstituted)amino carboxamide, protected carboxamide, N-(C$_1$ to C$_6$alkyl) carboxamide, protected N-(C$_1$ to C$_6$ alkyl)carboxamide, N, N-di($C_1$ to $C_6$ alkyl), trifluoromethyl, N-(($C_1$ to $C_6$ alkyl) sulfonyl)amino or N-(phenylsulfonyl)amino groups. The term "aminosubstituted heterocyclic ring" is a heterocyclic ring substituted with at least one amino group and the term "substituted aminosubstituted heterocyclic ring is an aminosubstituted heterocyclic ring substituted with one or more of the above identified substituents for a substituted heterocyclic ring.

The abbreviation "Ar" stands for an aryl group. Aryl groups which can be used with present invention include phenyl, substituted phenyl, as defined above, heteroaryl, and substituted heteroaryl. The term "heteroaryl" means a heterocyclic aromatic derivative which is a five-membered or six-membered ring system having from 1 to 4 heteroatoms, such as oxygen, sulfur and/or nitrogen, in particular nitrogen, either alone or in conjunction with sulfur or oxygen ring atoms. Examples of heteroaryls include pyridinyl, pyrimidinyl, and pyrazinyl, pyridazinyl, pyrrolo, furano, oxazolo, isoxazolo, thiazolo and the like.

The term "substituted heteroaryl" means the above-described heteroaryl is substituted with, for example, one or more, and preferably one or two, substituents which are the same or different which substituents can be halogen, hydroxy, protected hydroxy, cyano, nitro, $C_1$ to $C_6$ alkyl, $C_1$ to $C_7$ alkoxy, $C_1$ to $C_7$ acyl, $C_1$ to $C_7$ acyloxy, carboxy, protected carboxy, carboxymethyl, protected carboxymethyl, hydroxymethyl, protected hydroxymethyl, amino, protected amino, (monosubstituted) amino, protected (monosubstituted) amino, (disubstituted)amino carboxamide, protected carboxamide, N-($C_1$ to $C_6$alkyl) carboxamide, protected N-($C_1$ to $C_6$ alkyl)carboxamide, N, N-di($C_1$ to $C_6$ alkyl), trifluoromethyl, N-(($C_1$ to $C_6$ alkyl) sulfonyl)amino or N-(phenylsulfonyl)amino groups.

The term "$C_7$ to $C_{12}$ phenylalkyl" denotes a $C_1$ to $C_6$ alkyl group substituted at any position by a phenyl ring. Examples of such a group include benzyl, 2-phenylethyl, 3-phenyl(n-propyl), 4-phenylhexyl, 3-phenyl(n-amyl), 3-phenyl(sec-butyl) and the like. Preferred $C_7$ to $C_{12}$ phenylalkyl groups are the benzyl and the phenylethyl groups.

The term "$C_7$ to $C_{12}$ substituted phenylalkyl" denotes a $C_7$ to $C_{12}$ phenylalkyl group substituted on the $C_1$ to $C_6$ alkyl portion with one or more, and preferably one or two, groups chosen from halogen, hydroxy, protected hydroxy, oxo, protected oxo, amino, protected amino, monosubstituted) amino, protected (monosubstituted) amino, (disubstituted) amino, guanidino, heterocyclic ring, substituted heterocyclic ring, $C_1$ to $C_7$ alkoxy, $C_1$ to $C_7$ acyl, $C_1$ to $C_7$ acyloxy, nitro, carboxy, protected carboxy, carbamoyl, carboxamide, protected carboxamide, N-($C_1$ to $C_6$ alkyl)carboxamide, protected N-($C_1$ to $C_6$ alkyl)carboxamide, N, N-($C_1$ to $C_6$dialkyl)carboxamide, cyano, N-($C_1$ to $C_6$ alkylsulfonyl) amino, thiol, $C_1$ to $C_4$ alkylthio, $C_1$ to $C_4$ alkylsulfonyl groups; and/or the phenyl group may be substituted with one or more, and preferably one or two, substituents chosen from halogen, hydroxy, protected hydroxy, cyano, nitro, $C_1$ to $C_6$ alkyl, $C_1$ to $C_7$ alkoxy, $C_1$ to $C_7$ acyl, $C_1$ to $C_7$ acyloxy, carboxy, protected carboxy, carboxymethyl, protected carboxymethyl, hydroxymethyl, protected hydroxymethyl, amino, protected amino, (monosubstituted)amino, protected (monosubstituted)amino, (disubstituted)amino, carboxamide, protected carboxamide, N-($C_1$ to $C_6$ alkyl) carboxamide, protected N-($C_1$ to $C_6$ alkyl) carboxamide, N, N-di($C_1$ to $C_6$ alkyl)carboxamide, trifluoromethyl, N-(($C_1$ to $C_6$ alkyl)sulfonyl)amino, N-(phenylsulfonyl)amino or a phenyl group, substituted or unsubstituted, for a resulting biphenyl group. The substituted alkyl or phenyl groups may be substituted with one or more, and preferably one or two, substituents which can be the same or different.

Examples of the term "$C_7$ to $C_{12}$ substituted phenylalkyl" include groups such as 2-phenyl-1-chloroethyl, 2-(4-methoxyphenyl)ethyl, 4-(2,6-dihydroxy phenyl)-n-hexyl, 2-(5-cyano-3-methoxyphenyl)-n-pentyl, 3-(2,6-dimethylphenyl)-n-propyl, 4-chloro-3-aminobenzyl, 6-(4-methoxyphenyl)-3-carboxy(n-hexyl), 5-(4-aminomethylphenyl)-3-(aminomethyl)-n-pentyl, 5-phenyl-3-oxo-n-pent-1-yl and the like.

The term "substituted phenyl" specifies a phenyl group substituted with one or more, and preferably one or two, moieties chosen from the groups consisting of halogen, hydroxy, protected hydroxy, cyano, nitro, $C_1$ to $C_6$ alkyl, $C_1$ to $C_7$ alkoxy, $C_1$ to $C_7$ acyl, $C_1$ to $C_7$ acyloxy, carboxy, protected carboxy, carboxymethyl, protected carboxymethyl, hydroxymethyl, protected hydroxymethyl, amino, protected amino, (monosubstituted)amino, protected (monosubstituted)amino, (disubstituted)amino, carboxamide, protected carboxamide, N-($C_1$ to $C_6$ alkyl) carboxamide, protected N-($C_1$ to $C_6$ alkyl)carboxamide, N, N-di ($C_1$ to $C_6$ alkyl) carboxamide, trifluoromethyl, N-(($C_1$ to $C_6$ alkyl)sulfonyl)amino, N-(phenylsulfonyl)amino or phenyl, substituted or unsubstituted, such that, for example, a biphenyl results.

Examples of the term "substituted phenyl" include a mono- or di(halo)phenyl group such as 2, 3 or 4-chlorophenyl, 2,6-dichlorophenyl, 2,5-dichlorophenyl, 3,4-dichlorophenyl, 2, 3 or 4-bromophenyl, 3,4-dibromophenyl, 3-chloro-4-fluorophenyl, 2, 3 or 4-fluorophenyl and the like; a mono or di(hydroxy)phenyl group such as 2, 3 or 4-hydroxyphenyl, 2,4-dihydroxyphenyl, the protected-hydroxy derivatives thereof and the like; a nitrophenyl group such as 2, 3 or 4-nitrophenyl; a cyanophenyl group, for example, 2, 3 or 4-cyanophenyl; a mono- or di(alkyl)phenyl group such as 2, 3 or 4-methylphenyl, 2,4-dimethylphenyl, 2, 3 or 4-(isopropyl)phenyl, 2, 3 or 4-ethylphenyl, 2, 3 or 4-(n-propyl) phenyl and the like; a mono or di(alkoxyl)phenyl group, for example, 2,6-dimethoxyphenyl, 2, 3 or 4-methoxyphenyl, 2, 3 or 4-ethoxyphenyl, 2, 3 or 4-(isopropoxy)phenyl, 2, 3 or 4-(t-butoxy)phenyl, 3-ethoxy-4-methoxyphenyl and the like; 2, 3 or 4-trifluoromethylphenyl; a mono- or dicarboxyphenyl or (protected carboxy)phenyl group such as 2, 3 or 4-carboxyphenyl or 2,4-di(protected carboxy)phenyl; a mono-or di(hydroxymethyl)phenyl or (protected hydroxymethyl)phenyl such as 2, 3, or 4-(protected hydroxymethyl)phenyl or 3,4-di(hydroxymethyl)phenyl; a mono- or di(aminomethyl)phenyl or (protected aminomethyl)phenyl such as 2, 3 or 4-(aminomethyl)phenyl or 2,4-(protected aminomethyl)phenyl; or a mono- or di(N-(methylsulfonylamino))phenyl such as 2, 3 or 4-(N-(methylsulfonylamino))phenyl. Also, the term "substituted phenyl" represents disubstituted phenyl groups wherein the substituents are different, for example, 3-methyl-4-hydroxyphenyl, 3-chloro-4-hydroxyphenyl, 2-methoxy-4-bromophenyl, 4-ethyl-2-hydroxyphenyl, 3-hydroxy-4-nitrophenyl, 2-hydroxy 4-chlorophenyl and the like.

Phenylthio, phenyl sulfoxide, and phenylsulfonyl compounds are known in the art and these terms have their art recognized definition. By "substituted phenylthio," "substituted phenyl sulfoxide," and "substituted phenylsulfonyl" is meant that the phenyl can be substituted as described above in relation to "substituted phenyl."

The term "substituted aniline" specifies an aniline group substituted with one or more, and preferably one or two, moieties chosen from the groups consisting of halogen, hydroxy, protected hydroxy, cyano, nitro, $C_1$ to $C_6$ alkyl, $C_1$ to $C_7$ alkoxy, $C_1$ to $C_7$ acyl, $C_1$ to $C_7$ acyloxy, carboxy, protected carboxy, carboxymethyl, protected carboxymethyl, hydroxymethyl, protected hydroxymethyl, amino, protected amino, (monosubstituted)amino, protected (monosubstituted)amino, (disubstituted)amino, carboxamide, protected carboxamide, N-($C_1$ to $C_6$ alkyl) carboxamide, protected N-($C_1$ to $C_6$ alkyl)carboxamide, N, N-di($C_1$ to $C_6$ alkyl)carboxamide, trifluoromethyl, N-(($C_1$ to $C_6$ alkyl)sulfonyl)amino and N-(phenylsulfonyl)amino.

Examples of substituted aniline include 2-fluoroanilinyl, 3-fluoroanilinyl, 4-fluoroanilinyl, 2-chloroanilinyl, 3-chloroanilinyl, 4-chloroanilinyl, 2-bromoanilinyl, 3-bromoanilinyl, 4-bromoanilinyl, 2-methoxyanilinyl, 3-methoxyanilinyl, 4-methoxyanilinyl, 2-hydroxyanilinyl, 3-hydroxyanilinyl, 4-hydroxyanilinyl, 2-carboethoxyanilinyl, 3-carboethoxyanilinyl, 4-carboethoxyanilinyl, 2-trifluoromethylanilinyl, 3-trifluoromethylanilinyl, 4-trifluoromethylanilinyl, 2-dimethylaminoanilinyl, 3-dimethylaminoanilinyl, 4-dimethylaminoanilinyl, 2-phenoxyanilinyl, 3-phenoxyanilinyl, 4-phenoxyanilinyl, 3,4-methylenedioxyanilinyl, 2,3-methylenedioxyanilinyl, 2,3-difluoroanilinyl, 2,3-dibromoanilinyl, 3,4-dibromoanilinyl, 2,3-dimethoxyanilinyl, 3,4-dimethoxyanilinyl, 1-amino-5,6,7,8-tetrahydronaphthyl, 2-hydroxy-3-amino-5,6,7,8-tetrahydronaphthyl, 2-aminonaphthyl, 1-amino-4-chloronaphthyl, 1-amino-4-bromonaphthyl, 5-amino-1-hydroxynaphthyl, 1-amino-2-hydroxynaphthyl, 5-aminoindanyl, 1-aminofluorenyl, 2-aminofluorenyl and N-methylanilinyl.

The term "substituted naphthyl" specifies a naphthyl group substituted with one or more, and preferably one or two, moieties either on the same ring or on different rings chosen from the groups consisting of halogen, hydroxy, protected hydroxy, cyano, nitro, $C_1$ to $C_6$ alkyl, $C_1$ to $C_7$ alkoxy, $C_1$ to $C_7$ acyl, $C_1$ to $C_7$ acyloxy, carboxy, protected carboxy, carboxymethyl, protected carboxymethyl, hydroxymethyl, protected hydroxymethyl, amino, protected amino, (monosubstituted)amino, protected (monosubstituted)amino, (disubstituted)amino, carboxamide, protected carboxamide, N-($C_1$ to $C_6$ alkyl) carboxamide, protected N-($C_1$ to $C_6$ alkyl)carboxamide, N, N-di($C_1$ to $C_6$ alkyl)carboxamide, trifluoromethyl, N-(($C_1$ to $C_6$ alkyl)sulfonyl)amino or N-(phenylsulfonyl)amino.

Examples of the term "substituted naphthyl" include a mono or di(halo)naphthyl group such as 1, 2, 3, 4, 5, 6, 7 or 8-chloronaphthyl, 2, 6-dichloronaphthyl, 2, 5-dichloronaphthyl, 3, 4-dichloronaphthyl, 1, 2, 3, 4, 5, 6, 7 or 8-bromonaphthyl, 3, 4-dibromonaphthyl, 3-chloro-4-fluoronaphthyl, 1, 2, 3, 4, 5, 6, 7 or 8-fluoronaphthyl and the like; a mono or di(hydroxy)naphthyl group such as 1, 2, 3, 4, 5, 6, 7 or 8-hydroxynaphthyl, 2, 4-dihydroxynaphthyl, the protected-hydroxy derivatives thereof and the like; a nitronaphthyl group such as 3- or 4-nitronaphthyl; a cyanonaphthyl group, for example, 1, 2, 3, 4, 5, 6, 7 or 8-cyanonaphthyl; a mono- or di(alkyl)naphthyl group such as 2, 3, 4, 5, 6, 7 or 8-methylnaphthyl, 1, 2, 4-dimethylnaphthyl, 1, 2, 3, 4, 5, 6, 7 or 8-(isopropyl) naphthyl, 1, 2, 3, 4, 5, 6, 7 or 8-ethylnaphthyl, 1, 2, 3, 4, 5, 6, 7 or 8-(n-propyl)naphthyl and the like; a mono or di(alkoxy)naphthyl group, for example, 2, 6-dimethoxynaphthyl, 1, 2, 3, 4, 5, 6, 7 or 8-methoxynaphthyl, 1, 2, 3, 4, 5, 6, 7 or 8-ethoxynaphthyl, 1, 2, 3, 4, 5, 6, 7 or 8-(isopropoxy)naphthyl, 1, 2, 3, 4, 5, 6, 7 or 8-(t-butoxy)naphthyl, 3-ethoxy-4-methoxynaphthyl and the like; 1, 2, 3, 4, 5, 6, 7 or 8-trifluoromethylnaphthyl; a mono- or dicarboxynaphthyl or (protected carboxy)naphthyl group such as 1, 2, 3, 4, 5, 6, 7 or 8-carboxynaphthyl or 2, 4-di(-protected carboxy)naphthyl; a mono-or di(hydroxymethyl)naphthyl or (protected hydroxymethyl) naphthyl such as 1, 2, 3, 4, 5, 6, 7 or 8-(protected hydroxymethyl)naphthyl or 3,4-di(hydroxymethyl) naphthyl; a mono- or di(amino)naphthyl or (protected amino)naphthyl such as 1, 2, 3, 4, 5, 6, 7 or 8-(amino) naphthyl or 2, 4-(protected amino)-naphthyl, a mono- or di(aminomethyl)naphthyl or (protected aminomethyl) naphthyl such as 2, 3, or 5 4-(aminomethyl)naphthyl or 2,4-(protected aminomethyl)-naphthyl; or a mono- or di-(N-methylsulfonylamino) naphthyl such as 1, 2, 3, 4, 5, 6, 7 or 8-(N-methylsulfonylamino)naphthyl. Also, the term "substituted naphthyl" represents disubstituted naphthyl groups wherein the substituents are different, for example, 3-methyl-4-hydroxynaphth-1-yl, 3-chloro-4-hydroxynaphth-2-yl, 2-methoxy-4-bromonaphth-1-yl, 4-ethyl-2-hydroxynaphth-1-yl, 3-hydroxy-4-nitronaphth-2-yl, 2-hydroxy-4-chloronaphth-1-yl, 2-methoxy-7-bromonaphth-1-yl, 4-ethyl-5-hydroxynaphth-2-yl, 3-hydroxy-8-nitronaphth-2-yl, 2-hydroxy-5-chloronaphth-1-yl and the like.

The terms "halo" and "halogen" refer to the fluoro, chloro, bromo or iodo groups. There can be one or more halogen, which are the same or different. Preferred halogens are bromo, fluoro and chloro.

The term "(monosubstituted)amino" refers to an amino group with one substituent chosen from the group consisting of phenyl, substituted phenyl, $C_1$ to $C_6$ alkyl, $C_1$ to $C_6$ substituted alkyl, $C_1$ to $C_7$ acyl, $C_2$ to $C_7$ alkenyl, $C_2$ to $C_7$ substituted alkenyl, $C_2$ to $C_7$ alkynyl, $C_2$ to $C_7$ substituted alkynyl, $C_7$ to $C_{12}$ phenylalkyl, $C_7$ to $C_{12}$ substituted phenylalkyl and heterocyclic ring. The (monosubstituted)amino can additionally have an amino-protecting group as encompassed by the term "protected (monosubstituted)amino."

Examples of the term (monosubstituted)amino include methylamino, ethylamino, cyclohexylamino, cyclohexylmethyl, cyclohexylethyl, cyclopentylamino, anilinyl, 2-methoxyanilinyl, benzylamino, 2-hydroxybenzylamino, phenethylamino, 2-methoxyphenethylamino and the like.

The term "(disubstituted)amino" refers to amino groups with two substituents chosen from the group consisting of phenyl, substituted phenyl, $C_1$ to $C_6$ alkyl, $C_1$ to $C_6$ substituted alkyl, $C_1$ to $C_7$ acyl, $C_2$ to $C_7$ alkenyl, $C_2$ to $C_7$ alkynyl, $C_7$ to $C_{12}$ phenylalkyl, and $C_7$ to $C_{12}$ substituted phenylalkyl. The two substituents can be the same or different.

The term "amino-protecting group" as used herein refers to substituents of the amino group commonly employed to block or protect the amino functionality while reacting other functional groups of the molecule. The term "protected (monosubstituted)amino" means there is an amino-protecting group on the monosubstituted amino nitrogen atom. In addition, the term "protected carboxamide" means there is an amino-protecting group on the carboxamide nitrogen.

Examples of such amino-protecting groups include the formyl ("For") group, the trityl group, the phthalimido group, the trichloroacetyl group, the chloroacetyl, bromoacetyl, and iodoacetyl groups, urethane-type blocking groups, such as t-butoxycarbonyl ("Boc"), 2-(4-biphenylyl) propyl-2-oxycarbonyl ("Bpoc"), 2-phenylpropyl-2-oxycarbonyl ("Poc"), 2-(4-xenyl)isopropoxycarbonyl, 1,1-diphenylethyl-1-oxycarbonyl, 1,1-diphenylpropyl-1-oxycarbonyl, 2-(3,5-dimethoxyphenyl)propyl-2-oxycarbonyl ("Ddz"), 2-(p-toluyl)propyl-2-oxycarbonyl, cyclopentanyloxycarbonyl, 1-methylcyclopentanyloxycarbonyl, cyclohexanyloxycarbonyl, 1-methylcyclohexanyloxycarbonyl, 2-methylcyclohexanyloxycarbonyl, 2-(4-toluylsulfonyl)ethoxycarbonyl, 2-(methylsulfonyl)ethoxycarbonyl, 2-(triphenylphosphino)-ethoxycarbonyl, 9-fluorenylmethoxycarbonyl ("Fmoc"), 2-(trimethylsilyl)ethoxycarbonyl, allyloxycarbonyl, 1-(trimethylsilylmethyl)prop-1-enyloxycarbonyl, 5-benzisoxalylmethoxycarbonyl, 4-acetoxybenzyloxycarbonyl, 2,2,2-trichloroethoxycarbonyl, 2-ethynyl-2-propoxycarbonyl, cyclopropylmethoxycarbonyl, isobornyloxycarbonyl, 1-piperidyloxycarbonyl, benzyloxycarbonyl ("Cbz"), 4-phenylbenzyloxycarbonyl, 2-methylbenzyloxy-carbonyl, α2,4,5, -tetramethylbenzyloxycarbonyl ("Tmz"), 4-methoxybenzyloxycarbonyl, 4-fluorobenzyloxycarbonyl, 4-chlorobenzyloxycarbonyl, 3-chlorobenzyloxycarbonyl, 2-chlorobenzyloxycarbonyl, 2,4-dichlorobenzyloxycarbonyl, 4-bromobenzyloxycarbonyl, 3-bromobenzyloxycarbonyl, 4-nitrobenzyloxycarbonyl, 4-cyanobenzyloxycarbonyl, 4-(decyloxy)benzyloxycarbonyl and the like; the benzoylmethylsulfonyl group, dithiasuccinoyl ("Dts"), the 2-(nitro)phenylsulfenyl group ("Nps"), the diphenyl-phosphine oxide group and like amino-protecting groups. The species of amino-protecting group employed is not critical so long as the derivatized amino group is stable to the conditions of the subsequent reaction(S) and can be removed at the appropriate point without disrupting the remainder of the compounds. Preferred amino-protecting groups are Boc, Cbz and Fmoc. Further examples of amino-protecting groups embraced by the above term are well known in organic synthesis and the peptide art and are described by, for example, T. W. Greene and P. G. M. Wuts, "Protective Groups in Organic Synthesis," 2nd ed., John Wiley and Sons, New York, N.Y., 1991, Chapter 7, M. Bodanzsky, "Principles of Peptide Synthesis," 1st and 2nd revised ed., Springer-Verlag, New York, N.Y., 1984 and 1993, and Stewart and Young, "Solid Phase Peptide Synthesis," 2nd ed., Pierce Chemical Co., Rockford, Ill., 1984, each of which is incorporated herein by reference. The related term "protected amino" defines an amino group substituted with an amino-protecting group discussed above. In addition, the term "protected carboxamide" means there is an amino-protecting group on the carboxamide nitrogen.

The term "carboxy-protecting group" as used herein refers to one of the ester derivatives of the carboxylic acid group commonly employed to block or protect the carboxylic acid group while reactions are carried out on other functional groups on the compound. Examples of such carboxylic acid protecting groups include t-butyl, 4-nitrobenzyl, 4-methoxybenzyl, 3,4-dimethoxybenzyl, 2,4-dimethoxybenzyl, 2,4,6-trimethoxybenzyl, 2,4,6-trimethylbenzyl, pentamethylbenzyl, 3,4-methylenedioxybenzyl, benzhydryl, 4,4'-dimethoxytrityl, 4,4',4"-trimethoxytrityl, 2-phenylpropyl, trimethylsilyl, t-butyldimethylsilyl, phenacyl, 2,2,2-trichloroethyl, β-(trimethylsilyl)ethyl, β-(di(n-butyl)methylsilyl)ethyl, p-toluenesulfonylethyl, 4-nitrobenzylsulfonylethyl, allyl, cinnamyl, 1-(trimethylsilylmethyl)-propenyl and like moieties. The species of carboxy-protecting group employed is not critical so long as the derivatized carboxylic acid is stable to the conditions of subsequent reaction(S) and can be removed at the appropriate point without disrupting the remainder of the molecule. Further examples of these groups are found in E. Haslam, "Protective Groups in Organic Chemistry," J. G. W. McOmie, Ed., Plenum Press, New York, N.Y., 1973, Chapter 5, and T. W. Greene and P. G. M. Wuts, "Protective Groups in Organic Synthesis," 2nd ed., John Wiley and Sons, New York, N.Y., 1991, Chapter 5, each of which is incorporated herein by reference. A related term is "protected carboxy," which refers to a carboxy group substituted with one of the above carboxy-protecting groups.

The term "hydroxy-protecting group" refers to readily cleavable groups bonded to hydroxyl groups, with the hydroxy becoming a "protected hydroxy". In addition, the term "protected hydroxymethyl" means there is a readily cleavable groups bonded to hydroxyl portion of the hydroxymethyl group. Examples of such readily cleavable groups bonded to hydroxyl groups include the tetrahydropyranyl, 2-methoxypropyl, 1-ethoxyethyl, methoxymethyl, 2-methoxyethoxymethyl, methylthiomethyl, t-butyl, t-amyl, trityl, 4-methoxytrityl, 4,4'-dimethoxytrityl, 4,4',4"-trimethoxytrityl, benzyl, allyl, trimethylsilyl, (t-butyl)dimethylsilyl, 2,2,2-trichloroethoxycarbonyl groups and the like. The species of hydroxy-protecting groups is not critical so long as the derivatized hydroxyl group is stable to the conditions of subsequent reaction(S) and can be removed at the appropriate point without disrupting the remainder of the molecule. Further examples of hydroxy-protecting groups are described by C. B. Reese and E. Haslam, "Protective Groups in Organic Chemistry," J. G. W. McOmie, Ed., Plenum Press, New York, N.Y., 1973, Chapters 3 and 4, respectively, and T. W. Greene and P. G. M. Wuts, "Protective Groups in Organic Synthesis," 2nd ed., John Wiley and Sons, New York, N.Y., 1991, Chapters 2 and 3.

The term "$C_1$ to $C_4$ alkylthio" refers to sulfide groups such as methylthio, ethylthio, n-propylthio, isopropylthio, n-butylthio, t-butylthio and like groups.

The term "$C_1$ to $C_4$ alkylsulfoxide" indicates sulfoxide groups such as methylsulfoxide, ethylsulfoxide, n-propylsulfoxide, isopropylsulfoxide, n-butylsulfoxide, sec-butylsulfoxide and the like.

The term "$C_1$ to $C_4$ alkylsulfonyl" encompasses groups such as methylsulfonyl, ethylsulfonyl, n-propylsulfonyl, isopropylsulfonyl, n-butylsulfonyl, t-butylsulfonyl and the like.

By "substituted phenylthio," "substituted phenyl sulfoxide," and "substituted phenylsulfonyl" is meant that the phenyl can be substituted as described above in relation to "substituted phenyl."

The terms "cyclic $C_2$ to $C_7$ alkylene," "substituted cyclic $C_2$ to $C_7$ alkylene," "cyclic $C_2$ to $C_7$ heteroalkylene," and "substituted cyclic $C_2$ to $C_7$ heteroalkylene," define such a cyclic group bonded ("fused") to the phenyl radical resulting in a bicyclic ring system. The cyclic group may be saturated or contain one or two double bonds. Furthermore, the cyclic group may have one or two methylene or methine groups replaced by one or two oxygen, nitrogen or sulfur atoms which are the the cyclic $C_2$ to $C_7$ heteroalkylene.

The cyclic alkylene or heteroalkylene group may be substituted once or twice by the same or different substituents selected from the group consisting of the following moieties: hydroxy, protected hydroxy, carboxy, protected carboxy, oxo, protected oxo, $C_1$ to $C_4$ acyloxy, formyl, $C_1$ to $C_7$ acyl, $C_1$ to $C_6$ alkyl, carbamoyl, $C_1$ to $C_7$ alkoxy, $C_1$ to $C_4$ alkylthio, $C_1$ to $C_4$ alkylsulfoxide, $C_1$ to $C_4$ alkylsulfonyl, halo, amino, protected amino, (monosubstituted)amino, protected (monosubstitued)amino, (disubstituted)amino, hydroxymethyl or a protected hydroxymethyl.

The cyclic alkylene or heteroalkylene group fused onto the benzene radical can contain two to ten ring members, but it preferably contains three to six members. Examples of such saturated cyclic groups are when the resultant bicyclic ring system is 2,3-dihydro-indanyl and a tetralin ring. When the cyclic groups are unsaturated, examples occur when the resultant bicyclic ring system is a naphthyl ring or indolyl. Examples of fused cyclic groups which each contain one nitrogen atom and one or more double bond, preferably one or two double bonds, are when the phenyl is fused to a pyridino, pyrano, pyrrolo, pyridinyl, dihydropyrrolo, or dihydropyridinyl ring. Examples of fused cyclic groups which each contain one oxygen atom and one or two double bonds are when the phenyl ring is fused to a furo, pyrano, dihydrofurano, or dihydropyrano ring. Examples of fused cyclic groups which each have one sulfur atom and contain one or two double bonds are when the phenyl is fused to a thieno, thiopyrano, dihydrothieno or dihydrothiopyrano ring. Examples of cyclic groups which contain two heteroatoms selected from sulfur and nitrogen and one or two double bonds are when the phenyl ring is fused to a thiazolo, isothiazolo, dihydrothiazolo or dihydroisothiazolo ring. Examples of cyclic groups which contain two heteroatoms selected from oxygen and nitrogen and one or two double bonds are when the benzene ring is fused to an oxazolo, isoxazolo, dihydrooxazolo or dihydroisoxazolo ring. Examples of cyclic groups which contain two nitrogen heteroatoms and one or two double bonds occur when the benzene ring is fused to a pyrazolo, imidazolo, dihydropyrazolo or dihydroimidazolo ring or pyrazinyl.

The term "amino acid" includes any one of the twenty naturally-occurring amino acids or the D-form of any one of the naturally-occurring amino acids. In addition, the term "amino acid" also includes other non-naturally occurring amino acids besides the D-amino acids, which are functional equivalents of the naturally-occurring amino acids. Such non-naturally-occurring amino acids include, for example, norleucine ("Nle"), norvaline ("Nva"), β-Alanine, L- or D-naphthalanine, ornithine ("Orn"), homoarginine (homoArg) and others well known in the peptide art, such as those described in M. Bodanzsky, "Principles of Peptide Synthesis," 1st and 2nd revised ed., Springer-Verlag, New York, N.Y., 1984 and 1993, and Stewart and Young, "Solid Phase Peptide Synthesis," 2nd ed., Pierce Chemical Co., Rockford, Ill., 1984, both of which are incorporated herein by reference. Amino acids and amino acid analogs can be purchased commercially (Sigma Chemical Co.; Advanced Chemtech) or synthesized using methods known in the art.

The amino acids are indicated herein by either their full name or by the commonly known three letter code. Further, in the naming of amino acids, "D-" designates an amino acid having the "D" configuration, as opposed to the naturally occurring L-amino acids. Where no specific configuration is indicated, one skilled in the art would understand the amino acid to be an L-amino acid. The amino acids can, however, also be in racemic mixtures of the D- and L-configuration.

As used herein, the phrase "any one of the twenty naturally-occurring amino acids" means any one of the following: Ala, Arg, Asn, Asp, Cys, Gln, Glu, Gly, His, Ile, Leu, Lys, Met, Phe, Pro, Ser, Thr, Trp, Tyr, and Val. As used herein, the language "the D-form of a naturally-occurring amino acid" means the D-isomer of any one of these naturally-occurring amino acids, with the exception of Gly, which does not occur as D or L isomers.

One or more of the isoquinoline derivatives, even within a given library, may be present as a salt. The term "salt" encompasses those salts that form with the carboxylate anions and amine nitrogens and include salts formed with the organic and inorganic anions and cations discussed below. Furthermore, the term includes salts that form by standard acid-base reactions with basic groups (such as amino groups) and organic or inorganic acids. Such acids include hydrochloric, sulfuric, phosphoric, acetic, succinic, citric lactic, maleic, fumaric, palmitic, cholic, pamoic, mucic, D-glutamic, d-camphoric, glutaric, phthalic, tartaric, lauric, stearic, salicyclic, methanesulfonic, benzenesulfonic, sorbic, picric, benzoic, cinnamic, and like acids.

The term "organic or inorganic cation" refers to counterions for the carboxylate anion of a carboxylate salt. The counter-ions are chosen from the alkali and alkaline earth metals, (such as lithium, sodium, potassium, barium, aluminum and calcium); ammonium and mono-, di- and tri-alkyl amines such as trimethylamine, cyclohexylamine; and the organic cations, such as dibenzylammonium, benzylammonium, 2-hydroxyethylammonium, bis(2-hydroxyethyl)ammonium, phenylethylbenzylammonium, dibenzylethylenediammonium, and like cations. See, for example, "Pharmaceutical Salts," Berge et al., *J. Pharm. Sci.*, 66:1–19 (1977), which is incorporated herein by reference. Other cations encompassed by the above term include the protonated form of procaine, quinine and N-methylglucosamine, and the protonated forms of basic amino acids such as glycine, ornithine, histidine, phenylglycine, lysine and arginine. Furthermore, any zwitterionic form of the instant compounds formed by a carboxylic acid and an amino group is referred to by this term. For example, a cation for a carboxylate anion will exist when $R_2$ or $R_3$ is substituted with a (quaternary ammonium) methyl group. A preferred cation for the carboxylate anion is the sodium cation.

The compounds of the above formula can also exist as solvates and hydrates. Thus, these compounds may crystallize with, for example, waters of hydration, or one, a number of, or any fraction thereof of molecules of the mother liquor solvent. The solvates and hydrates of such compounds are included within the scope of this invention.

One or more isoquinoline derivatives, even when in a library, can be in the biologically active ester form, such as the non-toxic, metabolically-labile ester-form. Such ester forms induce increased blood levels and prolong the efficacy of the corresponding non-esterified forms of the compounds. Ester groups which can be used include the lower alkoxymethyl groups, for example, methoxymethyl, ethoxymethyl, isopropoxymethyl and the like; the $\alpha$-($C_1$ to $C_7$) alkoxyethyl groups, for example methoxyethyl, ethoxyethyl, propoxyethyl, isopropoxyethyl and the like; the 2-oxo-1,3-diooxlen-4-ylmethyl groups, such as 5-methyl-2-oxo-1,3-dioxolen-4-ylmethyl, 5-phenyl-2-oxo-1,3-dioxolen-4-ylmethyl and the like; the $C_1$ to $C_4$ alkylthiomethyl groups, for example methylthiomethyl, ethylthiomethyl, isopropylthiomethyl and the like; the acyloxymethyl groups, for example pivaloyloxymethyl, pivaloyloxyethyl, $\alpha$-acetoxymethyl and the like; the ethoxycarbonyl-1-methyl group; the a-acetoxyethyl; the 1-($C_1$ to $C_7$ alkyloxycarbonyloxy)ethyl groups such as the 1-(ethoxycarbonyloxy)ethyl group; and the 1-($C_1$ to $C_7$ alkylaminocarbonyloxy)ethyl groups such as the 1-(methylaminocarbonyloxy)ethyl group.

The term "array" is used merely to catagorize or group a collection of individually synthesized compounds based on certain commonality of one or more R substituents. Although compounds individually synthesized and screened as in ensuing examples, libraries containing such compounds can also be prepared by the synthetic scheme of the examples below using well known combinatorial chemistry. Therefore, libraries containing isoquinoline compounds as disclosed herein are included within the invention.

The library prepared from the above mentioned method can be useful for screening the library on the resin or alternatively can be cleaved from the resin as discrete compounds and screened in absence of resin. Preferably, the methods described above further comprise the step of cleaving the library from the resin to give discrete compounds.

As used herein, a chemical or combinatorial "library" is an intentionally created collection of differing molecules which can be prepared by the synthetic means provided below or otherwise and screened for biological activity in a variety of formats (e.g., libraries of soluble molecules, libraries of compounds attached to resin beads, silica chips or other solid supports). The libraries can be screened in any variety of melanocortin receptor and related activity assays, such as those detailed below as well as others known in the art. The libraries will generally have at least one active compound and are generally prepared in such that the compounds are in equimolar quantities.

Compounds disclosed in previous work that are not in an intentially created collection are not part of a "combinatorial library" of the invention. In addition, compounds that are in an unintentional or undesired mixture are not part of a "combinatorial library" of the invention.

"Combinatorial chemistry" or "combinatorial synthesis" refers to the parallel synthesis of diverse compounds by sequential addition of reagents which leads to the generation of large chemical libraries having molecular diversity. Combinatorial chemistry, therefore, involves the systematic and repetitive, covalent connection of a set of different "building blocks" of varying structures to yield large arrays of diverse molecular entities.

A combinatorial library of the invention can contain two or more of the above-described compounds. The invention further provides a combinatorial library containing five or more of the above-described compounds. In another embodiment of the invention, a combinatorial library can contain ten or more of the above-described compounds. In yet another embodiment of the invention, a combinatorial library can contain fifty or more of the above-described compounds. If desired, a combinatorial library of the invention can contain 100,000 or more, or even 1,000,000 or more, of the above-described compounds.

By way of example, the preparation of the combinatorial libraries can use the "split resin approach." The split resin approach is described by, for example, U.S. Pat. No. 5,010,175 to Rutter, WO PCT 91/19735 to Simon, and Gallop et al., *J. Med. Chem.*, 37:1233–1251 (1994), all of which are incorporated herein by reference.

In addition to the above isoquinoline compounds, which are MC receptor ligands, other isoquinoline compounds can also function as MC receptor ligands. Other isoquinoline compounds that can function as MC receptor ligands include the isoquinoline derivatives and isoquinoline compound libraries described in Kiely et al., "Isoquinoline Derivatives and Isoquinoline Combinatorial Libraries," U.S. Patent application Ser. No. 08/734,516, filed Oct. 18, 1996, which is incorporated herein by reference.

MC receptor ligands such as the isoquinoline compounds disclosed herein can be synthesized using the methods of synthesis described in Example I below. The choice of chemical functional groups incorporated into specific positions on isoquinoline compounds will depend, in part, on the specific physical, chemical or biological characteristics required of the MC receptor ligand. Such characteristics are determined, in part, by the route by which the MC receptor ligand will be administered or the location in a subject to which the MC receptor ligand will be directed.

As used herein, the term "ligand" means a molecule that can selectively bind to a receptor. For example, a MC receptor ligand can selectively bind to a MC receptor. Those skilled in the art know what is meant by the term ligand. The isoquinoline compounds described herein are MC receptor ligands. A ligand can function as an agonist or antagonist. As used herein, the term "agonist" means that a ligand has the function of mimicking the physiological activity of another molecule. For example, a MC receptor ligand that functions as an agonist mimics the physiological activity of a MC receptor ligand such as MSH, which stimulates MC receptor activity. Similarly, the term "antagonist" means that a ligand has the function of reducing the physiological activity of another molecule, for example, by preventing the activation or inhibiting the activity of a receptor. For example, a MC receptor ligand that functions as an antagonist reduces the physiological activity of a MC receptor. A reduction in MC receptor activity can be due to the antagonist binding to the MC receptor and inhibiting activation or to the antagonist preventing the binding of a ligand that stimulates MC receptor activity.

The invention provides methods for altering the activity of a MC receptor in a subject by administering to the subject an effective amount of a MC receptor ligand, wherein the MC receptor ligand comprises an isoquinoline compound. The MC receptor ligands can be the isoquinoline compounds having the structures described above.

Many of the physiological effects of known MC receptor ligands on MC receptor activity are mediated by cytokines, and MC receptor ligands alter cytokine activity. Due to the effect of MC receptor signaling on cytokines, the MC receptor ligands of the invention can function as cytokine regulatory agents by regulating the aberrant or altered expression of one or more cytokines that occurs in various conditions, including, for example, pathologies, immune responses and inflammatory responses. Such conditions are considered together for purposes of the present invention in that they are characterized, in part, by altered or aberrant cytokine activity and, therefore, are amenable to regulation by one or more cytokine regulatory agents such as the MC receptor ligands disclosed herein.

It should be recognized, however, that while the MC receptor ligands of the invention can function as cytokine regulatory agents, no specific mechanism of action is proposed as to how a MC receptor ligand acts to affect a condition. The MC receptor ligands of the invention can be used to treat conditions characterized by altered or aberrant cytokine activity. However, the conditions treatable with the MC receptor ligands of the invention are not restricted to those conditions or diseases involving altered cytokine activity. The MC receptor ligands are useful for treating a disease or condition if the MC receptor ligand prevents the disease or improves signs or symptoms of the disease, regardless of the mechanism causing the signs or symptoms of the disease.

The effects of isoquinoline compounds, which bind to MC receptors and have the structures described above, on cytokines are similar to those for cytokine regulatory agents such as HP 228, which has the amino acid sequence Ac-Nle-Gln-His-(D)Phe-Arg-(D)Trp-Gly-$NH_2$ (see Examples VI to IX). The amino acids are designated by their well known three letter codes, with the amino acids in the L- configuration except those specifically indicated as the D- configuration. Nle represents norleucine. The amino-terminus is acetylated and the carboxyl-terminus is amidated. The effect of HP 228 on cytokines and the uses provided thereby are described, for example, in U.S. Pat. No. 5,420,109, WO 95/13086 and WO 96/27386, each of which is incorporated herein by reference. The present invention provides a method of restraining a pathologically elevated cytokine activity in a subject by administering to the subject an effective amount of MC receptor ligands such as isoquinoline compounds. The pathologically elevated cytokine activity can be due, for example, to inflammation, cachexia, or a patho-immunogenic disease.

Aberrant cytokine expression can result in damage to healthy tissue in a subject and, in extreme cases, can lead to severe disability and death. Cytokines can be expressed at a site of localized infection or can be expressed systemically, for example, in an immune response or in response to bacterial endotoxin-induced sepsis. Cytokine expression can induce pyrexia (fever) and hyperalgesia (extreme sensitivity to pain) in a subject, as well as macrophage and monocyte activation, which produces or further contributes to an inflammatory response in a subject.

As used herein, the terms "regulate" or "regulatory" mean to control by enhancing, limiting, restricting, restraining, modulating or moderating. Such regulation includes the pleiotropic, redundant, synergistic or antagonistic effects that occur due to the activity of biological agents such as cytokines, which can affect a variety of biological functions directly or indirectly through cascade or biofeedback mechanisms.

As used herein, the term "cytokine regulatory agent" means an agent that controls cytokine activity by enhancing, limiting, restricting, restraining, modulating or moderating the biological activity of a cytokine. It should be recognized, however, that while the cytokine regulating agents generally can regulate cytokine activity, no specific mechanism of action is proposed as to how a cytokine regulatory agent acts to affect a condition characterized by altered or aberrant cytokine activity.

Cytokines are well known in the art and include, but are not limited to the tumor necrosis factors (TNFs), colony stimulating factors (CSFs), interferons (INFs), interleukins (IL-1, IL-2, IL-3, IL-4, IL-5, IL-6, IL-7, IL-8, IL-9, IL-10, IL-11, IL-12, IL-13, IL-14, and IL-15), transforming growth factors (TGFs), oncostatin M (OSM), leukemia inhibiting factor (LIF), platelet activating factor (PAF) and other soluble immunoregulatory peptides that mediate host defense responses, cell regulation and cell differentiation (see, for example, Kuby, *Immunology* 3rd ed. (W. H. Freeman and Co., New York (1997); see Chapter 13, which is incorporated herein by reference).

As used herein, the term "characterized by" means contributes or affects, at least in part. Though cytokine contribution can be, it does not have to be, the only, primary, or even a major factor of the condition. For example, it is well understood in the art that an infection has altered cytokine levels and is, therefore, a condition characterized by cytokine activity, although cytokine activity is only a part of the infectious condition.

As used herein, the term "condition characterized by altered or aberrant cytokine activity" includes all cytokine regulated or modulated pathologies and injuries, including the immune, inflammatory and healing processes associated with an injury or disease. The skilled artisan can recognize such a condition by detecting an increased or decreased level or activity of a particular cytokine as compared to the normal level of the cytokine expected to be found in a healthy individual. Methods for determining such normal levels are well known in the art and can be determined by sampling a statistically significant number of subjects in the population.

As used herein, the term "pathologically elevated" means that a cytokine activity is elevated above a range of activities which is expected in a normal population of such subjects and which is associated with a pathological response. For example, a normal range of interleukin activity, such as IL-1β activity, present in a specific tissue can be determined by sampling a number of subjects in the population. A subject having a pathology characterized by cytokine-induced pathological effects can be readily identified by determining that the cytokine activity in the subject is pathologically elevated above the normal range. In particular, a pathologically elevated level of cytokine activity is at least about one standard deviation above the normal, and can be at least two standard deviations above the normal range.

A MC receptor ligand of the invention, such as an isoquinoline compound, can function as a cytokine regulatory agent and can be used to decrease the activity of a cytokine. For example, a particular pathological condition can cause an increase in the level or activity of a cytokine. A MC receptor ligand that functions to restrain cytokine activity can be used to reduce the level or activity of the elevated cytokine. Such a reduction in cytokine activity can alleviate the symptoms of the pathological condition. As disclosed herein, isoquinoline compounds of the invention can effectively decrease the level of TNF-α (see Example VI and Table 4). Isoquinoline compounds that are particularly effective at decreasing TNF-α include TRG 2405-190, TRG 2405-241, TRG 2405-252, TRG 2405-253 and TRG 2408-30.

A MC receptor ligand of the present invention can function as a cytokine regulatory agent, or composition containing the agent, and can be used to increase the physiologic level of one or more cytokines. For example, a particular condition can decrease the level or activity of a cytokine, which can inhibit all or part of an immune response or the immune system. Administration of a cytokine regulatory agent in a pharmacologically efficacious dose can enhance the level or activity of the cytokine, thereby reducing the level of immunosuppression.

A MC receptor ligand such as the isoquinoline compounds disclosed herein can function as a cytokine regulatory agent and increase the levels of IL-10 in a mammal such as a human. IL-10 can block the activation of some inflammatory cytokines, including TNF, IL-1 and IL-6, while up-regulating cytokines such as IL-12. IL-10 also stimulates the proliferation of mast cells and thymocytes. IL-10 inhibits several monocyte and macrophage functions, including, for example, antigen presentation to T cells by depressing Class II MHC expression; synthesis of IL-1, IL-6, IL-8, CSF, and TNF; and microbicidal activities. The inhibited microbicidal activities include suppressing production of nitrogen oxides and bactericidal metabolites. As a consequence of monocyte and macrophage IL-10 mediated inhibition, activity of some types of helper T cells is inhibited. Particularly, the $T_H 1$ cells, which are responsible for cell-mediated functions such as delayed-type hypersensitivity cells, and cytotoxic T cells are inhibited. As a further consequence of $T_H 1$ cell inhibition, activity of the $T_H 2$ cells is augmented, particularly the T cell subset that augments B cell activation, bacterial and helminthic resistance and allergic reactions.

As disclosed herein, administration of a MC receptor ligand can increase the plasma levels of IL-10 in mammals (see Example VII and Table 4) and, therefore, can be useful for modulating, for example, immunoresponsiveness in a subject. Isoquinoline compounds that are particularly effective at increasing IL-10 include TRG 2405-190, TRG 2405-241, TRG 2405-252, TRG 2405-253 and TRG 2408-30.

The binding of a MC receptor ligand to a MC receptor results in a wide range of physiological responses. MC receptors are G protein-coupled receptors that activate adenylate cylcase and produce cAMP in response to binding of ligands such as MSH. Although many of the physiological effects of MC receptor signaling are mediated by cytokines, MC receptor ligands of the invention are not limited to those that regulate cytokine activity, as discussed above, but can be any MC receptor ligand that functions to alleviate the signs or symptoms of a disease or condition. Therefore, MC receptor ligands are useful for exploiting the various physiological responses mediated by MC receptor signaling.

The diversity of physiological responses to MC receptor signaling can be advantageously used to alter or regulate a physiological pathway that mediates or moderates a pathological condition or disease. The recent elucidation of the role of specific MC receptors in particular physiological pathways supports the use of ligands that activate specific MC receptors to modulate a physiological effect that results in a a given condition or disease. Therefore, MC receptor ligands of the invention, which alter the activity of a MC receptor that mediates or moderates a given condition or disease, are useful for treating that condition or disease.

MCR-1 is involved in pain and inflammation and, therefore, MC receptor ligands that alter the activity of MCR-1 are particularly useful for treating pain and inflammation. In one embodiment, a MC receptor ligand such as an isoquinoline compound can be used as an analgesic or anti-inflammatory agent. α-MSH has been shown to inhibit migration and chemotaxis of neutrophils, which express MCR-1 (Catania et al., supra). The inhibition by α-MSH was associated with changes in neutrophil cyclic AMP (cAMP) levels. MC receptors are G-protein coupled receptors that couple to adenylate cyclase and produce cAMP upon activation. The inhibition of neutrophil chemotaxis is associated with the anti-inflammatory activity of α-MSH. Since α-MSH has anti-inflammatory activity, the MC receptor ligands of the invention, such as isoquinoline compounds, can similarly function as anti-inflammatory agents, for example, by reducing neutrophil chemotaxis.

MC receptor ligands such as isoquinoline compounds are useful for reducing inflammation. As described in Example VIII, administration of TRG 2405-190, TRG 2405-241, TRG 2405-252, TRG 2405-253, TRG 2409-2 and TRG 2409-14 reduced inflammation in response to arachadonic acid administration. These results show that MC receptor ligands such as isoquinoline compounds, and particularly TRG 2405-190, TRG 2405-241, TRG 2405-252, TRG 2405-253, TRG 2409-2 and TRG 2409-14, are useful for reducing inflammation.

Nitric oxide (NO) is induced during 25 inflammation by a variety of proinflammatory cytokines. α-MSH was shown to inhibit production of NO through reduction of NO synthase and NO synthase mRNA (Star et al., *Proc. Natl. Acad. Sci. USA* 92:8016–8020 (1995)). Similarly, MC receptor ligands of the invention, such as isoquinoline compounds, can be used to inhibit NO production, thereby reducing inflammation.

MC receptor ligands that activate MCR-4 are particularly useful for decreasing body weight. MCR-4 has been shown to function in regulating food intake and weight gain. Targeted disruption of MCR-4 causes mice to develop a maturity onset obesity associated with hyperphagia, hyperinsulinemia and hyperglycemia (Huszar et al., supra). Further evidence for the role of MC receptors in regulating food intake and weight gain involves the function of the agouti protein, which is a MCR-4 antagonist. An agouti-related protein functions as a selective antagonist of MCR-3 and MCR-4 and causes obesity in transgenic mice expressing agouti-related protein (Ollman et al., *Science* 278:135–137 (1997)). Furthermore, agouti analogs were injected into the brains of mice, and those analogs that functioned as MC receptor agonists inhibited feeding while those agouti analogs that functioned as antagonists increased feeding (Fan et al. supra). Thus, a functional role for MC receptors in regulating food intake and weight gain has been established. Therefore, the MC receptor ligands of the invention such as isoquinoline compounds are useful for treating obesity by decreasing food intake and body weight gain.

As disclosed herein, administration of an isoquinoline compound to rats resulted in a significant decrease in the rate of body weight gain and a significant decrease in body weight (see Example IX). As used herein, the term "decrease in body weight" is used broadly to mean an actual decrease in body weight or a decrease in the rate of body weight gain over time, as compared to the normal weight gain expected in the period of time. The isoquinoline compounds TRG 2405-190, TRG 2405-241, TRG 2405-252 and TRG 2405-253 are particularly effective at reducing body weight and food consumption. These results indicate that a MC receptor ligand can cause a decrease in the rate of body weight gain and a decrease in food consumption.

An association between MC receptor signaling and body energy and metabolism has been reported (Huszar et al., supra). The MC receptor ligand HP 228 has been shown to modulate acute resting oxygen consumption (Omholt et al., *The Pharmacologist*, 39:53 (1997)), which is incorporated herein by reference. Therefore, MC receptor ligands of the invention can also be used for modulating the metabolic rate or acute oxygen consumption in a subject. The modulated metabolic rate can lead to a decrease in body weight. Thus, MC receptor ligands that can modulate the metabolic rate or acute oxygen consumption in a subject are particularly useful for decreasing body weight in a subject. The MC receptor ligands of the invention can be used to treat obesity and can independently or in combination affect body weight by decreasing food consumption or modulating metabolic rate or oxygen consumption.

In addition to MC receptor ligands that function as agonists that stimulate MC receptor activity, the invention also provides MC receptor ligands, such as isoquinoline compounds, that function as antagonists that inhibit MC receptor activity. MC receptor antagonists can be used, for example, to increase food intake and body weight analogous to that observed with the MC receptor antagonist agouti protein and the agouti analogs that function as antagonists (Fan et al., supra). MC receptor ligands that function as antagonists are particularly useful for increasing food intake and body weight in an individual suffering from cachexia, a general weight loss that occurs during chronic disease or emotional disturbance.

MC receptor ligands of the invention can also function as cytokine regulatory agents that are useful for treating diabetes. A link exists between obesity and non-insulin dependent diabetes mellitus (NIDDM) (Hotamisligil and Spiegelman, *Diabetes* 43:1271–1278 (1994a)). Therefore, MC receptor ligands are useful for decreasing the weight of an obese subject to prevent or alleviate the symptoms associated with NIDDM. Increased TNF-α expression has been detected in the adipose tissue of obese individuals and has been suggested to have a role in the appearance of NIDDM in these individuals (Hotamisligil et al., *J. Clin. Invest*, 95:2409–2415 (1995)). However, efforts to neutralize TNF activity using an antibody that binds the TNF receptor did not result in significant weight loss when examined in a rat obesity/diabetes model, the Zucker fa/fa rat model (Hotamisligil et al., *J. Clin Invest*, 94:1543–1549 (1994b)). Therefore, MC receptor ligands of the invention that decrease TNF-α are particularly useful for treating diabetes and associated obesity.

The α-MSH analog MELANOTAN-II has been shown to cause penile erections in human subjects in pilot phase I clinical studies (Dorr et al., *Life Sciences* 58:1777–1784 (1996)). Therefore, MC receptors ligands of the invention can be used to treat erectile dysfunction in a subject (see Example X and FIGS. 8 and 9). Further examples of compounds include any of the isoquinolines described herein, including those in TRG 2411.

Other conditions that can be treated with the MC receptor ligands of the invention such as isoquinoline compounds include, but are not limited to, disuse deconditioning; organ damage such as occurs in response to organ transplantation or ischemic injury such as that which can occur after reperfusion or stroke; adverse reactions associated with cancer chemotherapy; diseases such as atherosclerosis that are mediated by free radicals and nitric oxide action; bacterial endotoxic sepsis and related shock; adult respiratory distress syndrome; and autoimmune or other patho-immunogenic diseases or reactions such as allergic reactions or anaphylaxis, rheumatoid arthritis, inflammatory bowel disease, ulcerative colitis, glomerulonephritis, systemic lupus erythematosus, transplant atherosclerosis and parasitic mediated immune dysfunctions such as Chagas' Disease. Many of these conditions are characterized by altered or aberrant cytokine activity.

A variety of assays can be used to identify or characterize MC receptor ligands of the invention. For example, the ability of an isoquinoline compound to compete for binding of a known MC receptor ligand can be used to assess the affinity and specificity of an isoquinoline compound for one or more MC receptors. Any MC receptor ligand can be used so long as the ligand can be labeled with a detectable moiety. The detectable moiety can be, for example, a radiolabel, fluorescent label or chromophore, or any detectable functional moiety so long as the MC receptor ligand exhibits specific MC receptor binding. As described in Example II, a particularly useful detectable MC receptor ligand for identifying and characterizing other MC receptor ligands is $^{125}$I-HP 467, which has the amino acid sequence Ac-Nle-Gln-His-(p(I)-D-Phe)-Arg-(D-Trp)-Gly-NH$_2$ and is described in Dooley et al., "Melanocortin Receptor Ligands and Methods of Using Same," U.S. patent application Ser. No. 09/027,108, filed Feb. 20, 1998, which is incorporated herein by reference. HP 467 is a para-iodinated form of HP 228. The results described in Example IV below indicate that a number of MC receptor ligands can be identified using a detectable MC receptor ligand.

Using assay methods such as those described above and in Example II, binding kinetics and competition with radiolabeled HP 467 confirmed that isoquinoline compounds of the invention bind to one or more MC receptors (see Examples II and IV). Furthermore, the assays revealed that isoquinoline compounds of the invention exhibited a range of affinities and specificity for various MC receptors.

A variety of isoquinoline compounds that bind to MCR-1 and MCR-4 and are MC receptor ligands are shown in Table 1. Isoquinoline compounds that are particularly effective MC receptor ligands include TRG 2405-190, TRG 2405-239, TRG 2405-241, TRG 2405-252, TRG 2405-253, TRG 2408-30, TRG 2408-57, TRG 2408-62, TRG 2409-2, TRG 2409-14, TRG 2411-26, TRG 2411-50, TRG 2411-60, TRG 2411-111 and TRG 2411-186.

Some of the isoquinoline compounds were further tested for binding activity to MCR-3 and MCR-5. The results of these MCR-3 and MCR-5 binding studies are shown in Table 2. Various isoquinoline compounds of the invention exhibit binding activity to one or more MC receptors.

The invention provides MC receptor ligands that bind to several MC receptors with similar affinity (see Tables 1 and 2). In addition, the invention also provides MC receptor ligands that show selectivity for one or more MC receptors. As used herein, the term "selectivity" means that the affinity of a MC receptor ligand differs between one MC receptor and another by about 10-fold, generally about 20- to 50-fold, and particularly about 100-fold. In some cases, a MC receptor ligand having broad specificity is desired. In other cases, it is desirable to use MC receptor ligands having selectivity for a particular MC receptor. For example, MCR-1 ligands are particularly useful for treating pain and inflammation, whereas MCR-4 ligands are useful for treating obesity. The binding characteristics and specificity of a given MC receptor ligand can be selected based on the particular disease or physiological effect that is desired to be altered.

Another assay useful for identifying or characterizing MC receptor ligands measures signaling of MC receptors. MC receptors are G protein-coupled receptors that couple to adenylate cyclase and produce cAMP. Therefore, measuring cAMP production in a cell expressing a MC receptor and treated with a MC receptor ligand can be used to assess the function of the MC receptor ligand in activating a MC receptor. One method for measuring cAMP production in cells expressing a MC receptor ligand and treated with an isoquinoline compound of the invention is described in Example III. The results described in Example V show that isoquinoline compounds can activate MC receptors and stimulate cAMP production. A variety of isoquinoline compounds that activate MC receptors are shown in Table 3.

The invention also relates to pharmaceutical compositions comprising a MC receptor ligand such as an isoquinoline compound and a pharmaceutically acceptable carrier. Pharmaceutically acceptable carriers are well known in the art and include aqueous solutions such as physiologically buffered saline or other solvents or vehicles such as glycols, glycerol, oils such as olive oil or injectable organic esters.

A pharmaceutically acceptable carrier can contain physiologically acceptable compounds that act, for example, to stabilize the MC receptor ligand or increase the absorption of the agent. Such physiologically acceptable compounds include, for example, carbohydrates, such as glucose, sucrose or dextrans, antioxidants, such as ascorbic acid or glutathione, chelating agents, low molecular weight proteins or other stabilizers or excipients. One skilled in the art would know that the choice of a pharmaceutically acceptable carrier, including a physiologically acceptable compound, depends, for example, on the route of administration of the MC receptor ligand and on the particular physico-chemical characteristics of the specific MC receptor ligand.

The invention further relates to methods of administering a pharmaceutical composition comprising an MC receptor ligand such as an isoquinoline compound to a subject in order to restrain pathologically elevated cytokine activity in the subject, to treat inflammation or to treat obesity. For example, an isoquinoline compound can be administered to a subject as a treatment for inflammation, pain, obesity or cachexia.

The invention also relates to methods of administering a pharmaceutical composition comprising an MC receptor ligand such as an isoquinoline compound to a subject in order to enhance a cytokine activity that restrains pathologically elevated cytokine activity in a subject. For example, IL-10 is known to decrease the activity of certain pathologically elevated cytokines such as TNF-α, IL-1, IL-6 and IL-8 (Platzer et al., *International Immunol.* 7:517–523 (1995)). A normal range of IL-10 activity present in a specific tissue can be determined by sampling a statistically significant number of normal, healthy subjects in the population. An isoquinoline compound is administered to increase IL-10 activity above the normal range in order to restrain pathologically elevated cytokine activity. In particular, IL-10 cytokine activity is increased at least about one standard deviation above the normal, and can be two standard deviations or greater above the normal range.

A pharmaceutical composition comprising an MC receptor ligand such as an isoquinoline compound can be administered to a subject having pathologically elevated cytokine activity by various routes including, for example, orally, intravaginally, rectally, or parenterally, such as intravenously, intramuscularly, subcutaneously, intraorbitally, intracapsularly, intraperitoneally, intracisternally or by passive or facilitated absorption through the skin using, for example, a skin patch or transdermal iontophoresis, respectively. Furthermore, the composition can be administered by injection, intubation or topically, the latter of which can be passive, for example, by direct application of an ointment or powder, or active, for example, using a nasal spray or inhalant. An MC receptor ligand also can be administered as a topical spray, in which case one component of the composition is an appropriate propellant. The pharmaceutical composition also can be incorporated, if desired, into liposomes, microspheres or other polymer matrices (Gregoriadis, *Liposome Technology*, Vols. I to III, 2nd ed., CRC Press, Boca Raton, Fla. (1993), which is incorporated herein by reference). Liposomes, for example, which consist of phospholipids or other lipids, are nontoxic, physiologically acceptable and metabolizable carriers that are relatively simple to make and administer.

Since cytokine expression can be localized or systemic, one skilled in the art would select a particular route and method of administration of an isoquinoline compound based on the source and distribution of cytokines in a subject. For example, in a subject suffering from a systemic condition such as bacterial endotoxin-induced sepsis, a pharmaceutical composition comprising an isoquinoline compound can be administered intravenously, orally or by another method that distributes the compound systemically. However, in a subject suffering from a pathology caused by localized cytokine expression such as acute respiratory distress syndrome, an isoquinoline compound can be suspended or dissolved in the appropriate pharmaceutically acceptable carrier and administered directly into the lungs using a nasal spray or other inhalation device.

In order to restrain the biological activity of a cytokine, an isoquinoline compound must be administered in an effective dose, which is about 0.0001 to 100 mg/kg body weight. The total effective dose can be administered to a subject as a single dose, either as a bolus or by infusion over a relatively short period of time, or can be administered using a fractionated treatment protocol, in which the multiple doses are administered over a more prolonged period of time. One skilled in the art would know that the concentration of an isoquinoline compound required to obtain an effective dose in a subject depends on many factors including the age and general health of the subject as well as the route of administration and the number of treatments to be administered. In view of these factors, the skilled artisan would adjust the particular dose so as to obtain an effective dose for altering the activity of a MC receptor.

The following examples are intended to illustrate but not limit the invention.

EXAMPLE I

Synthesis of Isoquinoline Compounds

This example shows the synthesis of isoquinoline compounds.

Isoquinoline compounds were synthesized essentially as described previously in U.S. patent application Ser. No. 08/734,516, which is incorporated herein by reference.

An example of the reaction scheme representative of the synthesis of isoquinoline compounds is shown in FIGS. 1A and 1B. FIGS. 1A and 1B show a reaction scheme for synthesis of tetrahydroisoquinoline aromatic amines.

Briefly, for solid-phase synthesis of discrete 15 tetrahydroisoquinoline aromatic amines, the appropriate number of porous polypropylene teabags were prepared, each containing polystyrene methylbenzhydrylamine (MBHA) resin (974 mg, 0.750 milliequivalents). One teabag was placed in a 60 mL bottle and washed with 5% (v/v) N,N,-diisopropylethylamine/dichloromethane (3×30 mL) followed by dichloromethane (DCM, 5×30 mL). A solution of N-(t-butyloxycarbonyl)glycine (657 mg, 3.75 mmoles), N-hydroxybenzotriazole (HOBt) (507 mg, 3.75 mmoles), and N,N-diisopropylcarbodiimide (DIC) (0.705 mL, 4.5 mmoles) was prepared in dimethylformamide (DMF) (37.5 mL) and added to the resin packet. After shaking for 16 hours the teabag was washed with DMF (3×30 mL) and DCM (3×30 mL). The same coupling procedure was performed on the remaining teabags, each being reacted with a separate amino acid from the following ($R^1$) list:

(S)-2-N-(t-butyloxycarbonyl)-3-N-(9-fluorenylmethoxycarbonyl)-diaminopropanoic acid, (S)-2-N-(t-butyloxycarbonyl)-4-N-(9-fluorenylmethoxycarbonyl)-diaminobutanoic acid, (S)-2-N-(t-butyloxycarbonyl)-5-N-(9-fluorenylmethoxycarbonyl)-diaminopentanoic acid, (S)-2-N-(t-butyloxycarbonyl)-6-N-(9-fluorenylmethoxycarbonyl)-diaminohexanoic acid.

The teabag containing N-(t-butyloxycarbonyl)glycine on resin was washed with DCM (2×50 mL), shaken twice in 55% (v/v) trifluoroacetic acid (TFA)/DCM (30 mL, 30 min) and then washed with DCM (30 mL), isopropyl alcohol (2×30 mL), DCM (2×30 mL), 5% (v/v) diisopropylethylamine (DIEA)/DCM (3×30 mL, 2 min each) and DCM (3×30 mL). The remaining teabag was placed in one bottle and washed with DCM (150 mL, 15 minutes) and then treated with 20% (v/v) piperidine/DMF (150 mL, 10 minutes then again for 20 minutes). The bag was then washed with DMF (4×150 mL) and DCM (4×150 mL) and allowed to dry at room temperature.

The teabag containing glycine on resin was placed in a 20 mL bottle and treated with a solution of benzaldehyde (0.508 mL, 5 mmoles) and anhydrous trimethylorthoformate (1.094 mL, 10 mmoles) in anhydrous DMF (9 mL). After shaking for 3 hours, the packet was washed with anhydrous DMF (3×8 mL). A solution of homophthalic anhydride (801 mg, 5 mmoles) and triethylamine (0.044 mL, 0.3 mmoles) was prepared in DMF (10 mL) and added to the teabag. After shaking at room temperature for 16 hours the packet was washed with DMF (6×30 mL) and DCM (4×30 mL) and dried at room temperature.

The remaining teabags of amino acid on resin were each reacted as above in separate reactions with the following 94 aldehydes such that all combinations of 4-carboxy disubstituted dihydroisoquinolones were formed as indicated in the following (R2) list:
2-hydroxybenzaldehyde (salicylaldehyde),
1,4-benzodioxan-6-carboxaldehyde,
1-methyl-2-pyrrolecarboxaldehyde, 1-naphthaldehyde,
2,3,4-trifluorobenzaldehyde, 2,3,5-trichlorobenzaldehyde,
2,3-(methylenedioxy)benzaldehyde,
2,3-difluorobenzaldehyde, 2,4-dichlorobenzaldehyde,
2,6-difluorobenzaldehyde, 2-bromobenzaldehyde,
2-chloro-5-nitrobenzaldehyde,
2-chloro-6-fluorobenzaldehyde, 2-cyanobenzaldehyde,
2-fluorobenzaldehyde, 2-furaldehyde,
2-imidazolecarboxaldehyde, 2-methoxybenzaldehyde (o-anisaldehyde), 2-naphthaldehyde,
2-pyridinecarboxaldehyde, 2-quinolinecarboxaldehyde,
2-thiophenecarboxaldehyde,
3,4-(methylenedioxy)benzaldehyde (piperonal),
3,4-dibenzyloxybenzaldehyde, 3,4-dichlorobenzaldehyde,
3,4-difluorobenzaldehyde,
3,5-bis(trifluoromethyl)benzaldehyde,
3,5-dibenzyloxybenzaldehyde, 3,5-dichlorobenzaldehyde,
3,5-dimethoxybenzaldehyde,
3,5-dimethyl-4-hydroxybenzaldehyde,
3-(3,4-dichlorophenoxy)benzaldehyde,
3-(4-methoxyphenoxy)benzaldehyde,
3-(trifluoromethyl)benzaldehyde,
3-bromo-4-fluorobenzaldehyde, 3-bromobenzaldehyde,
3-carboxybenzaldehyde, 3-cyanobenzaldehyde,
3-fluoro-4-methoxybenzaldehyde, 3-fluorobenzaldehyde,
3-furaldehyde, 3-hydroxybenzaldehyde,
3-methoxy-4-hydroxy-5-nitrobenzaldehyde,
3-methoxybenzaldehyde (m-anisaldehyde),
3-methyl-4-methoxybenzaldehyde, 3-methylbenzaldehyde (m-tolualdehyde), 3-nitro-4-chlorobenzaldehyde,
3-nitrobenzaldehyde, 3-phenoxybenzaldehyde,
3-pyridinecarboxaldehyde, 3-quinolinecarboxaldehyde,
3-thiophenecarboxaldehyde,
4-(3-dimethylaminopropoxy)benzaldehyde,
4-(dimethylamino)benzaldehyde,
4-(methylcarboxylate)benzaldehyde,
4-(methylthio)benzaldehyde,
4-(trifluoromethyl)benzaldehyde, 4-acetamidobenzaldehyde,
4-methoxybenzaldehyde (p-anisaldehyde),
4-biphenylcarboxaldehyde, 4-bromobenzaldehyde,
4-carboxybenzaldehyde, 4-cyanobenzaldehyde,
4-fluorobenzaldehyde, 4-hydroxybenzaldehyde,
4-isopropylbenzaldehyde, 4-methoxy-1-naphthaldehyde,
4-methylbenzaldehyde (p-tolualdehyde),
3-hydroxy-4-nitrobenzaldehyde, 4-nitrobenzaldehyde,
4-phenoxybenzaldehyde, 4-propoxybenzaldehyde,
4-pyridinecarboxaldehyde, 4-quinolinecarboxaldehyde,
5-(hydroxymethyl)-2-furaldehyde,
3-methoxy-4-hydroxy-5-bromobenzaldehyde,
5-methyl-2-thiophenecarboxaldehyde,
5-methyl-2-furaldehyde (5-methylfurfural),
5-nitro-2-furaldehyde, 6-methyl-2-pyridinecarboxaldehyde,
8-hydroxyquinoline-2-carboxaldehyde,
9-ethyl-3-carbazolecarboxaldehyde,
9-formyl-8-hydroxyjulolidine, pyrrole-2-carboxaldehyde,
3-hydroxy-4-methoxybenzaldehyde,
4-methylsulphonylbenzaldehyde, 4-methoxy-3-(sulfonic acid, Na)benzaldehyde, 5-bromo-2-furaldehyde,
2-thiazolecarboxaldehyde, 4-ethoxybenzaldehyde,
4-propoxybenzaldehyde, 4-butoxybenzaldehyde,
4-pentylaminobenzaldehyde, 4-amylbenzaldehyde.

The teabag containing glycine on resin (converted to the 4-carboxy disubstituted dihydroisoquinolone with benzaldehyde at R2) was placed in a 20 mL bottle. The teabag was treated with a solution of HOBt (410 mg, 3.0 mmoles), and DIC (0.56 mL, 3.6 mmoles) in anhydrous DMF (10 mL, 300 mM solution) and shaken for 20 minutes. The HOBt/DIC solution was decanted off of the teabags and anhydrous DMF (6.9 mL) and aniline (0.683 mL, 7.5 mmoles) was added. After shaking for 1 hour, the aniline solution was removed, and the bag was washed with anhydrous DMF (2×8 mL). The HOBt/DIC treatment was repeated followed by decanting and addition of a second aniline solution. This reaction was shaken at room temperature for 24 hours. The bag was then washed with DMF (3×8 mL), water (8 mL, 60 minutes), DMF (3×8 mL), DCM (3×8 mL), and allowed to dry.

The remaining teabags (containing 4-carboxy dihydroisoquinolones) were reacted as above in reactions with the following amines such that all combinations of trisubstituted dihydroisoquinolones were formed and denoted as a group as (X): N-methylaniline, 2-chloroaniline, 2-methoxyaniline, 3-chloroaniline, 3-ethoxyaniline, 3-aminophenol, 4-chloroaniline, 4-Methoxyaniline, benzylamine, N-benzylmethylamine, 2-chlorobenzylamine, 2-(trifluoromethyl)benzylamine, 2-methoxybenzylamine, 2-ethoxybenzylamine, 3-methoxybenzylamine, 3-(trifluoromethyl)benzylamine, 4-chlorobenzylamine, 4-methoxybenzylamine, 4-(trifluoromethyl)benzylamine, phenethylamine, 2-chlorophenethylamine, 2-methoxyphenethylamine, 3-chlorophenethylamine, 4-methoxyphenethylamine, 3-phenyl-1-propylamine, cyclopentylamine, isopropylamine, cycloheptylamine, N-methylcyclohexylamine, (aminomethyl)cyclohexane, piperidine, morpholine, 1-aminopiperidine, diethylamine, allylamine, isopropylamine, (2-aminoethyl)-trimethylammonium Cl—HCl, ammonia.

One teabag was left as the free carboxylic acid. Additional diversity at the R2 site was obtained using teabags with attached trisubstituted dihydroisoquinolones that contain 4-nitrobenzaldehyde group in the R2 position. The teabags were washed with DCM (2×50 mL), and shaken with SnC12 (20 g) in DMF (50 mL, 2 M). After shaking for 24 hours the teabag was washed with DMF (5×50 mL), DCM (5×50 mL), 5% (v/v) DIEA/DCM (50 mL, 2×10 minutes), DCM (2×50 mL), DMF (2×50 mL), MeOH (2×50 mL), DCM (4×50 mL) and allowed to dry.

A solution of benzoic acid (492 mg, 3.75 mmoles), HOBt (507 mg, 3.75 mmoles), and DIC (0.705 mL, 4.5 mmoles) was prepared in DMF (37.5 mL) and added to a resin packet with attached trisubstituted dihydroisoquinolone. After shaking for 16 hours, the teabag was washed with DMF (3×30 mL) and DCM (3×30 mL). The same coupling procedure was performed on the resulting aniline derived from reduction of the 4-NO$_2$ of (R2), each being reacted with a separate carboxylic acid from the following (R2) list: propionic acid, butyric acid, cyclohexane carboxylic acid, isobutyric acid, methoxyacetic acid, p-anisic acid, phenylacetic acid, 4-methoxyphenylacetic acid, 2-norbornaneacetic acid, 3,4-dichlorophenylacetic acid, 4-chlorobenzoic acid, valeric acid.

The teabags with attached trisubstituted dihydroisoquinolones were washed with DCM (2×50 mL), shaken twice in 55% (v/v) TFA/DCM (30 mL, 30 minutes), then washed with DCM (30 mL), isopropyl alcohol (2×30 mL), DCM (2×30 mL), 5% (v/v) DIEA/DCM (3×30 mL, 2 minutes each) and DCM (3×30 mL) and allowed to dry at room temperature. One bag was left as the Boc protected amine (R8=methyl, after reduction).

A solution of phenylacetic acid (657 mg, 3.75 mmoles), HOBt (507 mg, 3.75 mmoles), and DIC (0.705 mL, 4.5 mmoles) was prepared in DMF (37.5 mL) and added to a resin packet with attached trisubstituted dihydroisoquinolone. After shaking for 16 hours, the teabag was washed with DMF (3×30 mL) and DCM (3×30 mL). The same coupling procedure was performed on the remaining teabags, each being reacted with a separate carboxylic acid from the list (R8): acetic acid, phenylacetic acid, Boc-glycine, glycine, Boc-alanine, hydroxy acetic acid, Boc-phenylalanine, succinic anhydride, methoxyacetic acid, butyric acid, cyclohexanecarboxylic acid, benzoic acid, 4-bromophenylacetic acid, 4-methoxyphenylacetic acid, 4-chlorobenzoic acid, 4-methoxybenzoic acid, 2-naphthylacetic acid, cyclohexylacetic acid. Additionally, one bag was left non-acylated (R8=H).

The teabag containing trisubstituted dihydroisoquinoline on resin (R1=glycine, R2=benzaldehyde, X=aniline, R8=phenylacetic acid) was placed in a 50 mL KIMAX glass tube and treated under nitrogen gas with a solution of: 1 M $BH_3$ in anhydrous tetrahydrofuran (15 mL), boric acid (315 mg) and trimethyl borate (0.5 mL). After the solution's bubbling slowed to a slight fizz, the tube was capped tightly and heated at 65° C. for 96 hours. After cooling, the borane solution was decanted and the bag washed with methanol (1×25 mL), tetrahydrofuran (1×25 mL), and again with methanol (4×25 mL). During this reaction all carbonyl groups were converted to methylenes and Boc protecting groups were converted to methyl groups.

After drying, the bag was returned to a 50 mL KIMAX glass tube, submerged completely in piperidine, sealed and heated at 65° C. for 16 hours. After cooling, the piperidine was decanted off of the teabag, and the bag was washed with DMF (2×25 mL), DCM (2×25 mL), methanol (1×25 mL), DMF (2×25 mL), DCM (2×25 mL), and again with methanol (1×25 mL) and allowed to dry at room temperature. The remaining teabags were treated in the same manner.

Each teabag prepared above was cleaved separately via standard HF procedures. The isoquinolone was cleaved off of the resin by treatment with HF (5 ml) at −15° C. for 9 hrs with the addition of 0.2 ml anisole to each HF cleavage reaction, as a scavenger, followed by warming to room temperature while removing HF with a nitrogen stream. The packet and HF tube were washed with $CH_3CN$, $H_2O$, acetic acid (45:45:10) (2×5 ml), and the two washes were transferred to a scintillation vial and lyophilized to provide a white crystalline solid.

The isoquinoline compounds were dissolved in an appropriate solvent and tested in a variety of assays. The compounds were characterized by HPLC and mass spectra.

EXAMPLE II

Melanocortin Receptor Assay

This example describes methods for assaying binding to MC receptors.

All cell culture media and reagents were obtained from GibcoBRL (Gaithersburg Md.), except for COSMIC CALF SERUM (HyClone; Logan UT). HEK 293 cell lines were transfected with the human MC receptors hMCR-1, hMCR-3, and hMCR-4 (Gantz et al., *Biochem. Biophys. Res. Comm.* 200:1214–1220 (1994); Gantz et al., *J. Biol. Chem.* 268:8246–8250 (1993); Gantz et al. *J. Biol. Chem.* 268:15174–15179 (1993); Haskell-Leuvano et al., *Biochem. Biophys. Res. Comm.* 204:1137–1142 (1994); each of which is incorporated herein by reference). Vectors for construction of an hMCR-5 expressing cell line were obtained, and a line of HEK 293 cells expressing hMCR-5 was constructed (Gantz, supra, 1994). hMCR-5 has been described previously (Franberg et al., *Biochem. Biophys. Res. Commun.* 236:489–492 (1997); Chowdhary et al., *Cytogenet. Cell Genet.* 68:1–2 (1995); Chowdhary et al., Cytogenet. Cell Genet. 68:79–81 (1995), each of which is incorporated herein by reference). HEK 293 cells were maintained in DMEM, 25 mM HEPES, 2 mM glutamine, non-essential amino acids, vitamins, sodium pyruvate, 10% COSMIC CALF SERUM, 100 units/ml penicillin, 100 μg/ml streptomycin and 0.2 mg/ml G418 to maintain selection.

Before assaying, cells were washed once with phosphate buffered saline ("PBS"; without $Ca^{2+}$ and $Mg^{2+}$), and stripped from the flasks using 0.25% trypsin and 0.5 mM EDTA. Cells were suspended in PBS, 10% COSMIC CALF SERUM and 1 mM $CaCl_2$. Cell suspensions were prepared at a density of $2 \times 10^4$ cells/ml for HEK 293 cells expressing hMCR-3, hMCR-4 or hMCR-5, and $1 \times 10^5$ cells/ml for HEK 293 cells expressing hMCR-1. Suspensions were placed in a water bath and allowed to warm to 37° C. for 1 hr.

Binding assays were performed in a total volume of 250 μl for HEK 293 cells. Control and test compounds were dissolved in distilled water. $^{125}$I-HP 467 (50,000 dpm) (2000 Ci/mmol) (custom labeled by Amersham; Arlington Heights Ill.) was prepared in 50 mM Tris, pH 7.4, 2 mg/ml BSA, 10 mM $CaCl_2$, 5 mM $MgCl_2$, 2 mM EDTA and added to each tube. To each tube was added $4 \times 10^3$ HEK 293 cells expressing hMCR-3, hMCR-4 or hMCR-5, or $2 \times 10^4$ cells expressing hMCR-1. Assays were incubated for 2.5 hr at 37° C.

GF/B filter plates were prepared by soaking for at least one hour in 5 mg/ml BSA and 10 mM $CaCl_2$. Assays were filtered using a Brandel 96-well cell harvester (Brandel Inc.; Gaithersburg, Md.). The filters were washed four times with cold 50 mM Tris, pH 7.4, the filter plates were dehydrated for 2 hr and 35 μl of MICROSCINT was added to each well. Filter plates were counted using a Packard Topcount (Packard Instrument Co.) and data analyzed using GraphPad PRISM v2.0 (GraphPad Software Inc.; San Diego Calif.) and Microsoft EXCEL v5.0a (Microsoft Corp.; Redmond Wash.).

To assay isoquinoline compounds, binding assays were performed in duplicate in a 96 well format. HP 467 was prepared in 50 mM Tris, pH 7.4, and $^{125}$I-HP 467 was diluted to give 100,000 dpm per 50 μl. An isoquinoline compound, synthesized as described in Example I, was added to the well in 25 μl aliquots. A 25 μl aliquot of $^{125}$I-HP 467 was added to each well. A 0.2 ml aliquot of suspended cells was added to each well to give the cell numbers indicate above, and the cells were incubated at 37° C. for 2.5 hr. Cells were harvested on GF/B filter plates as described above and counted.

EXAMPLE III cAMP Assay for Melanocortin Receptors

This example describes methods for assaying cAMP production from G-protein coupled MC receptors.

HEK 293 cells expressing MCR-1, MCR-3, MCR-4 and MCR-5 were used (see Example II). Cells were plated at 20,000 cells per well in a 96-well plate coated with collagen. The next day, cells were pretreated with 75 μl of 0.4 mM 3-isobutyl-1-methylxanthine (IBMX) in low serum medium containing DMEM, 25 mM HEPES, non-essential amino acids, vitamins, 100 units/ml penicillin, 100 μg/ml streptomycin and 0.1% COSMIC CALF SERUM. IBMX is an inhibitor of cAMP phosphodiesterase. The pretreatment was carried out for 10 min at 37° C.

Following pretreatment, 25 μl of diluted isoquinoline compound was added to the wells, and cells were incubated for 15 min at 37° C. Cells were lysed by adding 25 μl saponin lysis buffer and incubating 2 to 5 min. Plates were covered and stored at −20° C.

cAMP concentration was determined by ELISA. Briefly, 96 well ELISA plates were coated with goat anti-cAMP antibody in PBS for 12 to 72 hr at 4° C. 50 μl of sample was mixed with 50 μl of cAMP ELISA buffer containing 1% bovine serum albumin, 10% heat inactivated donor horse serum, 1% normal mouse serum and 0.05% TWEEN-20 in PBS, and the diluted sample was added to the coated ELISA plate. Standards of known concentrations of cAMP were added to separate wells. 25 μl of 16 ng/ml cAMP-conjugated horse radish peroxidase (HRP) (cAMP-HRP) was added to each well, and the plates were incubated hr at room temperature. Plates were washed and the binding of cAMP-HRP was detected with 3,3',5,5'-tetramethylbenzidine (TMB) and hydrogen peroxide using standard immunoassay procedures.

EXAMPLE IV

Melanocortin Receptor Binding Profile of Isoquinoline Compounds

This example describes MC receptor binding affinity and specificity for various isoquinoline compounds.

Various isoquinoline compounds were tested for in vitro binding activity to HEK 293 cells expressing MCR-1 or MCR-4 as described in Example II. Table 1 shows the IC50 values, the concentration giving 50% inhibition of binding of $^{125}$I-HP 467, for various isoquinoline compounds. Table 1 also shows for some isoquinoline compounds the percentage of displacement (% Disp.) (in duplicate) of $^{125}$1-HP 467 when HEK 293 cells expressing is MCR-1 were incubated in the presence of 10 μM isoquinoline compound. As shown in Table 1, isoquinoline compounds exhibited a range of affinities to MCR-1 and MCR-4, including ligands with nM affinities. Some isoquinoline compounds exhibited specificity of about 10-fold for at least one MC receptor over another MC receptor, for example, TRG 2405-241, TRG 2405-252, TRG 2405-253 and TRG 2408-30.

Isoquinoline compounds that are particularly effective MC receptor ligands include TRG 2405-190, TRG 2405-239, TRG 2405-241, TRG 2405-252, TRG 2405-253, TRG 2408-30, TRG 2408-57, TRG 2408-62, TRG 2409-2, TRG 2409-14, TRG 2411-26, TRG 2411-50, TRG 2411-60, TRG 2411-111 and TRG 2411-186, as well as the other ligands described above and claimed below individually.

In describing each compound, Table 1 refers to the starting material used at each position. When describing TRG 2403 to TRG 2413 libraries in Table 1, "R3" refers to the "X" position. Additionally, in the TRG 2419 and 2420 libraries described in Table 1, two compounds contribute to the "R8" position (and are therefore each designated "R8 in Table 1). The anhydride compound is coupled to the amine compound to form the caroxylic acid of R8. When reduced, the carboxylic acid becomes a substituted alkyl.

TABLE 1

| Cpd # | R1: Amino Acid | R8 = Boc R2: Aldehyde | R3: amine | M.W. | obs. (M + 1) M.W. | >85% LCQ | Mc-1 IC50 uM | MC-4 IC50 uM | MC-1 IC50 mM | MC-4 IC50 mM |
|---|---|---|---|---|---|---|---|---|---|---|
| | TRG 2403 | | | | | | | | | |
| 3 | (S)-2,6-Diaminohexanoic acid | 4-Acetamidobenzaldehyde | 2-Methoxybenzylamine | 516 | 517 | Y | Y | | 0.5 | >10 |
| | TRG 2404 | | | | | | | | | |
| 3 | (S)-2,6-Diaminohexanoic acid | 4-Bromobenzaldehyde | 2-Methoxybenzylamine | 552 | 553 | Y | Y | | 2.5 | 0.8 |

| Cpd # | R1 = Cyclohexlamine R1: Amino Acids | R8 = Boc R2: Aldehydes | R3: amines | prod. MW | obs.(M + 1) M.W. | >85% LCQ | Mc-1 IC50 uM | MC-4 IC50 uM | % Disp. MC-1 10 uM | MC-1 10 uM |
|---|---|---|---|---|---|---|---|---|---|---|
| | TRG 2405 | | | | | | | | | |
| 1 | Glycine | Benzaldehyde | Cyclohexylamine | 364 | 365 | Y | | | 85.3 | 24.1 |
| 2 | Glycine | 2-Hydroxybenzaldehyde (salicylaldehyde) | Cyclohexylamine | 380 | 381 | Y | | | 42.9 | 40.8 |
| 3 | Glycine | 1,4-Benzodioxan-6-carboxaldehyde | Cyclohexylamine | 422 | 423 | Y | | | 46.8 | 44.2 |
| 4 | Glycine | 1-Methyl-2-pyrrolecarboxaldehyde | Cyclohexylamine | 367 | | N | 2.17 | 11.64 | 76.8 | 77.7 |
| 5 | Glycine | 1-Naphthaldehyde | Cyclohexylamine | 414 | 415 | Y | | | 53.6 | 53.8 |
| 6 | Glycine | 2,3,4-Trifluorobenzaldehyde | Cyclohexylamine | 418 | 419 | Y | | | 45.7 | 50 |
| 7 | Glycine | 2,3,5-Trichlorobenzaldehyde | Cyclohexylamine | 467 | 468 | Y | | | 50.3 | 54.8 |
| 8 | Glycine | 2,3-(Methylenedioxy)benzaldehyde | Cyclohexylamine | 408 | 409 | Y | | | 0 | 26.1 |
| 9 | Glycine | 2,3-Difluorobenzaldehyde | Cyclohexylamine | 400 | 401 | Y | | | 36.4 | 33.4 |
| 10 | Glycine | 2,4-Dichlorobenzaldehyde | Cyclohexylamine | 433 | 434 | Y | | | 56.9 | 53 |
| 11 | Glycine | 2,6-Difluorobenzaldehyde | Cyclohexylamine | 400 | 401 | Y | | | 45.1 | 27 |
| 12 | Glycine | 2-Bromobenzaldehyde | Cyclohexylamine | 443 | 444 | Y | | | 38.7 | 41.8 |
| 13 | Glycine | 2-Chloro-5-nitrobenzaldehyde | Cyclohexylamine | 414 | 415 | Y | | | 36 | 32.1 |
| 14 | Glycine | 2-Chloro-6-fluorobenzaldehyde | Cyclohexylamine | 417 | 418 | Y | | | 34.2 | 29.6 |
| 15 | Glycine | 2-Cyanobenzaldehyde | Cyclohexylamine | 393 | 394 | Y | | | 23.5 | 52.5 |
| 16 | Glycine | 2-Fluorobenzaldehyde | Cyclohexylamine | 382 | 383 | Y | | | 26.8 | 40.3 |
| 17 | Glycine | 2-Furaldehyde | Cyclohexylamine | 354 | | N | | | 36 | 32.8 |
| 18 | Glycine | 2-Imidazolecarboxaldehyde | Cyclohexylamine | 354 | 355 | Y | | | 35.9 | 34.7 |
| 19 | Glycine | 2-Methoxybenzaldehyde (o-anisaldehyde) | Cyclohexylamine | 394 | 395 | Y | | | 42.2 | 36.2 |
| 20 | Glycine | 2-Naphthaldehyde | Cyclohexylamine | 414 | 415 | Y | | | 59.8 | 53.8 |
| 21 | Glycine | 2-Pyridinecarboxaldehyde | Cyclohexylamine | 365 | | N | | | 47.7 | 42.5 |
| 22 | Glycine | 2-Quinolinecarboxaldehyde | Cyclohexylamine | 415 | | N | | | 29.7 | 43.4 |
| 23 | Glycine | 2-Thiophenecarboxaldehyde | Cyclohexylamine | 370 | 371 | Y | | | 43 | 47.8 |
| 24 | Glycine | 3,4-(Methylenedioxy)benzaldehyde (piperonal) | Cyclohexylamine | 396 | 397 | Y | | | 0 | 19.4 |
| 25 | Glycine | 3,4-Dibenzyloxybenzaldehyde | Cyclohexylamine | 396 | 397 | Y | | | 21.6 | 31.9 |
| 26 | Glycine | 3,4-Dichlorobenzaldehyde | Cyclohexylamine | 433 | 434 | Y | | | 59.6 | 64.6 |
| 27 | Glycine | 3,4-Difluorobenzaldehyde | Cyclohexylamine | 400 | 401 | Y | | | 52.1 | 43.8 |
| 28 | Glycine | 3,5-Bis(trifluoromethyl)benzaldehyde | Cyclohexylamine | 500 | 501 | Y | 8.75 | 9.24 | 52 | 52.5 |
| 29 | Glycine | 3,5-Dibenzyloxybenzaldehyde | Cyclohexylamine | 396 | 397 | Y | | | 28.5 | 26.2 |
| 30 | Glycine | 3,5-Dichlorobenzaldehyde | Cyclohexylamine | 433 | 434 | Y | | | 54.7 | 52.8 |
| 31 | Glycine | 3,5-Dimethoxybenzaldehyde | Cyclohexylamine | 424 | 425 | Y | | | 40.7 | 48.5 |
| 32 | Glycine | 3,5-Dimethylbenzaldehyde | Cyclohexylamine | 408 | 409 | Y | | | 10.1 | 38.3 |
| 33 | Glycine | 3-(3,4-Dichlorophenoxy)benzaldehyde | Cyclohexylamine | 525 | 526 | Y | | | 54.2 | 48.7 |
| 34 | Glycine | 3-(4-Methoxyphenoxy)benzaldehyde | Cyclohexylamine | 486 | 487 | Y | | | 55.6 | 56.1 |
| 35 | Glycine | 3-(Trifluoromethyl)benzaldehyde | Cyclohexylamine | 432 | 433 | Y | | | 54.6 | 55 |

TABLE 1-continued

| # | Amino acid | Amine | Aldehyde | ID1 | ID2 | Y/N | Val A | Val B | Val C | Val D |
|---|---|---|---|---|---|---|---|---|---|---|
| 36 | Glycine | Cyclohexylamine | 3-Bromo-4-fluorobenzaldehyde | 461 | 462 | Y | | | 51.8 | 53.6 |
| 37 | Glycine | Cyclohexylamine | 3-Bromobenzaldehyde | 443 | 444 | Y | | | 49.7 | 54.4 |
| 38 | Glycine | Cyclohexylamine | 3-Carboxybenzaldehyde | 476 | 477 | Y | | | 35.2 | 39.2 |
| 39 | Glycine | Cyclohexylamine | 3-Cyanobenzaldehyde | 393 | 394 | Y | | | 23.2 | 16.9 |
| 40 | Glycine | Cyclohexylamine | 3-Fluoro-4-Methoxybenzaldehyde | 412 | 413 | Y | | | 22.4 | 35.5 |
| 41 | Glycine | Cyclohexylamine | 3-Fluorobenzaldehyde | 382 | 383 | Y | | | 19.6 | 19.8 |
| 42 | Glycine | Cyclohexylamine | 3-Furaldehyde | 354 | | N | | | 43.6 | 40.7 |
| 43 | Glycine | Cyclohexylamine | 3-Hydroxybenzaldehyde | 380 | 381 | Y | | | 32.3 | 23.1 |
| 44 | Glycine | Cyclohexylamine | 3-Methoxy-4-Hydroxy-5-nitrobenzaldehyde | 425 | 426 | Y | | | 35.4 | 22 |
| 45 | Glycine | Cyclohexylamine | 3-Methoxybenzaldehyde (m-anisaldehyde) | 394 | 395 | Y | | | 40.6 | 31.9 |
| 46 | Glycine | Cyclohexylamine | 3-Methyl-4-methoxybenzaldehyde | 408 | 409 | Y | | | 46.8 | 40.3 |
| 47 | Glycine | Cyclohexylamine | 3-Methylbenzaldehyde (m-tolualdehyde) | 378 | 379 | Y | 14.3 | 18.93 | 42.3 | 45.8 |
| 48 | Glycine | Cyclohexylamine | 3-Nitro-4-chlorobenzaldehyde | 414 | 415 | Y | | | 20.5 | 50.8 |
| 49 | Glycine | Cyclohexylamine | 3-Nitrobenzaldehyde | 409 | 410 | Y | | | 37.2 | 42.4 |
| 50 | Glycine | Cyclohexylamine | 3-Phenoxybenzaldehyde | 456 | 457 | Y | | | 61.9 | 50.8 |
| 51 | Glycine | Cyclohexylamine | 3-Pyridinecarboxaldehyde | 365 | | N | | | 30.6 | 23.1 |
| 52 | Glycine | Cyclohexylamine | 3-Quinolinecarboxaldehyde | 415 | | N | | | 42.4 | 42.3 |
| 53 | Glycine | Cyclohexylamine | 3-Thiophenecarboxaldehyde | 370 | 371 | Y | | | 43.3 | 43.4 |
| 54 | Glycine | Cyclohexylamine | 4-(3-Dimethylaminopropoxy)benzaldehyde | 465 | 466 | Y | | | 1.3 | 9 |
| 55 | Glycine | Cyclohexylamine | 4-(Dimethylamino)benzaldehyde | 407 | 408 | Y | | | 32.6 | 38.1 |
| 56 | Glycine | Cyclohexylamine | 4-(Methylcarboxylate)benzaldehyde | 484 | 485 | Y | | | 35.3 | 43.6 |
| 57 | Glycine | Cyclohexylamine | 4-(Methylthio)benzaldehyde | 410 | 411 | Y | | | 17.4 | 42.8 |
| 58 | Glycine | Cyclohexylamine | 4-(Trifluoromethyl)benzaldehyde | 432 | 433 | Y | | | 56.3 | 46.6 |
| 59 | Glycine | Cyclohexylamine | 4-Acetamidobenzaldehyde | 407 | 408 | Y | | | 34.3 | 40.1 |
| 60 | Glycine | Cyclohexylamine | 4-Methoxybenzaldehyde (p-anisaldehyde) | 394 | 395 | Y | | | 41.4 | 42.4 |
| 61 | Glycine | Cyclohexylamine | 4-Biphenylcarboxaldehyde | 440 | 441 | Y | | | 54.7 | 61.9 |
| 62 | Glycine | Cyclohexylamine | 4-Bromobenzaldehyde | 443 | 444 | Y | | | 32.1 | 54.3 |
| 63 | Glycine | Cyclohexylamine | 4-Carboxybenzaldehyde | 476 | 477 | Y | | | 41.6 | 49.1 |
| 64 | Glycine | Cyclohexylamine | 4-Cyanobenzaldehyde | 393 | 394 | Y | | | 0 | 0 |
| 65 | Glycine | Cyclohexylamine | 4-Fluorobenzaldehyde | 382 | 383 | Y | | | 49.6 | 33.9 |
| 66 | Glycine | Cyclohexylamine | 4-Hydroxybenzaldehyde | 380 | 381 | Y | | | 81.6 | 11.3 |
| 67 | Glycine | Cyclohexylamine | 4-Isopropylbenzaldehyde | 406 | 407 | Y | | | 54 | 51.3 |
| 68 | Glycine | Cyclohexylamine | 4-Methoxy-1-naphthaldehyde | 444 | 445 | Y | | | 55.3 | 52.3 |
| 69 | Glycine | Cyclohexylamine | 4-Methylbenzaldehyde (p-tolualdehyde) | 378 | 379 | Y | | | 49.8 | 49 |
| 70 | Glycine | Cyclohexylamine | 3-Hydroxy-4-nitrobenzaldehyde | 425 | | N | | | 19.9 | 46.7 |
| 71 | Glycine | Cyclohexylamine | 4-Nitrobenzaldehyde | 409 | 410 | Y | | | 28.2 | 40 |
| 72 | Glycine | Cyclohexylamine | 4-Phenoxybenzaldehyde | 456 | 457 | Y | | | 50.1 | 57.7 |
| 73 | Glycine | Cyclohexylamine | 4-Propoxybenzaldehyde | 422 | 423 | Y | | | 60.1 | 60.5 |
| 74 | Glycine | Cyclohexylamine | 4-Pyridinecarboxaldehyde | 365 | 366 | Y | | | 35.3 | 0 |
| 75 | Glycine | Cyclohexylamine | 4-Quinolinecarboxaldehyde | 415 | | N | | | 38.9 | 11.6 |
| 76 | Glycine | Cyclohexylamine | 5-(Hydroxymethyl)-2-furaldehyde | 474 | | N | | | 22.8 | 32.7 |
| 77 | Glycine | Cyclohexylamine | 3-Methoxy-1-hydroxy-5-bromobenzaldehyde | 477 | 478 | Y | 4.21 | >10 | 61.3 | 67.9 |
| 78 | Glycine | Cyclohexylamine | 5-Methyl-2-thiophenecarboxaldehyde | 384 | | N | | | 33.3 | 40.8 |
| 79 | Glycine | Cyclohexylamine | 5-Methyl-2-furaldehyde (5-methylfurfural) | 368 | | N | | | 17.3 | 26.3 |
| 80 | Glycine | Cyclohexylamine | 5-Nitro-2-furaldehyde | 399 | | N | 8.66 | 20.81 | 30.8 | 52.9 |
| 81 | Glycine | Cyclohexylamine | 6-Methyl-2-pyridinecarboxaldehyde | 379 | | N | | | 0 | 43.1 |
| 82 | Glycine | Cyclohexylamine | 8-Hydroxyquinoline-2-carboxaldehyde | 431 | | N | | | 18.5 | 29.6 |
| 83 | Glycine | Cyclohexylamine | 9-Ethyl-3-carbazolecarboxaldehyde | 481 | 482 | Y | | | 39.1 | 46.9 |
| 84 | Glycine | Cyclohexylamine | 9-Formyl-8-hydroxyjulolidine | 475 | | N | 5.98 | 33.47 | 18.2 | 37.5 |
| 85 | Glycine | Cyclohexylamine | Pyrrole-2-carboxaldehyde | 353 | | N | | | 57.1 | 59.8 |
| 86 | Glycine | Cyclohexylamine | 3-Hydroxy-4-methoxybenzeldehyde | 396 | 397 | Y | | | 12.9 | 31.6 |
| 87 | Glycine | Cyclohexylamine | 4-Methylsulphonylbenzaldehyde | 442 | 443 | Y | | | 21.9 | 22.1 |

TABLE 1-continued

| # | Amino acid | Aldehyde | Amine | | | | |
|---|---|---|---|---|---|---|---|
| 88 | Glycine | 4-Methoxy-3-(sulfonic acid, Na)benzaldehyde | Cyclohexylamine | | | 474 | 475 | 5.5 | 0 |
| 89 | Glycine | 5-Bromo-2-furaldehyde | Cyclohexylamine | | | 433 | 434 | 21.5 | 31.2 |
| 90 | Glycine | 2-Thiazolecarboxaldehyde | Cyclohexylamine | | | 371 | | 48.4 | 45.9 |
| 91 | (S)-2,3-Diaminopropionic acid | Benzaldehyde | Cyclohexylamine | | | 407 | 408 | 35.2 | 43.9 |
| 92 | (S)-2,3-Diaminopropionic acid | 2-Hydroxybenzaldehyde (salicylaldehyde) | Cyclohexylamine | | | 423 | 424 | 57.6 | 49.9 |
| 93 | (S)-2,3-Diaminopropionic acid | 1,4-Benzodioxan-6-carboxaldehyde | Cyclohexylamine | | | 465 | 466 | 43.2 | 56.2 |
| 94 | (S)-2,3-Diaminopropionic acid | 1-Methyl-2-pyrrolecarboxaldehyde | Cyclohexylamine | 2.11 | 10.46 | 410 | | 68.9 | 72 |
| 95 | (S)-2,3-Diaminopropionic acid | 1-Naphthaldehyde | Cyclohexylamine | | | 457 | 458 | 45.6 | 51.1 |
| 96 | (S)-2,3-Diaminopropionic acid | 2,3,4-Trifluorobenzaldehyde | Cyclohexylamine | | | 461 | 462 | 44.5 | 54.4 |
| 97 | (S)-2,3-Diaminopropionic acid | 2,5-Trichlorobenzaldehyde | Cyclohexylamine | | | 510 | 511 | 58.2 | 61.1 |
| 98 | (S)-2,3-Diaminopropionic acid | 2,3-(Methylenedioxy)benzeldehyde | Cyclohexylamine | | | 451 | 452 | 20.1 | 48.3 |
| 99 | (S)-2,3-Diaminopropionic acid | 2,3-Difluorobenzaldehyde | Cyclohexylamine | | | 443 | 444 | 34.7 | 54.2 |
| 100 | (S)-2,3-Diaminopropionic acid | 2,4-Dichlorobenzaldehyde | Cyclohexylamine | 12.18 | 11.22 | 476 | 477 | 54.2 | 59.6 |
| 101 | (S)-2,3-Diaminopropionic acid | 2,6-Difluorobenzaldehyde | Cyclohexylamine | | | 443 | 444 | 34 | 45.3 |
| 102 | (S)-2,3-Diaminopropionic acid | 2-Bromobenzaldehyde | Cyclohexylamine | | | 486 | 487 | 44.7 | 50.4 |
| 103 | (S)-2,3-Diaminopropionic acid | 2-Chloro-5-nitrobenzeldehyde | Cyclohexylamine | | | 457 | 458 | 44.6 | 45.2 |
| 104 | (S)-2,3-Diaminopropionic acid | 2-Chloro-6-fluorobenzaldehyde | Cyclohexylamine | | | 460 | 461 | 32.8 | 33.3 |
| 105 | (S)-2,3-Diaminopropionic acid | 2-Cyanobenzaldehyde | Cyclohexylamine | | | 436 | 437 | 20.2 | 49.9 |
| 106 | (S)-2,3-Diaminopropionic acid | 2-Fluorobenzeldehyde | Cyclohexylamine | | | 425 | 426 | 40.7 | 44.7 |
| 107 | (S)-2,3-Diaminopropionic acid | 2-Furaldehyde | Cyclohexylamine | | | 397 | | 43.1 | 52.1 |
| 108 | (S)-2,3-Diaminopropionic acid | 2-Imidazolecarboxaldehyde | Cyclohexylamine | | | 397 | 398 | 46 | 46.6 |
| 109 | (S)-2,3-Diaminopropionic acid | 2-Methoxybenzaldehyde (o-anisaldehyde) | Cyclohexylamine | | | 437 | 438 | 34.7 | 44.7 |
| 110 | (S)-2,3-Diaminopropionic acid | 2-Naphthaldehyde | Cyclohexylamine | | | 457 | 458 | 59.5 | 61.6 |
| 111 | (S)-2,3-Diaminopropionic acid | 2-Pyridinecarboxaldehyde | Cyclohexylamine | 7.48 | 17.13 | 408 | | 57.2 | 51 |
| 112 | (S)-2,3-Diaminopropionic acid | 2-Quinolinecarboxaldehyde | Cyclohexylamine | | | 458 | | 42.2 | 43.2 |
| 113 | (S)-2,3-Diaminopropionic acid | 2-Thiophenecarboxaldehyde | Cyclohexylamine | | | 413 | 414 | 40 | 58.5 |
| 114 | (S)-2,3-Diaminopropionic acid | 3,4-(Methylenedioxy)benzaldehyde (piperonal) | Cyclohexylamine | | | 439 | 440 | 30.6 | 40.9 |
| 115 | (S)-2,3-Diaminopropionic acid | 3,4-Dibenzyloxybenzaldehyde | Cyclohexylamine | | | 439 | 440 | 20.6 | 22.1 |
| 116 | (S)-2,3-Diaminopropionic acid | 3,4-Dichlorobenzaldehyde | Cyclohexylamine | | | 476 | 477 | 62.3 | 63 |
| 117 | (S)-2,3-Diaminopropionic acid | 3,4-Difluorobenzaldehyde | Cyclohexylamine | | | 443 | 444 | 40.9 | 55.7 |
| 118 | (S)-2,3-Diaminopropionic acid | 3,5-Bis(trifluoromethyl)benzaldehyde | Cyclohexylamine | | | 543 | 544 | 47.3 | 58.9 |
| 119 | (S)-2,3-Diaminopropionic acid | 3,5-Dibenzyloxybenzaldehyde | Cyclohexylamine | | | 439 | 440 | 25.9 | 39.8 |
| 120 | (S)-2,3-Diaminopropionic acid | 3,5-Dichlorobenzaldehyde | Cyclohexylamine | | | 476 | 477 | 52.4 | 54.3 |
| 121 | (S)-2,3-Diaminopropionic acid | 3,5-Dimethoxybenzaldehyde | Cyclohexylamine | | | 467 | 468 | 35.2 | 38.7 |
| 122 | (S)-2,3-Diaminopropionic acid | 3,5-Dimethyl-4-hydroxybenzaldehyde | Cyclohexylamine | | | 451 | 452 | 17.6 | 40.7 |
| 123 | (S)-2,3-Diaminopropionic acid | 3-(3,4-Dichlorophenoxy)benzaldehyde | Cyclohexylamine | | | 568 | 569 | 47.9 | 55.6 |
| 124 | (S)-2,3-Diaminopropionic acid | 3-(4-Methoxyphenoxy)benzaldehyde | Cyclohexylamine | 5.16 | 3.1 | 529 | 530 | 65.2 | 63 |
| 125 | (S)-2,3-Diaminopropionic acid | 3-(Trifluoromethyl)benzeldehyde | Cyclohexylamine | | | 475 | 476 | 59.1 | 58.4 |
| 126 | (S)-2,3-Diaminopropionic acid | 3-Bromo-4-fluorabenzaldehyde | Cyclohexylamine | 5.34 | 12.82 | 504 | 505 | 52.4 | 58.4 |
| 127 | (S)-2,3-Diaminopropionic acid | 3-Bromobenzaldehyde | Cyclohexylamine | | | 486 | 487 | 50.6 | 60.3 |
| 128 | (S)-2,3-Diaminopropionic acid | 3-Carboxybenzaldehyde | Cyclohexylamine | | | 519 | 520 | 52.9 | 54 |
| 129 | (S)-2,3-Diaminopropionic acid | 3-Cyanobenzaldehyde | Cyclohexylamine | | | 436 | 437 | 39.8 | 39.6 |
| 130 | (S)-2,3-Diaminopropionic acid | 3-Fluoro-1-methoxybenzaldehyde | Cyclohexylamine | | | 455 | 456 | 48.9 | 43.3 |
| 131 | (S)-2,3-Diaminopropionic acid | 3-Fluorobenzaldehyde | Cyclohexylamine | | | 425 | 426 | 39.2 | 55.7 |
| 132 | (S)-2,3-Diaminopropionic acid | 3-Furaldehyde | Cyclohexylamine | | | 397 | | 49 | 51.7 |
| 133 | (S)-2,3-Diaminopropionic acid | 3-Hydroxybenzaldehyde | Cyclohexylamine | 20.01 | 12.4 | 423 | 424 | 51.8 | 44.1 |
| 134 | (S)-2,3-Diaminopropionic acid | 3-Methoxy-4-hydroxy-5-nitrobenzaldehyde | Cyclohexylamine | | | 468 | 469 | 43.4 | 48 |
| 135 | (S)-2,3-Diaminopropionic acid | 3-Methoxybenzatdehyde (m-anisaldehyde) | Cyclohexylamine | | | 437 | 438 | 43.9 | 39.7 |
| 136 | (S)-2,3-Diaminopropionic acid | 3-Methyl-4-methoxybenzaldehyde | Cyclohexylamine | | | 451 | 452 | 49 | 51.8 |
| 137 | (S)-2,3-Diaminopropionic acid | 3-Methylbenzaldehyde (m-toltualdehyde) | Cyclohexylamine | | | 421 | 422 | 40.6 | 46 |
| 138 | (S)-2,3-Diaminopropionic acid | 3-Nitro-4-chlorobenzaldehyde | Cyclohexylamine | | | 4571 | 458 | 53.2 | 56.1 |
| 139 | (S)-2,3-Diaminopropionic acid | 3-Nitrobenzaldehyde | Cyclohexylamine | | | 452 | 453 | 40.3 | 45.5 |

TABLE 1-continued

| | | | | | | | |
|---|---|---|---|---|---|---|---|
| 140 | (S)-2,3-Diaminopropionic acid | 3-Phenoxybenzaldehyde | Cyclohexylamine | 499 | 500 | Y | | 67.6 | 67.8 |
| 141 | (S)-2,3-Diaminopropionic acid | 3-Pyridinecarboxaldehyde | Cyclohexylamine | 408 | 408 | N | | 15 | 16.2 |
| 142 | (S)-2,3-Diaminopropionic acid | 3-Quinolinecarboxaldehyde | Cyclohexylamine | 458 | | N | | 48.5 | 45.1 |
| 143 | (S)-2,3-Diaminopropionic acid | 3-Thiophenecarboxaldehyde | Cyclohexylamine | 413 | 414 | Y | | 54.6 | 50.4 |
| 144 | (S)-2,3-Diaminopropionic acid | 4-(3-Dimethylaminopropoxy)benzaldehyde | Cyclohexylamine | 508 | 509 | Y | | 29.6 | 41.7 |
| 145 | (S)-2,3-Diaminopropionic acid | 4(Dimethylamino)benzaldehyde | Cyclohexylamine | 450 | 451 | Y | | 41.2 | 49.7 |
| 146 | (S)-2,3-Diaminopropionic acid | 4-(Methylcarboxylate)benzaldehyde | Cyclohexylamine | 527 | 528 | Y | | 59.5 | 60.1 |
| 147 | (S)-2,3-Diaminopropionic acid | 4-(Methylthio)benzaldehyde | Cyclohexylamine | 453 | 454 | Y | | 31.6 | 38.9 |
| 148 | (S)-2,3-Diaminopropionic acid | 4-(Trifluoromethyl)benzaldehyde | Cyclohexylamine | 475 | 476 | Y | 10.29 | 8.95 | 63.7 | 57.4 |
| 149 | (S)-2,3-Diaminopropionic acid | 4-Acetamidobenzaldehyde | Cyclohexylamine | 450 | 451 | Y | | 30.1 | 52.3 |
| 150 | (S)-2,3-Diaminopropionic acid | 4-Methoxybenzaldehyde (p-anisaldehyde) | Cyclohexylamine | 437 | 438 | Y | | 37.6 | 54.7 |
| 151 | (S)-2,3-Diaminopropionic acid | 4-Biphenylcarboxaldehyde | Cyclohexylamine | 483 | 484 | Y | | 61.5 | 57.6 |
| 152 | (S)-2,3-Diaminopropionic acid | 4-Bromobenzaldehyde | Cyclohexylamine | 486 | 487 | Y | | 52.8 | 52.9 |
| 153 | (S)-2,3-Diaminopropionic acid | 4-Carboxybenzaldehyde | Cyclohexylamine | 519 | 520 | Y | | 42.1 | 58.6 |
| 154 | (S)-2,3-Diaminopropionic acid | 4-Cyanobenzaldehyde | Cyclohexylamine | 436 | 437 | Y | | 43.1 | 54.8 |
| 155 | (S)-2,3-Diaminopropionic acid | 4-Fluorobenzaldehyde | Cyclohexylamine | 425 | 426 | Y | | 52.3 | 55.6 |
| 156 | (S)-2,3-Diaminopropionic acid | 4-Hydroxybenzaldehyde | Cyclohexylamine | 423 | 424 | Y | 16.96 | 20.59 | 25.9 | 21.3 |
| 157 | (S)-2,3-Diaminopropionic acid | 4-Isopropylbenzaldehyde | Cyclohexylamine | 449 | 450 | Y | | 58.4 | 56.1 |
| 158 | (S)-2,3-Diaminopropionic acid | 4-Methoxy-1-naphthaldehyde | Cyclohexylamine | 487 | 488 | Y | | 45.6 | 45.8 |
| 159 | (S)-2,3-Diaminopropionic acid | 4-Methylbenzaldehyde (p-tolualdehyde) | Cyclohexylamine | 421 | 422 | Y | | 51 | 53.5 |
| 160 | (S)-2,3-Diaminopropionic acid | 3-Hydroxy-4-nitrobenzaldehyde | Cyclohexylamine | 468 | 469 | Y | | 26.1 | 41.7 |
| 161 | (S)-2,3-Diaminopropionic acid | 4-Nitrobenzaldehyde | Cyclohexylamine | 452 | 453 | Y | | 58.4 | 59.1 |
| 162 | (S)-2,3-Diaminopropionic acid | 4-Phenoxybenzaldehyde | Cyclohexylamine | 499 | 500 | Y | | 71 | 59.6 |
| 163 | (S)-2,3-Diaminopropionic acid | 4-Propoxybenzaldehyde | Cyclohexylamine | 465 | 466 | Y | | 62.4 | 58.1 |
| 164 | (S)-2,3-Diaminopropionic acid | 4-Pyridinecarboxaldehyde | Cyclohexylamine | 408 | 409 | Y | | 24.7 | 33.5 |
| 165 | (S)-2,3-Diaminopropionic acid | 4-Quinolinecarboxaldehyde | Cyclohexylamine | 458 | | Y | | 37.3 | 34.6 |
| 166 | (S)-2,3-Diaminopropionic acid | 5-(Hydroxymethyl)-2-furaldehyde | Cyclohexylamine | 517 | | N | | 38.9 | 41.8 |
| 167 | (S)-2,3-Diaminopropionic acid | Methoxy-4-hydroxy-5-Bromobenzaldehyde | Cyclohexylamine | 520 | 521 | Y | 18.27 | | 35.1 | 24.2 |
| 168 | (S)-2,3-Diaminopropionic acid | 5-Methyl-2-thiophenecarboxaldehyde | Cyclohexylamine | 427 | 428 | Y | | 44.9 | 24.1 |
| 169 | (S)-2,3-Diaminopropionic acid | 5-Methyl-2-furaldehyde (5-methylfurfural) | Cyclohexylamine | 411 | | N | | 62.2 | 51.5 |
| 170 | (S)-2,3-Diaminopropionic acid | 5-Nitro-2-furaldehyde | Cyclohexylamine | 442 | | Y | 4.81 | 10.17 | 68.4 | 57.5 |
| 171 | (S)-2,3-Diaminopropionic acid | 6-Methyl-2-pyridinecarboxaldehyde | Cyclohexylamine | 422 | | Y | 10.82 | >10 | 63.1 | 49.7 |
| 172 | (S)-2,3-Diaminopropionic acid | 8-Hydroxyquinoline-2-carboxaldehyde | Cyclohexylamine | 474 | 475 | N | | 59.4 | 43.9 |
| 173 | (S)-2,3-Diaminopropionic acid | 9-Ethyl-3-carbazolecarboxaldehyde | Cyclohexylamine | 524 | 525 | Y | | 67 | 59.3 |
| 174 | (S)-2,3-Diaminopropionic acid | 9-Formyl-8-hydroxyjulolidine | Cyclohexylamine | 518 | | N | | 41.9 | 38.8 |
| 175 | (S)-2,3-Diaminopropionic acid | Pyrrole-2-caboxaldehyde | Cyclohexylamine | 396 | | N | 5.86 | 15.75 | 88.5 | 56.6 |
| 176 | (S)-2,3-Diaminopropionic acid | 3-Hydroxy-4-methoxybenzaldehyde | Cyclohexylamine | 439 | 440 | Y | | 26.1 | 19.3 |
| 177 | (S)-2,3-Diaminopropionic acid | 4-Methylsulphonylbenzaldehyde | Cyclohexylamine | 485 | 486 | Y | | 39 | 30.7 |
| 178 | (S)-2,3-Diaminopropionic acid | 4-Methoxy-3-(sulfonic acid, Na)benzaldehyde | Cyclohexylamine | 517 | 518 | Y | | 25 | 22.1 |
| 179 | (S)-2,3-Diaminopropionic acid | 5-Bromo-2-furaldehyde | Cyclohexylamine | 476 | 477 | Y | | 61.1 | 56.8 |
| 180 | (S)-2,3-Diaminopropionic acid | 2-Thiazolecarboxaldehyde | Cyclohexylamine | 414 | | N | 3.88 | 10.83 | 72 | 64.6 |
| 181 | (S)-2,6-Diaminohexanoic acid | Benzaldehyde | Cyclohexylamine | 449 | 450 | Y | | 57.3 | 64.4 |
| 182 | (S)-2,6-Diaminohexanoic acid | 2-Hydroxybenzaldehyde (salicylaldehyde) | Cyclohexylamine | 465 | 466 | Y | | 37.5 | 44.4 |
| 183 | (S)-2,6-Diaminohexanoic acid | 1,4-Benzodioxan-6-carboxaldehyde | Cyclohexylamine | 507 | 508 | Y | | 58.9 | 64.1 |
| 184 | (S)-2,6-Diaminohexanoic acid | 1-Methyl-2-pyrrolecarboxaldehyde | Cyclohexylamine | 452 | 453 | Y | | 55.8 | 46 |
| 185 | (S)-2,6-Diaminohexanoic acid | 1-Naphthaldehyde | Cyclohexylamine | 499 | 500 | Y | | 68.1 | 60.4 |
| 186 | (S)-2,6-Diaminohexanoic acid | 2,3,4-Trifluorobenzaldehyde | Cyclohexylamine | 503 | 504 | Y | | 62.7 | 52.7 |
| 187 | (S)-2,6-Diaminohexanoic acid | 2,3,5-Trichlorobenzaldehyde | Cyclohexylamine | 552 | 553 | Y | | 64.6 | 59.3 |
| 188 | (S)-2,6-Diaminohexanoic acid | 2,3-(Methylenedioxy)benzaldehyde | Cyclohexylamine | 493 | 494 | Y | | 66.9 | 60.1 |
| 189 | (S)-2,6-Diaminohexanoic acid | 2,3-Difluorobenzaldehyde | Cyclohexylamine | 485 | 486 | Y | | 45 | 54.8 |
| 190 | (S)-2,6-Diaminohexanoic acid | 2,4-Dichlorobenzaldehyde | Cyclohexylamine | 518 | 519 | Y | 1.2 | 1.87 | 79.4 | 81 |
| 191 | (S)-2,6-Diaminohexanoic acid | 2,6-Difluorobenzaldehyde | Cyclohexylamine | 485 | 486 | Y | | 41.2 | 47.3 |

TABLE 1-continued

| # | | | | | | | | |
|---|---|---|---|---|---|---|---|---|
| 192 | (S)-2,6-Diaminohexanoic acid | 2-Bromobenzaldehyde | Cyclohexylamine | 528 | 529 | Y | | 73.8 | 50.9 |
| 193 | (S)-2,6-Diaminohexanoic acid | 2-Chloro-5-nitrobenzaldehyde | Cyclohexylamine | 499 | 500 | Y | | 54.8 | 54.6 |
| 194 | (S)-2,6-Diaminohexanoic acid | 2-Chloro-6-fluorobenzaldehyde | Cyclohexylamine | 502 | 503 | Y | | 50.7 | 51.4 |
| 195 | (S)-2,6-Diaminohexanoic acid | 2-Cyanobenzaldehyde | Cyclohexylamine | 478 | 479 | Y | | 44.7 | 35.7 |
| 196 | (S)-2,6-Diaminohexanoic acid | 2-Fluorobenzaldehyde | Cyclohexylamine | 467 | 468 | Y | | 69.1 | 64.6 |
| 197 | (S)-2,6-Diaminohexanoic acid | 2-Furaldehyde | Cyclohexylamine | 439 | | N | | 41.9 | 41.3 |
| 198 | (S)-2,6-Diaminohexanoic acid | 2-Imidazolecarboxaldehyde | Cyclohexylamine | 439 | 440 | Y | | 65.4 | 26.4 |
| 199 | (S)-2,6-Diaminohexanoic acid | 2-Methoxybenzaldehyde (o-anisaldehyde) | Cyclohexylamine | 479 | 480 | Y | 2.79 | 5.83 | 71.5 | 71.4 |
| 200 | (S)-2,6-Diaminohexanoic acid | 2-Naphthaldehyde | Cyclohexylamine | 499 | 500 | Y | 1.78 | 2.1 | 83.6 | 81 |
| 201 | (S)-2,6-Diaminohexanoic acid | 2-Pyridinecarboxaldehyde | Cyclohexylamine | 450 | | N | | | 61.1 | 43.4 |
| 202 | (S)-2,6-Diaminohexanoic acid | 2-Quinolinecarboxaldehyde | Cyclohexylamine | 500 | | N | | | 63 | 53.2 |
| 203 | (S)-2,6-Diaminohexanoic acid | 2-Thiophenecarboxaldehyde | Cyclohexylamine | 455 | 456 | Y | | | 58.1 | 49 |
| 204 | (S)-2,6-Diaminohexanoic acid | 3,4-(Methylenedioxy)benzaldehyde (piperonal) | Cyclohexylamine | 851 | 482 | Y | | | 32.1 | 25.8 |
| 205 | (S)-2,6-Diaminohexanoic acid | 3,4-Dibenzyloxybenzaldehyde | Cyclohexylamine | 481 | 482 | Y | | | 35.9 | 39 |
| 206 | (S)-2,6-Diaminohexanoic acid | 3,4-Dichlorobenzaldehyde | Cyclohexylamine | 518 | 519 | Y | 2.7 | 1.35 | 75 | 69 |
| 207 | (S)-2,6-Diaminohexanoic acid | 3,4-Difluorobenzaldehyde | Cyclohexylamine | 485 | 486 | Y | 3.99 | 3.16 | 65 | 65.5 |
| 208 | (S)-2,6-Diaminohexanoic acid | 3,5-Bis(trifluoromethyl)benzaldehyde | Cyclohexylamine | 585 | 586 | Y | 3.34 | 2.99 | 79.5 | 67.5 |
| 209 | (S)-2,6-Diaminohexanoic acid | 3,5-Dibenzyloxybenzaldehyde | Cyclohexylamine | 481 | 482 | Y | | | 19.7 | 24.3 |
| 210 | (S)-2,6-Diaminohexanoic acid | 3,5-Dichlorobenzaldehyde | Cyclohexylamine | 518 | 519 | Y | | | 76.5 | 69.6 |
| 211 | (S)-2,6-Diaminohexanoic acid | 3,5-Dimethoxybenzaldehyde | Cyclohexylamine | 509 | 510 | Y | | | 69.9 | 69 |
| 212 | (S)-2,6-Diaminohexanoic acid | 3,5-Dimethyl-4-hydroxybenzaldehyde | Cyclohexylamine | 493 | 494 | Y | | | 54.8 | 45.8 |
| 213 | (S)-2,6-Diaminohexanoic acid | 3-(3,4-Dichlorophenoxy)benzaldehyde | Cyclohexylamine | 610 | 611 | Y | | | 80 | 78.1 |
| 214 | (S)-2,6-Diaminohexanoic acid | 3-(4-Methoxyphenoxy)benzaldehyde | Cyclohexylamine | 571 | 572 | Y | | | 87.5 | 84.9 |
| 215 | (S)-2,6-Diaminohexanoic acid | 3-(Trifluoromethyl)benzaldehyde | Cyclohexylamine | 517 | 518 | Y | 2.76 | 6.36 | 75.9 | 70.8 |
| 216 | (S)-2,6-Diaminohexanoic acid | 3-Bromo-4-fluorobenzaldehyde | Cyclohexylamine | 546 | 547 | Y | 2.41 | 3.73 | 78.9 | 67.9 |
| 217 | (S)-2,6-Diaminohexanoic acid | 3-Bromobenzaldehyde | Cyclohexylamine | 528 | 529 | Y | | | 74.5 | 68.8 |
| 218 | (S)-2,6-Diaminohexanoic acid | 3-Carboxybenzaldehyde | Cyclohexylamine | 581 | 562 | Y | | | 61.4 | 57.2 |
| 219 | (S)-2,6-Diaminohexanoic acid | 3-Cyanobenzaldehyde | Cyclohexylamine | 478 | 479 | Y | | | 43.5 | 42.9 |
| 220 | (S)-2,6-Diaminohexanoic acid | 3-Fluoro-4-methoxybenzaldehyde | Cyclohexylamine | 497 | 498 | Y | | | 67.3 | 60.6 |
| 221 | (S)-2,6-Diaminohexanoic acid | 3-Fluorobenzaldehyde | Cyclohexylamine | 467 | 468 | Y | 3.91 | 5.46 | 65.2 | 62.7 |
| 222 | (S)-2,6-Diaminohexanoic acid | 3-Furaldehyde | Cyclohexylamine | 439 | | N | | | 34.3 | 39.3 |
| 223 | (S)-2,6-Diaminohexanoic acid | 3-Hydroxybenzaldehyde | Cyclohexylamine | 465 | 466 | Y | 20.92 | >10 | 33.6 | 21.2 |
| 224 | (S)-2,6-Diaminohexanoic acid | 3-Methoxy-4-hydroxy-5-nitrobenzaldehyde | Cyclohexylamine | 510 | 511 | Y | | | 54.8 | 36.6 |
| 225 | (S)-2,6-Diaminohexanoic acid | 3-Methoxybenzaldehyde (m-anisaldehyde) | Cyclohexylamine | 479 | 480 | Y | | | 69.8 | 69.4 |
| 226 | (S)-2,6-Diaminohexanoic acid | 3-Methyl-4-methoxybenzaldehyde | Cyclohexylamine | 493 | 494 | Y | 3.84 | 13.68 | 79.1 | 77.7 |
| 227 | (S)-2,6-Diaminohexanoic acid | 3-Methylbenzaldehyde (m-tolualdehyde) | Cyclohexylamine | 463 | 464 | Y | 1.55 | 5.59 | 78.2 | 74.6 |
| 228 | (S)-2,6-Diaminohexanoic acid | 3-Nitro-4-chlorobenzaldehyde | Cyclohexylamine | 499 | 500 | Y | | | 78.5 | 69.3 |
| 229 | (S)-2,6-Diaminohexanoic acid | 3-Nitrobenzaldehyde | Cyclohexylamine | 494 | 495 | Y | | | 58.6 | 48.8 |
| 230 | (S)-2,6-Diaminohexanoic acid | 3-Phenoxybenzaldehyde | Cyclohexylamine | 541 | 542 | Y | 2.12 | 3.88 | 89.2 | 84.2 |
| 231 | (S)-2,6-Diaminohexanoic acid | 3-Pyridinecarboxaldehyde | Cyclohexylamine | 450 | 451 | Y | | | 25 | 18.9 |
| 232 | (S)-2,6-Diaminohexanoic acid | 3-Quinolinecarboxaldehyde | Cyclohexylamine | 500 | | N | | | 36.1 | 34.2 |
| 233 | (S)-2,6-Diaminohexanoic acid | 3-Thiophenecarboxaldehyde | Cyclohexylamine | 455 | 456 | Y | | | 53.6 | 42.8 |
| 234 | (S)-2,6-Diaminohexanoic acid | 4-(Dimethylaminopropoxy)benzaldehyde | Cyclohexylamine | 550 | 551 | Y | | | 52.9 | 37.7 |
| 235 | (S)-2,6-Diaminohexanoic acid | 4-(Dimethylamino)benzaldehyde | Cyclohexylamine | 492 | 493 | Y | 5.91 | 11.04 | 64.2 | 26.3 |
| 236 | (S)-2,6-Diaminohexanoic acid | 4-(Methylcarboxylate)benzaldehyde | Cyclohexylamine | 569 | 570 | Y | | | 75.7 | 69.7 |
| 237 | (S)-2,6-Diaminohexanoic acid | 4-(Methylthio)benzaldehyde | Cyclohexylamine | 495 | 496 | Y | | | 62.2 | 47.8 |
| 238 | (S)-2,6-Diaminohexanoic acid | 4-(Trifluoromethyl)benzaldehyde | Cyclohexylamine | 517 | 518 | Y | 2.54 | retest | 76.8 | 72.8 |
| 239 | (S)2,6-Diaminohexanoic acid | 4-Acetamido benzaldehyde | Cyclohexylamine | 492 | 493 | Y | 0.58 | 49.7 | 86.6 | 85.2 |
| 240 | (S)-2,6-Diaminohexanoic acid | 4-Methoxybenzaldehyde (p-anisaldehyde) | Cyclohexylamine | 479 | 480 | Y | 3.16 | 12.49 | 69.6 | 66.5 |
| 241 | (S)-2,6-Diaminohexanoic acid | 4-Biphenylcarboxaldehyde | Cyclohexylamine | 525 | 526 | Y | 1.11 | 10.07 | 89.5 | 88.8 |
| 242 | (S)-2,6-Diaminohexanoic acid | 4-Bromobenzaldehyde | Cyclohexylamine | 528 | 529 | Y | 2.12 | 0.69 | 86 | 83.4 |
| 243 | (S)-2,6-Diaminohexanoic acid | 4-Carboxybenzaldehyde | Cyclohexylamine | 561 | 562 | Y | | | 42 | 47.9 |

TABLE 1-continued

| | R1: Amino Acids | R2: Aldehydes | R3: amines | M.W. | obs.(M + 1) M.W. | >85% LCQ | MC-1 IC50 uM | | MC-4 IC50 uM |
|---|---|---|---|---|---|---|---|---|---|
| 244 | (S)-2,6-Diaminohexanoic acid | 4-Cyanobenzaldehyde | Cyclohexylamine | 478 | 479 | Y | | 29.7 | 22.5 |
| 245 | (S)-2,6-Diaminohexanoic acid | 4-Fluorobenzaldehyde | Cyclohexylamine | 467 | 468 | Y | 6.64 | 56.6 | 56.8 |
| 246 | (S)-2,6-Diaminohexanoic acid | 4-Hydroxybenzaldehyde | Cyclohexylamine | 465 | 466 | Y | 48.11 | 26.5 | 20.7 |
| 247 | (S)-2,6-Diaminohexanoic acid | 4-Isopropylbenzaldehyde | Cyclohexylamine | 491 | 492 | Y | 1.59 | 83 | 85.3 |
| 248 | (S)-2,6-Diaminohexanoic acid | 4-Methoxy-1-naphthaldehyde | Cyclohexylamine | 529 | 530 | Y | 8.66 | 56.5 | 67.9 |
| 249 | (S)-2,6-Diaminohexanoic acid | 4-Methylbenzaldehyde (p-tolualdehyde) | Cyclohexylamine | 463 | 464 | Y | 1.87 | 82.3 | 83 |
| 250 | (S)-2,6-Diaminohexanoic acid | 3-Hydroxy-4-nitrobenzaldehyde | Cyclohexylamine | 510 | 511 | Y | | 34.7 | 50.5 |
| 251 | (S)-2,6-Diaminohexanoic acid | 4-Nitrobenzaldehyde | Cyclohexylamine | 494 | 495 | Y | 13.11 | 49.4 | 46.9 |
| 252 | (S)-2,6-Diaminohexanoic acid | 4-Phenoxybenzaldehyde | Cyclohexylamine | 541 | 542 | Y | 0.58 | 95.1 | 95.5 |
| 253 | (S)-2,6-Diaminohexanoic acid | 4-Propoxybenzaldehyde | Cyclohexylamine | 507 | 508 | Y | 0.73 | 93.9 | 92.2 |
| 254 | (S)-2,6-Diaminohexanoic acid | 4-Pyridinecarboxaldehyde | Cyclohexylamine | 450 | 451 | Y | | 24.9 | 29.1 |
| 255 | (S)-2,6-Diaminohexanoic acid | 4-Quinolinecarboxeldehyde | Cyclohexylamine | 500 | | Y | | 29.2 | 25.3 |
| 256 | (S)-2,6-Diaminohexanoic acid | 5-(Hydroxymethyl)-2-furaldehyde | Cyclohexylamine | 559 | | N | | 38.9 | 38.9 |
| 257 | (S)-2,6-Diaminohexanoic acid | 3-Methoxy-4-hydroxy-5-bromobenzaldehyde | Cyclohexylamine | 562 | 563 | N | >10 | 26.3 | 28.4 |
| 258 | (S)-2,6-Diaminohexanoic acid | 5-Methyl-2-thiophenecarboxaldehyde | Cyclohexylamine | 469 | 470 | Y | 2.42 | 80.7 | 81.9 |
| 259 | (S)-2,6-Diaminohexanoic acid | 5-Methyl-2-furaldehyde (5-methylfurfural) | Cyclohexylamine | 453 | 454 | Y | 7.27 | 42.5 | 48.1 |
| 260 | (S)-2,6-Diaminohexanoic acid | 5-Nitro-2-furaldehyde | Cyclohexylamine | 484 | | N | | 43 | 39 |
| 261 | (S)-2,6-Diaminohexanoic acid | 6-Methyl-2-pyridinecarboxaldehyde | Cyclohexylamine | 464 | | N | | 48.9 | 47.8 |
| 262 | (S)-2,6-Diaminohexanoic acid | 8-Hydroxyquinoline-2-carboxaldehyde | Cyclohexylamine | 516 | 517 | Y | 4.17 | 66.1 | 68.8 |
| 263 | (S)-2,6-Diaminohexanoic acid | 9-Ethyl-3-carbazolecarboxaldehyde | Cyclohexylamine | 566 | 567 | Y | | 61.6 | 65.3 |
| 264 | (S)-2,6-Diaminohexanoic acid | 9-Formyl-8-hydroxyjulolidine | Cyclohexylamine | 560 | 561 | Y | | 35 | 39.4 |
| 265 | (S)-2,6-Diaminohexanoic acid | Pyrrole-2-carboxaldehyde | Cyclohexylamine | 438 | 439 | Y | | 60.5 | 54.1 |
| 266 | (S)-2,6-Diaminohexanoic acid | 3-Hydroxy-4-methoxybenzaldehyde | Cyclohexylamine | 481 | 482 | Y | >10 | 36.4 | 31.8 |
| 267 | (S)-2,6-Diaminohexanoic acid | 4-Methylsulphonylbenzaldehyde | Cyclohexylamine | 527 | 528 | Y | | 21.5 | 8.4 |
| 268 | (S)-2,6-Diaminohexanoic acid | 4-Methoxy-3-(sulfanic acid, Na)benzaldehyde | Cyclohexylamine | 559 | 560 | Y | | 0 | 3.6 |
| 269 | (S)-2,6-Diaminohexanoic acid | 5-Bromo-2-furaldehyde | Cyclohexylamine | 518 | 519 | Y | | 55.9 | 57.7 |
| 270 | (S)-2,6-Diaminohexanoic acid | 2-Thiazolecarboxaldehyde | Cyclohexylamine | 456 | | N | | 41.1 | 337 |

| Cmpd # | R1: Amino Acids | R8 = Boc R2: Aldehydes | R3: amines | M.W. | obs.(M + 1) M.W. | >85% LCQ | MC-1 IC50 uM | MC-4 IC50 uM |
|---|---|---|---|---|---|---|---|---|
| | TRG 2406 | | | | | | | |
| 1 | (S)-2,6-Diaminohexanoic acid | 1-Methyl-2-pyrrolecarboxaldehyde | 2-Hydroxybenzylamine | 474 | 475 | Y | 3.79 | 5.85 |
| 2 | Glycine | 3-(3,4-Dichlorophenoxy)benzaldehyde | 2-Hydroxybenzylamine | 547 | 548 | Y | 7.98 | 3.86 |
| 3 | (S)-2,3-Diaminopropionic acid | 3-(3,4-Dichlorophenoxy)benzaldehyde | 2-Hydroxybenzylamine | 590 | 591 | Y | 12.34 | 9.69 |
| 4 | (S)-2,6-Diaminohexanoic acid | 3-(3,4-Dichlorophenoxy)benzaldehyde | 2-Hydroxybenzylamine | 632 | 633 | Y | 1.72 | 3.78 |
| 5 | Glycine | 3-(4-Methoxyphenoxy)benzaldehyde | 2-Hydroxybenzylamine | 508 | 509 | Y | 6.16 | 3.41 |
| 6 | (S)-2,3-Diaminopropionic acid | 3-(4-Methoxyphenoxy)benzaldehyde | 2-Hydroxybenzylamine | 551 | 552 | Y | 3.17 | 1.36 |
| 7 | (S)-2,6-Diaminohexanoic acid | 3-(4-Methoxyphenoxy)benzaldehyde | 2-Hydroxybenzylamine | 593 | 594 | Y | 1.23 | 1.74 |
| 8 | Glycine | 3-Phenoxybenzaldehyde | 2-Hydroxybenzylamine | 478 | 479 | Y | 7.48 | 5.67 |
| 9 | (S)-2,3-Diaminopropionic acid | 3-Phenoxybenzaldehyde | 2-Hydroxybenzylamine | 521 | 522 | Y | 3.66 | 2.1 |
| 10 | (S)-2,6-Diaminohexanoic acid | 3-Phenoxybenzaldehyde | 2-Hydroxybenzylamine | 563 | 564 | Y | 0.85 | 0.26 |
| 11 | Glycine | 4-Phenoxybenzaldehyde | 2-Hydroxybenzylamine | 478 | 479 | Y | 10.47 | 7 |
| 12 | (S)-2,3-Diaminopropionic acid | 4-Phenoxybenzaldehyde | 2-Hydroxybenzylamine | 521 | 522 | Y | 5.44 | 2.62 |
| 13 | (S)-2,6-Diaminohexanoic acid | 4-Phenoxybenzaldehyde | 2-Hydroxybenzylamine | 563 | 564 | Y | 0.15 | 1.29 |
| 14 | Glycine | 4-Propoxybenzaldehyde | 2-Hydroxybenzylamine | 444 | 445 | Y | 8.31 | 5.36 |
| 15 | (S)-2,3-Diaminopropionic acid | 4-Propoxybenzaldehyde | 2-Hydroxybenzylamine | 487 | 488 | Y | 7.22 | 2.75 |
| 16 | (S)-2,6-Diaminohexanoic acid | 4-Propoxybenzaldehyde | 2-Hydroxybenzylamine | 529 | 530 | Y | 2.12 | 11.64 |
| 17 | Glycine | 3-Methoxy-4-hydroxy-5-bromobenzaldehyde | 2-Hydroxybenzylamine | 499 | 500 | Y | 15.6 | |
| 18 | (S)-2,3-Diaminopropionic acid | 3-Methoxy-4-hydroxy-5-bromobenzaldehyde | 2-Hydroxybenzylamine | 542 | 543 | Y | 4.32 | 35.08 |
| 19 | (S)-2,6-Diaminohexanoic acid | 3-Methoxy-4-hydroxy-5-bromobenzaldehyde | 2-Hydroxybenzylamine | 584 | 585 | Y | 26.5 | |

TABLE 1-continued

| Cpd # | R1 | R8 = Boc R2: Aldehyde | R3: Amine | prod. MW | obs.(M + 1) M.W. | >85% LCQ | MC-1 IC50 uM | MC-4 IC50 uM |
|---|---|---|---|---|---|---|---|---|
| 20 | Glycine | 9-Ethyl-3-carbazolecarboxaldehyde | 2-Hydroxybenzylamine | | 503 | Y | 10.8 | 3.3 |
| 21 | (S)-2,3-Diaminopropionic acid | 9-Ethyl-3-carbazolecarboxaldehyde | 2-Hydroxybenzylamine | | 547 | Y | 6.25 | 1.53 |
| 22 | (S)-2,6-Diaminohexanoic acid | 9-Ethyl-3-carbazolecarboxaldehyde | 2-Hydroxybenzylamine | | 588 | Y | 2.12 | 1.79 |

TRG 2407

| Cpd # | R1 | R2: Aldehyde | R3: Amine | prod. MW | obs.(M + 1) M.W. | >85% LCQ | MC-1 IC50 uM | MC-4 IC50 uM |
|---|---|---|---|---|---|---|---|---|
| 1 | L-Lysine | 2,4-dichlorobensaldehyde | Aniline | 512 | 513 | Y | 5.57 | 10.65 |
| 2 | L-Lysine | 2,4-dichlorobensaldehyde | N-methylaniline | 526 | 527 | Y | 5.75 | 6.26 |
| 3 | L-Lysine | 2,4-dichlorobensaldehyde | 2-chloroaniline | 546 | 547 | Y | 8.46 | 9.45 |
| 4 | L-Lysine | 2,4-dichlorobensaldehyde | 2-Methoxyaniline | 542 | 543 | Y | 3.65 | 4.12 |
| 5 | L-Lysine | 2,4-dichlorobensaldehyde | 3-chloroaniline | 546 | 547 | Y | 8.82 | 14.66 |
| 6 | L-Lysine | 2,4-dichlorobensaldehyde | 3-ethoxyaniline | 556 | 557 | Y | 3.42 | 6.97 |
| 7 | L-Lysine | 2,4-dichlorobensaldehyde | 3-aminophenol | 528 | 529 | Y | 4.38 | no fit |
| 8 | L-Lysine | 2,4-dichlorobensaldehyde | 4-chloroaniline | 546 | 547 | Y | 10.88 | 21.23 |
| 9 | L-Lysine | 2,4-dichlorobensaldehyde | 4-Methoxyaniline | 542 | 543 | Y | 2.53 | 6.22 |
| 10 | L-Lysine | 2,4-dichiorobenzaldehyde | Benzylamine | 526 | 527 | Y | 4.13 | 3.85 |
| 11 | L-Lysine | 2,4-dichlorobenzaldehyde | N-benzymethylamine | 540 | 541 | Y | 5.31 | 6.17 |
| 12 | L-Lysine | 2,4-dichlorobenzaldehyde | 2-chlorobenzylamine | 560 | 561 | Y | 2.70 | 3.23 |
| 13 | L-Lysine | 2,4-dichlorobenzaldehyde | 2-(trifluoromethyl)benzylamine | 594 | 595 | Y | 8.50 | 9.25 |
| 14 | L-Lysine | 2,4-dichlorobenzaldehyde | 2-Methoxybenzylamine | 556 | 557 | Y | 0.37 | 0.41 |
| 15 | L-Lysine | 2,4-dichlorobenzaldehyde | 2-ethoxybenzylamine | 570 | 571 | Y | 1.20 | 0.78 |
| 16 | L-Lysine | 2,4-dichlorobenzaldehyde | 3-methoxybenzylamine | 556 | 557 | Y | 5.83 | 1.81 |
| 17 | L-Lysine | 2,4-dichlorobenzaldehyde | 3-(trifluoromethyl)benzylamine | 594 | 595 | Y | 10.07 | 9.22 |
| 18 | L-Lysine | 2,4-dichlorobenzaldehyde | 4-Chlorobenzylamine | 560 | 561 | Y | 3.31 | 2.83 |
| 19 | L-Lysine | 2,4-dichiorobenzaldehyde | 4-methoxybenzylamine | 556 | 557 | Y | 2.29 | 2.04 |
| 20 | L-Lysine | 2,4-dichlorobenzaldehyde | 4-(trifluoromethyl)benzylamine | 594 | 595 | Y | 3.78 | 3.49 |
| 21 | L-Lysine | 2,4-dichlorobenzaldehyde | phenethylamine | 540 | 541 | Y | 1.03 | 0.36 |
| 22 | L-Lysine | 2,4-dichlorobenzaldehyde | 2-chlorophenethylamine | 574 | 575 | Y | 1.34 | 0.69 |
| 23 | L-Lysine | 2,4-dichlorobenzaldehyde | 2-methoxyphenethylamine | 570 | 571 | Y | 0.94 | 0.69 |
| 24 | L-Lysine | 2,4-dichlorobenzaldehyde | 3-chlorophemethylamine | 574 | 575 | Y | 1.79 | 0.80 |
| 25 | L-Lysine | 2,4-dichlorobenzaldehyde | 4-methoxyphenthylamine | 570 | 571 | Y | 1.47 | 0.62 |
| 26 | L-Lysine | 2,4-dichlorobenzaldehyde | 3-phenyl-1-propylamine | 554 | 555 | Y | 0.70 | 0.83 |
| 27 | L-Lysine | 2,4-dichlorobenzaldehyde | Cyclopentylamine 99% | 504 | 505 | Y | 0.57 | 0.53 |
| 28 | L-Lysine | 4-biphenylcarboxaldehyde | Isopropylamine | 485 | 486 | Y | 0.31 | 3.60 |
| 29 | L-Lysine | 2,4-dichlorobensaldehyde | Cycloheptylamine 99% | 532 | 533 | Y | 0.64 | 0.77 |
| 30 | L-Lysine | 2,4-dichlorobenzaldehyde | N-methylcyclohexylamine | 532 | 533 | Y | 3.15 | 2.10 |
| 31 | L-Lysine | 2,4-dichlorobenzaldehyde | (aminomethyl)cyclohexane | 532 | 533 | Y | 1.11 | 1.02 |
| 32 | L-Lysine | 2,4-dichlorobenzaldehyde | Piperidine 99.5% | 504 | 505 | Y | 3.29 | 2.14 |
| 33 | L-Lysine | 2,4-dichlorobenzaldehyde | Morpholine 99.5 + % | 506 | 507 | Y | 6.90 | 6.02 |
| 34* | L-Lysine | 2,4-dichlorocbenzaldehyde | 1-aminopiperidine | 519 | 520 | N | 3.97 | 2.01 |
| 35 | L-Lysine | 2,4-dichlorobenzaldehyde | Diethylamine 99.5% | 492 | 493 | Y | 6.52 | 3.41 |
| 36 | L-Lysine | 2,4-dichlorobenzaldehyde | Allylamine | 476 | 477 | Y | 0.43 | 0.46 |
| 37 | L-Lysine | 2,4-dichlorobenzaldehyde | Isopropylamine | 478 | 479 | Y | 0.91 | 0.54 |
| 38* | L-Lysine | 2,4-dichlorobenzaldehyde | (2-Aminoethyl)-trimethylammonium | 594 | 595 | N | 3.21 | 3.82 |
| 39 | L-Lysine | 2,4-dichlorobenzaldehyde | ammonia | 435 | 436 | Y | 0.91 | 0.11 |
| 40 | L-Lysine | 2,4-dichlorobenzaldehyde | none (OH) | 436 | 437 | Y | 4.74 | 4.94 |
| 41 | L-Lysine | 4-acetamidobenzaldehyde | Aniline | 486 | 487 | Y | 5.87 | 16.96 |
| 42 | L-Lysine | 4-acetamidobenzaldehyde | N-methylaniline | 500 | 501 | Y | 4.23 | 7.90 |
| 43 | L-Lysine | 4-acetamidobenzaldehyde | 2-chloroaniline | 520 | 521 | Y | 7.07 | 11.20 |

TABLE 1-continued

| | | | | | | | | |
|---|---|---|---|---|---|---|---|---|
| 44 | L-Lysine | 4-acetamidobenzaldehyde | 2-Methoxyaniline | Y | 516 | 517 | 1.15 | 10.38 |
| 45 | L-Lysine | 4-acetamidobenzaldehyde | 3-chloroaniline | Y | 520 | 521 | 7.91 | 10.95 |
| 46 | L-Lysine | 4-acetamidobenzaldehyde | 3-ethoxyaniline | Y | 530 | 531 | 1.63 | 16.39 |
| 47 | L-Lysine | 4-acetamidobenzaldehyde | 3-aminophenol | Y | 502 | 503 | 0.84 | no fit |
| 48 | L-Lysine | 4-acetamidobenzaldehyde | 4-chloroaniline | Y | 520 | 521 | 4.48 | 10.81 |
| 49 | L-Lysine | 4-acetamidobenzaldehyde | 4-Methoxyaniline | Y | 516 | 517 | 2.36 | no fit |
| 50 | L-Lysine | 4-acetamidobenzaldehyde | Benzylamine | Y | 500 | 501 | 0.35 | 9.10 |
| 51 | L-Lysine | 4-acetamidobenzaldehyde | N-benzylmethylamine | Y | 514 | 515 | 2.16 | 13.49 |
| 52 | L-Lysine | 4-acetamidobenzaldehyde | 2-chlorobenzylamine | Y | 534 | 535 | 0.44 | 1.56 |
| 53 | L-Lysine | 4-acetamidobenzaldehyde | 2-(trifluoromethyl)benzylamine | Y | 568 | 569 | 1.27 | 0.79 |
| 54* | L-Lysine | 4-biphenylcarboxaldehyde | (2-Aminoethyl)-trimethylammonium | N | 601 | 602 | 4.23 | 14.82 |
| 55 | L-Lysine | 4-acetamidobenzaldehyde | 2-ethoxybenzylamine | Y | 544 | 545 | 0.19 | 14.89 |
| 56 | L-Lysine | 4-acetamidobenzaldehyde | 3-methoxybenzylamine | Y | 530 | 531 | 1.50 | 12.09 |
| 57 | L-Lysine | 4-acetamidobenzaldehyde | 3-(trifluoromethyl)benzylamine | Y | 568 | 569 | 2.46 | 3.65 |
| 58 | L-Lysine | 4-acetamidobenzaldehyde | 4-Chlorobenzylamine | Y | 534 | 535 | 0.54 | 2.78 |
| 59 | L-Lysine | 4-acetamidobenzaldehyde | 4-methoxybenzylamine | Y | 530 | 531 | 0.89 | 9.99 |
| 60 | L-Lysine | 4-acetamidobenzaldehyde | 4-(trifluoromethyl)benzylamine | Y | 568 | 569 | 0.77 | 3.32 |
| 61 | L-Lysine | 4-acetamidobenzaldehyde | phenellhylamino | Y | 514 | 515 | 0.18 | 12.28 |
| 62 | L-Lysine | 4-acetamidobenzaldehyde | 2-chlorophenethylamine | Y | 548 | 549 | 0.23 | 4.22 |
| 63 | L-Lysine | 4-acetamidobenzaldehyde | 2-methoxyphenethylamine | Y | 544 | 545 | 0.28 | 10.08 |
| 64 | L-Lysine | 4-acetamidobenzaldehyde | 3-chlorophenethylamine | Y | 548 | 549 | 0.87 | 5.41 |
| 65 | L-Lysine | 4-acetamidobenzaldehyde | 4-methoxyphenthylamine | Y | 544 | 545 | 0.21 | 5.40 |
| 66 | L-Lysine | 4-acetamidobenzaldehyde | 3-phenyl-1-propylamine | Y | 528 | 529 | 0.23 | 3.29 |
| 67 | L-Lysine | 4-acetamidobenzaldehyde | Cyclopentylamine 99% | Y | 478 | 479 | 0.52 | no fit |
| 68 | L-Lysine | 4-acetamidobenzaldehyde | ammonia | Y | 443 | 444 | 0.35 | 4.86 |
| 69 | L-Lysine | 4-acetamidobenzaldehyde | Cycloheptylamine 99% | Y | 506 | 507 | 0.29 | 15.30 |
| 70 | L-Lysine | 4-acetamidobenzaldehyde | N-methylcyclohexylamine | Y | 506 | 507 | 1.02 | 43.56 |
| 71 | L-Lysine | 4-acetamidobenzaldehyde | (aminomethyl)cyclohexane | Y | 506 | 507 | 0.64 | 13.50 |
| 72 | L-Lysine | 4-acetamidobenzaldehyde | Piperidine 99.5% | Y | 478 | 479 | 1.86 | no fit |
| 73 | L-Lysine | 4-acetamidobenzaldehyde | Morpholine 99.5 + % | Y | 480 | 481 | 10.55 | no fit |
| 74* | L-Lysine | 4-acetamidobenzaldehyde | 1-aminopiperidine | N | 493 | | 2.73 | no fit |
| 75 | L-Lysine | 4-acetamidobenzaldehyde | Diethylamine 99.5% | Y | 466 | 467 | 5.50 | no fit |
| 76* | L-Lysine | 4-acetamidobenzaldehyde | Allylamine | N | 450 | | 0.51 | no fit |
| 77 | L-Lysine | 4-acetamidobenzaldehyde | Isopropylamine | Y | 452 | 453 | 1.24 | no fit |
| 78* | L-Lysine | 4-acetamidobenzaldehyde | (2-Aminoethyl)-trimethylammonium | N | 568 | | 4.60 | no fit |
| 79 | L-Lysine | 4-acetamidobenzaldehyde | ammonia | Y | 410 | 411 | 1.44 | no fit |
| 80 | L-Lysine | 4-acetamidobenzaldehyde | none | Y | 411 | 412 | 11.60 | no fit |
| 81 | L-Lysine | 4-biphenylcarboxaldehyde | Aniline | Y | 519 | 520 | 6.40 | 13.23 |
| 82 | L-Lysine | 4-biphenylcarboxaldehyde | N-methylaniline | Y | 533 | 534 | 5.40 | 8.61 |
| 83 | L-Lysine | 4-biphenylcarboxaldehyde | 2-chloroaniline | Y | 553 | 554 | 7.02 | 9.53 |
| 84 | L-Lysine | 4-biphenylcarboxaldehyde | 2-Methoxyaniline | Y | 549 | 550 | 3.12 | 15.01 |
| 85 | L-Lysine | 4-biphenylcarboxaldehyde | 3-chloroaniline | Y | 553 | 554 | 7.09 | 12.47 |
| 86 | L-Lysine | 4-biphenylcarboxaldehyde | 3-ethoxyaniline | Y | 563 | 564 | 4.16 | 15.86 |
| 87 | L-Lysine | 4-biphenylcarboxaldehyde | 3-aminophenol | Y | 535 | 536 | 4.25 | 29.33 |
| 88 | L-Lysine | 4-biphenylcarboxaldehyde | 4-chloroaniline | Y | 553 | 554 | 8.24 | 12.47 |
| 89 | L-Lysine | 4-biphenylcarboxaldehyde | 4-Methoxyaniline | Y | 549 | 550 | 4.48 | 6.49 |
| 90 | L-Lysine | 4-biphenylcarboxaldehyde | Benzylamine | Y | 533 | 534 | 3.43 | 5.45 |
| 91 | L-Lysine | 4-biphenylcarboxaldehyde | N-benzylmethylamine | Y | 547 | 548 | 6.20 | 12.82 |
| 92 | L-Lysine | 4-biphenylcarboxaldehyde | 2-chlorobenzylamine | Y | 567 | 568 | 2.36 | 6.95 |
| 93 | L-Lysine | 4-biphenylcarboxaldehyde | 2-(trifluoromethyl)benzylamine | Y | 601 | 602 | 19.12 | 25.10 |
| 94 | L-Lysine | 4-biphenylcarboxaldehyde | 2-Methoxybenzylamine | Y | 563 | 564 | 0.92 | 5.88 |
| 95 | L-Lysine | 4-biphenylcarboxaldehyde | 2-ethoxybenzylamine | Y | 577 | 578 | 2.37 | 8.05 |

TABLE 1-continued

| | R1: Amino Acids | R2: Aldehydes | R3: amines | R8: Substit. on R1 (C2-N) | M.W. | obs. (M + 1) M.W. | >85% LCQ | MC-1 IC50 | uM | MC-4 IC50 uM |
|---|---|---|---|---|---|---|---|---|---|---|
| 96 | L-Lysine | 4-biphenylcarboxaldehyde | 3-methoxybenzylamine | | 563 | 564 | Y | 1.15 | | 4.07 |
| 97 | L-Lysine | 4-biphenylcarboxaldehyde | 3-(trifluoromethyl)benzylamine | | 601 | 602 | Y | 11.94 | | 15.11 |
| 98 | L-Lysine | 4-biphenylcarboxaldehyde | 4-Chlorobenzylamine | | 567 | 568 | Y | 3.04 | | 6.27 |
| 99 | L-Lysine | 4-biphenylcarboxaldehyde | 4-methoxybenzylamine | | 563 | 564 | Y | 3.24 | | 9.05 |
| 100 | L-Lysine | 4-biphenylcarboxaldehyde | 4-(trifluoromethyl)benzylamine | | 601 | 602 | Y | 2.76 | | 6.49 |
| 101 | L-Lysine | 4-biphenylcarboxaldehyde | phenethylamine | | 547 | 548 | Y | 0.93 | | 4.18 |
| 102 | L-Lysine | 4-biphenylcarboxaldehyde | 2-chlorophenethylamine | | 581 | 582 | Y | 1.53 | | 3.62 |
| 103 | L-Lysine | 4-biphenylcarboxaldehyde | 2-methoxyphenethylamine | | 577 | 578 | Y | 1.72 | | 9.61 |
| 104 | L-Lysine | 4-biphenylcarboxaldehyde | 3-chlorophenethylamine | | 581 | 582 | Y | 3.98 | | 7.74 |
| 105 | L-Lysine | 4-biphenylcarboxaldehyde | 4-methoxyphenethylamine | | 577 | 578 | Y | 1.67 | | 2.05 |
| 106 | L-Lysine | 4-biphenylcarboxaldehyde | 3-phenyl-1-propylamine | | 561 | 562 | Y | 2.21 | | 4.53 |
| 107 | L-Lysine | 4-biphenylcarboxaldehyde | Cyclopentylamine 99% | | 511 | 512 | Y | 0.92 | | 5.56 |
| 108 | L-Lysine | 4-biphenylcarboxaldehyde | none | | 444 | 445 | Y | 3.54 | | 10.78 |
| 109 | L-Lysine | 4-biphenylcarboxaldehyde | Cycloheptylamine 99% | | 539 | 540 | Y | 1.19 | | 5.36 |
| 110 | L-Lysine | 4-biphenylcarboxaldehyde | N-methylcyclohexylamine | | 539 | 540 | Y | 2.34 | | 4.15 |
| 111 | L-Lysine | 4-biphenylcarboxaldehyde | (aminonethyl)cyclohexane | | 539 | 540 | Y | 1.43 | | 4.57 |
| 112 | L-Lysine | 4-biphenylcarboxaldehyde | Piperidine 99.5% | | 511 | 512 | Y | 1.66 | | 6.99 |
| 113 | L-Lysine | 4-biphenylcarboxaldehyde | Morpholine 99.5 + % | | 513 | 514 | Y | 5.57 | | 10.34 |
| 114* | L-Lysine | 4-biphenylcarboxaldehyde | 1-aminopiperidine | | 526 | | N | 3.04 | | 10.00 |
| 115 | L-Lysine | 4-biphenylcarboxaldehyde | Diethylamine 99.5% | | 499 | 500 | Y | 2.94 | | 8.91 |
| 116 | L-Lysine | 4-biphenylcarboxaldehyde | Allylamine | | 483 | 484 | Y | 0.60 | | 18.67 |

| Cmpd 190 | R1: Amino Acids | R2: Aldehydes | R3: amines | R8: Substit. on R1 (C2-N) | M.W. | obs. (M + 1) M.W. | >85% LCQ | MC-1 IC50 | uM | MC-4 IC50 uM |
|---|---|---|---|---|---|---|---|---|---|---|
| TRG 2408 | | | | | | | | | | |
| 1 | (S)-2,6-Diaminohexanoic acid | 4-Acetamidobenzaldehyde | 2-Methoxybenzylamine | Hydrogen | 501 | 502 | Y | 0.51 | | 15.06 |
| 2 | (S)-2,6-Diamihohexanoic acid | 4-Acetamidobenzaldehyde | 2-Methoxybenzylamine | Phenylacetic acid | 605 | 606 | Y | 1.18 | | 8.55 |
| 3 | (S)-2,6-Diaminohexanoic acid | 4-Acetamidobenzaldehyde | 2-Methoxybenzylamine | Glycine | 544 | 545 | Y | 0.96 | | 14.77 |
| 4 | (S)-2,6-Diaminohexanoic acid | 4-Acetamidobenzaldehyde | 2-Methoxybenzylamine | Boc-Gly | 558 | 559 | Y | 1.66 | | 17.64 |
| 5 | (S)-2,6-Diaminohexanoic acid | 4-Acetamidobenzaldehyde | Cyclohexylamine | Hydrogen | 477 | 478 | Y | 1.66 | | 31.82 |
| 6 | (S)-2,6-Diaminohexanoic acid | 4-Acetamidobenzaldehyde | Cyclohexylamine | Phenylacetic acid | 581 | 582 | Y | 0.61 | | 7.16 |
| 7 | (S)-2,6-Diaminohexanoic acid | 4-Acetamidobenzaldehyde | Cyclohexylamine | Glycine | 520 | 521 | Y | 1.30 | | 44.54 |
| 8 | (S)-2,6-Diaminohexanoic acid | 4-Acetamidobenzaldehyde | Cyclohexylamine | Boc-Gly | 534 | 535 | Y | 2.31 | | 43.26 |
| 9 | (S)-2,6-Diaminohexanoic acid | 2,4-Dichlorobenzaldehyde | 2-Methoxybenzylamine | Hydrogen | 526 | 527 | Y | 1.81 | | 2.17 |
| 10 | (S)-2,6-Diaminohexanoic acid | 2,4-Dichlorobenzaldehyde | 2-Methoxybenzylamine | Phenylacetic acid | 630 | 631 | Y | 4.34 | | 10.94 |
| 11 | (S)-2,6-Diaminohexanoic acid | 2,4-Dichlorobenzaldehyde | 2-Methoxybenzylamine | Glycine | 569 | 570 | Y | 2.50 | | 8.10 |
| 12 | (S)-2,6-Diaminohexanoic acid | 2,4-Dichlorobenzaldehyde | 2-Methoxybenzylamine | Boc-Gly | 583 | 584 | Y | 1.84 | | 4.90 |
| 13 | (S)-2,6-Diaminohexanoic acid | 2,4-Dichlorobenzaldehyde | Cyclohexylamine | Hydrogen | 502 | 503 | Y | 1.72 | | 1.58 |
| 14 | (S)-2,6-Diaminohexanoic acid | 2,4-Dichlorobenzaldehyde | Cyclohexylamine | Phenylacetic acid | 606 | 607 | Y | 2.11 | | 5.52 |
| 15 | (S)-2,6-Diaminohexanoic acid | 2,4-Dichlorobenzaldehyde | Cyclohexylamine | Glycine | 545 | 546 | Y | 0.76 | | 6.30 |
| 16 | (S)-2,6-Diaminohexanoic acid | 2,4-Dichlorobenzaldehyde | Cyclohexylamine | Boc-Gly | 559 | 560 | Y | 1.79 | | 6.11 |
| 17 | (S)-2,6-Diaminohexanoic acid | 4-Biphenylcarboxaldehyde | 2-Methoxybenzylamine | Hydrogen | 534 | 535 | Y | 2.34 | | 15.05 |
| 18 | (S)-2,6-Diaminohexanoic acid | 4-Biphenylcarboxaldehyde | 2-Methoxybenzylamine | Phenylacetic acid | 638 | 639 | Y | 4.06 | | 12.48 |
| 19 | (S)-2,6-Diaminohexanoic acid | 4-Biphenylcarboxaldehyde | 2-Methoxybenzylamine | Glycine | 577 | 578 | Y | 2.64 | | 21.81 |
| 20 | (S)-2,6-Diaminohexanoic acid | 4-Biphenylcarboxaldehyde | 2-Methoxybenzylamine | Boc-Gly | 591 | 592 | Y | 1.32 | | 14.81 |
| 21 | (S)-2,6-Diaminohexanoic acid | 4-Biphenylcarboxaldehyde | Cyclohexylamine | Hydrogen | 510 | 511 | Y | 1.73 | | 17.39 |
| 22 | (S)-2,6-Diaminohexanoic acid | 4-Biphenylcarboxaldehyde | Cyclohexylamine | Phenylacetic acid | 614 | 615 | Y | 2.77 | | 11.44 |
| 23 | (S)-2,6-Diaminohexanoic acid | 4-Biphenylcarboxaldehyde | Cyclohexylamine | Glycine | 553 | 554 | Y | 0.82 | | 20.46 |
| 24 | (S)-2,6-Diaminohexanoic acid | 4-Biphenylcarboxaldehyde | Cyclohexylamine | Boc-Gly | 567 | 568 | Y | 1.94 | | 17.09 |
| 25 | (R)-2,6-Diaminohexanoic acid | 4-Acetamidobenzaldehyde | 2-Methoxybenzylamine | Boc | 515 | 516 | Y | 1.02 | | 38.03 |

TABLE 1-continued

| | | | | | | | | | |
|---|---|---|---|---|---|---|---|---|---|
| 26 | (R)-2,6-Diaminohexanoic acid | 4-Acetamidobenzaldehyde | 2-Methoxybenzylamine | Hydrogen | 501 | 502 | Y | 1.14 | 38.91 |
| 27 | (R)-2,6-Diaminohexanoic acid | 4-Acetamidobenzaldehyde | 2-Methoxybenzylamine | Phenylacetic acid | 605 | 606 | Y | 1.57 | 9.71 |
| 28 | (R)-2,6-Diaminohexanoic acid | 4-Acetamidobenzaldehyde | 2-Methoxybenzylamine | Glycine | 544 | 545 | Y | 0.47 | 12.57 |
| 29 | (R)-2,6-Diaminohexanoic acid | 4-Acetamidobenzaldehyde | 2-Methoxybenzylamine | Boc-Gly | 558 | 559 | Y | 0.68 | 21.83 |
| 30 | (R)-2,6-Diaminohexanoic acid | 4-Acetamidobenzaldehyde | Cyclohexylamine | Boc | 491 | 492 | Y | 1.17 | 45.56 |
| 31 | (R)-2,6-Diaminohexanoic acid | 4-Acetamidobenzaldehyde | Cyclohexylamine | Hydrogen | 477 | 478 | Y | 1.27 | 46.49 |
| 32 | (R)-2,6-Diaminohexanoic acid | 4-Acetamidobenzaldehyde | Cyclohexylamine | Phenylacetic acid | 581 | 582 | Y | 1.15 | 9.44 |
| 33 | (R)-2,6-Diaminohexanoic acid | 4-Acetamidobenzaldehyde | Cyclohexylamine | Glycine | 520 | 521 | Y | 1.06 | 38.66 |
| 34 | (R)-2,6-Diaminohexanoic acid | 4-Acetamidobenzaldehyde | Cyclohexylamine | Boc-Gly | 534 | 535 | Y | 2.14 | 33.62 |
| 35 | (R)-2,6-Diaminohexanoic acid | 2,4-Dichlorobenzaldehyde | 2-Methoxybenzylamine | Boc | 540 | 541 | Y | 2.77 | 4.89 |
| 36 | (R)-2,6-Diaminohexanoic acid | 2,4-Dichlorobenzaldehyde | 2-Methoxybenzylamine | Hydrogen | 526 | 527 | Y | 1.60 | 3.66 |
| 37 | (R)-2,6-Diaminohexanoic acid | 2,4-Dichlorobenzaldehyde | 2-Methoxybenzylamine | Phenylacetic acid | 630 | 631 | Y | 4.76 | 11.69 |
| 38 | (R)-2,6-Diaminohexanoic acid | 2,4-Dichlorobenzaldehyde | 2-Methoxybenzylamine | Glycine | 569 | 570 | Y | 1.70 | 5.57 |
| 39 | (R)-2,6-Diaminohexanoic acid | 2,4-Dichlorobenzaldehyde | 2-Methoxybenzylamine | Boc-Gly | 583 | 584 | Y | 1.80 | 6.05 |
| 40 | (R)-2,6-Diaminohexanoic acid | 2,4-Dichlorobenzaldehyde | Cyclohexylamine | Boc | 516 | 517 | Y | 2.43 | 8.28 |
| 41 | (R)-2,6-Diaminohexanoic acid | 2,4-Dichlorobenzaldehyde | Cyclohexylamine | Hydrogen | 502 | 503 | Y | 1.03 | 3.88 |
| 42 | (R)-2,6-Diaminohexanoic acid | 2,4-Dichlorobenzaldehyde | Cyclohexylamine | Phenylacetic acid | 606 | 607 | Y | 1.93 | 4.24 |
| 43 | (R)-2,6-Diaminohexanoic acid | 2,4-Dichlorobenzaldehyde | Cyclohexylamine | Glycine | 545 | 546 | Y | 1.63 | 7.49 |
| 44 | (R)-2,6-Diaminohexanoic acid | 2,4-Dichlorobenzaldehyde | Cyclohexylamine | Boc-Gly | 559 | 560 | Y | 1.27 | 5.06 |
| 45 | (R)-2,6-Diaminohexanoic acid | 4-Biphenylcarboxaldehyde | 2-Methoxybenzylamine | Boc | 548 | 549 | Y | 1.55 | 15.19 |
| 46 | (R)-2,6-Diaminohexanoic acid | 4-Biphenylcarboxaldehyde | 2-Methoxybenzylamine | Hydrogen | 534 | 535 | Y | 1.85 | 20.35 |
| 47 | (R)-2,6-Diaminohexanoic acid | 4-Biphenylcarboxaldehyde | 2-Methoxybenzylamine | Phenylacetic acid | 638 | 639 | Y | 8.81 | 18.12 |
| 48 | (R)-2,6-Diaminohexanoic acid | 4-Biphenylcarboxaldehyde | 2-Methoxybenzylamine | Glycine | 577 | 578 | Y | 4.24 | 28.82 |
| 49 | (R)-2,6-Diaminohexanoic acid | 4-Biphenylcarboxaldehyde | 2-Methoxybenzylamine | Boc-Gly | 591 | 592 | Y | 1.70 | 19.03 |
| 50 | (R)-2,6-Diaminohexanoic acid | 4-Biphenylcarboxaldehyde | Cyclohexylamine | Boc | 524 | 525 | Y | 1.55 | 13.30 |
| 51 | (R)-2,6-Diaminohexanoic acid | 4-Biphenylcarboxaldehyde | Cyclohexylamine | Hydrogen | 510 | 511 | Y | 3.19 | 29.34 |
| 52 | (R)-2,6-Diaminohexanoic acid | 4-Biphenylcarboxaldehyde | Cyclohexylamine | Phenylacetic acid | 614 | 615 | Y | 3.69 | 12.29 |
| 53 | (R)-2,6-Diaminohexanoic acid | 4-Biphenylcarboxaldehyde | Cyclohexylamine | Glycine | 553 | 554 | Y | 1.00 | 14.78 |
| 54 | (R)-2,6-Diaminohexanoic acid | 4-Biphenylcarboxaldehyde | Cyclohexylamine | Boc-Gly | 567 | 568 | Y | 0.61 | 26.78 |
| 55 | (R)-2,6-Diaminohexanoic acid | 4-Acetamidobenzaldehyde | 2-Methoxybenzylamine | Boc | 501 | 502 | Y | 0.89 | 27.89 |
| 56 | (S)-2,5-Diaminopentanoic acid | 4-Acetamidobenzaldehyde | 2-Methoxybenzylamine | Hydrogen | 487 | 488 | Y | 0.71 | 38.21 |
| 57 | (S)-2,5-Diaminopentanoic acid | 4-Acetamidobenzaldehyde | 2-Methoxybenzylamine | Phenylacetic acid | 591 | 592 | Y | 0.28 | 6.02 |
| 58 | (S)-2,5-Diaminopentanoic acid | 4-Acetamidobenzaldehyde | 2-Methoxybenzylamine | Glycine | 530 | 531 | Y | 1.44 | 16.39 |
| 59 | (S)-2,5-Diaminopentanoic acid | 4-Acetamidobenzaldehyde | 2-Methoxybenzylamine | Boc-Gly | 544 | 545 | Y | 0.91 | 13.38 |
| 60 | (S)-2,5-Diaminopentanoic acid | 4-Acetamidobenzaldehyde | Cyclohexylamine | Boc | 477 | 478 | Y | 0.69 | 20.70 |
| 61 | (S)-2,5-Diaminopentanoic acid | 4-Acetamidobenzaldehyde | Cyclohexylamine | Hydrogen | 463 | 464 | Y | 0.69 | 35.18 |
| 62 | (S)-2,5-Diaminopentanoic acid | 4-Acetamidobenzaldehyde | Cyclohexylamine | Phenylacetic acid | 567 | 568 | Y | 0.12 | 2.61 |
| 63 | (S)-2,5-Diaminopentanoic acid | 4-Acetamidobenzaldehyde | Cyclohexylamine | Glycine | 506 | 507 | Y | 0.69 | 18.74 |
| 64 | (S)-2,5-Diaminopentanoic acid | 4-Acetamidobenzaldehyde | Cyclohexylamine | Boc-Gly | 520 | 521 | Y | 2.67 | 24.97 |
| 65 | (S)-2,5-Diaminopentanoic acid | 2,4-Dichlorobenzaldehyde | 2-Methoxybenzylamine | Boc | 526 | 527 | Y | 2.07 | 4.36 |
| 66 | (S)-2,5-Diaminopentanoic acid | 2,4-Dichlorobenzaldehyde | 2-Methoxybenzylamine | Hydrogen | 512 | 513 | Y | 2.21 | 9.44 |
| 67 | (S)-2,5-Diaminopentanoic acid | 2,4-Dichlorobenzaldehyde | 2-Methoxybenzylamine | Phenylacetic acid | 616 | 617 | Y | 4.66 | 13.28 |
| 68 | (S)-2,5-Diaminopentanoic acid | 2,4-Dichlorobenzaldehyde | 2-Methoxybenzylamine | Glycine | 555 | 556 | Y | 1.66 | 4.51 |
| 69 | (S)-2,5-Diaminopentanoic acid | 2,4-Dichlorobenzaldehyde | 2-Methoxybenzylamine | Boc-Gly | 569 | 570 | Y | 1.66 | 3.88 |
| 70 | (S)-2,5-Diaminopentanoic acid | 2,4-Dichlorobenzaldehyde | Cyclohexylamine | Boc | 502 | 503 | Y | 1.46 | 2.50 |
| 71 | (S)-2,5-Diaminopentanoic acid | 2,4-Dichlorobenzaldehyde | Cyclohexylamine | Hydrogen | 488 | 489 | Y | 1.19 | 3.03 |
| 72 | (S)-2,5-Diaminopentanoic acid | 2,4-Dichlorobenzaldehyde | Cyclohexylamine | Phenylacetic acid | 592 | 593 | Y | 1.94 | 5.87 |
| 73 | (S)-2,5-Diaminopentanoic acid | 2,4-Dichlorobenzaldehyde | Cyclohexylamine | Glycine | 531 | 532 | Y | 1.08 | 4.05 |
| 74 | (S)-2,5-Diaminopentanoic acid | 2,4-Dichlorobenzaldehyde | Cyclohexylamine | Boc-Gly | 545 | 546 | Y | 1.56 | 4.28 |
| 75 | (S)-2,5-Diaminopentanoic acid | 4-Biphenylcarboxaldehyde | 2-Methoxybenzylamine | Boc | 534 | 535 | Y | 3.58 | 11.17 |
| 76 | (S)-2,5-Diaminopentanoic acid | 4-Biphenylcarboxaldehyde | 2-Methoxybenzylamine | Hydrogen | 520 | 521 | Y | 2.54 | 12.51 |
| 77 | (S)-2,5-Diaminopentanoic acid | 4-Biphenylcarboxaldehyde | 2-Methoxybenzylamine | Phenylacetic acid | 624 | 625 | Y | 8.22 | 27.59 |

TABLE 1-continued

| Cpd # | R1: Amino Acids | R8 = Boc R2: Aldehydes | R3: amines | R5: Substit. on R2 NH2 | M.W. | obs.(M + 1) M.W. | >85% LCQ | MC-1 IC50 uM | MC-4 IC50 uM |
|---|---|---|---|---|---|---|---|---|---|
| 78 | (S)-2,5-Diaminopentanoic acid | 4-Biphenylcarboxaldehyde | 2-Methoxybenzylamine | Glycine | 563 | 564 | Y | 1.33 | 17.75 |
| 79 | (S)-2,5-Diaminopentanoic acid | 4-Biphenylcarboxaldehyde | 2-Methoxybenzylamine | Boc-Gly | 577 | 578 | Y | 2.38 | 20.22 |
| 80 | (S)-2,5-Diaminopentanoic acid | 4-Biphenylcarboxaldehyde | Cyclohexylamine | Boc | 510 | 511 | Y | 2.18 | 12.24 |
| 81 | (S)-2,5-Diaminopentanoic acid | 4-Biphenylcarboxaldehyde | Cyclohexylamine | Hydrogen | 496 | 497 | Y | 4.41 | 18.03 |
| 82 | (S)-2,5-Diaminopentanoic acid | 4-Biphenylcarboxaldehyde | Cyclohexylamine | Phenylacetic acid | 600 | 601 | Y | 10.19 | 16.44 |
| 83 | (S)-2,5-Diaminopentanoic acid | 4-Biphenylcarboxaldehyde | Cyclohexylamine | Glycine | 539 | 540 | Y | 1.77 | 11.08 |
| 84 | (S)-2,5-Diaminopentanoic acid | 4-Biphenylcarboxaldehyde | Cyclohexylamine | Boc-Gly | 553 | 554 | Y | 2.50 | 15.36 |
| 85 | (S)-2,4-Diaminobutanoic acid | 4-Acetamidobenzaldehyde | 2-Methoxybenzylamine | Boc | 487 | 488 | Y | 3.08 | 21.26 |
| 86 | (S)-2,4-Diaminobutanoic acid | 4-Acetamidobenzaldehyde | 2-Methoxybenzylamine | Hydrogen | 473 | 474 | Y | 3.31 | 15.94 |
| 87 | (S)-2,4-Diaminobutanoic acid | 4-Acetamidobenzaldehyde | 2-Methoxybenzylamine | Phenylacetic acid | 577 | 578 | Y | 3.27 | 7.07 |
| 88 | (S)-2,4-Diaminobutanoic acid | 4-Acetamidobenzaldehyde | 2-Methoxybenzylamine | Glycine | 516 | 517 | Y | 2.76 | 23.26 |
| 89 | (S)-2,4-Diaminobutanoic acid | 4-Acetamidobenzaldehyde | 2-Methoxybenzylamine | Boc-Gly | 530 | 531 | Y | 1.82 | 21.73 |
| 90 | (S)-2,4-Diaminobutanoic acid | 4-Acetamidobenzaldehyde | Cyclohexylamine | Boc | 463 | 464 | Y | 5.90 | 25.19 |
| 91 | (S)-2,4-Diaminobutanoic acid | 4-Acetamidobenzaldehyde | Cyclohexylamine | Hydrogen | 449 | 450 | Y | 9.94 | 28.06 |
| 92 | (S)-2,4-Diaminobutanoic acid | 4-Acetamidobenzaldehyde | Cyclohexylamine | Phenylacetic acid | 553 | 554 | Y | 4.51 | 1.54 |
| 93 | (S)-2,4-Diaminobutanoic acid | 4-Acetamidobenzaldehyde | Cyclohexylamine | Glycine | 492 | 493 | Y | 4.01 | 36.28 |
| 94 | (S)-2,4-Diaminobutanoic acid | 4-Acetamidobenzaldehyde | Cyclohexylamine | Boc-Gly | 506 | 507 | Y | 3.89 | 27.08 |
| 95 | (S)-2,4-Diaminobutanoic acid | 2,4-Dichlorobenzaldehyde | 2-Methoxybenzylamine | Boc | 512 | 513 | Y | 5.09 | 7.85 |
| 96 | (S)-2,4-Diaminobutanoic acid | 2,4-Dichlorobenzaldehyde | 2-Methoxybenzylamine | Hydrogen | 498 | 499 | Y | 6.33 | 8.72 |
| 97 | (S)-2,4-Diaminobutanoic acid | 2,4-Dichlorobenzaldehyde | 2-Methoxybenzylamine | Phenylacetic acid | 602 | 603 | Y | 9.06 | 6.90 |
| 98 | (S)-2,4-Diaminobutanoic acid | 2,4-Dichlorobenzaldehyde | 2-Methoxybenzylamine | Glycine | 541 | 542 | Y | 3.71 | 8.04 |
| 99 | (S)-2,4-Diaminobutanoic acid | 2,4-Dichlorobenzaldehyde | 2-Methoxybenzylamine | Boc-Gly | 555 | 556 | Y | 3.87 | 6.47 |
| 100 | (S)-2,4-Diaminobutanoic acid | 2,4-Dichlorobenzaldehyde | Cyclohexylamine | Boc | 488 | 489 | Y | 6.98 | 6.10 |
| 101 | (S)-2,4-Diaminobutanoic acid | 2,4-Dichlorobenzaldehyde | Cyclohexylamine | Hydrogen | 474 | 475 | Y | 7.89 | 5.68 |
| 102 | (S)-2,4-Diaminobutanoic acid | 2,4-Dichlorobenzaldehyde | Cyclohexylamine | Phenylacetic acid | 578 | 579 | Y | 7.05 | 1.88 |
| 103 | (S)-2,4-Diaminobutanoic acid | 2,4-Dichlorobenzaldehyde | Cyclohexylamine | Glycine | 517 | 518 | Y | 5.41 | 8.80 |
| 104 | (S)-2,4-Diaminobutanoic acid | 2,4-Dichlorobenzaldehyde | Cyclohexylamine | Boc-Gly | 531 | 532 | Y | 5.65 | 9.06 |
| 105 | (S)-2,4-Diaminobutanoic acid | 4-Biphenylcarboxaldehyde | 2-Methoxybenzylamine | Boc | 520 | 521 | Y | 6.72 | 10.84 |
| 106 | (S)-2,4-Diaminobutanoic acid | 4-Biphenylcarboxaldehyde | 2-Methoxybenzylamine | Hydrogen | 506 | 507 | Y | 6.70 | 14.92 |
| 107 | (S)-2,4-Diaminobutanoic acid | 4-Biphenylcarboxaldehyde | 2-Methoxybenzylamine | Phenylacetic acid | 610 | 611 | Y | 14.68 | 16.40 |
| 108 | (S)-2,4-Diaminobutanoic acid | 4-Biphenylcarboxaldehyde | 2-Methoxybenzylamine | Glycine | 549 | 550 | Y | 4.61 | 17.54 |
| 109 | (S)-2,4-Diaminobutanoic acid | 4-Biphenylcarboxaldehyde | 2-Methoxybenzylamine | Boc-Gly | 563 | 564 | Y | 4.75 | 9.73 |
| 110 | (S)-2,4-Diaminobutanoic acid | 4-Biphenylcarboxaldehyde | Cyclohexylamine | Boc | 496 | 497 | Y | 5.37 | 9.01 |
| 111 | (S)-2,4-Diaminobutanoic acid | 4-Biphenylcarboxaldehyde | Cyclohexylamine | Hydrogen | 482 | 483 | Y | 7.52 | 12.02 |
| 112 | (S)-2,4-Diaminobutanoic acid | 4-Biphenylcarboxaldehyde | Cyclohexylamine | Phenylacetic acid | 586 | 587 | Y | 8.79 | 10.36 |
| 113 | (S)-2,4-Diaminobutanoic acid | 4-Biphenylcarboxaldehyde | Cyclohexylamine | Glycine | 525 | 526 | Y | 3.78 | 12.67 |
| 114 | (S)-2,4-Diaminobutanoic acid | 4-Biphenylcarboxaldehyde | Cyclohexylamine | Boc-Gly | 539 | 540 | Y | 3.24 | 10.52 |

TRG 2409

| 1 | (S)-2,6-Diaminohexanoic acid | 4-nitrobenzaldehyde | 2-Methoxybenzylamine | Benzoic acid | 577 | 578 | Y | 0.54 | 10.47 |
| 2 | (S)-2,6-Diaminohexanoic acid | 4-nitrobenzaldehyde | 2-Methoxybenzylamine | Butyric acid | 543 | 544 | Y | 0.22 | 10.69 |
| 3 | (S)-2,6-Diaminohexanoic acid | 4-nitrobenzaldehyde | 2-Methoxybenzylamine | Cyclohexane carboxylic acid | 583 | 584 | Y | 2.47 | 15.28 |
| 4 | (S)-2,6-Diaminohexanoic acid | 4-nitrobenzaldehyde | 2-Methoxybenzylamine | Isobutyric acid | 543 | 544 | Y | 0.68 | 15.82 |
| 5 | (S)-2,6-Diaminohexanoic acid | 4-nitrobenzaldehyde | 2-Methoxybenzylamine | Methoxyacetic acid | 545 | 546 | Y | 1.15 | 18.35 |
| 6 | (S)-2,6-Diaminohexanoic acid | 4-nitrobenzaldehyde | 2-Methoxybenzylamine | p-anisic acid | 607 | 608 | Y | 4.00 | 13.37 |
| 7 | (S)-2,6-Diaminohexanoic acid | 4-nitrobenzaldehyde | 2-Methoxybenzylamine | Phenylacetic acid | 591 | 592 | Y | 1.03 | 9.81 |
| 8 | (S)-2,6-Diaminohexanoic acid | 4-nitrobenzaldehyde | 2-Methoxybenzylamine | Propionic acid | 529 | 530 | Y | 0.64 | 12.59 |
| 9 | (S)-2,6-Diaminohexanoic acid | 4-nitrobenzaldehyde | 2-Methoxybenzylamine | 4-Methoxyphenylacetic acid | 621 | 622 | Y | 1.70 | 20.99 |

TABLE 1-continued

| Cpd # | R1: Amino Acid | R2: Aldehyde | R3: amine | R8: Substit. on R1 a-NH2 | M.W. | obs.(M + 1) M.W. | >85% LCQ | MC-1 IC50 uM | MC-4 IC50 uM |
|---|---|---|---|---|---|---|---|---|---|
| 10 | (S)-2,6-Diaminohexanoic acid | 4-nitrobenzaldehyde | 2-Methoxybenzylamine | 2-Norbornaneacetic acid | 609 | 610 | Y | 2.60 | 20.72 |
| 11 | (S)-2,6-Diaminohexanoic acid | 4-nitrobenzaldehyde | 2-Methoxybenzylamine | 3,4-Dichlorophenylacetic acid | 660 | 661 | Y | 9.82 | 49.83 |
| 12 | (S)-2,6-Diaminohexanoic acid | 4-nitrobenzaldehyde | 2-Methoxybenzylamine | 4-Chlorobenzoic acid | 611 | 612 | Y | 5.04 | 22.86 |
| 13 | (S)-2,6-Diaminohexanoic acid | 4-nitrobenzaldehyde | Cyclohexylamine | Benzoic acid | 553 | 554 | Y | 1.46 | 17.41 |
| 14 | (S)-2,6-Diaminohexanoic acid | 4-nitrobenzaldehyde | Cyclohexylamine | Butyric acid | 519 | 520 | Y | 0.10 | 15.09 |
| 15 | (S)-2,6-Diaminohexanoic acid | 4-nitrobenzaldehyde | Cyclohexylamine | Cyclohexane carboxylic acid | 559 | 560 | Y | 1.65 | 16.22 |
| 16 | (S)-2,6-Diaminohexanoic acid | 4-nitrobenzaldehyde | Cyclohexylamine | Isobutyric acid | 519 | 520 | Y | 0.95 | 20.96 |
| 17 | (S)-2,6-Diaminohexanoic acid | 4-nitrobenzaldehyde | Cyclohexylamine | Methoxyacetic acid | 521 | 522 | Y | 2.72 | 27.50 |
| 18 | (S)-2,6-Diaminohexanoic acid | 4-nitrobenzaldehyde | Cyclohexylamine | p-anisic acid | 583 | 584 | Y | 7.51 | 16.88 |
| 19 | (S)-2,6-Diaminohexanoic acid | 4-nitrobenzaldehyde | Cyclohexylamine | Phenylacetic acid | 567 | 568 | Y | 2.08 | 15.50 |
| 20 | (S)-2,6-Diaminohexanoic acid | 4-nitrobenzaldehyde | Cyclohexylamine | Propionic acid | 505 | 506 | Y | 0.88 | 19.80 |
| 21 | (S)-2,6-Diaminohexanoic acid | 4-nitrobenzaldehyde | Cyclohexylamine | 4-Methoxyphenylacetic acid | 597 | 598 | Y | 2.63 | 14.70 |
| 22 | (S)-2,6-Diaminohexanoic acid | 4-nitrobenzaldehyde | Cyclohexylamine | 2-Norbornaneacetic acid | 585 | 586 | Y | 1.53 | 12.32 |
| 23 | (S)-2,6-Diaminohexanoic acid | 4-nitrobenzaldehyde | Cyclohexylamine | 3,4-Dichlorophenylacetic acid | 636 | 637 | Y | 4.77 | 19.59 |
| 24 | (S)-2,6-Diaminohexanoic acid | 4-nitrobenzaldehyde | Cyclohexylamine | 4-Chlorobenzoic acid | 587 | 588 | Y | 3.95 | 12.15 |
| 221 | (S)-2,5-Diaminopentanoic acid | 4-Butyramidobenzaldehyde | Ammonia | Phenylacetic acid | 513 | 514 | Y | 0.08 | 0.85 |
| 222 | (S)-2,5-Diaminopentanoic acid | 4-Butyramidobenzaldehyde | Ammonia | 4-Bromophenylacetic acid | 591 | 592 | Y | 0.12 | |
| 223 | (S)-2,5-Diaminopentanoic acid | 4-Butyramidobenzaldehyde | Ammonia | 4-Methoxyphenylacetic acid | 543 | 544 | Y | 0.10 | 0.63 |
| 224 | (S)-2,5-Diaminopentanoic acid | 4-Butyramidobenzaldehyde | Ammonia | Benzoic acid | 499 | 500 | Y | 0.12 | 1.32 |
| 225 | (S)-2,5-Diaminopentanoic acid | 4-Butyramidobenzaldehyde | Ammonia | 4-Chlorobenzoic acid | 533 | 534 | Y | 0.12 | 1.12 |
| 226 | (S)-2,5-Diaminopentanoic acid | 4-Butyramidobenzaldehyde | Ammonia | 4-Methoxybenzoic acid | 529 | 530 | Y | 0.10 | |
| 227 | (S)-2,5-Diaminopentanoic acid | 4-Butyramidobenzaldehyde | Ammonia | 2-Naphthylacetic acid | 563 | 564 | Y | 0.17 | |
| 228 | (S)-2,5-Diaminopentanoic acid | 4-Butyramidobenzaldehyde | Ammonia | Cyclohexylacetic acid | 519 | 520 | Y | | |
| 229 | (S)-2,6-Diaminohexanoic acid | 4-Butyramidobenzaldehyde | Cyclohexylamine | Glycine | 452 | 453 | Y | 0.23 | |

TRG 2411

| 1 | (S)-2,6-Diaminohexanoic acid | 4-Biphenylcarboxaldehyde | Phenethylamine | Hydrogen | 532 | 533 | Y | 0.60 | 1.22 |
| 2 | (S)-2,6-Diaminohexanoic acid | 4-Biphenylcarboxaldehyde | Phenethylamine | Acetic acid | 560 | 561 | Y | 0.55 | |
| 3 | (S)-2,6-Diaminohexanoic acid | 4-Biphenylcarboxaldehyde | Phenethylamine | Phenylacetic acid | 636 | 637 | Y | 0.88 | |
| 4 | (S)-2,6-Diaminohexanoic acid | 4-Biphenylcarboxaldehyde | Phenethylamine | Boc-Gly | 589 | 590 | Y | 0.70 | |
| 5 | (S)-2,6-Diaminohexanoic acid | 4-Biphenylcarboxaldehyde | Phenethylamine | Gly | 575 | 576 | Y | 0.79 | |
| 6 | (S)-2,6-Diaminohexanoic acid | 4-Biphenylcarboxaldehyde | Phenethylamine | Boc-Ala | 603 | 604 | Y | 0.47 | |
| 7 | (S)-2,6-Diaminohexanoic acid | 4-Biphenylcarboxaldehyde | Phenethylamine | Hydroxy Acetic acid | 576 | 577 | Y | 0.63 | |
| 8 | (S)-2,6-Diaminohexanoic acid | 4-Biphenylcarboxaldehyde | Phenethylamine | Boc-Phe | 679 | 680 | Y | 0.76 | |
| 9 | (S)-2,6-Diaminohexanoic acid | 4-Biphenylcarboxaldehyde | Phenethylamine | Succinic anhydride | 586 | 646 | Y | 0.13 | 1.27 |
| 10 | (S)-2,6-Diaminohexanoic acid | 4-Biphenylcarboxaldehyde | Phenethylamine | Methoxyacetic acid | 590 | 591 | Y | 1.10 | |
| 11 | (S)-2,6-Diaminohexanoic acid | 4-Biphenylcarboxaldehyde | Phenethylamine | Butyric acid | 588 | 589 | Y | 0.83 | 1.80 |
| 12 | (S)-2,6-Diaminohexanoic acid | 4-Biphenylcarboxaldehyde | Phenethylamine | Cyclohexanecarboxylic acid | 628 | 629 | Y | 0.73 | |
| 13 | (S)-2,6-Diaminohexanoic acid | 4-Biphenylcarboxaldehyde | Phenethylamine | Benzoic acid | 622 | 623 | Y | 1.36 | |
| 14 | (S)-2,6-Diaminohexanoic acid | 4-Biphenylcarboxaldehyde | Cyclohexylamine | Acetic acid | 538 | 539 | Y | 0.46 | |

TABLE 1-continued

| | | | | | | | |
|---|---|---|---|---|---|---|---|
| 15 | (S)-2,6-Diaminohexanoic acid | 4-Biphenylcarboxaldehyde | Cyclohexylamine | Boc-Ala | 581 | 582 | Y | 0.73 |
| 16 | (S)-2,6-Diaminohexanoic acid | 4-Biphenylcarboxaldehyde | Cyclohexylamine | Hydroxy Acetic acid | 554 | 555 | Y | 0.90 |
| 17 | (S)-2,6-Diaminohexanoic acid | 4-Biphenylcarboxaldehyde | Cyclohexylamine | Boc-Phe | 657 | 658 | Y | 0.39 |
| 18 | (S)-2,6-Diaminohexanoic acid | 4-Biphenylcarboxaldehyde | Cyclohexylamine | Succinic anhydride | 564 | 624 | Y | 0.08 |
| 19 | (S)-2,6-Diaminohexanoic acid | 4-Biphenylcarboxaldehyde | Cyclohexylamine | Methoxyacetic acid | 568 | 569 | Y | 0.49 |
| 20 | (S)-2,6-Diaminohexanoic acid | 4-Biphenylcarboxaldehyde | Cyclohexylamine | Butyric acid | 566 | 567 | Y | 0.61 | 0.77 |
| 21 | (S)-2,6-Diaminohexanoic acid | 4-Biphenylcarboxaldehyde | Cyclohexylamine | Cyclohexanecarboxylic acid | 606 | 607 | Y | 0.27 | 1.01 |
| 22 | (S)-2,6-Diaminohexanoic acid | 4-Biphenylcarboxaldehyde | Cyclohexylamine | Benzoic acid | 600 | 601 | Y | 0.42 | 1.73 |
| 23 | (S)-2,6-Diaminohexanoic acid | 4-Biphenylcarboxaldehyde | Ammonia | Hydrogen | 428 | 429 | Y | 0.59 | |
| 24 | (S)-2,6-Diaminohexanoic acid | 4-Biphenylcarboxaldehyde | Ammonia | Acetic acid | 456 | 457 | Y | 0.53 | |
| 25 | (S)-2,6-Diaminohexanoic acid | 4-Biphenylcarboxaldehyde | Ammonia | Phenylacetic acid | 532 | 533 | Y | 0.35 | |
| 26 | (S)-2,6-Diaminohexanoic acid | 4-Biphenylcarboxaldehyde | Ammonia | Boc-Gly | 485 | 486 | Y | 0.09 | 6.17 |
| 27 | (S)-2,6-Diaminohexanoic acid | 4-Biphenylcarboxaldehyde | Ammonia | Gly | 471 | 472 | Y | 0.66 | |
| 28 | (S)-2,6-Diaminohexanoic acid | 4-Biphenylcarboxaldehyde | Ammonia | Boc-Ala | 499 | 500 | Y | 0.56 | 1.23 |
| 29 | (S)-2,6-Diaminohexanoic acid | 4-Biphenylcarboxaldehyde | Ammonia | Hydroxy Acetic acid | 472 | 473 | Y | 0.30 | 1.42 |
| 30 | (S)-2,6-Diaminohexanoic acid | 4-Biphenylcarboxaldehyde | Ammonia | Boc-Phe | 575 | 576 | Y | 0.97 | 1.33 |
| 31 | (S)-2,6-Diaminohexanoic acid | 4-Biphenylcarboxaldehyde | Ammonia | Succinic anhydride | 482 | 542 | Y | 0.55 | |
| 32 | (S)-2,6-Diaminohexanoic acid | 4-Biphenylcarboxaldehyde | Ammonia | Methoxyacetic acid | 486 | 487 | Y | 0.39 | |
| 33 | (S)-2,6-Diaminohexanoic acid | 4-Biphenylcarboxaldehyde | Ammonia | Butyric acid | 484 | 485 | Y | 0.35 | 1.73 |
| 34 | (S)-2,6-Diaminohexanoic acid | 4-Biphenylcarboxaldehyde | Ammonia | Cyclohexanecarboxylic acid | 524 | 525 | Y | 0.51 | |
| 35 | (S)-2,6-Diaminohexanoic acid | 4-Biphenylcarboxaldehyde | Ammonia | Benzoic acid | 518 | 519 | Y | 0.13 | |
| 36 | (S)-2,6-Diaminohexanoic acid | 4-Biphenylcarboxaldehyde | Phenethylamine | Hydrogen | 499 | 500 | Y | 0.13 | |
| 37 | (S)-2,6-Diaminohexanoic acid | 4-Biphenylcarboxaldehyde | Phenethylamine | Acetic acid | 527 | 528 | Y | 0.09 | 1.33 |
| 38 | (S)-2,6-Diaminohexanoic acid | 4-Acetamidobenzaldehyde | Phenethylamine | Butyric acid | 555 | 556 | Y | 0.03 | |
| 39 | (S)-2,6-Diaminohexanoic acid | 4-Acetamidobenzaldehyde | Phenethylamine | Succinic anhydride | 553 | 59 | Y | 0.19 | 1.00 |
| 40 | (S)-2,6-Diaminohexanoic acid | 4-Acetamidobenzaldehyde | Phenethylamine | Phenylacetic acid | 603 | 604 | Y | 0.49 | 1.64 |
| 41 | (S)-2,6-Diaminohexanoic acid | 4-Acetamidobenzaldehyde | Phenethylamine | 4-Bromophenylacetic acid | 681 | 682 | Y | 0.32 | 1.56 |
| 42 | (S)-2,6-Diaminohexanoic acid | 4-Acetamidobenzaldehyde | Phenethylamine | 4-Methoxyphenylacetic acid | 633 | 634 | Y | 0.19 | 1.03 |
| 43 | (S)-2,6-Diaminohexanoic acid | 4-Acetamidobenzaldehyde | Phenethylamine | Benzoic acid | 589 | 590 | Y | 0.16 | 1.04 |
| 44 | (S)-2,6-Diaminohexanoic acid | 4-Acetamidobenzaldehyde | Phenethylamine | 4-Chlorobenzoic acid | 619 | 620 | Y | 0.12 | 0.84 |
| 45 | (S)-2,6-Diaminohexanoic acid | 4-Acetamidobenzaldehyde | Phenethylamine | 4-Methoxybenzoic acid | 623 | 624 | Y | 0.89 | 1.33 |
| 46 | (S)-2,6-Diaminohexanoic acid | 4-Acetamidobenzaldehyde | Phenethylamine | 2-Naphthylacetic acid | 653 | 654 | Y | 0.22 | |
| 47 | (S)-2,6-Diaminohexanoic acid | 4-Acetamidobenzaldehyde | Phenethylamine | Cyclohexylacetic acid | 609 | 610 | Y | 0.30 | |
| 48 | (S)-2,6-Diaminohexanoic acid | 4-Acetamidobenzaldehyde | Phenethylamine | Glycine | 542 | 543 | Y | 0.22 | |
| 49 | (S)-2,6-Diaminohexanoic acid | 4-Acetamidobenzaldehyde | Cyclohexylamine | Acetic acid | 505 | 506 | Y | 0.08 | |
| 50 | (S)-2,6-Diaminohexanoic acid | 4-Acetamidobenzaldehyde | Cyclohexylamine | Butyric acid | 533 | 534 | Y | | |
| 51 | (S)-2,6-Diaminohexanoic acid | 4-Acetamidobenzaldehyde | Cyclohexylamine | Succinic anhydride | 531 | 591 | Y | | |
| 52 | (S)-2,6-Diaminohexanoic acid | 4-Acetamidobenzaldehyde | Cyclohexylamine | 4-Bromophenylacetic acid | 659 | 660 | Y | 0.55 | 0.86 |
| 53 | (S)-2,6-Diaminohexanoic acid | 4-Acetamidobenzaldehyde | Cyclohexylamine | 4-Methoxyphenylacetic acid | 611 | 612 | Y | 0.28 | 1.65 |
| 54 | (S)-2,6-Diaminohexenoic acid | 4-Acetamidobenzeldehyde | Cyclohexylamine | Benzoic acid | 567 | 568 | Y | 0.13 | 1.79 |
| 55 | (S)-2,6-Diaminohexanoic acid | 4-Acetemidobenzaldehyde | Cyclohexylamine | 4-Chlorobenzoic acid | 601 | 602 | Y | 0.09 | 2.05 |
| 56 | (S)-2,6-Diaminohexanoic acid | 4-Acetamidobenzaldehyde | Cyclohexylamine | 4-Methoxybenzoic acid | 597 | 598 | Y | 0.13 | |
| 57 | (S)-2,6-Diaminohexanoic acid | 4-Acetamidobenzaldehyde | Cyclohexylamine | 2-Naphthylacetic acid | 631 | 632 | Y | 0.92 | 1.19 |
| 58 | (S)-2,6-Diaminohexanoic acid | 4-Acetamidobenzaldehyde | Cyclohexylamine | Cyclohexylacetic acid | 587 | 588 | Y | 0.22 | 1.11 |
| 59 | (S)-2,6-Diaminohexanoic acid | 4-Acetamidobenzaldehyde | Ammonia | Hydrogen | 395 | 396 | Y | 0.37 | |
| 60 | (S)-2,6-Diaminohexanoic acid | 4-Acetamidobenzaldehyde | Ammonia | Acetic acid | 423 | 424 | Y | 0.05 | |
| 61 | (S)-2,6-Diaminohexanoic acid | 4-Acetamidobenzaldehyde | Ammonia | Butyric acid | 451 | 452 | Y | 0.11 | |
| 62 | (S)-2,6-Diaminohexanoic acid | 4-Acetamidobenzaldehyde | Ammonia | Succinic anhydride | 449 | 509 | Y | | |
| 63 | (S)-2,6-Diaminohexanoic acid | 4-Acetamidobenzaldehyde | Ammonia | Phenylacetic acid | 499 | 500 | Y | 0.24 | 1.82 |
| 64 | (S)-2,6-Diaminohexanoic acid | 4-Acetamidobenzaldehyde | Ammonia | 4-Bromophenylacetic acid | 577 | 578 | Y | 0.48 | |
| 65 | (S)-2,6-Diaminohexanoic acid | 4-Acetamidobenzaldehyde | Ammonia | 4-Methoxyphenylacetic acid | 529 | 530 | Y | 0.39 | |
| 66 | (S)-2,6-Diaminohexanoic acid | 4-Acetamidobenzaldehyde | Ammonia | Benzoic acid | 485 | 486 | Y | 0.11 | |

TABLE 1-continued

| | | | | | | |
|---|---|---|---|---|---|---|
| 67 | (S)-2,6-Diaminohexanoic acid | 4-Acetamidobenzaldehyde | Ammonia | 4-Chlorobenzoic acid | 519 | 520 | Y | 0.21 | |
| 68 | (S)-2,6-Diaminohexanoic acid | 4-Acetamidobenzaldehyde | Ammonia | 4-Methoxybenzoic acid | 515 | 516 | Y | 0.12 | |
| 69 | (S)-2,6-Diaminohexanoic acid | 4-Acetamidobenzaldehyde | Ammonia | 2-Naphthylacetic acid | 549 | 550 | Y | 0.37 | |
| 70 | (S)-2,6-Diaminohexanoic acid | 4-Acetamidobenzaldehyde | Ammonia | Cyclohexylacetic acid | 505 | 506 | Y | 0.16 | |
| 71 | (S)-2,6-Diaminohexanoic acid | 4-Acetamidobenzaldehyde | Ammonia | Glycine | 438 | 439 | Y | 0.39 | |
| 72 | (S)-2,6-Diaminohexanoic acid | 4-Acetamidobenzaldehyde | Phenethylamine | Hydrogen | 527 | 528 | Y | 0.25 | |
| 73 | (S)-2,6-Diaminohexanoic acid | 4-Acetamidobenzaldehyde | Phenethylamine | Boc | 541 | 542 | Y | 0.19 | |
| 74 | (S)-2,6-Diaminohexanoic acid | 4-Butyramidobenzaldehyde | Phenethylamine | Acetic acid | 555 | 556 | Y | 0.11 | 2.24 |
| 75 | (S)-2,6-Diaminohexanoic acid | 4-Butyramidobenzaldehyde | Phenethylamine | Butyric acid | 583 | 584 | Y | 0.13 | 1.05 |
| 76 | (S)-2,6-Diaminohexanoic acid | 4-Butyramidobenzaldehyde | Phenethylamine | Succinic anhydride | 581 | 641 | Y | | |
| 77 | (S)-2,6-Diaminohexanoic acid | 4-Butyramidobenzaldehyde | Phenethylamine | Phenylacetic acid | 631 | 632 | Y | 0.22 | 1.49 |
| 78 | (S)-2,6-Diaminohexanoic acid | 4-Butyramidobenzaldehyde | Phenethylamine | 4-Bromophenylacetic acid | 709 | 710 | Y | 0.45 | 1.32 |
| 79 | (S)-2,6-Diaminohexanoic acid | 4-Butyramidobenzaldehyde | Phenethylamine | 4-Methoxyphenylacetic acid | 661 | 662 | Y | 0.37 | |
| 80 | (S)-2,6-Diaminohexanoic acid | 4-Butyramidobenzaldehyde | Phenethylamine | Benzoic acid | 617 | 618 | Y | 0.17 | 1.83 |
| 81 | (S)-2,6-Diaminohexanoic acid | 4-Butyramidobenzaldehyde | Phenethylamine | 4-Chlorobenzoic acid | 651 | 652 | Y | 0.18 | 1.38 |
| 82 | (S)-2,6-Diaminohexanoic acid | 4-Butyramidobenzaldehyde | Phenethylamine | 4-Methoxybenzoic acid | 647 | 648 | Y | 0.29 | 1.46 |
| 83 | (S)-2,6-Diaminohexanoic acid | 4-Butyramidobenzaldehyde | Phenethylamine | 2-Naphthylacetic acid | 681 | 682 | Y | 0.57 | 1.06 |
| 84 | (S)-2,6-Diaminohexanoic acid | 4-Butyramidobenzaldehyde | Phenethylamine | Cyclohexylacetic acid | 637 | 638 | Y | 0.22 | 0.76 |
| 85 | (S)-2,6-Diaminohexanoic acid | 4-Butyramidobenzaldehyde | Phenethylamine | Glycine | 570 | 571 | Y | 0.31 | |
| 86 | (S)-2,6-Diaminohexanoic acid | 4-Butyramidobenzaldehyde | Cyclohexylamine | Hydrogen | 505 | 506 | Y | | |
| 87 | (S)-2,6-Diaminohexanoic acid | 4-Butyramidobenzaldehyde | Cyclohexylamine | Acetic acid | 533 | 534 | Y | 0.23 | 0.83 |
| 88 | (S)-2,6-Diaminohexanoic acid | 4-Butyramidobenzaldehyde | Cyclohexylamine | Butyric acid | 561 | 562 | Y | 0.24 | 1.50 |
| 89 | (S)-2,6-Diaminochexanoic acid | 4-Butyramidobenzaldehyde | Cyclohexylamine | Succinic anhydride | 559 | 619 | Y | 0.06 | |
| 90 | (S)-2,6-Diaminohexanoic acid | 4-Butyramidobenzaldehyde | Cyclohexylamine | Phenylacetic acid | 609 | 610 | Y | 0.25 | 1.17 |
| 91 | (S)-2,6-Diaminohexanoic acid | 4-Butyramidobenzaldehyde | Cyclohexylamine | 4-Bromophenylacetic acid | 687 | 688 | Y | 0.64 | |
| 92 | (S)-2,6-Diaminohexanoic acid | 4-Butyramidobenzaldehyde | Cyclohexylamine | 4-Methoxyphenylacetic acid | 639 | 640 | Y | 0.30 | |
| 93 | (S)-2,6-Diaminohexanoic acid | 4-Butyramidobenzaldehyde | Cyclohexylamine | Benzoic acid | 595 | 596 | Y | 0.13 | |
| 94 | (S)-2,6-Diaminohexanoic acid | 4-Butyramidobenzaldehyde | Cyclohexylamine | 4-Chlorobenzoic acid | 629 | 630 | Y | 0.09 | 1.71 |
| 95 | (S)-2,6-Diaminohexanoic acid | 4-Butyramidobenzaldehyde | Cyclohexylamine | 4-Methoxybenzoic acid | 625 | 626 | Y | 0.11 | 1.03 |
| 96 | (S)-2,6-Diaminohexanoic acid | 4-Butyramidobenzaldehyde | Cyclohexylamine | 2-Naphthylacetic acid | 659 | 660 | Y | 0.60 | 1.65 |
| 97 | (S)-2,6-Diaminohexanoic acid | 4-Butyramidobenzaldehyde | Cyclohexylamine | Cyclohexylacetic acid | 615 | 616 | Y | | |
| 98 | (S)-2,6-Diaminohexanoic acid | 4-Butyramidobenzaldehyde | Cyclohexylamine | Glycine | 548 | 549 | Y | | |
| 99 | (S)-2,6-Diaminohexanoic acid | 4-Butyramidobenzaldehyde | Ammonia | Hydrogen | 423 | 424 | Y | 0.27 | |
| 100 | (S)-2,6-Diaminohexanoic acid | 4-Butyramidobenzaldehyde | Ammonia | Boc | 437 | 438 | Y | 0.13 | |
| 101 | (S)-2,6-Diaminohexanoic acid | 4-Butyramidobenzaldehyde | Ammonia | Acetic acid | 451 | 452 | Y | 0.10 | |
| 102 | (S)-2,6-Diaminohexanoic acid | 4-Butyramidobenzaldehyde | Ammonia | Butyric acid | 479 | 480 | Y | 0.09 | 1.17 |
| 103 | (S)-2,6-Diaminohexanoic acid | 4-Butyramidobenzaldehyde | Ammonia | Succinic anhydride | 477 | 537 | Y | 0.02 | |
| 104 | (S)-2,6-Diaminohexanoic acid | 4-Butyramidobenzaldehyde | Ammonia | Phenylacetic acid | 527 | 528 | Y | 0.16 | 0.59 |
| 105 | (S)-2,6-Diaminohexanoic acid | 4-Butyramidobenzaldehyde | Ammonia | 4-Bromophenylacetic acid | 605 | 606 | Y | 0.21 | 0.91 |
| 106 | (S)-2,6-Diaminohexanoic acid | 4-Butyramidobenzaldehyde | Ammonia | 4-Methoxyphenylacetic acid | 557 | 558 | Y | 0.37 | |
| 107 | (S)-2,6-Diaminohexanoic acid | 4-Butyramidobenzaldehyde | Ammonia | Benzoic acid | 513 | 514 | Y | 0.34 | |
| 108 | (S)-2,6-Diaminohexanoic acid | 4-Butyramidobenzaldehyde | Ammonia | 4-Chlorobenzoic acid | 547 | 548 | Y | 0.16 | |
| 109 | (S)-2,6-Diaminohexanoic acid | 4-Butyramidobenzaldehyde | Ammonia | 4-Methoxybenzoic acid | 543 | 544 | Y | 0.10 | 1.40 |
| 110 | (S)-2,6-Diaminohexanoic acid | 4-Butyramidobenzaldehyde | Ammonia | 2-Naphthylacetic acid | 577 | 578 | Y | 0.10 | 1.05 |
| 111 | (S)-2,6-Diaminohexanoic acid | 4-Butyramidobenzaldehyde | Ammonia | Cyclohexylamine acid | 533 | 534 | Y | 0.04 | 1.47 |
| 112 | (S)-2,6-Diaminohexanoic acid | 4-Butyramidobenzaldehyde | Ammonia | Glycine | 466 | 467 | Y | 0.20 | 1.45 |
| 113 | (S)-2,5-Diaminopentanoic acid | 4-Biphenylcarboxaldehyde | Phenethylamine | Hydrogen | 518 | 519 | Y | 0.50 | |
| 114 | (S)-2,5-Diaminopentanoic acid | 4-Biphenylcarboxaldehyde | Phenethylamine | Boc | 532 | 533 | Y | 0.76 | |
| 115 | (S)-2,5-Diaminopentanoic acid | 4-Biphenylcarboxaldehyde | Phenethylamine | Acetic acid | 546 | 547 | Y | 0.82 | 1.43 |
| 116 | (S)-2,5-Diaminopentanoic acid | 4-Biphenylcarboxaldehyde | Phenethylamine | Phenylacetic acid | 622 | 623 | Y | 1.24 | 1.98 |
| 117 | (S)-2,5-Diaminopentanoic acid | 4-Biphenylcarboxaldehyde | Phenethylamine | Boc-Gly | 575 | 576 | Y | 0.97 | |
| 118 | (S)-2,5-Diaminopentanoic acid | 4-Biphenylcarboxaldehyde | Phenethylamine | Gly | 561 | 562 | Y | 0.35 | |

TABLE 1-continued

| # | | | | | | |
|---|---|---|---|---|---|---|
| 119 | (S)-2,5-Diaminopentanoic acid | 4-Biphenylcarboxaldehyde | Phenethylamine | Boc-Ala | 589 | 590 | Y | 0.37 |
| 120 | (S)-2,5-Diaminopentanoic acid | 4-Biphenylcarboxaldehyde | Phenethylamine | Hydroxy Acetic acid | 562 | 563 | Y | 1.70 |
| 121 | (S)-2,5-Diaminopentanoic acid | 4-Biphenylcarboxaldehyde | Phenethylamine | Boc-Phe | 665 | 666 | Y | 1.07 |
| 122 | (S)-2,5-Diaminopentanoic acid | 4-Biphenylcarboxaldehyde | Phenethylamine | Succinic anhydride | 572 | 632 | Y | 0.15 |
| 123 | (S)-2,5-Diaminopentanoic acid | 4-Biphenylcarboxaldehyde | Phenethylamine | Methoxyacetic acid | 576 | 577 | Y | 1.54 |
| 124 | (S)-2-5-Diaminopentanoic acid | 4-Biphenylcarboxaldehyde | Phenethylamine | Butyric acid | 574 | 575 | Y | 1.54 |
| 125 | (S)-2,5-Diaminopentanoic acid | 4-Biphenylcarboxaldehyde | Phenethylamine | Cyclohexanecarboxylic acid | 614 | 615 | Y | 0.82 |
| 126 | (S)-2,5-Diaminopentanoic acid | 4-Biphenylcarboxaldehyde | Cyclohexylamine | Benzoic acid | 608 | 609 | Y | 1.32 |
| 127 | (S)-2,5-Diaminopentanoic acid | 4-Biphenylcarboxaldehyde | Cyclohexylamine | Acetic acid | 524 | 525 | Y | 1.48 | 1.49 |
| 128 | (S)-2,5-Diaminopentanoic acid | 4-Biphenylcarboxaldehyde | Cyclohexylamine | Boc-Ala | 567 | 568 | Y | 1.57 |
| 129 | (S)-2,5-Diaminopentanoic acid | 4-Biphenylcarboxaldehyde | Cyclohexylamine | Hydroxy Acetic acid | 540 | 541 | Y | |
| 130 | (S)-2,5-Diaminopentanoic acid | 4-Biphenylcarboxaldehyde | Cyclohexylamine | Boc-Phe | 643 | 644 | Y | 0.92 |
| 131 | (S)-2,5-Diaminopentanoic acid | 4-Biphenylcarboxaldehyde | Cyclohexylamine | Succinic anhydride | 550 | 610 | Y | 0.23 |
| 132 | (S)-2,5-Diaminopentanoic acid | 4-Biphenylcarboxaldehyde | Cyclohexylamine | Methoxyacetic acid | 554 | 555 | Y | |
| 133 | (S)-2,5-Diaminopentanoic acid | 4-Biphenylcarboxaldehyde | Cyclohexylamine | Butyric acid | 552 | 553 | Y | 1.46 | 1.59 |
| 134 | (S)-2,5-Diaminopentanoic acid | 4-Biphenylcarboxaldehyde | Cyclohexylamine | Cyclohexanecarboxylic acid | 592 | 593 | Y | 1.48 |
| 135 | (S)-2,5-Diaminopentanoic acid | 4-Biphenylcarboxaldehyde | Cyclohexylamine | Benzoic acid | 586 | 587 | Y | 1.98 |
| 136 | (S)-2,5-Diaminopentanoic acid | 4-Biphenylcarboxaldehyde | Ammonia | Hydrogen | 414 | 415 | Y | 1.73 |
| 137 | (S)-2,5-Diaminopentanoic acid | 4-Biphenylcarboxaldehyde | Ammonia | Boc | 428 | 429 | Y | 1.62 |
| 138 | (S)-2,5-Diaminopentanoic acid | 4-Biphenylcarboxaldehyde | Ammonia | Acetic acid | 442 | 443 | Y | 1.27 |
| 139 | (S)-2,5-Diaminopentanoic acid | 4-Biphenylcarboxaldehyde | Ammonia | Phenylacetic acid | 518 | 519 | Y | 1.46 |
| 140 | (S)-2,5-Diaminopentanoic acid | 4-Biphenylcarboxaldehyde | Ammonia | Boc-Gly | 471 | 472 | Y | 1.36 |
| 141 | (S)-2,5-Diaminopentanoic acid | 4-Biphenylcarboxaldehyde | Ammonia | Gly | 457 | 458 | Y | 1.15 |
| 142 | (S)-2,5-Diaminopentanoic acid | 4-Biphenylcarboxaldehyde | Ammonia | Boc-Ala | 485 | 486 | Y | 1.28 |
| 143 | (S)-2,5-Diaminopentanoic acid | 4-Biphenylcarboxaldehyde | Ammonia | Hydroxy Acetic acid | 458 | 459 | Y | |
| 144 | (S)-2,5-Diaminopentanoic acid | 4-Biphenylcarboxaldehyde | Ammonia | Boc-Phe | 561 | 562 | Y | 1.22 |
| 145 | (S)-2,5-Diaminopentanoic acid | 4-Biphenylcarboxaldehyde | Ammonia | Succinic anhydride | 468 | 528 | Y | 0.11 |
| 146 | (S)-2,5-Diaminopentanoic acid | 4-Biphenylcarboxaldehyde | Ammonia | Methoxyacetic acid | 472 | 473 | Y | 1.22 |
| 147 | (S)-2,5-Diaminopentanoic acid | 4-Biphenylcarboxaldehyde | Ammonia | Butyric acid | 470 | 471 | Y | 1.26 |
| 148 | (S)-2,5-Diaminopentanoic acid | 4-Biphenylcarboxaldehyde | Ammonia | Cyclohexanecarboxylic acid | 510 | 511 | N | 0.96 |
| 149 | (S)-2,5-Diaminopentanoic acid | 4-Biphenylcarboxaldehyde | Ammonia | Benzoic acid | 504 | 505 | N | 1.17 |
| 150 | (S)-2,5-Diaminopentanoic acid | 4-Acetamidobenzaldehyde | Phenethylamine | Hydrogen | 485 | 486 | N | 0.49 |
| 151 | (S)-2,5-Diaminopentanoic acid | 4-Acetamidobenzaldehyde | Phenethylamine | Boc | 499 | 500 | Y | 0.12 |
| 152 | (S)-2,5-Diaminopentanoic acid | 4-Acetamidobenzaldehyde | Phenethylamine | Acetic acid | 513 | 514 | Y | 4.54 |
| 153 | (S)-2,5-Diaminopentanoic acid | 4-Acetamidobenzaldehyde | Phenethylamine | Butyric acid | 541 | 542 | Y | 1.78 |
| 154 | (S)-2,5-Diaminopentanoic acid | 4-Acetamidobenzaldehyde | Phenethylamine | Succinic anhydride | 539 | 599 | Y | 0.09 |
| 155 | (S)-2,5-Diaminopentanoic acid | 4-Acetamidobenzaldehyde | Phenethylamine | Phenylacetic acid | 589 | 590 | Y | 0.52 |
| 156 | (S)-2,5-Diaminopentanoic acid | 4-Acetamidobenzaldehyde | Phenethylamine | 4-Bromophenylacetic acid | 667 | 668 | Y | 0.06 |
| 157 | (S)-2,5-Diaminopentanoic acid | 4-Acetamidobenzaldehyde | Phenethylamine | 4-Methoxyphenylacetic acid | 619 | 620 | Y | 0.59 |
| 158 | (S)-2,5-Diaminopentanoic acid | 4-Acetamidobenzaldehyde | Phenethylamine | Benzoic acid | 575 | 576 | Y | 0.08 |
| 159 | (S)-2,5-Diaminopentanoic acid | 4-Acetamidobenzaldehyde | Phenethylamine | 4-Chlorobenzoic acid | 609 | 610 | Y | 2.30 |
| 160 | (S)-2,5-Diaminopentanoic acid | 4-Acetamidobenzaldehyde | Phenethylamine | 4-Methoxybenzoic acid | 605 | 606 | Y | 0.01 |
| 161 | (S)-2,5-Diaminopentanoic acid | 4-Acetamidobenzaldehyde | Phenethylamine | 2-Naphthylacetic acid | 639 | 640 | Y | 0.09 |
| 162 | (S)-2,5-Diaminopentanoic acid | 4-Acetamidobenzaldehyde | Phenethylamine | Cyclohexylacetic acid | 595 | 596 | Y | 0.72 |
| 163 | (S)-2,5-Diaminopentanoic acid | 4-Acetamidobenzaldehyde | Phenethylamine | Glycine | 528 | 529 | Y | 0.66 |
| 164 | (S)-2,5-Diaminopentanoic acid | 4-Acetamidobenzaldehyde | Phenethylamine | Acetic acid | 491 | 492 | Y | 0.67 |
| 165 | (S)-2,5-Diaminopentanoic acid | 4-Acetamidobenzaldehyde | Cyclohexylamine | Butyric acid | 519 | 520 | Y | 0.41 |
| 166 | (S)-2,5-Diaminopentanoic acid | 4-Acetamidobenzaldehyde | Cyclohexylamine | Succinic anhydride | 517 | 577 | Y | 0.10 |
| 167 | (S)-2,5-Diaminopentanoic acid | 4-Acetamidobenzaldehyde | Cyclohexylamine | 4-Bromophenylacetic acid | 645 | 646 | Y | 0.35 | 4.02 |
| 168 | (S)-2,5-Diaminopentanoic acid | 4-Acetamidobenzaldehyde | Cyclohexylamine | 4-Methoxyphenylacetic acid | 597 | 598 | Y | 0.09 |
| 169 | (S)-2,5-Diaminopentanoic acid | 4-Acetamidobenzaldehyde | Cyclohexylamine | Benzoic acid | 553 | 554 | Y | 0.16 |
| 170 | (S)-2,5-Diaminopentanoic acid | 4-Acetamidobenzaldehyde | Cyclohexylamine | 4-Chlorobenzoic acid | 587 | 588 | Y | 0.51 |

TABLE 1-continued

| # | | | | | | | | |
|---|---|---|---|---|---|---|---|---|
| 171 | (S)-2,5-Diaminopentanoic acid | 4-Acetamidobenzaldehyde | Cyclohexylamine | 4-Methoxybenzoic acid | 583 | 584 | Y | 0.15 |
| 172 | (S)-2,5-Diaminopentanoic acid | 4-Acetamidobenzaldehyde | Cyclohexylamine | 2-Naphthylacetic acid | 617 | 618 | Y | 0.22 |
| 173 | (S)-2,5-Diaminopentanoic acid | 4-Acetamidobenzaldehyde | Cyclohexylamine | Cyclohexylacetic acid | 573 | 574 | Y | 0.14 | 1.59 |
| 174 | (S)-2,5-Diaminopentanoic acid | 4-Acetamidobenzaldehyde | Ammonia | Hydrogen | 381 | 382 | Y | 0.48 |
| 175 | (S)-2,5-Diaminopentanoic acid | 4-Acetamidobenzaldehyde | Ammonia | Boc | 395 | 396 | Y | 0.29 |
| 176 | (S)-2,5-Diaminopentanoic acid | 4-Acetamidobenzaldehyde | Ammonia | Acetic acid | 409 | 410 | Y | 0.22 |
| 177 | (S)-2,5-Diaminopentanoic acid | 4-Acetamidobenzaldehyde | Ammonia | Butyric acid | 437 | 438 | Y | 0.11 |
| 178 | (S)-2,5-Diaminopentanoic acid | 4-Acetamidobenzaldehyde | Ammonia | Succinic anhydride | 435 | 495 | Y | 0.02 |
| 179 | (S)-2,5-Diaminopentanoic acid | 4-Acetamidobenzaldehyde | Ammonia | Pheylacetic acid | 485 | 486 | Y | 0.07 |
| 180 | (S)-2,5-Diaminopentanoic acid | 4-Acetamidobenzaldehyde | Ammonia | 4-Bromophenylacetic acid | 563 | 564 | Y | 0.12 | 1.43 |
| 181 | (S)-2,5-Diaminopentanoic acid | 4-Acetamidobenzaldehyde | Ammonia | 4-Methoxyphenylacetic acid | 515 | 516 | Y | 0.11 | 1.06 |
| 182 | (S)-2,5-Diaminopentanoic acid | 4-Acetamidobenzaldehyde | Ammonia | Benzoic acid | 471 | 472 | Y | 0.20 |
| 183 | (S)-2,5-Diaminopentanoic acid | 4-Acetamidobenzaldehyde | Ammonia | 4-Chlorobenzoic acid | 505 | 506 | Y | 0.13 |
| 184 | (S)-2,5-Diaminopentanoic acid | 4-Acetamidobenzaldehyde | Ammonia | 4-Methoxybenzoic acid | 501 | 502 | Y | 0.09 | 1.61 |
| 185 | (S)-2,5-Diaminopentanoic acid | 4-Acetamidobenzaldehyde | Ammonia | 2-Naphthylacetic acid | 535 | 536 | Y | 0.10 |
| 186 | (S)-2,5-Diaminopentanoic acid | 4-Acetamidobenzaldehyde | Ammonia | Cyclohexylacetic acid | 491 | 492 | Y | 0.03 | 0.58 |
| 187 | (S)-2,5-Diaminopentanoic acid | 4-Acetamidobenzaldehyde | Ammonia | Glycine | 424 | 425 | Y | 0.06 |
| 188 | (S)-2,5-Diaminopentanoic acid | 4-Butyramidobenzaldehyde | Phenethylamine | Hydrogen | 513 | 100 | Y | 0.13 |
| 189 | (S)-2,5-Diaminopentanoic acid | 4-Butyramidobenzaldehyde | Phenethylamine | Boc | 527 | 528 | Y | 0.12 |
| 190 | (S)-2,5-Diaminopentanoic acid | 4-Butyramidobenzaldehyde | Phenethylamine | Acetic acid | 541 | 542 | Y | 0.19 | 0.21 |
| 191 | (S)-2,5-Diaminopentanoic acid | 4-Butyramidobenzaldehyde | Phenethylamine | Butyric acid | 569 | 570 | Y | 0.12 | 0.52 |
| 192 | (S)-2,5-Diaminopentanoic acid | 4-Butyramidobenzaldehyde | Phenethylamine | Succinic anhydride | 567 | 627 | Y | 0.07 | 0.88 |
| 193 | (S)-2,5-Diaminopentanoic acid | 4-Butyramidobenzaldehyde | Phenethylamine | Phenylacetic acid | 617 | 618 | Y | 0.15 | 1.24 |
| 194 | (S)-2,5-Diaminopentanoic acid | 4-Butyramidobenzaldehyde | Phenethylamine | 4-Bromophenylacetic acid | 695 | 696 | Y | 0.24 | 1.36 |
| 195 | (S)-2,5-Diaminopentanoic acid | 4-Butyramidobenzaldehyde | Phenethylamine | 4-Methoxypheneylacetic acid | 647 | 648 | Y | 0.16 | 1.44 |
| 196 | (S)-2,5-Diaminopentanoic acid | 4-Butyramidobenzaldehyde | Phenethylamine | Benzoic acid | 603 | 604 | Y | 0.12 | 1.05 |
| 197 | (S)-2,5-Diaminopentanoic acid | 4-Butyramidobenzaldehyde | Phenethylamine | 4-Chlorobenzoic acid | 637 | 638 | Y | 0.08 |
| 198 | (S)-2,5-Diaminopentanoic acid | 4-Butyramidobenzaldehyde | Phenethylamine | 4-Methoxybenzoic acid | 633 | 634 | Y | 0.12 |
| 199 | (S)-2,5-Diaminopentanoic acid | 4-Butyramidobenzaldehyde | Phenethylamine | 2-Naphthylacetic acid | 667 | 668 | Y | 0.17 |
| 200 | (S)-2,5-Diaminopentanoic acid | 4-Butyramidobenzaldehyde | Phenethylamine | Cyclohexylacetic acid | 623 | 624 | Y | 0.13 | 1.34 |
| 201 | (S)-2,5-Diaminopentanoic acid | 4-Butyramidobenzaldehyde | Phenethylamine | Glycine | 556 | 557 | Y | 0.30 |
| 202 | (S)-2,5-Diaminopentanoic acid | 4-Butyramidobenzaldehyde | Cyclohexylamine | Hydrogen | 491 | 492 | Y | 0.22 |
| 203 | (S)-2,5-Diaminopentanoic acid | 4-Butyramidobenzaldehyde | Cyclohexylamine | Boc | 505 | 506 | Y | 0.17 |
| 204 | (S)-2,5-Diaminopentanoic acid | 4-Butyramidobenzaldehyde | Cyclohexylamine | Acetic acid | 519 | 520 | Y | 0.15 |
| 205 | (S)-2,5-Diaminopentanoic acid | 4-Butyramidobenzaldehyde | Cyclohexylamine | Butyric acid | 547 | 548 | Y | 0.25 |
| 206 | (S)-2,5-Diaminopentanoic acid | 4-Butyramidobenzaldehyde | Cyclohexylamine | Succinic anhydride | 545 | 605 | Y | 0.07 |
| 207 | (S)-2,5-Diaminopentanoic acid | 4-Butyramidobenzaldehyde | Cyclohexylamine | Phenylacetic acid | 595 | 596 | Y | 0.19 |
| 208 | (S)-2,5-Diaminopentanoic acid | 4-Butyramidobenzaldehyde | Cyclohexylamine | 4-Bromophenylacetic acid | 673 | 674 | Y | 0.47 | 0.86 |
| 209 | (S)-2,5-Diaminopentanoic acid | 4-Butyramidobenzaldehyde | Cyclohexylamine | 4-Methoxyphenylacetic acid | 625 | 626 | Y | 0.35 | 1.33 |
| 210 | (S)-2,5-Diaminopentanoic acid | 4-Butyramidobenzaldehyde | Cyclohexylamine | Benzoic acid | 581 | 582 | Y | 0.30 |
| 211 | (S)-2,5-Diaminopentanoic acid | 4-Butyramidobenzaldehyde | Cyclohexylamine | 4-Chlorobenzoic acid | 615 | 616 | Y | 0.10 |
| 212 | (S)-2,5-Diaminopentanoic acid | 4-Butyramidobenzaldehyde | Cyclohexylamine | 4-Methoxybenzoic acid | 611 | 612 | Y | 0.10 | 1.93 |
| 213 | (S)-2,5-Diaminopentanoic acid | 4-Butyramidobenzaldehyde | Cyclohexylamine | 2-Naphthylacetic acid | 645 | 646 | Y | 0.22 | 1.95 |
| 214 | (S)-2,5-Diaminopentanoic acid | 4-Butyramidobenzaldehyde | Cyclohexylamine | Cyclohexylacetic acid | 601 | 602 | Y | 0.08 |
| 215 | (S)-2,5-Diaminopentanoic acid | 4-Butyramidobenzaldehyde | Cyclohexylamine | Glycine | 534 | 535 | Y | 0.38 |
| 216 | (S)-2,5-Diaminopentanoic acid | 4-Butyramidobenzaldehyde | Ammonia | Hydrogen | 409 | 410 | Y | 0.11 |
| 217 | (S)-2,5-Diaminopentanoic acid | 4-Butyramidobenzaldehyde | Ammonia | Boc | 423 | 424 | Y | 0.09 |
| 218 | (S)-2,5-Diaminopentanoic acid | 4-Butyramidobenzaldehyde | Ammonia | Acetic acid | 437 | 438 | Y | 0.07 | 9.59 |
| 219 | (S)-2,5-Diaminopentanoic acid | 4-Butyramidobenzaldehyde | Ammonia | Butyric acid | 465 | 466 | Y | 0.10 | 2.97 |
| 220 | (S)-2,5-Diaminopentanoic acid | 4-Butyramidobenzaldehyde | Ammonia | Succinic anhydride | 463 | 523 | Y | 0.02 |

TABLE 1-continued

| Cpd # | R1: Amino Acid | R2: Aldehyde | R3: amine | R8: Substit. on R1 a-NH2 | M.W. | obs.(M + 1) M.W. | >85% LCQ | MC-1 IC50 uM | MC-4 IC50 uM |
|---|---|---|---|---|---|---|---|---|---|
| TRG 2412 | | | | | | | | | |
| 1 | (S)-2,6-Diaminohexanoic acid | 4-Valeramidobenzaldehyde | Phenethylamine | Boc | 555 | 556 | Y | 0.38 | |
| 2 | (S)-2,6-Diaminohexanoic acid | 4-Valeramidobenzaldehyde | Phenethylamine | Phenylacetic acid | 645 | 646 | Y | 0.47 | |
| 3 | (S)-2,6-Diaminohexanoic acid | 4-Valeramidobenzaldehyde | Phenethylamine | Benzoic acid | 631 | 632 | Y | 0.36 | |
| 4 | (S)-2,6-Diaminohexanoic acid | 4-Ethoxybenzaldehyde | Phenethylamine | Boc | 514 | 515 | Y | 0.31 | 0.32 |
| 5 | (S)-2,6-Diaminohexanoic acid | 4-Ethoxybenzaldehyde | Phenethylamine | Phenylacetic acid | 604 | 605 | Y | 0.49 | |
| 6 | (S)-2,6-Diaminohexanoic acid | 4-Ethoxybenzaldehyde | Phenethylamine | Benzoic acid | 590 | 591 | Y | 0.59 | |
| 7 | (S)-2,6-Diaminohexanoic acid | 4-Propoxybenzaldehyde | Phenethylamine | Boc | 528 | 529 | Y | 0.42 | |
| 8 | (S)-2,6-Diaminohexanoic acid | 4-Propoxybenzaldehyde | Phenethylamine | Phenylacetic acid | 618 | 619 | Y | 0.83 | |
| 9 | (S)-2,6-Diaminohexanoic acid | 4-Propoxybenzaldehyde | Phenethylamine | Benzoic acid | 604 | 605 | Y | 0.57 | |
| 10 | (S)-2,6-Diaminohexanoic acid | 4-Butoxybenzaldehyde | Phenethylamine | Boc | 542 | 543 | Y | 0.31 | |
| 11 | (S)-2,6-Diaminohexanoic acid | 4-Butoxybenzaldehyde | Phenethylamine | Phenylacetic acid | 632 | 633 | Y | 0.82 | |
| 12 | (S)-2,6-Diaminohexanoic acid | 4-Butoxybenzaldehyde | Phenethylamine | Benzoic acid | 618 | 619 | Y | 0.54 | |
| 13 | (S)-2,6-Diaminohexanoic acid | 4-Amylbenzaldehyde | Phenethylamine | Boc | 540 | 541 | Y | 0.45 | |
| 14 | (S)-2,6-Diaminohexanoic acid | 4-Amylbenzaldehyde | Phenethylamine | Phenylacetic acid | 630 | 631 | Y | 0.88 | |
| 15 | (S)-2,6-Diaminohexanoic acid | 4-Amylbenzaldehyde | Phenethylamine | Benzoic acid | 618 | 619 | Y | 0.75 | |
| 16 | (S)-2,5-Diaminopentanoic acid | 4-Valeramidobenzaldehyde | Phenethylamine | Boc | 541 | 542 | Y | 0.09 | 1.48 |
| 17 | (S)-2,5-Diaminopentanoic acid | 4-Valeramidobenzaldehyde | Phenethylamine | Pheneylacetic acid | 631 | 632 | Y | 0.27 | 1.15 |
| 18 | (S)-2,5-Diaminopentanoic acid | 4-Valeramidobenzaldehyde | Phenethylamine | Benzoic acid | 617 | 618 | Y | 0.19 | |
| 19 | (S)-2,5-Diaminopentanoic acid | 4-Ethoxybenzaldehyde | Phenethylamine | Boc | 500 | 501 | Y | 0.16 | |
| 20 | (S)-2,5-Diaminopentanoic acid | 4-Ethoxybenzaldehyde | Phenethylamine | Phenylacetic acid | 590 | 591 | Y | 0.15 | |
| 21 | (S)-2,5-Diaminopentanoic acid | 4-Ethoxybenzaldehyde | Phenethylamine | Benzoic acid | 576 | 577 | Y | 0.17 | 0.23 |
| 22 | (S)-2,5-Diaminopentanoic acid | 4-Propoxybenzaldehyde | Phenethylamine | Boc | 514 | 515 | Y | 0.20 | |
| 23 | (S)-2,5-Diaminopentanoic acid | 4-Propoxybenzaldehyde | Phenethylamine | Phenylacetic acid | 604 | 605 | Y | 0.35 | |
| 24 | (S)-2,5-Diaminopentanoic acid | 4-Propoxybenzaldehyde | Phenethylamine | Benzoic acid | 590 | 591 | Y | 0.41 | |
| 25 | (S)-2,5-Diaminopentanoic acid | 4-Butoxybenzaldehyde | Phenethylamine | Boc | 528 | 529 | Y | 0.16 | 1.06 |
| 26 | (S)-2,5-Diaminopentanoic acid | 4-Butoxybenzaldehyde | Phenethylamine | Phenylacetic acid | 618 | 619 | Y | 0.20 | |
| 27 | (S)-2,5-Diaminopentanoic acid | 4-Butoxybenzaldehyde | Phenethylamine | Benzoic acid | 604 | 605 | Y | 0.25 | |
| 28 | (S)-2,5-Diaminopentanoic acid | 4-Amylbenzaldehyde | Phenethylamine | Boc | 526 | 527 | Y | 0.27 | |
| 29 | (S)-2,5-Diaminopentanoic acid | 4-Amylbenzaldehyde | Phenethylamine | Phenylacetic acid | 616 | 617 | Y | 0.50 | |
| 30 | (S)-2,5-Diaminopentanoic acid | 4-Amylbenzaldehyde | Phenethylamine | Benzoic acid | 602 | 603 | Y | 0.62 | 1.06 |

| Cpd # | R1: Amino Acid | R2: Aldehyde | R3: amine | R8: Subst., R1 a-NH2 | M.W. | obs.(M + 1) M.W. | >85% LCQ | MC-1 IC50 uM | MC-4 IC50 |
|---|---|---|---|---|---|---|---|---|---|
| TRG 2413 | | | | | | | | | |
| 1 | (R)-2,6-Diaminohexanoic acid | 4-Biphenylcarboxaldehyde | Phenethylamine | Boc-Gly | 589 | 590 | Y | 0.44 | |
| 2 | (R)-2,6-Diaminohexanoic acid | 4-Biphenylcarboxaldehyde | Ammonia | Boc-Gly | 485 | 486 | Y | 0.54 | |
| 3 | (R)-2,6-Diaminohexanoic acid | 4-Acetamidobenzaldehyde | Ammonia | Boc-Gly | 452 | 453 | Y | 1.56 | |
| 4 | (R)-2,6-Diaminohexanoic acid | 4-Acetamidobenzaldehyde | Phenethylamine | Boc-Gly | 556 | 557 | Y | 0.34 | |
| 5 | (R)-2,6-Diaminohexanoic acid | 4-Nitrobenzaldehyde | Phenethylamine | Boc | 515 | 516 | Y | 4.88 | |
| 6 | (R)-2,6-Diaminohexanoic acid | 4-Nitrobenzaldehyde | Ammonia | Boc | 412 | 413 | | 6.51 | |
| 7 | (R)-2,5-Diaminopentanoic acid | 4-Biphenylcarboxaldehyde | Ammonia | Gly | 457 | 458 | Y | 1.54 | |

TABLE 1-continued

| | | | | | | |
|---|---|---|---|---|---|---|
| 8 | (R)-2,5-Diaminopentanoic acid | 4-Biphenylcarboxaldehyde | Ammonia | Boc | 428 | 429 | Y | 1.84 |
| 9 | (R)-2,5-Diaminopentanoic acid | 4-Acetamidobenzaldehyde | Phenethylamine | Phenylacetic acid | 589 | 590 | Y | 0.26 |
| 10 | (R)-2,5-Diaminopentanoic acid | 4-Acetamidobenzaldehyde | Cyclohexylamine | Phenylacetic acid | 567 | 568 | Y | 0.31 |
| 11 | (R)-2,5-Diaminopentanoic acid | 4-Acetamidobenzaldehyde | Ammonia | Boc | 485 | 486 | Y | 0.13 |
| 12 | (R)-2,5-Diaminopentanoic acid | 4-Acetamidobenzaldehyde | Phenethylamine | Phenylacetic acid | 499 | 500 | Y | 0.19 |
| 13 | (R)-2,5-Diaminopentanoic acid | 4-Nitrobenzaldehye | Phenethylamine | Phenylacetic acid | 591 | 592 | Y | 1.07 |
| 14 | (R)-2,5-Diaminopentanoic acid | 4-Nitrobenzaldehyde | Cyclohexylamine | Phenylacetic acid | 569 | 570 | Y | 1.57 | 1.34 |
| 15 | (R)-2,5-Diaminopentanoic acid | 4-Nitrobenzaldehyde | Ammonia | Boc | 487 | 458 | Y | 1.92 |
| 16 | (R)-2,5-Diaminopentanoic acid | 4-Nitrobenzaldehyde | Phenethylamine | Boc | 501 | 502 | Y | 1.27 | 0.40 |

| Cmpd # | TRG 2414 R2: Aldehydes | X: amines | R8: acids | M.W. | obs.(M + 1) M.W. | >85% LCQ | MC-1 IC50 μM | MC-4 IC50 μM |
|---|---|---|---|---|---|---|---|---|
| 1 | 2,4-Dichlorobenzaldehyde | 2-(trifluoromethyl)benzylamine | H | 578 | 579 | Y | | 7.59 |
| 2 | 2,4-Dichlorobenzaldehyde | 2-(trifluoromethyl)benzylamine | Phenylacetic | 682 | 683 | Y | | 29.27 |
| 3 | 2,4-Dichlorobenzaldehyde | 2-(trifluoromethyl)benzylamine | Benzoic | 668 | 669 | Y | | 65.55 |
| 4 | 2,4-Dichlorobenzaldehyde | 2-(trifluoromethyl)benzylamine | IBP | 752 | 753 | Y | | no fit |
| 5 | 2,4-Dichlorobenzaldehyde | 2-ethoxybenzylamine | H | 554 | 555 | Y | | 0.48 |
| 6 | 2,4-Dichlorobenzaldehyde | 2-ethoxybenzylamine | Phenylacetic | 658 | 659 | Y | | 5.54 |
| 7 | 2,4-Dichlorobenzaldehyde | 2-ethoxybenzylamine | Benzoic | 644 | 645 | Y | | 4.56 |
| 8 | 2,4-Dichlorobenzaldehyde | 2-ethoxybenzylamine | IBP | 728 | 729 | Y | | 13.84 |
| 9 | 2,4-Dichlorobenzaldehyde | 2-methoxyphenethylamine | H | 554 | 555 | Y | 1.103 | 0.7 |
| 10 | 2,4-Dichlorobenzaldehyde | 2-methoxyphenethylamine | Phenylacetic | 658 | 659 | Y | 2.926 | 4.88 |
| 11 | 2,4-Dichlorobenzaldehyde | 2-methoxyphenethylamine | Benzoic | 644 | 645 | Y | 1.803 | 3.48 |
| 12 | 2,4-Dichlorobenzaldehyde | 2-methoxyphenethylamine | IBP | 728 | 729 | Y | 11.741 | 34.45 |
| 13 | 2,4-Dichlorobenzaldehyde | 3-chlorophenethylamine | H | 558 | 559 | Y | 2.185 | 1.18 |
| 14 | 2,4-Dichlorobenzaldehyde | 3-chlorophenethylamine | Phenylacetic | 662 | 663 | Y | 3.228 | 2.92 |
| 15 | 2,4-Dichlorobenzaldehyde | 3-chlorophenethylamine | Benzoic | 648 | 649 | Y | 6.409 | 6.93 |
| 16 | 2,4-Dichlorobenzaldehyde | 3-chlorophenethylamine | IBP | 732 | 733 | Y | no fit | 33.41 |
| 17 | 2,4-Dichlorobenzaldehyde | 3-methoxybenzylamine | H | 540 | 541 | Y | 3.083 | 1.63 |
| 18 | 2,4-Dichlorobenzaldehyde | 3-methoxybenzylamine | Phenylacetic | 644 | 645 | Y | 4.974 | 8.22 |
| 19 | 2,4-Dichlorobenzaldehyde | 3-methoxybenzylamine | Benzoic | 630 | 631 | Y | 3.274 | 7.31 |
| 20 | 2,4-Dichlorobenzaldehyde | 3-methoxybenzylamine | IBP | 714 | 715 | Y | 27.444 | 38.09 |
| 21 | 2,4-Dichlorobenzaldehyde | 4-methoxybenzylamine | H | 540 | 541 | Y | 1.121 | 1.57 |
| 22 | 2,4-Dichlorobenzaldehyde | 4-methoxybenzylamine | Phenylacetic | 644 | 645 | Y | 3.563 | 5.02 |
| 23 | 2,4-Dichlorobenzaldehyde | 4-methoxybenzylamine | Benzoic | 630 | 631 | Y | 3.187 | 6.14 |
| 24 | 2,4-Dichlorobenzaldehyde | 4-methoxybenzylamine | IBP | 714 | 715 | Y | 25.549 | 37.48 |
| 25 | 2,4-Dichlorobenzaldehyde | 4-methoxyphenethylamine | H | 554 | 555 | Y | 1.386 | 0.52 |
| 26 | 2,4-Dichlorobenzaldehyde | 4-methoxyphenethylamine | Phenylacetic | 658 | 659 | Y | 3.947 | 2.52 |
| 27 | 2,4-Dichlorobenzaldehyde | 4-methoxyphenethylamine | Benzoic | 644 | 645 | Y | 2.654 | 2.6 |
| 28 | 2,4-Dichlorobenzaldehyde | 4-methoxyphenethylamine | IBP | 728 | 729 | Y | 13.937 | 7.42 |
| 29 | 2,4-Dichlorobenzaldehyde | Benzylamine | H | 510 | 511 | Y | 5.658 | 4.4 |
| 30 | 2,4-Dichlorobenzaldehyde | Benzylamine | Phenylacetic | 614 | 615 | Y | 5.392 | 6.21 |
| 31 | 2,4-Dichlorobenzaldehyde | Benzylamine | Benzoic | 600 | 601 | Y | 3.896 | 7.03 |
| 32 | 2,4-Dichlorobenzaldehyde | Benzylamine | IBP | 684 | 685 | Y | 28.308 | 32.08 |
| 33 | 2,4-Dichlorobenzaldehyde | Cycloheptylamine | H | 516 | 517 | Y | 1.901 | 0.72 |
| 34 | 2,4-Dichlorobenzaldehyde | Cycloheptylamine | Phenylacetic | 620 | 621 | Y | 3.551 | 4.42 |
| 35 | 2,4-Dichlorobenzaldehyde | Cycloheptylamine | Benzoic | 606 | 607 | Y | 2.169 | 5.67 |
| 36 | 2,4-Dichlorobenzaldehyde | Cycloheptylamine | IBP | 690 | 691 | Y | 8.654 | 9.92 |
| 37 | 2,4-Dichlorobenzaldehyde | Cyclohexylamine | H | 502 | 503 | Y | 0.992 | 1.3 |
| 38 | 2,4-Dichlorobenzaldehyde | Cyclohexylamine | Phenylacetic | 606 | 607 | Y | 1.916 | 3.96 |
| 39 | 214-Dichlorobenzaldehyde | Cyclohexylamine | Benzoic | 592 | 593 | Y | 2.12 | 4.37 |
| 40 | 2,4-Dichlorobenzaldehyde | Cyclohexylamine | IBP | 676 | 677 | Y | 8.638 | 17.48 |
| 41 | 3,5-Bis(trifluoromethyl)benzaldehyde | 2-(trifluoromethyl)benzylamine | H | 646 | 647 | Y | 34.166 | 15.56 |
| 42 | 3,5-Bis(trifluoromethyl)benzaldehyde | 2-(trifluoromethyl)benzylamine | Phenylacetic | 750 | 751 | Y | 32.808 | 30.25 |
| 43 | 3,5-Bis(trifluoromethyl)benzaldehyde | 2-(trifluoromethyl)benzylamine | Benzoic | 736 | 737 | Y | 56.885 | 41.96 |
| 44 | 3,5-Bis(trifluoromethyl)benzaldehyde | 2-(trifluoromethyl)benzylamine | IBP | 820 | 821 | Y | no fit | no fit |
| 45 | 3,5-Bis(trifluoromethyl)benzaldehyde | 2-ethoxybenzylamine | H | 622 | 623 | Y | 6.34 | 0.92 |
| 46 | 3,5-Bis(trifluoromethyl)benzaldehyde | 2-ethoxybenzylamine | Phenylacetic | 726 | 727 | Y | 6.545 | 4.25 |
| 47 | 3,5-Bis(trifluoromethyl)benzaldehyde | 2-ethoxybenzylamine | Benzoic | 712 | 713 | Y | 7.744 | 7.51 |
| 48 | 3,5-Bis(trifluoromethyl)benzaldehyde | 2-ethoxybenzylamine | IBP | 796 | 797 | Y | 33.523 | 38.82 |
| 49 | 3,5-Bis(trifluoromethyl)benzaldehyde | 2-methoxyphenethylamine | H | 622 | 623 | Y | 3.768 | 0.32 |
| 50 | 3,5-Bis(trifluoromethyl)benzaldehyde | 2-methoxyphenethylamine | Phenylacetic | 726 | 727 | Y | 8.086 | 4.94 |
| 51 | 3,5-Bis(trifluoromethyl)benzaldehyde | 2-methoxyphenethylamine | Benzoic | 712 | 713 | Y | 6.448 | 2.16 |
| 52 | 3,5-Bis(trifluoromethyl)benzaldehyde | 2-methoxyphenethylamine | IBP | 796 | 797 | Y | 22.082 | 17.47 |
| 53 | 3,5-Bis(trifluoromethyl)benzaldehyde | 3-chlorophenethylamine | H | 626 | 627 | Y | 9.779 | 0.64 |
| 54 | 3,5-Bis(trifluoromethyl)benzaldehyde | 3-chlorophenethylamine | Phenylacetic | 730 | 731 | Y | 9.813 | 3.06 |
| 55 | 3,5-Bis(trifluoromethyl)benzaldehyde | 3-chlorophenethylamine | Benzoic | 716 | 717 | Y | 12.493 | 3.12 |
| 56 | 3,5-Bis(trifluoromethyl)benzaldehyde | 3-chlorophenethylamine | IBP | 800 | 801 | Y | no fit | 42.56 |
| 57 | 3,5-Bis(trifluoromethyl)benzaldehyde | 3-methoxybenzylamine | H | 608 | 609 | Y | 7.702 | 1.55 |
| 58 | 3,5-Bis(trifluoromethyl)benzaldehyde | 3-methoxybenzylamine | Phenylacetic | 712 | 713 | Y | 6.718 | 3.45 |
| 59 | 3,5-Bis(trifluoromethyl)benzaldehyde | 3-methoxybenzylamine | Benzoic | 698 | 699 | Y | 9.641 | 6.76 |
| 60 | 3,5-Bis(trifluoromethyl)benzaldehyde | 3-methoxybenzylamine | IBP | 782 | 783 | Y | no fit | 52.58 |
| 61 | 3,5-Bis(trifluoromethyl)benzaldehyde | 4-methoxybenzylamine | H | 608 | 609 | Y | 10.5 | 1.67 |
| 62 | 3,5-Bis(trifluoromethyl)benzaldehyde | 4-methoxybenzylamine | Phenylacetic | 712 | 713 | Y | 15.497 | 6.87 |
| 63 | 3,5-Bis(trifluoromethyl)benzaldehyde | 4-methoxybenzylamine | Benzoic | 698 | 699 | Y | 14.465 | 5.34 |
| 64 | 3,5-Bis(trifluoromethyl)benzaldehyde | 4-methoxybenzylamine | IBP | 782 | 783 | Y | 34.482 | 45.45 |
| 65 | 3,5-Bis(trifluoromethyl)benzaldehyde | 4-methoxyphenethylamine | H | 622 | 623 | Y | 3.304 | 0.26 |
| 66 | 3,5-Bis(trifluoromethyl)benzaldehyde | 4-methoxyphenethylamine | Phenylacetic | 726 | 727 | Y | 10.524 | 3.2 |
| 67 | 3,5-Bis(trifluoromethyl)benzaldehyde | 4-methoxyphenethylamine | Benzoic | 712 | 713 | Y | 0.033 | 5.21 |
| 68 | 3,5-Bis(trifluoromethyl)benzaldehyde | 4-methoxyphenethylamine | IBP | 796 | 797 | Y | no fit | 17.66 |
| 69 | 3,5-Bis(trifluoromethyl)benzaldehyde | Benzylamine | H | 578 | 579 | Y | 9.449 | 0.64 |
| 70 | 3,5-Bis(trifluoromethyl)benzaldehyde | Benzylamine | Phenylacetic | 682 | 683 | Y | 18.286 | 9.29 |
| 71 | 3,5-Bis(trifluoromethyl)benzaldehyde | Benzylamine | Benzoic | 668 | 669 | Y | 17.03 | 9.06 |
| 72 | 3,5-Bis(trifluoromethyl)benzaldehyde | Benzylamine | IBP | 752 | 753 | Y | no fit | 44.21 |
| 73 | 3,5-Bis(trifluoromethyl)benzaldehyde | Cycloheptylamine | H | 584 | 585 | Y | 5.769 | 1.01 |
| 74 | 3,5-Bis(trifluoromethyl)benzaldehyde | Cycloheptylamine | Phenylacetic | 688 | 689 | Y | 11.233 | 4.57 |
| 75 | 3,5-Bis(trifluoromethyl)benzaldehyde | Cycloheptylamine | Benzoic | 674 | 675 | Y | 1.917 | 3.24 |
| 76 | 3,5-Bis(trifluoromethyl)benzaldehyde | Cycloheptylamine | IBP | 758 | 759 | Y | no fit | 54.4 |

-continued

| Cmpd # | TRG 2414 R2: Aldehydes | X: amines | R8: acids | M.W. | obs.(M + 1) M.W. | >85% LCQ | MC-1 IC50 μM | MC-4 IC50 μM |
|---|---|---|---|---|---|---|---|---|
| 77 | 3,5-Bis(trifluoromethyl)benzaldehyde | Cyclohexylamine | H | 570 | 571 | Y | 3.863 | 0.63 |
| 78 | 3,5-Bis(trifluoromethyl)benzaldehyde | Cyclohexylamine | Phenylacetic | 674 | 675 | Y | 6.275 | 4.26 |
| 79 | 3,5-Bis(trifluoromethyl)benzaldehyde | Cyclohexylamine | Benzoic | 660 | 661 | Y | 10.396 | 4.99 |
| 80 | 3,5-Bis(trifluoromethyl)benzaldehyde | Cyclohexylamine | IBP | 744 | 745 | Y | 23.708 | 26.99 |
| 81 | 3-Phenoxybenzaldehyde | 2-(trifluoromethyl)benzylamine | H | 602 | 603 | Y | 10.768 | 9.87 |
| 82 | 3-Phenoxybenzaldehyde | 2-(trifluoromethyl)benzylamine | Phenylacetic | 706 | 707 | Y | no fit | 42.56 |
| 83 | 3-Phenoxybenzaldehyde | 2-(trifluoromethyl)benzylamine | Benzoic | 692 | 693 | Y | 31.546 | no fit |
| 84 | 3-Phenoxybenzaldehyde | 2-(trifluoromethyl)benzylamine | IBP | 776 | 777 | Y | no fit | no fit |
| 85 | 3-Phenoxybenzaldehyde | 2-ethoxybenzylamine | H | 578 | 579 | Y | 2.434 | 2.17 |
| 86 | 3-Phenoxybenzaldehyde | 2-ethoxybenzylamine | Phenylacetic | 682 | 683 | Y | 11.848 | 16.21 |
| 87 | 3-Phenoxybenzaldehyde | 2-ethoxybenzylamine | Benzoic | 668 | 669 | Y | 6.652 | 11.18 |
| 88 | 3-Phenoxybenzaldehyde | 2-ethoxybenzylamine | IBP | 752 | 753 | Y | 36.516 | no fit |
| 89 | 3-Phenoxybenzaldehyde | 2-methoxyphenethylamine | H | 578 | 579 | Y | 1.26 | 0.73 |
| 90 | 3-Phenoxybenzaldehyde | 2-methoxyphenethylamine | Phenylacetic | 682 | 683 | Y | 3.524 | 4.06 |
| 91 | 3-Phenoxybenzaldehyde | 2-methoxyphenethylamine | Benzoic | 668 | 669 | Y | 3.206 | 2.74 |
| 92 | 3-Phenoxybenzaldehyde | 2-methoxyphenethylamine | IBP | 752 | 753 | Y | 42.645 | no fit |
| 93 | 3-Phenoxybenzaldehyde | 3-chlorophenethylamine | H | 582 | 583 | Y | 6.302 | 3.8 |
| 94 | 3-Phenoxybenzaldehyde | 3-chlorophenethylamine | Phenylacetic | 686 | 687 | Y | 16.888 | 8.2 |
| 95 | 3-Phenoxybenzaldehyde | 3-chlorophenethylamine | Benzoic | 672 | 673 | Y | 8.663 | 5.26 |
| 96 | 3-Phenoxybenzaldehyde | 3-chlorophenethylamine | IBP | 756 | 757 | Y | no fit | 50.55 |
| 97 | 3-Phenoxybenzaldehyde | 3-methoxybenzylamine | H | 564 | 565 | Y | 4.51 | 2.5 |
| 98 | 3-Phenoxybenzaldehyde | 3-methoxybenzylamine | Phenylacetic | 668 | 669 | Y | 13.154 | 9.61 |
| 99 | 3-Phenoxybenzaldehyde | 3-methoxybenzylamine | Benzoic | 654 | 655 | Y | 5.859 | 6.93 |
| 100 | 3-Phenoxybenzaldehyde | 3-methoxybenzylamine | IBP | 738 | 739 | Y | no fit | no fit |
| 101 | 3-Phenoxybenzaldehyde | 4-methoxybenzylamine | H | 564 | 565 | Y | 2.496 | 1.26 |
| 102 | 3-Phenoxybenzaldehyde | 4-methoxybenzylamine | Phenylacetic | 668 | 669 | Y | 12.229 | 6.91 |
| 103 | 3-Phenoxybenzaldehyde | 4-methoxybenzylamine | Benzoic | 654 | 655 | Y | 8.135 | 7.48 |
| 104 | 3-Phenoxybenzaldehyde | 4-methoxybenzylamine | IBP | 738 | 739 | Y | no fit | 46.21 |
| 105 | 3-Phenoxybenzaldehyde | 4-methoxyphenethylamine | H | 578 | 579 | Y | 3.71 | 2.68 |
| 106 | 3-Phenoxybenzaldehyde | 4-methoxyphenethylamine | Phenylacetic | 682 | 683 | Y | 12.947 | 10.04 |
| 107 | 3-Phenoxybenzaldehyde | 4-methoxyphenethylamine | Benzoic | 668 | 669 | Y | 6.548 | 8.21 |
| 108 | 3-Phenoxybenzaldehyde | 4-methoxyphenethylamine | IBP | 752 | 753 | Y | no fit | 49.18 |
| 109 | 3-Phenoxybenzaldehyde | Benzylamine | H | 534 | 535 | Y | 3.063 | 0.91 |
| 110 | 3-Phenoxybenzaldehyde | Benzylamine | Phenylacetic | 638 | 639 | Y | 11.106 | 10.04 |
| 111 | 3-Phenoxybenzaldehyde | Benzylamine | Benzoic | 624 | 625 | Y | 7.735 | 13.11 |
| 112 | 3-Phenoxybenzaldehyde | Benzylamine | IBP | 708 | 709 | Y | no fit | 51.34 |
| 113 | 3-Phenoxybenzaldehyde | Cycloheptylamine | H | 540 | 541 | Y | 2.955 | 1.78 |
| 114 | 3-Phenoxybenzaldehyde | Cycloheptylamine | Phenylacetic | 644 | 645 | Y | 8.96 | 4.83 |
| 115 | 3-Phenoxybenzaldehyde | Cycloheptylamine | Benzoic | 630 | 631 | Y | 3.712 | 5.6 |
| 116 | 3-Phenoxybenzaldehyde | Cycloheptylamine | IBP | 714 | 715 | Y | 53.662 | no fit |
| 117 | 3-Phenoxybenzaldehyde | Cyclohexylamine | H | 526 | 527 | Y | 1.935 | 1.27 |
| 118 | 3-Phenoxybenzaldehyde | Cyclohexylamine | Phenylacetic | 630 | 631 | Y | 8.444 | 4.49 |
| 119 | 3-Phenoxybenzaldehyde | Cyclohexylamine | Benzoic | 616 | 617 | Y | 5.008 | 4.77 |
| 120 | 3-Phenoxybenzaldehyde | Cyclohexylamine | IBP | 700 | 701 | Y | 25.013 | 58.77 |
| 121 | 4-Phenoxybenzaldehyde | 2-(trifluoromethyl)benzylamine | H | 602 | 603 | Y | 8.135 | 27.78 |
| 122 | 4-Phenoxybenzaldehyde | 2-(trifluoromethyl)benzylamine | Phenylacetic | 766 | 707 | Y | no fit | 55.54 |
| 123 | 4-Phenoxybenzaldehyde | 2-(trifluoromethyl)benzylamine | Benzoic | 692 | 693 | Y | 17.576 | no fit |
| 124 | 4-Phenoxybenzaldehyde | 2-(trifluoromethyl)benzylamine | IBP | 776 | 777 | Y | no fit | no fit |
| 125 | 4-Phenoxybenzaldehyde | 2-ethoxybenzylamine | H | 578 | 579 | Y | 0.7 | 8.08 |
| 126 | 4-Phenoxybenzaldehyde | 2-ethoxybenzylamine | Phenylacetic | 682 | 683 | Y | 6.428 | 18.69 |
| 127 | 4-Phenoxybenzaldehyde | 2-ethoxybenzylamine | Benzoic | 668 | 669 | Y | 2.135 | 26.79 |
| 128 | 4-Phenoxybenzaldehyde | 2-ethoxybenzylamine | IBP | 752 | 753 | Y | 25.006 | no fit |
| 129 | 4-Phenoxybenzaldehyde | 2-methoxyphenethylamine | H | 578 | 579 | Y | 0.146 | 5.58 |
| 130 | 4-Phenoxybenzaldehyde | 2-methoxyphenethylamine | Phenylacetic | 682 | 683 | Y | 4.632 | 13.37 |
| 131 | 4-Phenoxybenzaldehyde | 2-methoxyphenethylamine | Benzoic | 668 | 669 | Y | 1.645 | 14.59 |
| 132 | 4-Phenoxybenzaldehyde | 2-methoxyphenethylamine | IBP | 752 | 753 | Y | 27.369 | no fit |
| 133 | 4-Phenoxybenzaldehyde | 3-chlorophenethylamine | H | 582 | 583 | Y | 5.802 | 15.92 |
| 134 | 4-Phenoxybenzaldehyde | 3-chlorophenethylamine | Phenylacetic | 686 | 687 | Y | 40.222 | no fit |
| 135 | 4-Phenoxybenzaldehyde | 3-chlorophenethylamine | Benzoic | 672 | 673 | Y | 10.053 | 45.97 |
| 136 | 4-Phenoxybenzaldehyde | 3-chlorophenethylamine | IBP | 756 | 757 | Y | no fit | no fit |
| 137 | 4-Phenoxybenzaldehyde | 3-methoxybenzylamine | H | 564 | 565 | Y | 1.207 | 5.26 |
| 138 | 4-Phenoxybenzaldehyde | 3-methoxybenzylamine | Phenylacetic | 668 | 669 | Y | 10.559 | 16.64 |
| 139 | 4-Phenoxybenzaldehyde | 3-methoxybenzylamine | Benzoic | 654 | 655 | Y | 0.788 | 12.57 |
| 140 | 4-Phenoxybenzaldehyde | 3-methoxybenzylamine | IBP | 738 | 739 | Y | 36.973 | no fit |
| 141 | 4-Phenoxybenzaldehyde | 4-methoxybenzylamine | H | 564 | 565 | Y | 2.042 | 4.21 |
| 142 | 4-Phenoxybenzaldehyde | 4-methoxybenzylamine | Phenylacetic | 668 | 669 | Y | 4.378 | 11.26 |
| 143 | 4-Phenoxybenzaldehyde | 4-methoxybenzylamine | Benzoic | 654 | 655 | Y | 2.355 | 14.02 |
| 144 | 4-Phenoxybenzaldehyde | 4-methoxybenzylamine | IBP | 738 | 739 | Y | no fit | no fit |
| 145 | 4-Phenoxybenzaldehyde | 4-methoxyphenethylamine | H | 578 | 579 | Y | 2.046 | 3.47 |
| 146 | 4-Phenoxybenzaldehyde | 4-methoxyphenethylamine | Phenylacetic | 682 | 683 | Y | 8.205 | 16.76 |
| 147 | 4-Phenoxybenzaldehyde | 4-methoxyphenethylamine | Benzoic | 668 | 669 | Y | 1.626 | 8.5 |
| 148 | 4-Phenoxybenzaldehyde | 4-methoxyphenethylamine | IBP | 752 | 753 | Y | no fit | no fit |
| 149 | 4-Phenoxybenzaldehyde | Benzylamine | H | 534 | 535 | Y | 2.858 | 2.69 |
| 150 | 4-Phenoxybenzaldehyde | Benzylamine | Phenylacetic | 638 | 639 | Y | 9.417 | 16.28 |
| 151 | 4-Phenoxybenzaldehyde | Benzylamine | Benzoic | 624 | 625 | Y | 1.813 | 14.69 |
| 152 | 4-Phenoxybenzaldehyde | Benzylamine | IBP | 708 | 709 | Y | no fit | no fit |

-continued

| Cmpd # | TRG 2414 R2: Aldehydes | X: amines | R8: acids | M.W. | obs.(M + 1) M.W. | >85% LCQ | MC-1 IC50 μM | MC-4 IC50 μM |
|---|---|---|---|---|---|---|---|---|
| 153 | 4-Phenoxybenzaldehyde | Cycloheptylamine | H | 540 | 541 | Y | 0.772 | 4.09 |
| 154 | 4-Phenoxybenzaldehyde | Cycloheptylamine | Phenylacetic | 644 | 645 | Y | 4.852 | 7.52 |
| 155 | 4-Phenoxybenzaldehyde | Cycloheptylamine | Benzoic | 630 | 631 | Y | 2.031 | 8.94 |
| 156 | 4-Phenoxybenzaldehyde | Cycloheptylamine | IBP | 714 | 715 | Y | 18.583 | no fit |
| 157 | 4-Phenoxybenzaldehyde | Cyclohexylamine | H | 526 | 527 | Y | 1.115 | 4.11 |
| 158 | 4-Phenoxybenzaldehyde | Cyclohexylamine | Phenylacetic | 630 | 631 | Y | 2.74 | 6.71 |
| 159 | 4-Phenoxybenzaldehyde | Cyclohexylamine | Benzoic | 616 | 617 | Y | 1.397 | 9.82 |
| 160 | 4-Phenoxybenzaldehyde | Cyclohexylamine | IBP | 700 | 701 | Y | 17.528 | no fit |
| 161 | 4-Propoxybenzaldehyde | 2-(trifluoromethyl)benzylamine | H | 568 | 569 | Y | 7.981 | 11 |
| 162 | 4-Propoxybenzaldehyde | 2-(trifluoromethyl)benzylamine | Phenylacetic | 672 | 673 | Y | 19.061 | 18.41 |
| 163 | 4-Propoxybenzaldehyde | 2-(trifluoromethyl)benzylamine | Benzoic | 658 | 659 | Y | 2.732 | 22.61 |
| 164 | 4-Propoxybenzaldehyde | 2-(trifluoromethyl)benzylamine | IBP | 742 | 743 | Y | no fit | no fit |
| 165 | 4-Propoxybenzaldehyde | 2-ethoxybenzylamine | H | 544 | 545 | Y | 0.994 | 5.06 |
| 166 | 4-Propoxybenzaldehyde | 2-ethoxybenzylamine | Phenylacetic | 648 | 649 | Y | 8.815 | 8.58 |
| 167 | 4-Propoxybenzaldehyde | 2-ethoxybenzylamine | Benzoic | 634 | 635 | Y | 2.16 | 7.03 |
| 168 | 4-Propoxybenzaldehyde | 2-ethoxybenzylamine | IBP | 718 | 719 | Y | 21.754 | 44.44 |
| 169 | 4-Propoxybenzaldehyde | 2-methoxyphenethylamine | H | 544 | 545 | Y | 0.518 | 5.34 |
| 170 | 4-Propoxybenzaldehyde | 2-methoxyphenethylamine | Phenylacetic | 648 | 649 | Y | 1.772 | 7.34 |
| 171 | 4-Propoxybenzaldehyde | 2-methoxyphenethylamine | Benzoic | 634 | 635 | Y | 1.1 | 4.8 |
| 172 | 4-Propoxybenzaldehyde | 2-methoxyphenethylamine | IBP | 718 | 719 | Y | 15.681 | 39.65 |
| 173 | 4-Propoxybenzaldehyde | 3-chlorophenethylamine | H | 548 | 549 | Y | 1.963 | 4.22 |
| 174 | 4-Propoxybenzaldehyde | 3-chlorophenethylamine | Phenylacetic | 652 | 653 | Y | 4.297 | 5.42 |
| 175 | 4-Propoxybenzaldehyde | 3-chlorophenethylamine | Benzoic | 638 | 639 | Y | 4.14 | 6.08 |
| 176 | 4-Propoxybenzaldehyde | 3-chlorophenethylamine | IBP | 722 | 723 | Y | 21.873 | no fit |
| 177 | 4-Propoxybenzaldehyde | 3-methoxybenzylamine | H | 530 | 531 | Y | 0.739 | 5.07 |
| 178 | 4-Propoxybenzaldehyde | 3-methoxybenzylamine | Phenylacetic | 634 | 635 | Y | 2.175 | 8.13 |
| 179 | 4-Propoxybenzaldehyde | 3-methoxybenzylamine | Benzoic | 620 | 621 | Y | 0.998 | 5.48 |
| 180 | 4-Propoxybenzaldehyde | 3-methoxybenzylamine | IBP | 704 | 705 | Y | 8.189 | 47.14 |
| 181 | 4-Propoxybenzaldehyde | 4-methoxybenzylamine | H | 530 | 531 | Y | 0.468 | 6.83 |
| 182 | 4-Propoxybenzaldehyde | 4-methoxybenzylamine | Phenylacetic | 634 | 635 | Y | 1.476 | 4.11 |
| 183 | 4-Propoxybenzaldehyde | 4-methoxybenzylamine | Benzoic | 620 | 621 | Y | 1.089 | 4.95 |
| 184 | 4-Propoxybenzaldehyde | 4-methoxybenzylamine | IBP | 704 | 705 | Y | 17.019 | 27.94 |
| 185 | 4-Propoxybenzaldehyde | 4-methoxyphenethylamine | H | 544 | 545 | Y | 0.542 | 4.26 |
| 186 | 4-Propoxybenzaldehyde | 4-methoxyphenethylamine | Phenylacetic | 648 | 649 | Y | 2.809 | 8.09 |
| 187 | 4-Propoxybenzaldehyde | 4-methoxyphenethylamine | Benzoic | 634 | 635 | Y | 1.069 | 1.47 |
| 188 | 4-Propoxybenzaldehyde | 4-methoxyphenethylamine | IBP | 718 | 719 | Y | 7.902 | 19.99 |
| 189 | 4-Propoxybenzaldehyde | Benzylamine | H | 500 | 501 | Y | 0.869 | 2.31 |
| 190 | 4-Propoxybenzaldehyde | Benzylamine | Phenylacetic | 604 | 605 | Y | 1.443 | 5.42 |
| 191 | 4-Propoxybenzaldehyde | Benzylamine | Benzoic | 590 | 591 | Y | 1.949 | 5.53 |
| 192 | 4-Propoxybenzaldehyde | Benzylamine | IBP | 674 | 675 | Y | 11.374 | 15.98 |
| 193 | 4-Propoxybenzaldehyde | Cycloheptylamine | H | 506 | 507 | Y | 1.639 | 6.59 |
| 194 | 4-Propoxybenzaldehyde | Cycloheptylamine | Phenylacetic | 610 | 611 | Y | 3.861 | 5.09 |
| 195 | 4-Propoxybenzaldehyde | Cycloheptylamine | Benzoic | 596 | 597 | Y | 1.382 | 4.07 |
| 196 | 4-Propoxybenzaldehyde | Cycloheptylamine | IBP | 680 | 681 | Y | 13.28 | 37.02 |
| 197 | 4-Propoxybenzaldehyde | Cyclohexylamine | H | 492 | 493 | Y | 0.419 | 12.62 |
| 198 | 4-Propoxybenzaldehyde | Cyclohexylamine | Phenylacetic | 596 | 597 | Y | 2.998 | 3.68 |
| 199 | 4-Propoxybenzaldehyde | Cyclohexylamine | Benzoic | 582 | 583 | Y | 1.291 | 5.15 |
| 200 | 4-Propoxybenzaldehyde | Cyclohexylamine | IBP | 666 | 667 | Y | 7.589 | 16.84 |
| 201 | 2-Bromobenzaldehyde | 2-(trifluoromethyl)benzylamine | H | 588 | 589 | Y | no fit | no fit |
| 202 | 2-Bromobenzaldehyde | 2-(trifluoromethyl)benzylamine | Phenylacetic | 692 | 693 | Y | 21.849 | 34.09 |
| 203 | 2-Bromobenzaldehyde | 2-(trifluoromethyl)benzylamine | Benzoic | 678 | 679 | Y | 30.209 | 39.59 |
| 204 | 2-Bromobenzaldehyde | 2-(trifluoromethyl)benzylamine | IBP | 762 | 763 | Y | no fit | no fit |
| 205 | 2-Bromobenzaldehyde | 2-ethoxybenzylamine | H | 564 | 565 | Y | 2.334 | 1.5 |
| 206 | 2-Bromobenzaldehyde | 2-ethoxybenzylamine | Phenylacetic | 668 | 669 | Y | 7.045 | 6.2 |
| 207 | 2-Bromobenzaldehyde | 2-ethoxybenzylamine | Benzoic | 654 | 655 | Y | 7.675 | 6.43 |
| 208 | 2-Bromobenzaldehyde | 2-ethoxybenzylamine | IBP | 738 | 739 | Y | 34.365 | 21.12 |
| 209 | 2-Bromobenzaldehyde | 2-methoxyphenethylamine | H | 564 | 565 | Y | 1.707 | 1.37 |
| 210 | 2-Bromobenzaldehyde | 2-methoxyphenethylamine | Phenylacetic | 668 | 669 | Y | 3.704 | 4.43 |
| 211 | 2-Bromobenzaldehyde | 2-methoxyphenethylamine | Benzoic | 654 | 655 | Y | 3.561 | 4.21 |
| 212 | 2-Bromobenzaldehyde | 2-methoxyphenethylamine | IBP | 738 | 739 | Y | 18.335 | 16.61 |
| 213 | 2-Bromobenzaldehyde | 3-chlorophenethylamine | H | 568 | 569 | Y | 6.48 | 2.06 |
| 214 | 2-Bromobenzaldehyde | 3-chlorophenethylamine | Phenylacetic | 672 | 673 | Y | 7.381 | 4.76 |
| 215 | 2-Bromobenzaldehyde | 3-chlorophenethylamine | Benzoic | 658 | 659 | Y | 8.508 | 6.43 |
| 216 | 2-Bromobenzaldehyde | 3-chlorophenethylamine | IBP | 742 | 743 | Y | 48.284 | 38.95 |
| 217 | 2-Bromobenzaldehyde | 3-methoxybenzylamine | H | 550 | 551 | Y | 5.563 | 2.42 |
| 218 | 2-Bromobenzaldehyde | 3-methoxybenzylamine | Phenylacetic | 654 | 655 | Y | 8.203 | 10.85 |
| 219 | 2-Bromobenzaldehyde | 3-methoxybenzylamine | Benzoic | 640 | 641 | Y | 10.287 | 9.59 |
| 220 | 2-Bromobenzaldehyde | 3-methoxybenzylamine | IBP | 724 | 725 | Y | 40.552 | 35.1 |
| 221 | 2-Bromobenzaldehyde | 4-methoxybenzylamine | H | 550 | 551 | Y | 6.605 | 1.83 |
| 222 | 2-Bromobenzaldehyde | 4-methoxybenzylamine | Phenylacetic | 654 | 655 | Y | 5.054 | 4.78 |
| 223 | 2-Bromobenzaldehyde | 4-methoxybenzylamine | Benzoic | 640 | 641 | Y | 10.555 | 8.22 |
| 224 | 2-Bromobenzaldehyde | 4-methoxybenzylamine | IBP | 724 | 725 | Y | 31.491 | 22.67 |
| 225 | 2-Bromobenzaldehyde | 4-methoxyphenethylamine | H | 564 | 565 | Y | 4.522 | 2.04 |
| 226 | 2-Bromobenzaldehyde | 4-methoxyphenethylamine | Phenylacetic | 668 | 669 | Y | 5.165 | 3.42 |
| 227 | 2-Bromobenzaldehyde | 4-methoxyphenethylamine | Benzoic | 654 | 655 | Y | 4.489 | 3.71 |
| 228 | 2-Bromobenzaldehyde | 4-methoxyphenethylamine | IBP | 738 | 739 | Y | 17.699 | 8.79 |

-continued

| Cmpd # | TRG 2414 R2: Aldehydes | X: amines | R8: acids | M.W. | obs.(M + 1) M.W. | >85% LCQ | MC-1 IC50 μM | MC-4 IC50 μM |
|---|---|---|---|---|---|---|---|---|
| 229 | 2-Bromobenzaldehyde | Benzylamine | H | 520 | 521 | Y | 8.629 | 1.29 |
| 230 | 2-Bromobenzaldehyde | Benzylamine | Phenylacetic | 624 | 625 | Y | 6.478 | 5.46 |
| 231 | 2-Bromobenzaldehyde | Benzylamine | Benzoic | 610 | 611 | Y | 11.028 | 9.13 |
| 232 | 2-Bromobenzaldehyde | Benzylamine | IBP | 694 | 695 | Y | 32.732 | 23.43 |
| 233 | 2-Bromobenzaldehyde | Cycloheptylamine | H | 526 | 527 | Y | 3.319 | 3.27 |
| 234 | 2-Bromobenzaldehyde | Cycloheptylamine | Phenylacetic | 630 | 631 | Y | 4.407 | 5.28 |
| 235 | 2-Bromobenzaldehyde | Cycloheptylamine | Benzoic | 616 | 617 | Y | 2.862 | 5.35 |
| 236 | 2-Bromobenzaldehyde | Cycloheptylamine | IBP | 700 | 701 | Y | 13.958 | 18.05 |
| 237 | 2-Bromobenzaldehyde | Cyclohexylamine | H | 512 | 513 | Y | 5.867 | 3.61 |
| 238 | 2-Bromobenzaldehyde | Cyclohexylamine | Phenylacetic | 616 | 617 | Y | 2.782 | 5.22 |
| 239 | 2-Bromobenzaldehyde | Cyclohexylamine | Benzoic | 602 | 603 | Y | 3.303 | 6.27 |
| 240 | 2-Bromobenzaldehyde | Cyclohexylamine | IBP | 686 | 687 | Y | 8.985 | 9.9 |
| 241 | 2,4-Dichlorobenzaldehyde | 2-methoxyphenethylamine | H | 596 | 597 | Y | no fit | no fit |
| 242 | 2,4-Dichlorobenzaldehyde | 2-methoxyphenethylamine | Phenylacetic | 714 | 715 | Y | no fit | no fit |
| 243 | 2,4-Dichlorobenzaldehyde | 2-methoxyphenethylamine | IBP | 784 | 785 | Y | no fit | no fit |
| 244 | 2,4-Dichlorobenzaldehyde | 3-chlorophenethylamine | H | 600 | 601 | Y | 44.099 | no fit |
| 245 | 2,4-Dichlorobenzaldehyde | 3-chlorophenethylamine | Phenylacetic | 718 | 719 | Y | no fit | no fit |
| 246 | 2,4-Dichlorobenzaldehyde | 3-chlorophenethylamine | Benzoic | 704 | 705 | Y | no fit | no fit |
| 247 | 2,4-Dichlorobenzaldehyde | 4-methoxybenzylamine | H | 582 | 583 | Y | no fit | no fit |
| 248 | 2,4-Dichlorobenzaldehyde | 4-methoxybenzylamine | Phenylacetic | 700 | 701 | Y | no fit | no fit |
| 249 | 2,4-Dichlorobenzaldehyde | 4-methoxybenzylamine | Benzoic | 686 | 687 | Y | no fit | no fit |
| 250 | 2,4-Dichlorobenzaldehyde | 4-methoxyphenethylamine | H | 596 | 597 | Y | no fit | no fit |
| 251 | 2,4-Dichlorobenzaldehyde | 4-methoxyphenethylamine | Phenylacetic | 714 | 715 | Y | no fit | no fit |
| 252 | 2,4-Dichlorobenzaldehyde | 4-methoxyphenethylamine | Benzoic | 700 | 701 | Y | no fit | no fit |
| 253 | 3,5-Bis(trifluoromethyl)benzaldehyde | 2-methoxyphenethylamine | H | 664 | 665 | Y | no fit | no fit |
| 254 | 3,5-Bis(trifluoromethyl)benzaldehyde | 2-methoxyphenethylamine | Phenylacetic | 782 | 783 | Y | no fit | no fit |
| 255 | 3,5-Bis(trifluoromethyl)benzaldehyde | 2-methoxyphenethylamine | Benzoic | 768 | 769 | Y | no fit | no fit |
| 256 | 3,5-Bis(trifluoromethyl)benzaldehyde | 3-chlorophenethylamine | H | 668 | 669 | Y | no fit | no fit |
| 257 | 3,5-Bis(trifluoromethyl)benzaldehyde | 3-chlorophenethylamine | Phenylacetic | 786 | 787 | Y | no fit | no fit |
| 258 | 3,5-Bis(trifluoromethyl)benzaldehyde | 3-chlorophenethylamine | IBP | 856 | 857 | Y | no fit | no fit |
| 259 | 3,5-Bis(trifluoromethyl)benzaldehyde | 4-methoxybenzylamine | H | 650 | 651 | Y | no fit | no fit |
| 260 | 3,5-Bis(trifluoromethyl)benzaldehyde | 4-methoxybenzylamine | Phenylacetic | 768 | 769 | Y | no fit | no fit |
| 261 | 3,5-Bis(trifluoromethyl)benzaldehyde | 4-methoxybenzylamine | Benzoic | 754 | 755 | Y | no fit | no fit |
| 262 | 3,5-Bis(trifluoromethyl)benzaldehyde | 4-methoxyphenethylamine | H | 664 | 665 | Y | no fit | no fit |
| 263 | 3,5-Bis(trifluoromethyl)benzaldehyde | 4-methoxyphenethylamine | Phenylacetic | 782 | 783 | Y | no fit | no fit |
| 264 | 3,5-Bis(trifluoromethyl)benzaldehyde | 4-methoxyphenethylamine | Benzoic | 768 | 769 | Y | no fit | no fit |
| 265 | 4-Phenoxybenzaldehyde | 2-methoxyphenethylamine | H | 620 | 621 | Y | no fit | no fit |
| 266 | 4-Phenoxybenzaldehyde | 2-methoxyphenethylamine | Phenylacetic | 738 | 739 | Y | no fit | no fit |
| 267 | 4-Phenoxybenzaldehyde | 2-methoxyphenethylamine | Benzoic | 892 | 893 | Y | no fit | no fit |
| 268 | 4-Phenoxybenzaldehyde | 3-chlorophenethylamine | H | 624 | 625 | Y | no fit | no fit |
| 269 | 4-Phenoxybenzaldehyde | 3-chlorophenethylamine | Phenylacetic | 742 | 743 | Y | no fit | no fit |
| 270 | 4-Phenoxybenzaldehyde | 3-chlorophenethylamine | Benzoic | 728 | 729 | Y | no fit | no fit |
| 271 | 4-Phenoxybenzaldehyde | 4-methoxybenzylamine | H | 606 | 607 | Y | no fit | no fit |
| 272 | 4-Phenoxybenzaldehyde | 4-methoxybenzylamine | Phenylacetic | 724 | 725 | Y | no fit | no fit |
| 273 | 4-Phenoxybenzaldehyde | 4-methoxybenzylamine | IBP | 794 | 795 | Y | no fit | no fit |
| 274 | 4-Phenoxybenzaldehyde | 4-methoxyphenethylamine | H | 620 | 621 | Y | no fit | no fit |
| 275 | 4-Phenoxybenzaldehyde | 4-methoxyphenethylamine | Phenylacetic | 738 | 739 | Y | no fit | no fit |
| 276 | 4-Phenoxybenzaldehyde | 4-methoxyphenethylamine | Benzoic | 724 | 725 | Y | no fit | no fit |
| 277 | 4-Propoxybenzaldehyde | 2-methoxyphenethylamine | H | 586 | 587 | Y | no fit | no fit |
| 278 | 4-Propoxybenzaldehyde | 2-methoxyphenethylamine | Phenylacetic | 704 | 705 | Y | no fit | no fit |
| 279 | 4-Propoxybenzaldehyde | 2-methoxyphenethylamine | Benzoic | 690 | 691 | Y | no fit | no fit |
| 280 | 4-Propoxybenzaldehyde | 3-chlorophenethylamine | H | 590 | 591 | Y | no fit | no fit |
| 281 | 4-Propoxybenzaldehyde | 3-chlorophenethylamine | Phenylacetic | 708 | 709 | Y | no fit | no fit |
| 282 | 4-Propoxybenzaldehyde | 3-chlorophenethylamine | Benzoic | 694 | 695 | Y | no fit | no fit |
| 283 | 4-Propoxybenzaldehyde | 4-methoxybenzylamine | H | 572 | 573 | Y | no fit | no fit |
| 284 | 4-Propoxybenzaldehyde | 4-methoxybenzylamine | Phenylacetic | 690 | 691 | Y | no fit | no fit |
| 285 | 4-Propoxybenzaldehyde | 4-methoxybenzylamine | Benzoic | 676 | 677 | Y | no fit | no fit |
| 286 | 4-Propoxybenzaldehyde | 4-methoxyphenethylamine | H | 586 | 587 | Y | no fit | no fit |
| 287 | 4-Propoxybenzaldehyde | 4-methoxyphenethylamine | Phenylacetic | 704 | 705 | Y | no fit | no fit |
| 288 | 4-Propoxybenzaldehyde | 4-methoxyphenethylamine | IBP | 774 | 775 | Y | no fit | no fit |

R1 = (S)-2,6-Diaminohexanoic acid
IBP = 4-isobutyl-α-methylphenyl acetic acid

TRG

| Cmpd # | R1: Amino Acid | R2: Aldehydes | X: Amines | R8: acids | M.W. | obs. (M + 1) M.W. | >85% LCQ | MC-1 IC50 μM | MC-4 IC50 μM |
|---|---|---|---|---|---|---|---|---|---|
| 1 | (S)-2,5-Diaminopentanoic acid | 4-butyramidobenzaldehyde | None (OH) | Cyclohexylacetic | 520 | 521 | Y | 1.934 | 5.04 |
| 2 | (S)-2,5-Diaminopentanoic acid | 4-hydroxybenzaldehyde | None (OH) | Cyclohexylacetic | 465 | 466 | Y | 2.24 | 0.94 |

-continued

TRG

| Cmpd # | R1: Amino Acid | R2: Aldehydes | X: Amines | R8: acids | M.W. | obs. (M + 1) M.W. | >85% LCQ | MC-1 IC50 µM | MC-4 IC50 µM |
|---|---|---|---|---|---|---|---|---|---|
| 3 | (S)-2,5-Diaminopentanoic acid | 4-Ethoxybenzaldehyde | None (OH) | Cyclohexylacetic | 493 | 494 | Y | 1.443 | 2.38 |
| 4 | (S)-2,5-Diaminopentanoic acid | 4-n-Propoxybenzaldehyde | None (OH) | Cyclohexylacetic | 507 | 508 | Y | 2.572 | 2.55 |
| 5 | (S)-2,5-Diaminopentanoic acid | 4-isopropoxybenzaldehyde | None (OH) | Cyclohexylacetic | 507 | 508 | Y | 2.517 | 0.96 |
| 6 | (S)-2,5-Diaminopentanoic acid | 4-n-butoxybenzaldehyde | None (OH) | Cyclohexylacetic | 521 | 522 | Y | 2.388 | 5 |
| 7 | (S)-2,5-Diaminopentanoic acid | 4-Ethylbenzaldehyde | None (OH) | Cyclohexylacetic | 477 | 478 | Y | 4.805 | 2.13 |
| 8 | (S)-2,5-Diaminopentanoic acid | 4-Amylbenzaldehyde | None (OH) | Cyclohexylacetic | 519 | 520 | Y | 6.213 | 13.81 |
| 9 | (S)-2,5-Diaminopentanoic acid | 4-hydroxybenzaldehyde | Ammonia | Cyclohexylacetic | 464 | 465 | Y | 3 | 1.95 |
| 10 | (S)-2,5-biaminopentanoic acid | 4-Ethoxybenzaldehyde | Ammonia | Cyclohexylacetic | 492 | 493 | Y | 0.46 | 1.76 |
| 11 | (S)-2,5-Diaminopentanoic acid | 4-n-Propoxybenzaldehyde | Ammonia | Cyclohexylacetic | 506 | 507 | Y | 0.441 | 1.52 |
| 12 | (S)-2,5-Diaminopentanoic acid | 4-n-butoxybenzaldehyde | Ammonia | Cyclohexylacetic | 520 | 521 | Y | 0.677 | 3.89 |
| 13 | (S)-2,5-Diaminopentanoic acid | 4-Ethylbenzaldehyde | Ammonia | Cyclohexylacetic | 476 | 477 | Y | 1.833 | 0.87 |
| 14 | (S)-2,5-Diaminopentanoic acid | 4-Amylbenzaldehyde | Ammonia | Cyclohexylacetic | 518 | 519 | Y | 1.69 | 9.39 |
| 15 | (S)-2,6-Diaminohexanoic acid | 4-hydroxybenzaldehyde | Ammonia | Acetic | 396 | 397 | Y | no fit | 63.91 |
| 16 | (S)-2,6-Diaminohexanoic acid | 4-Ethoxybenzaldehyde | Ammonia | Acetic | 424 | 425 | Y | 1.331 | 3.99 |
| 17 | (S)-2,6-Diaminohexanoic acid | 4-n-Propoxybenzaldehyde | Ammonia | Acetic | 438 | 439 | Y | 0.581 | 9.35 |
| 18 | (S)-2,6-Diaminohexanoic acid | 4-n-butoxybenzaldehyde | Ammonia | Acetic | 452 | 453 | Y | 0.306 | 7.95 |
| 19 | (S)-2,6-Diaminohexanoic acid | 4-Ethylbenzaldehyde | Ammonia | Acetic | 408 | 409 | Y | 1.461 | 2.04 |
| 20 | (S)-2,6-Diaminohexanoic acid | 4-Amylbenzaldehyde | Ammonia | Acetic | 450 | 451 | Y | 0.273 | 4.54 |

TRG 2419

R1 = (S)-2,5-Diaminopentanoic acid
R2 = 4-Acetimidobenzaldehyde
R8 = Succinic anhydride

| Cmpd # | X: Amine | R8: Amine | M.W. | obs. (M + 1) M.W. | >85% LCQ | MC-1 IC50 µM | MC-4 IC50 µM |
|---|---|---|---|---|---|---|---|
| 1 | Phenethylamine | Aniline | 632 | 633 | Y | 0.110 | 3.01 |
| 3 | Phenethylamine | Benzylamine | 646 | 647 | Y | 0.049 | 2.15 |
| 4 | Phenethylamine | Diethylamine | 612 | 613 | Y | 0.058 | 14.38 |
| 6 | Ammonia | Benzylamine | 542 | 543 | Y | 0.082 | 6.41 |
| 7 | Ammonia | Diethylamine | 508 | 509 | Y | 0.141 | 10.07 |
| 8 | Ammonia | None (OH) | 453 | 454 | Y | 1.088 | 6.91 |
| 9 | Ammonia | Aniline | 528 | 529 | Y | 0.239 | 10.00 |
| 10 | Ammonia | t-Butylamine | 508 | 509 |  | 0.093 | 4.32 |
| 11 | Ammonia | Ammonia | 452 | 453 | Y | 0.199 | 18.40 |
| 12 | Ammonia | Phenethylamine | 556 | 557 | Y | 0.073 | 16.67 |
| 13 | Ammonia | Piperidine | 520 | 521 | Y | 0.073 | 2.51 |

TRG 2420

R1 = (S)-2,5-Diaminopentanoic acid
R2 = 4-Acetimidobenzaldehyde

| Cmpd # | X: Amine | R8: Anhydride | R8: Amine | M.W. | obs. (M + 1) M.W. | >85% LCQ | MC-1 IC50 µM | MC-4 IC50 µM |
|---|---|---|---|---|---|---|---|---|
| 1 | phenethylamine | glutaric anhydride | isopropyl amine | 613 | 613 | Y | 0.046 | 1.50 |
| 2 | phenethylamine | glutaric anhydride | benzyl amine | 60 | 661 | Y | 0.076 | 4.05 |
| 3 | phenethylamine | glutaric anhydride | diethyl amine | 626 | 627 | Y | 0.030 | 8.23 |
| 4 | phenethylamine | glutaric anhydride | phenethylamine | 674 | 675 | Y | 0.068 | 4.17 |
| 5 | phenethylamine | 3-oxabicyclo(3.1.0)hexane-2,4-dione anhydride | isopropyl amine | 610 | 611 | Y | 0.043 | 9.88 |
| 6 | phenethylamine | 3-oxabicyclo(3.1.0)hexane-2,4-dione anhydride | benzyl amine | 658 | 659 | Y | 0.103 | 5.13 |
| 7 | phenethylamine | 3-oxabicyclo(3.1.0)hexane-2,4-dione anhydride | diethyl amine | 624 | 625 | Y | 0.063 | 1.81 |
| 8 | phenethylamine | 3-oxabicyclo(3.1.0)hexane-2,4-dione anhydride | phenethylamine | 672 | 673 | Y | 0.208 | 2.36 |
| 9 | phenethylamine | diglycolic anhydride | isopropyl amine | 614 | 615 | Y | 0.040 | 3.23 |
| 10 | phenethylamine | diglycolic anhydride | benzyl amine | 662 | 663 | Y | 0.055 | 0.94 |
| 11 | phenethylamine | diglycolic anhydride | diethyl amine | 628 | 629 | Y | 0.028 | 4.63 |
| 12 | phenethylamine | diglycolic anhydride | phenethylamine | 676 | 677 | Y | 0.079 | 1.53 |
| 13 | phenethylamine | phthalic anhydride | isopropyl amine | 646 | 647 | Y | 0.065 | 0.67 |
| 14 | phenethylamine | phthalic anhydride | benzyl amine | 694 | 695 | Y | 0.135 | 0.29 |
| 15 | phenethylamine | phthalic anhydride | diethyl amine | 660 | 661 | Y | 0.070 | 1.37 |
| 16 | phenethylamine | phthalic anhydride | phenethylamine | 708 | 709 | Y | 0.164 | 1.20 |

TRG 2420

R1 = (S)-2,5-Diaminopentanoic acid
R2 = 4-Acetimidobenzaldehyde

| Cmpd # | X: Amine | R8: Anhydride | R8: Amine | M.W. | obs. (M + 1) M.W. | >85% LCQ | MC-1 IC50 μM | MC-4 IC50 μM |
|---|---|---|---|---|---|---|---|---|
| 17 | phenethylamine | 3-(t-butyl dimethyl silyloxy) glutaric anhydride | isopropyl amine | 584 | 585 | Y | 0.099 | 2.30 |
| 18 | phenethylamine | 3-(t-butyl dimethyl silyloxy) glutaric anhydride | benzyl amine | 632 | 633 | Y | 0.057 | 3.40 |
| 19 | phenethylamine | 3-(t-butyl dimethyl silyloxy) glutaric anhydride | diethyl amine | 598 | 599 | Y | 0.060 | 10.66 |
| 20 | phenethylamine | 3-(t-butyl dimethyl silyloxy) glutaric anhydride | phenethylamine | 646 | 647 | Y | 0.123 | 7.59 |
| 21 | ammonia | glutaric anhydride | isopropyl amine | 628 | 629 | Y | 0.023 | 4.18 |
| 22 | ammonia | glutaric anhydride | benzyl amine | 676 | 677 | Y | 0.027 | 43.99 |
| 23 | ammonia | glutaric anhydride | diethyl amine | 642 | 643 | Y | 0.020 | 2.65 |
| 24 | ammonia | glutaric anhydride | phenethylamine | 690 | 691 | Y | 0.118 | 13.47 |
| 25 | ammonia | 3-oxabicyclo(3.1.0)hexane-2,4-dione anhydride | isopropyl aine | 508 | 509 | Y | 0.103 | 4.82 |
| 26 | ammonia | 3-oxabicyclo(3.1.0)hexane-2,4-dione anhydride | benzyl amine | 556 | 557 | Y | 0.093 | 5.01 |
| 27 | ammonia | 3-oxabicyclo(3.1.0)hexane-2,4-dione anhydride | diethyl amine | 522 | 523 | Y | 0.040 | 4.19 |
| 28 | ammonia | 3-oxabicyclo(3.1.0)hexane-2,4-dione anhydride | phenethylamine | 570 | 571 | Y | 0.203 | 4.08 |
| 29 | ammonia | diglycolic anhydride | isopropyl amine | 506 | 507 | Y | 0.129 | 35.02 |
| 30 | ammonia | diglycolic anhydride | benzyl amine | 554 | 555 | Y | 0.057 | 3.08 |
| 31 | ammonia | diglycolic anhydride | diethyl amine | 520 | 521 | Y | 0.121 | 48.31 |
| 32 | ammonia | diglycolic anhydride | phenethylamine | 568 | 569 | Y | 0.344 | 12.29 |
| 33 | ammonia | phthalic anhydride | isopropyl amine | 510 | 511 | Y | 0.307 | 4.30 |
| 34 | ammonia | phthalic anhydride | benzyl amine | 558 | 559 | Y | 0.271 | 0.94 |
| 35 | ammonia | phthalic anhydride | diethyl amine | 524 | 525 | Y | 0.218 | 1.42 |
| 36 | ammonia | phthalic anhydride | phenethylamine | 572 | 573 | Y | 0.257 | 0.54 |
| 37 | ammonia | 3-(t-butyldimethyl silyloxy) glutaric anhydride | isopropyl amine | 542 | 543 | Y | 0.186 | 2.17 |
| 38 | ammonia | 3-(t-butyldimethyl silyloxy) glutaric anhydride | benzyl amine | 590 | 591 | Y | 0.084 | 0.35 |
| 39 | ammonia | 3-(t-butyldimethyl silyloxy) glutaric anhydride | diethyl amine | 556 | 557 | Y | 0.237 | 33.10 |
| 40 | ammonia | 3-(t-butyldimethyl silyloxy) glutaric anhydride | phenethylamine | 604 | 605 | Y | 0.460 | 12.11 |

TRG 2421

R1 = L-Lysine

| Cmpd # | R2: benzaldehyde | X: amine | R8: acid | M.W. | obs. (M + 1) M.W. | >85% LCQ | MC-1 IC50 μM | MC-4 IC50 μM |
|---|---|---|---|---|---|---|---|---|
| 1 | 3,5-bis(trifluoromethyl)benzaldehyde | phenethylamine | benzoic acid | 683 | 684 | Y | 4.18 | 1.78 |
| 2 | 3,5-bis(trifluoromethyl)benzaldehyde | phenethylamine | p-toluic acid | 697 | 698 | Y | 3.73 | 3.03 |
| 3 | 3,5-bis(trifluoromethyl)benzaldehyde | phenethylamine | 4-bromobenzoic acid | 762 | 763 | Y | 4.91 | 9.64 |
| 4 | 3,5-bis(trifluoromethyl)benzaldehyde | phenethylamine | p-anisic acid | 713 | 714 | Y | 2.57 | 2.81 |
| 5 | 3,5-bis(trifluoromethyl)benzaldehyde | phenethylamine | 4-biphenylcarboxylic acid | 759 | 760 | Y | 11.24 | 9.41 |
| 6 | 3,5-bis(trifluoromethyl)benzaldehyde | tyramine | benzoic acid | 699 | 700 | Y | 2.25 | 0.76 |
| 7 | 3,5-bis(trifluoromethyl)benzaldehyde | tyramine | p-toluic acid | 713 | 714 | Y | 3.19 | 4.53 |
| 8 | 3,5-bis(trifluoromethyl)benzaldehyde | tyramine | 4-bromobenzoic acid | 778 | 779 | Y | 5.00 | 5.99 |
| 9 | 3,5-bis(trifluoromethyl)benzaldehyde | tyramine | p-anisic acid | 729 | 730 | Y | 1.50 | 1.75 |
| 10 | 3,5-bis(trifluoromethyl)benzaldehyde | tyramine | 4-biphenylcarboxylic acid | 775 | 776 | Y | 4.77 | |
| 11 | 3,5-bis(trifluoromethyl)benzaldehyde | 2-(4-methoxyphenyl)ethylamine | benzoic acid | 713 | 714 | Y | | |
| 12 | 3,5-bis(trifluoromethyl)benzaldehyde | 2-(4-methoxyphenyl)ethylamine | p-toluic acid | 727 | 728 | Y | 2.57 | 1.40 |
| 13 | 3,5-bis(trifluoromethyl)benzaldehyde | 2-(4-methoxyphenyl)ethylamine | 4-bromobenzoic acid | 792 | 793 | Y | 4.41 | 8.11 |
| 14 | 3,5-bis(trifluoromethyl)benzaldehyde | 2-(4-methoxyphenyl)ethylamine | p-anisic acid | 743 | 744 | Y | 3.47 | 1.69 |
| 15 | 3,5-bis(trifluoromethyl)benzaldehyde | 2-(4-methoxyphenyl)ethylamine | 4-biphenylcarboxylic acid | 789 | 790 | Y | 7.81 | |
| 16 | 3,5-bis(trifluoromethyl)benzaldehyde | 3,4 dimethoxyphenylethylamine | benzoic acid | 743 | 744 | Y | 2.42 | 0.36 |
| 17 | 3,5-bis(trifluoromethyl)benzaldehyde | 3,4 dimethoxyphenylethylamine | p-toluic acid | 757 | 758 | Y | 2.06 | 0.83 |
| 18 | 3,5-bis(trifluoromethyl)benzaldehyde | 3,4 dimethoxyphenylethylamine | 4-bromobenzoic acid | 822 | 823 | Y | 4.79 | 1.35 |
| 19 | 3,5-bis(trifluoromethyl)benzaldehyde | 3,4 dimethoxyphenylethylamine | p-anisic acid | 773 | 774 | Y | 1.63 | |
| 20 | 3,5-bis(trifluoromethyl)benzaldehyde | 3,4 dimethoxyphenylethylamine | 4-biphenylcarboxylic acid | 819 | 820 | Y | 4.22 | 1.97 |
| 21 | 3,5-bis(trifluoromethyl)benzaldehyde | 4-ethoxyphenethylamine | benzoic acid | 727 | 728 | Y | 2.59 | 3.98 |
| 22 | 3,5-bis(trifluoromethyl)benzaldehyde | 4-ethoxyphenethylamine | p-toluic acid | 741 | 742 | Y | 3.02 | 8.22 |
| 23 | 3,5-bis(trifluoromethyl)benzaldehyde | 4-ethoxyphenethylamine | 4-bromobenzoic acid | 806 | 807 | Y | 7.44 | 8.22 |
| 24 | 3,5-bis(trifluoromethyl)benzaldehyde | 4-ethoxyphenethylamine | p-anisic acid | 757 | 758 | Y | 2.35 | |
| 25 | 3,5-bis(trifluoromethyl)benzaldehyde | 4-ethoxyphenethylamine | 4-biphenylcarboxylic acid | 803 | 804 | Y | 10.00 | 10.93 |
| 26 | 3,5-bis(trifluoromethyl)benzaldehyde | 4-phenoxyphenethylamine | benzoic acid | 775 | 776 | Y | 11.39 | 12.91 |
| 27 | 3,5-bis(trifluoromethyl)benzaldehyde | 4-phenoxyphenethylamine | p-toluic acid | 789 | 790 | Y | 7.26 | 9.26 |
| 28 | 3,5-bis(trifluoromethyl)benzaldehyde | 4-phenoxyphenethylamine | 4-bromobenzoic acid | 854 | 855 | Y | 15.74 | |
| 29 | 3,5-bis(trifluoromethyl)benzaldehyde | 4-phenoxyphenethylamine | p-anisic acid | 805 | 806 | Y | 5.10 | 7.92 |
| 30 | 3,5-bis(trifluoromethyl)benzaldehyde | 4-phenoxyphenethylamine | 4-biphenylcarboxylic acid | 851 | 852 | Y | 36.36 | |
| 31 | 3,5-bis(trifluoromethyl)benzaldehyde | 2-(4-chlorophenyl)ethylamine | benzoic acid | 717 | 718 | Y | 5.90 | 2.77 |
| 32 | 3,5-bis(trifluoromethyl)benzaldehyde | 2-(4-chlorophenyl)ethylamine | p-toluic acid | 731 | 732 | Y | 5.77 | 4.15 |
| 33 | 3,5-bis(trifluoromethyl)benzaldehyde | 2-(4-chlorophenyl)ethylamine | 4-bromobenzoic acid | 796 | 797 | Y | 6.93 | |
| 34 | 3,5-bis(trifluoromethyl)benzaldehyde | 2-(4-chlorophenyl)ethylamine | p-anisic acid | 747 | 748 | Y | 4.98 | 2.64 |
| 35 | 3,5-bis(trifluoromethyl)benzaldehyde | 2-(4-chlorophenyl)ethylamine | 4-biphenylcarboxylic acid | 793 | 794 | Y | | |

-continued

TRG 2421

R1 = L-Lysine

| Cmpd # | R2: benzaldehyde | X: amine | R8: acid | M.W. | obs. (M + 1) M.W. | >85% LCQ | MC-1 IC50 μM | MC-4 IC50 μM |
|---|---|---|---|---|---|---|---|---|
| 36 | 3,5-bis(trifluoromethyl)benzaldehyde | 2-(3-methoxyphenyl)ethylamine | benzoic acid | 713 | 714 | Y | 3.99 | 0.89 |
| 37 | 3,5-bis(trifluoromethyl)benzaldehyde | 2-(3-methoxyphenyl)ethylamine | p-toluic acid | 727 | 728 | Y | 3.08 | |
| 38 | 3,5-bis(trifluoromethyl)benzaldehyde | 2-(3-methoxyphenyl)ethylamine | 4-bromobenzoic acid | 792 | 793 | Y | 7.47 | 1.34 |
| 39 | 3,5-bis(trifluoromethyl)benzaldehyde | 2-(3-methoxyphenyl)ethylamine | p-anisic acid | 743 | 744 | Y | 3.30 | 1.04 |
| 40 | 3,5-bis(trifluoromethyl)benzaldehyde | 2-(3-methoxyphenyl)ethylamine | 4-biphenylcarboxylic acid | 789 | 790 | Y | 12.10 | 3.98 |
| 41 | 3-(trifluoromethyl)benzaldehyde | phenethylamine | benzoic acid | 615 | 616 | Y | 2.51 | 1.72 |
| 42 | 3-(trifluoromethyl)benzaldehyde | phenethylamine | p-anisic acid | 645 | 646 | Y | 2.15 | |
| 43 | 3-(trifluoromethyl)benzaldehyde | 2-(4-methoxyphenyl)ethylamine | benzoic acid | 645 | 646 | Y | 2.15 | 1.76 |
| 44 | 3-(trifluoromethyl)benzaldehyde | 2-(4-methoxyphenyl)ethylamine | p-anisic acid | 675 | 676 | Y | 1.54 | 1.42 |
| 45 | 3-(trifluoromethyl)benzaldehyde | 4-ethoxyphenethylamine | benzoic acid | 659 | 660 | Y | 0.98 | 2.73 |
| 46 | 3-(trifluoromethyl)benzaldehyde | 4-ethoxyphenethylamine | p-anisic acid | 689 | 690 | Y | 1.58 | |
| 47 | 3-(trifluoromethyl)benzaldehyde | 2-(3-methoxyphenyl)ethylamine | benzoic acid | 645 | 646 | Y | 2.71 | 1.37 |
| 48 | 3-(trifluoromethyl)benzaldehyde | 2-(3-methoxyphenyl)ethylamine | p-anisic acid | 675 | 676 | Y | 1.74 | 0.95 |

TRG 2422

| Cmpd # | R1: Amino Acid | R1a: Amino Acid | R2: Aldehyde | X: Amine |
|---|---|---|---|---|
| 1 | Fmoc-5-Aminovaleric acid | t-Boc-L-glycine | 4-acetamidobenzaldehyde | 2-methoxybenzylamine |
| 2 | Fmoc-5-Aminovaleric acid | t-Boc-L-glycine | 4-acetamidobenzaldehyde | 4-methoxybenzylamine |
| 3 | Fmoc-5-Aminovaleric acid | t-Boc-L-glycine | 4-acetamidobenzaldehyde | cyclohexylamine |
| 4 | Fmoc-5-Aminovaleric acid | t-Boc-L-glycine | 4-acetamidobenzaldehyde | phenethylamine |
| 5 | Fmoc-5-Aminovaleric acid | t-Boc-L-glycine | 4-acetamidobenzaldehyde | ammonia |

TRG 2424

| Cmpd # | R1 | R2 | X | R8 | M.W. | obs. (M + 1) M.W. | >85% LCQ | MC-1 IC50 μM IC50 | MC-4 IC50 μM IC50 |
|---|---|---|---|---|---|---|---|---|---|
| 2424#1 | L-ornithine | 4-acetamidobenzaldehyde | ammonia | valeric acid | 454 | 455 | Y | 0.19 | 53.95 |
| 2424#2 | L-ornithine | 4-acetamidobenzaldehyde | ammonia | 4-phenoxybutyric acid | 530 | 531 | Y | 0.05 | 7.77 |
| 2424#3 | L-ornithine | 4-acetamidobenzaldehyde | ammonia | glutaric anhydride | 452 | 453 | Y | 0.09 | 3.04 |
| 2424#4 | L-ornithine | 4-acetamidobenzaldehyde | phenethylamine | valeric acid | 558 | 559 | Y | 0.02 | 4.37 |
| 2424#5 | L-ornithine | 4-acetamidobenzaldehyde | phenethylamine | 4-phenoxybutyric acid | 634 | 635 | Y | 0.05 | 1.51 |
| 2424#6 | L-ornithine | 4-acetamidobenzaldehyde | phenethylamine | glutaric anhydride | 556 | 557 | Y | 0.11 | 0.91 |
| 2424#7 | L-lysine | 4-acetamidobenzaldehyde | ammonia | valeric acid | 468 | 469 | Y | 0.46 | |
| 2424#8 | L-lysine | 4-acetamidobenzaldehyde | ammonia | 4-phenoxybutyric acid | 544 | 545 | Y | 0.22 | 5.18 |
| 2424#9 | L-lysine | 4-acetamidobenzaldehyde | ammonia | glutaric anhydride | 466 | 467 | Y | 0.19 | 3.25 |
| 2424#10 | L-lysine | 4-acetamidobenzaldehyde | phenethylamine | valeric acid | 572 | 573 | Y | 0.08 | 12.86 |
| 2424#11 | L-lysine | 4-acetamidobenzaldehyde | phenethylamine | 4-phenoxybutyric acid | 648 | 649 | Y | 0.21 | 3.51 |
| 2424#12 | L-lysine | 4-acetamidobenzaldehyde | phenethylamine | glutaric anhydride | 570 | 571 | Y | 0.14 | 0.78 |

Some of the isoquinoline compounds were further tested for binding to MCR-3 and MCR-5. Table 2 shows the $IC_{50}$ values for some of the isoquinoline compounds shown in Table 1. As shown in Table 2, various isoquinoline compounds bound to MCR-3 and MCR-5. Several isoquinoline compounds exhibited similar affinities between all four MC receptors whereas other isoquinoline compounds showed specificity for at least one MC receptor over another MC receptor (compare Tables 1 and 2).

TABLE 2

Binding of Isoquinoline Compounds to MCR-3 and MCR-5
IN VITRO MELANOCORTIN RECEPTOR PROFILE
RECEPTOR BINDING RESULTS

| Array/ Compound # | R1: Amino Acids | R2: Aldehydes | R3: amines | R4: Substit. on R1 | MW | M-3 IC50 ($\mu$M) | MC-5 IC50 ($\mu$M) |
|---|---|---|---|---|---|---|---|
| TRG 2403 | | | | | | | |
| 3 | L-Lys | 4-Acetamido-benzaldehyde | 2-methoxybenzylamine | | 516 | >10 | >10 |
| TRG 2404 | | | | | | | |
| 3 | L-Lys | 4-Bromobenzaldehyde | 2-methoxybenzylamine | | 552 | 0.9 | 1 |
| TRG 2405 | | | | | | | |
| 64 | Glycine | 4-Cyanobenzaldehyde | Cyclohexylamine | | 393 | | |
| 77 | Glycine | 3-Methoxy-4-hydroxy-5-bromobenzaldehyde | Cyclohexylamine | | 477 | >10 | >10 |
| 156 | (S)-2,3-Diamino-propionic acid | 4-Hydroxybenzaldehyde | Cyclohexylamine | | 423 | 23.71 | 2.83 |
| 190 | (S)-2,6-Diamino-hexanoic acid | 2,4-Dichlorobenzaldehyde | Cyclohexylamine | | 518 | 2.24[2] | 0.80 |
| 235 | (S)-2,6-Diamino-hexanoic acid | 4-(Dimethylamino)benzaldehyde | Cyclohexylamine | | 492 | 22.27 | 2.82 |
| 238 | (S)-2,6-Diamino-hexanoic acid | 4-(Trifluoromethyl)benzaldehyde | Cyclohexylamine | | 517 | >10 | 0.43 |
| 239 | (S)-2,6-Diamino-hexanoic acid | 4-Acetamidobenzaldehyde | Cyclohexylamine | | 492 | 39.79 | 8.72 |
| 241 | (S)-2,6-Diamino-hexanoic acid | 4-Biphenylcarboxaldehyde | Cyclohexylamine | | 525 | 7.45 | 1.04 |
| 242 | (S)-2,6-Diamino-hexanoic acid | 4-Bromobenzaldehyde | Cyclohexylamine | | 528 | 0.55[2] | 0.41 |
| 246 | (S)-2,6-Diamino-hexanoic acid | 4-Hydroxybenzaldehyde | Cyclohexylamine | | 465 | >10 | >10 |
| 252 | (S)-2,6-Diamino-hexanoic acid | 4-Phenoxybenzaldehyde | Cyclohexylamine | | 541 | 6.49 | 1.86 |
| 253 | (S)-2,6-Diamino-hexanoic acid | 4-Propoxybenzaldehyde | Cyclohexylamine | | 507 | 9.68 | 2.77 |
| 262 | (S)-2,6-Diamino-hexanoic acid | 8-Hydroxy-quinoline-2-carboxaldehyde | Cyclohexylamine | | | >10 | >10 |
| 268 | (S)-2,6-Diamino-hexanoic acid | 4-Methoxy-3-(sulfonic acid)benzaldehyde | Cyclohexylamine | | 559 | | |
| TRG 2407 | | | | | | | |
| 39 | (S)-2,6-Diamino-hexanoic acid | 2,4-Dichlorobenzaldehyde | Ammonia | | 435 | 0.28 | 0.24 |
| 67 | (S)-2,6-Diamino-hexanoic acid | 4-Acetamidobenzaldehyde | Cyclopentylamine | | 478 | 20.86 | 4.16 |

TABLE 2-continued

Binding of Isoquinoline Compounds to MCR-3 and MCR-5
IN VITRO MELANOCORTIN RECEPTOR PROFILE
RECEPTOR BINDING RESULTS

| Array/ Compound # | R1: Amino Acids | R2: Aldehydes | R3: amines | R4: Substit. on R1 | MW | M-3 IC50 ($\mu$M) | MC-5 IC50 ($\mu$M) |
|---|---|---|---|---|---|---|---|
| TRG 2408 | | | | | | | |
| 30 | (R)-2,6-Diamino-hexanoic acid | 4-Acetamidobenzaldehyde | Cyclohexylamine | Boc | 491 | 40.43 | 9.35 |
| 57 | (S)-2,5-Diamino-pentanoic acid | 4-Acetamidobenzaldehyde | 2-Methoxybenzylamine | Phenyl-acetic acid | 591 | 5.17 | 1.70 |
| 62 | (S)-2,5-Diamino-pentanoic acid | 2,4-Dichlorobenzaldehyde | 2-Methoxybenzylamine | Glycine | 555 | 5.71 | 2.79 |
| TRG 2409 | | | | | | | |
| 2 | (S)-2,6-Diamino-hexanoic acid | 4-Nitrobenzaldehyde | 2-Methoxybenzylamine | R5: Butyric Acid | 543 | | |
| 14 | (S)-2,6-Diamino-hexanoic acid | 4-Nitrobenzaldehyde | Cyclohexylamine | R5: Butyric Acid | 519 | | |

These results show that isoquinoline compounds are MC receptor ligands.

EXAMPLE V

Effect of Isoquinoline Compounds on Melanocortin Receptor Signaling

This example shows the effect of isoquinoline compounds on MC receptor signaling.

Various isoquinoline compounds were tested for their ability to activate MC receptor by measuring cAMP as described in Example III. Table 3 shows the EC50 values, the effective concentration for achieving 50% of maximal cAMP production, for various isoquinoline compounds administered to HEK 293 cells expressing MCR-1, MCR-3, MCR-4 or MCR-5. The EC50 values shown in Table 3 are $\mu$M. Table 3 also shows the maximum amount (in pmol) of cAMP produced in response to a given isoquinoline compound. As shown in Table 3, isoquinoline compounds were able to activate various MC receptors with a range of affinities.

TABLE 3

In vitro Binding and Activation of Isoquinoline Compounds to Melanocortin Receptors
IN VITRO MELANOCORTIN RECEPTOR PROFILE
Functional (cAMP) Results

| Array/ Compound # | R1: Amino Acids | R2: Aldehydes | R3: amines | R4: Substit. on R1 | MW | MC-1 EC50 | Max (pmole) | MC-3 EC50 | MC-4 EC50 | Max (pmole) | MC-5 EC50 |
|---|---|---|---|---|---|---|---|---|---|---|---|
| TRG 2403 | | | | | | | | | | | |
| 3 | L-Lys | 4-Acetamido-benzaldehyde | 2-methoxybenzyl-amine | | 516 | 1.1 | 20 | | 47.64 | 50.71 | |
| TRG 2404 | | | | | | | | | | | |
| 3 | L-Lys | 4-Bromobenz-aldehyde | 2-methoxybenzyl-amine | | 552 | 2.2 | 20 | | | | |
| TRG 2405 | | | | | | | | | | | |
| 64 | Glycine | 4-Cyanobenz-aldehyde | Cyclohexyl-amine | | 393 | | | | | | |

TABLE 3-continued

In vitro Binding and Activation of Isoquinoline Compounds to Melanocortin Receptors
IN VITRO MELANOCORTIN RECEPTOR PROFILE
Functional (cAMP) Results

| Array/ Compound # | R1: Amino Acids | R2: Aldehydes | R3: amines | R4: Substit. on R1 | MW | MC-1 EC50 | MC-1 Max (pmole) | MC-3 EC50 | MC-4 EC50 | MC-4 Max (pmole) | MC-5 EC50 |
|---|---|---|---|---|---|---|---|---|---|---|---|
| 77 | Glycine | 3-Methoxy-4-hydroxy-5-bromobenzaldehyde | Cyclohexylamine | | 477 | >50 | | >50 | >50 | | >50 |
| 156 | (S)-2,3-Diaminopropionic acid | 4-Hydroxybenzaldehyde | Cyclohexylamine | | 423 | 20.64 | 16.01 | >50 | >50 | | >50 |
| 190 | (S)-2,6-Diaminohexanoic acid | 2,4-Dichlorobenzaldehyde | Cyclohexylamine | | 518 | 8.52 | 33.56 | | 46.29 | 100.48 | |
| 235 | (S)-2,6-Diaminohexanoic acid | 4-(Dimethylamino)benzaldehyde | Cyclohexylamine | | 492 | 29.9 | 17.07 | | >50 | | |
| 238 | (S)-2,6-Diaminohexanoic acid | 4-(Trifluoromethyl)benzaldehyde | Cyclohexylamine | | 517 | 19.92 | 29.82 | >50 | >50 | | >50 |
| 239 | (S)-2,6-Diaminohexanoic acid | 4-Acetamidobenzaldehyde | Cyclohexylamine | | 492 | 3.67 | 20.6 | >50 | >50 | | >50 |
| 241 | (S)-2,6-Diaminohexanoic acid | 4-Biphenylcarboxaldehyde | Cyclohexylamine | | 525 | 10.36 | 66.67 | >50 | 28.48 | 32.32 | >50 |
| 242 | (S)-2,6-Diaminohexanoic acid | 4-Bromobenzaldehyde | Cyclohexylamine | | 528 | 13.05 | 55.89 | >50 | >50 | | >50 |
| 246 | (S)-2,6-Diaminohexanoic acid | 4-Hydroxybenzaldehyde | Cyclohexylamine | | 465 | 23.72 | 12.48 | >50 | >50 | | >50 |
| 252 | (S)-2,6-Diaminohexanoic acid | 4-Phenoxybenzaldehyde | Cyclohexylamine | | 541 | 15.97 | 33.07 | >50 | 18.48 | 39.24 | >50 |
| 253 | (S)-2,6-Diaminohexanoic acid | 4-Propoxybenzaldehyde | Cyclohexylamine | | 507 | 8.5 | 22.55 | >50 | 16.61 | 69.11 | >50 |
| 262 | (S)-2,6-Diaminohexanoic acid | 8-Hydroxyquinoline-2-carboxaldehyde | Cyclohexylamine | | | >50 | | >50 | >50 | | >50 |
| 268 | (S)-2,6-Diaminohexanoic acid | 4-Methoxy-3-(sulfonic acid)benzaldehyde | Cyclohexylamine | | 559 | | | | | | |
| TRG 2407 | | | | | | | | | | | |
| 39 | (S)-2,6-Diaminohexanoic acid | 2,4-Dichlorobenzaldehyde | Ammonia | | 435 | | | | | | |
| 67 | (S)-2,6-Diaminohexanoic acid | 4-Acetamidobenzaldehyde | Cyclopentylamine | | 478 | | | | | | |
| TRG 2408 | | | | | | | | | | | |
| 30 | (R)-2,6-Diaminohexanoic acid | 4-Acetamidobenzaldehyde | Cyclohexylamine | Boc | 491 | 2.83 | 125.79 | | | | |

TABLE 3-continued

In vitro Binding and Activation of Isoquinoline Compounds to Melanocortin Receptors
IN VITRO MELANOCORTIN RECEPTOR PROFILE
Functional (cAMP) Results

| Array/ Compound # | R1: Amino Acids | R2: Aldehydes | R3: amines | R4: Substit. on R1 | MW | MC-1 EC50 | Max (pmole) | MC-3 EC50 | MC-4 EC50 | Max (pmole) | MC-5 EC50 |
|---|---|---|---|---|---|---|---|---|---|---|---|
| 57 | (S)-2,5-Diamino-pentanoic acid | 4-Acetamido-benzaldehyde | 2-Methoxy-benzylamine | Phenyl-acetic acid | 591 | <0.1 | | | | | |
| 62 | (S)-2,5-Diamino-pentanoic acid | 2,4-Dichlorobenz-aldehyde | 2-Methoxy-benzylamine | Glycine | 555 | <0.1 | | | | | |
| TRG 2409 | | | | | | | | | | | |
| 2 | (S)-2,6-Diamino-hexanoic acid | 4-Nitrobenz-aldehyde | 2-Methoxy-benzylamine | R5: Butyric Acid | 543 | $1.01 \pm 0.26^3$ | 200 | | | | |
| 14 | (S)-2,6-Diamino-hexanoic acid | 4-Nitrobenz-aldehyde | Cyclohexyl-amine | R5: Butyric Acid | 519 | $0.87 \pm 0.2^3$ | 170 | | | | |

These results show that isoquinoline compounds are MC receptor ligands that can activate MC receptors.

EXAMPLE VI

Reduction of Lipopolysaccharide-Induced Tumor Necrosis Factor Levels in Mice

This example describes the effectiveness of isoquinoline compounds for decreasing tumor necrosis factor (TNF) levels in lipopolysaccharide (LPS; endotoxin) treated mice.

BALB/c female mice weighing approximately 20 g were placed into a control group and a treated group. Five mg/kg of LPS in 0.9% saline was administered (100 μl to give 100 μg LPS per mouse) by intraperitoneal (IP) injection to all mice. Mice in the treatment group received either 30, 100, 300 or 600 μg of various isoquinoline compounds per mouse in a volume of 100 μl of PBS. Control mice received 100 μl of saline alone. One minute after initial injections all mice received the LPS injection. As a positive control, 100 μg of HP 228 was injected per mouse.

Blood samples were collected from the orbital sinus of treated and control mice 90 minutes or 105 minutes after LPS administration. The plasma was separated by centrifugation at 3000×g for 5 min and stored at −20° C. Samples were thawed and diluted, if TNF-α concentration was greater than 3200 μg/ml, with PBS containing 1% bovine serum albumin, 10% donor horse serum, 1% normal mouse serum, 0.05% TWEEN-20 and 0.05% thimerosal. A 100 μl sample of plasma was assayed by ELISA for TNF-α. Briefly, ELISA plates were coated with hamster anti-mouse TNF-α antibody (Genzyme; Cambridge Mass.). Samples or known concentrations of TNF-α were added to the coated plates and incubated for 2 hr at 37° C. Plates were washed and subsequently incubated with biotinylated rabbit anti-mouse TNG-α for 1 hr at 37° C. Plates were washed and incubated with streptavidin-HRP for 1 hr at 37° C., and HRP activity was detected with hydrogen peroxide and o-phenylenediamine (OPD) using standard immunoassay procedures.

The mean (±SEM) TNG-α level in five mice from each group was determined and the percent reduction in TNG-α levels was calculated. As shown in Table 4, treatment of mice with various isoquinoline compounds decreased the levels of TNG-α in a dose dependent manner when compared to saline controls. TRG 2408-30 was particularly effective at inhibiting TNG-α using both i.p. and oral administration.

TABLE 4

Effect of Isoquinoline Compounds on Cytokines
IN VIVO MELANOCORTIN RECEPTOR PROFILE
In Vivo Cytokine Data for Compounds Received
90 or 105 Minutes

| Array/ Compound # | % TNF-α Inhibition | | | | | % IL-10 Induction | | | | |
|---|---|---|---|---|---|---|---|---|---|---|
| | IP | | | Oral | | IP | | | Oral | |
| | 30 | 100 | 300 | 300 | 600 | 30 | 100 | 300 | 300 | 600 |
| TRG 2403 | | | | | | | | | | |
| 3 | 34 ± 14 | | 83 ± 11* | | | 50 ± 16 | | 180 ± 50* | | |
| TRG 2404 | | | | | | | | | | |
| 3 | 39 ± 4 | | 81 ± 12* | | | 82 ± 24 | | 246 ± 75** | | |

TABLE 4-continued

Effect of Isoquinoline Compounds on Cytokines
IN VIVO MELANOCORTIN RECEPTOR PROFILE
In Vivo Cytokine Data for Compounds Received
90 or 105 Minutes

| Array/ | % TNF-α Inhibition | | | | | % IL-10 Induction | | | | |
|---|---|---|---|---|---|---|---|---|---|---|
| Compound | IP | | | Oral | | IP | | | Oral | |
| # | 30 | 100 | 300 | 300 | 600 | 30 | 100 | 300 | 300 | 600 |
| TRG 2405 | | | | | | | | | | |
| 64 | 34 ± 12 | | 87 ± 2* | | | −13 ± 12 | | 57 ± 28 | | |
| 77 | 52 ± 13* | 5 ± 7 | 85 ± 13* | | | −14 ± 8 | 9 ± 9 | 68 ± 14 | | |
| 156 | 30 ± 13 | 12 ± 7 | 48 ± 16 | | | 17 ± 23 | −5 ± 11 | 43 ± 34 | | |
| 190 | 70 ± 11* | −6 ± 7 | 83 ± 11* | | | 25 ± 30 | 13 ± 14 | 109 ± 31** | | |
| 235 | 8 ± 7 | 39 ± 7 | 50 ± 9 | | | −11 ± 13 | 45 ± 18 | 113 ± 15** | | |
| 238 | 19 ± 7 | 73 ± 1* | 84 ± 18* | | 6 ± 28 | −17 ± 7 | 151 ± 26** | 118 ± 25** | | 65 ± 15* |
| 239 | 13 ± 8 | 10 ± 6 | 66 ± 9* | | 9 ± 14 | 44 ± 35 | −29 ± 6 | 197 ± 34** | | 46 ± 14 |
| 241 | 26 ± 15 | 75 ± 3* | 45 ± 9 | 38 ± 9* | 74 ± 8* | 117 ± 21 | 310 ± 35** | 406 ± 46** | 9 ± 23 | 77 ± 37* |
| 242 | 21 ± 8 | 60 ± 4* | 68 ± 5* | | | | −9 ± 7 | | | |
| 246 | 27 ± 9 | | 80 ± 3* | | −29 ± 31* | | | | | 30 ± 5* |
| 252 | 49 ± 14* | | 90 ± 2* | | 55 ± 13* | 2 ± 13 | | 307 ± 43* | | 69 ± 19* |
| 253 | 46 ± 8 | | 80 ± 7 | | | 7 ± 21 | | 325 ± 73** | | |
| 262 | | | 83 ± 3* | | | | | 191 ± 53* | | |
| 268 | −58 ± 18 | | 9 ± 23 | | | −3 ± 16 | | 6 ± 17 | | |
| TRG 2407 | | | | | | | | | | |
| 39 | 24 ± 17 | | 72 ± 5* | | | 34 ± 13 | | 366 ± 12** | | |
| 67 | 8 ± 14 | | 73 ± 3* | | | −3 ± 15 | | 29 ± 8 | | |
| TRG 2408 | | | | | | | | | | |
| 30 | 30 ± 14 | | 78 ± 3* | 42 ± 14* | 74 ± 4* | −20 ± 14 | | 24 ± 12 | 33 ± 18 | 136 ± 41* |
| 57 | 76 ± 8* | 83 ± 2* 87 ± 5* | 86 ± 2* | 21 ± 11 | 72 ± 7* | 123 ± 30 | 247 ± 75* 225 ± 31* | 386 ± 25* | 57 ± 11* | 104 ± 16* |
| 62 | 71 ± 6* | | 84 ± 8* | 45 ± 11 | 35 ± 5 | 51 ± 15 | | 270 ± 71* | 43 ± 20 | 27 ± 10 |
| TRG 2409 | | | | | | | | | | |
| 2 | 57 ± 6* | | 65 ± 14 | 58 ± 2* | 65 ± 2* | −30 ± 11 | | 157 ± 57* | 39 ± 15 | 82 ± 19* |
| 14 | 31 ± 7 | | 76 ± 7* | 41 ± 9* | 67 ± 4* | −27 ± 8 | | 150 ± 50* | 79 ± 29 | 193 ± 50* |

Significantly different from saline (*p < 0.05, **p < 0.01)
italic values compounds tested at 105 minutes
Compounds originally chosen as negative controls based on single point binding data (10 μM)

These results indicate that isoquinoline compounds can restrain LPS-induced cytokine activity.

EXAMPLE VII

Increasing Levels of IL-10 in Mice

This example describes the effectiveness of isoquinoline compounds in increasing the levels of IL-10 in mammals.

Table 4 shows the IL-10 inducing effect of various isoquinoline compounds in mouse plasma. Isoquinoline compounds were administered intraperitoneally to mice in doses of 30, 100 or 300 μg/mouse or orally in doses of 300 or 600 μg/mouse. Levels of IL-10 were measured 90 or 105 minutes after administration as indicated. Samples were collected and diluted, when appropriate, as described in Example VI. A 100 μl sample of plasma was assayed by ELISA for IL-10. Briefly, ELISA plates were coated with rat anti-mouse IL-10 monoclonal antibody (Pharmingen; San Diego Calif.). Samples or known concentrations of IL-10 were added to the coated plates and incubated for 2 hr at 37° C. Plates were washed and incubated with biotinylated rat anti-mouse IL-10 (R&D Systems; Minneapolis Minn.) for 1 hr at 37° C. Plates were washed and incubated with streptavidin-HRP 30 min at 37° C., and HRP activity was detected with hydrogen peroxide and TMB using standard immunoassay procedures.

Table 4 shows a dose dependent increase in IL 10 levels up to 400% greater than control mice administered saline. Oral administration also caused a significant increase in IL-10 of up to 200%. TRG 2408-30 is particularly effective at increasing IL-10 when administered orally.

These results demonstrate that isoquinoline compounds can significantly increase the levels of IL-10.

EXAMPLE VIII

Effect of Isoquinoline Compounds on Arachidonic Acid Induced Dermal Inflammation This example describes the effect of isoquinoline compounds on arachidonic acid induced dermal inflammation.

Female BALB/c mice (17–22 g) were used and administered the test isoquinoline compounds or positive control compounds 30 to 60 min prior to topical application of arachidonic acid. Indomethacin and HP 228 were used as positive controls. Compounds were administered orally (p.o.) or intraperitoneally (i.p.). Initial ear thickness (left and right) was measured using spring loaded micro-calipers. Arachidonic acid was applied to mice anesthetized with a cocktail of ketamine/xylazine (7.0 mg/ml and 0.6 mg/ml, respectively) administered i.p. (300 μl/mouse). Utilizing a micro-pipette, 20 μl of arachidonic acid solution (100 mg/ml ethanol or acetone) was applied to the right ear (10 μl to inner and 10 μl to outer surfaces of both ears for a total of 2 mg arachidonic acid per right ear), and 20 μl of vehicle (ethanol or acetone) was applied to the left ear. Mice were returned to their cages to recover. Mice were again anesthetized 50 min after arachidonic acid application and their ears measured.

Dermal inflammation was determined by subtracting the difference of the vehicle treated left ear ($L_{60}-L_0$) from the difference of the arachidonic acid treated right ear ($R_{60}-R_0$). Ear thickness measurements were averaged for each group, and the responses in the vehicle treated control group (Cr; saline or PBS) were subtracted from the response noted in the isoquinoline compound treated group (Tr) to give the relative inflammatory response for each treatment group compared to the control group. The percent inhibition is defined by the equation: % inhibition=(Cr−Tr)/(Cr)×100.

FIG. 2 shows inhibition of arachidonic acid induced dermal inflammation with TRG 2405-241 (600 μg/mouse) comparable to that seen with indomethacin (1 mg/mouse) administered orally. FIG. 3 shows inhibition of arachidonic acid induced dermal inflammation with TRG 2405-241 (300 μg/mouse) comparable to that seen with with HP 228 (100 μg/mouse) administered intraperitoneally. FIG. 4 shows inhibition of arachidonic acid induced dermal inflammation with HP 228, TRG 2405-190, TRG 2405-241, TRG 2405-252 or TRG 2405-253 (100 μg/mouse) administered intraperitoneally. As shown in FIG. 5, TRG 2409-2 showed a dose dependent reduction in the level of arachidonic acid-induced dermal inflammation, comparable to the reduction seen with HP 228. TRG 2409-14 decreased dermal inflammation to a lesser extent than TRG 2409-2.

These results show that isoquinoline compounds significantly reduce arachidonic acid-induced dermal inflammation.

EXAMPLE IX

Reduction in Body Weight Due to Administration of Isoquinoline Compounds

This example demonstrates that administration of an isoquinoline compound can cause a decrease in the body weight of a subject.

Adult male Sprague-Dawley rats (175–225 g) were used to assess the effect of isoquinoline compounds on food uptake and body weight. Baseline body weight and food consumption measurements were taken for 3 days prior to start of the study (Day 0). On Day -1, the food was taken away from the animals at 5:00 PM. The next morning (Day 0), body weight measurements were taken, and the animals were divided into treatment groups with 6 animals in each group. The treatment groups were saline control, HP 228 positive control and test isoquinoline compounds. Saline was administered i.p. at 1 ml/kg. HP 228 and test isoquinoline compounds were administered i.p. at 5 mg/kg. The injections were initiated at 2:00 PM on Day 0.

Body weight and food consumption measurements were taken at 9 hr (Day 0; 11:00 PM) and at 18 hr (Day 1, 8:00 AM) after injection. At the end of the study, all evaluated parameters (9 and 18 hour body weight and food consumption) were analyzed by standard statistical methods. Significance (P<0.05) was determined by one-way ANOVA, ANOVA for repeated measures, or Student's t-test.

Figure 6B:
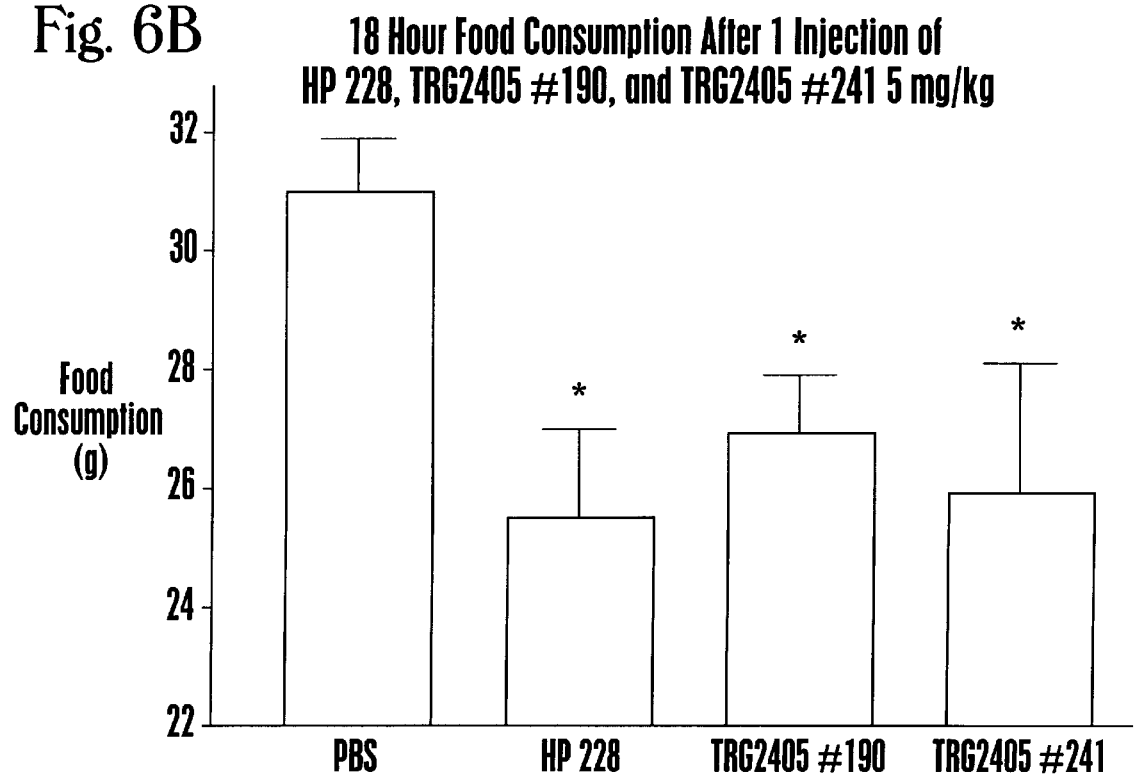

Administration of TRG 2405-190 or TRG 2405-241 caused a significant decrease in the weight gain and food consumption of rats at 18 hours after injection (see FIG. 6). The level of reduction was similar to that seen with HP 228. These results indicate that an isoquinoline compound can decrease weight gain and food intake in subjects. FIG. 7 shows that significant differences in body weight and food consumption relative to control could be observed at 9 hours as well as 18 hours in rats treated with TRG 2405-252 or TRG 2405-253.

These results indicate that a cytokine regulatory agent is useful for decreasing the body weight of a subject.

EXAMPLE X

Penile Erection Due to Administration of Isoquinoline Compound

Assay Method

Adult male rats were housed 2–3 per cage and were acclimated to the standard vivarium light cycle (12 hr. light, 12 hr. dark), rat chow and water for a least a week prior to testing. All experiments were performed between 9 a.m. and noon and rats were placed in cylindrical, clear plexiglass chambers during the 60 minute observation period. Mirrors were positioned below and to the sides of the chambers, to improve viewing.

Observations began 10 minutes after an unstraperitoneal injection of either saline or compound. An observer counted the number of grooming motions, stretches, yawns and penile erections (spontaneously occurring, not elicited by genital grooming) and recorder them every 5 minutes, for a total of 60 minutes (see FIGS. 8 and 9). The observer was unaware of the treatment and animals were tested once, with n=6 in each group. Values in the figures represent the group mean positive control for penile erections. Significant differences between groups were determined by an overall analysis of variance and the Student Neunmann-Keuls post hoc test was used to identify individual differences between groups (p≦0.05).

Although the invention has been described with reference to the examples provided above, it should be understood that various modifications can be made without departing from the spirit of the invention. Accordingly, the invention is limited only by the following claims.

We claim:

1. An isoquinoline compound of the formula:

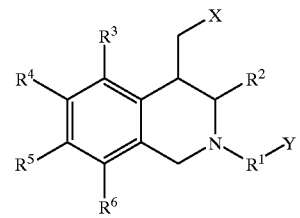

wherein:

$R^1$ is selected from the group consisting of $C_1$ to $C_9$ alkylene, $C_1$ to $C_9$ substituted alkylene, $C_2$ to $C_9$ alkenylene, $C_2$ to $C_9$ substituted alkenylene, $C_2$ to $C_9$ alkynylene, $C_2$ to $C_9$ substituted alkynylene, $C_7$ to $C_{12}$ phenylalkylene, $C_7$ to $C_{12}$ substituted phenylalkylene and a group of the formula:

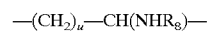

wherein u is selected from a number 1 to 8; and $R^8$ is selected from the group consisting of a hydrogen atom, $C_1$ to $C_9$ alkyl, $C_1$ to $C_9$ substituted alkyl, $C_7$ to $C_{12}$ phenylalkyl and $C_7$ to $C_{12}$ substituted phenylalkyl;

$R^2$ is selected from the group consisting of phenyl, substituted phenyl, naphthyl, substituted naphthyl, $C_7$ to $C_{12}$ phenylalkyl, $C_7$ to $C_{12}$ substituted phenylalkyl, a heterocyclic ring and a substituted heterocyclic ring;

$R^3$, $R^4$, $R^5$ and $R^6$ are, independently, a hydrogen atom, halo, hydroxy, protected hydroxy, cyano, nitro, $C_1$ to $C_6$ alkyl, $C_2$ to $C_7$ alkenyl, $C_2$ to $C_7$ alkynyl, $C_1$ to $C_6$ substituted alkyl, $C_2$ to $C_7$ substituted alkenyl, $C_2$ to $C_7$ substituted alkynyl, $C_1$ to $C_7$ alkoxy, $C_1$ to $C_7$ acyloxy, $C_1$ to $C_7$ acyl, $C_3$ to $C_7$ cycloalkyl, $C_3$ to $C_7$ substituted cycloalkyl, $C_5$ to $C_7$ cycloalkenyl, $C_5$ to $C_7$ substituted cycloalkenyl, a heterocyclic ring, $C_7$ to $C_{12}$ phenylalkyl, $C_7$ to $C_{12}$ substituted phenylalkyl, phenyl, substituted phenyl, naphthyl, substituted naphthyl, cyclic $C_2$ to $C_7$ alkylene, substituted cyclic $C_2$ to $C_7$ alkylene, cyclic $C_2$ to $C_7$ heteroalkylene, substituted cyclic $C_2$ to $C_7$ heteroalkylene, carboxy, protected carboxy, hydroxymethyl, protected hydroxymethyl, amino, protected amino, (monosubstituted)amino, protected (monosubstituted)amino, (disubstituted)amino, carboxamide, protected carboxamide, $C_1$ to $C_4$ alkylthio, $C_1$ to $C_4$ alkylsulfonyl, $C_1$ to $C_4$ alkylsulfoxide, phenylthio, substituted phenylthio, phenylsulfoxide, substituted phenylsulfoxide, phenylsulfonyl and substituted phenylsulfonyl;

X is selected from the group consisting of hydroxy, amino, protected amino, (monosubstituted)amino, (disubstituted)amino, an amino acid, aniline, substituted aniline, a heterocyclic ring, an aminosubstituted heterocyclic ring, and a heterocyclic ring substituted with secondary or tertiary amine; and Y is selected from the group consisting of $CH_2NHR^7$ and $C(O)NHR^7$, wherein $R^7$ is a hydrogen atom, $C_1$ to $C_6$ alkyl and $C_1$ to $C_6$ substituted alkyl.

2. The isoquinoline compound of claim 1, wherein:

$R^1$ is selected from the group consisting of $C_1$ to $C_9$ alkylene, $C_1$ to $C_9$ substituted alkylene and a group of the formula:

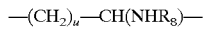

wherein u is selected from a number 1 to 8; and $R^8$ is selected from the group consisting of a hydrogen atom, $C_1$ to $C_9$ alkyl, $C_1$ to $C_9$ substituted alkyl, $C_7$ to $C_{12}$ phenylalkyl and $C_7$ to $C_{12}$ substituted phenylalkyl.

3. The isoquinoline compound of claim 1, wherein:

$R^2$ is selected from the group consisting of phenyl, substituted phenyl, a heterocyclic ring, amino substituted heterocyclic ring and a substituted heterocyclic ring.

4. The isoquinoline compound of claim 1, wherein:

$R^3$, $R^4$, $R^5$ and $R^6$ are, independently, a hydrogen atom.

5. The isoquinoline compound of claim 1, wherein:

X is selected from the group consisting of hydroxy, amino, protected amino, (monosubstituted)amino, (disubstituted)amino, aniline, substituted aniline, a heterocyclic ring, a substituted heterocyclic ring, an aminosubstituted heterocyclic ring, and a heterocyclic ring substituted with secondary or tertiary amine.

6. The isoquinoline compound of claim 1, wherein:

Y is $CH_2NHR^7$, wherein $R^7$ is selected from the group consisting of a hydrogen atom, $C_1$ to $C_6$ alkyl and $C_1$ to $C_6$ substituted alkyl.

7. The isoquinoline compound of claim 1, wherein:

$R^1$ is selected from the group consisting of $C_1$ to $C_9$ alkylene, $C_1$ to $C_9$ substituted alkylene and a group of the formula:

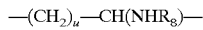

wherein u is selected from a number 1 to 8; and $R^8$ is selected from the group consisting of a hydrogen atom, $C_1$ to $C_9$ alkyl, $C_1$ to $C_9$ substituted alkyl, $C_7$ to $C_{12}$ phenylalkyl and $C_7$ to $C_{12}$ substituted phenylalkyl;

$R^2$ is selected from the group consisting of phenyl, substituted phenyl, a heterocyclic ring, amino substituted heterocyclic ring and a substituted heterocyclic ring;

$R^3$, $R^4$, $R^5$ and $R^6$ are, independently, a hydrogen atom;

X is selected from the group consisting of hydroxy, amino, protected amino, (monosubstituted)amino, (disubstituted)amino, aniline, substituted aniline, a heterocyclic ring, a substituted heterocyclic ring, an aminosubstituted heterocyclic ring, and a heterocyclic ring substituted with secondary or tertiary amine; and Y is $CH_2NHR^7$, wherein $R^7$ is selected from the group consisting of a hydrogen atom, $C_1$ to $C_6$ alkyl and $C_1$ to $C_6$ substituted alkyl.

8. The isoquinoline compound of claim 1, wherein:

$R^1$ is selected from the group consisting of methylene and a group of the formula:

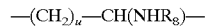

in either chiral form wherein u is selected from a number 1 to 4; and $R^8$ is selected from the group consisting of methyl, ethyl, phenethyl, 2-(N-methyl)aminoethyl, 2-aminoethyl, 2-(N-methyl)aminopropyl, hydroxyethyl, 2-(N-methyl)amino-2-phenethyl, a reduced and/or modified form of succinic anhydride, methoxyethyl, butyl, cyclohexanemethyl, benzyl, 4-bromophenethyl, 4-methoxyphenethyl, 4-chlorobenzyl, 4-methoxybenzyl, 2-naphthylethyl and cyclohexylethyl;

$R^2$ is selected from the group consisting of phenyl, 2-hydroxyphenyl, 1,4-benzodioxan-6-yl, 1-methyl-2-pyrrolyl, 1-naphthyl, 2,3,4-trifluorophenyl, 2,3,5-trichlorophenyl, 2,3-(methylenedioxy)phenyl, 2,3-difluorophenyl, 2,4-dichlorophenyl, 2,6-difluorophenyl, 2-bromophenyl, 2-chloro-5-nitrophenyl, 2-chloro-6-fluorophenyl, 2-aminomethylphenyl, 2-fluorophenyl, 2-imidazolyl, 2-methoxybenzyl, 2-naphthyl, 2-thiophene-yl, 3,4-(methylenedioxy)phenyl, 3,4-dihydroxyphenyl, 3,4-dichlorophenyl, 3,4-difluorophenyl, 3,5-bis(trifluoromethyl)phenyl, 3,5-dihydroxyphenyl, 3,5-dichlorophenyl, 3,5-dimethoxyphenyl, 3,5-dimethyl-4-hydroxyphenyl, 3-(3,4-dichlorophenoxy)phenyl, 3-(4-methoxyphenoxy)phenyl, 3-(trifluoromethyl)phenyl, 3-bromo-4-fluorophenyl, 3-bromophenyl, 3-hydroxymethylphenyl, 3-aminomethylphenyl, 3-fluoro-4-methoxyphenyl, 3-fluorophenyl, 3-hydroxyphenyl, 3-methoxy-4-hydroxy-5-nitrophenyl, 3-methoxyphenyl, 3-methyl-4-methoxyphenyl, 3-methylphenyl, 3-nitro-4-chlorophenyl, 3-nitrophenyl, 3-phenoxyphenyl, 3-pyridinyl, 3-thiophene-yl, 4-(3-dimethylaminopropoxy)phenyl, 4-(dimethylamino)phenyl, 4-hydroxymethylphenyl, 4-(methylthio)phenyl, 4-(trifluoromethyl)phenyl, 4-ethylaminophenyl, 4-methoxyphenyl (p-anisaldehyde), 4-biphenylcarboxaldehyde, 4-bromophenyl, 4-aminomethylphenyl, 4-fluorophenyl, 4-hydroxyphenyl, 4-isopropylphenyl, 4-methoxy-1-naphthaldehyde, 4-methylphenyl, 3-hydroxy-4-nitrophenyl, 4-nitrophenyl, 4-phenoxyphenyl, 4-propoxyphenyl, 4-pyridinyl, 3-methoxy-4-hydroxy-5-bromophenyl, 5-methyl-2-thiophene-yl, 5-methyl-2-furyl, 8-hydroxyquinoline-2-yl, 9-ethyl-3-carbazole-yl, 9-formyl-8-hydroxyjulolidin-yl, pyrrole-2-yl, 3-hydroxy-4-methoxyphenyl, 4-methylsulphonylphenyl, 4-methoxy-3-(sulfonic acid, Na)phenyl, 5-bromo-2-furyl, 4-ethoxyphenyl, 4-propoxyphenyl, 4-butoxyphenyl, 4-amylphenyl, 4-propylaminophenyl, 4-butylaminophenyl, 4-pentylaminophenyl, 4-cyclohexylmethylaminophenyl, 4-isobutylaminophenyl, 4-(2-methoxy)-ethylaminophenyl, 4-methoxybenzylaminophenyl, phenethylaminophenyl, 4-methoxyphenethylaminophenyl, 2-(2-norbornyl)-ethylaminophenyl, 3,4-dichlorphenethylaminophenyl, 4-benzylaminophenyl and 4-p-chlorobenzylaminophenyl;

$R^3$, $R^4$, $R^5$, $R^6$ are, independently, a hydrogen atom;

X is selected from the group consisting of anilinyl, N-methylanilinyl, 2-chloroanilinyl, 2-methoxyanilinyl, 3-chloroanilinyl, 3-ethoxyanilinyl, 3-aminophenol, 4-chloroanilinyl, 4-methoxyanilinyl, benzylamino, N-benzylmethylamino, 2-chlorobenzylamino, 2-(trifluoromethyl)benzylamino, 2-hydroxybenzylamino, 3-methoxybenzylamino, 3-(trifluoromethyl)benzylamino, 4-chlorobenzylamino, 4-methoxybenzylamino, 4-(trifluoromethyl)benzylamino, phenethylamino, 2-chlorophenethylamino, 2-methoxyphenethylamino, 3-chlorophenethylamino, 4-methoxyphenthylamino, 3-phenyl-1-propylamino, cyclopentylamino, isopropylamino, cycloheptylamino, N-methylcyclohexylamino, (aminomethyl)cyclohexane, piperidinyl, morpholinyl, 1-aminopiperidinyl, diethylamino, 3-hydroxypropyl, isopropylamino, (2-aminoethyl)-trimethylaminoethyl chloride, ammonia and hydroxy; and Y is $CH_2NH_2$.

9. The isoquinoline compound of claim 1, wherein:

$R^1$ is selected from the group consisting of methylene and a group of the formula:

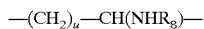

—$(CH_2)_u$—$CH(NHR_8)$— in either chiral form wherein u is selected from a number 1, 2 and 4 and $R^8$ is methyl;

$R^2$ is selected from the group consisting of phenyl, 2-hydroxyphenyl, 1,4-benzodioxan-6-yl, 1-methyl-2-pyrrolyl, 1-naphthyl, 2,3,4-trifluorophenyl, 2,3,5-trichlorophenyl, 2,3-(methylenedioxy)phenyl, 2,3-difluorophenyl, 2,4-dichlorophenyl, 2,6-difluorophenyl, 2-bromophenyl, 2-chloro-5-nitrophenyl, 2-chloro-6-fluorophenyl, 2-cyanophenyl, 2-fluorophenyl, 2-imidazolyl, 2-methoxybenzyl, 2-naphthyl, 2-thiophene-yl, 3,4-(methylenedioxy)phenyl, 3,4-dihydroxyphenyl, 3,4-dichlorophenyl, 3,4-difluorophenyl, 3,5-bis(trifluoromethyl)phenyl, 3,5-dihydroxyphenyl, 3,5-dichlorophenyl, 3,5-dimethoxyphenyl, 3,5-dimethyl-4-hydroxyphenyl, 3-(3,4-dichlorophenoxy)phenyl, 3-(4-methoxyphenoxy)phenyl, 3-(trifluoromethyl)phenyl, 3-bromo-4-fluorophenyl, 3-bromophenyl, 3-hydroxymethylphenyl, 3-aminomethylphenyl, 3-fluoro-4-methoxyphenyl, 3-fluorophenyl, 3-hydroxyphenyl, 3-methoxy-4-hydroxy-5-nitrophenyl, 3-methoxyphenyl, 3-methyl-4-methoxyphenyl, 3-methylphenyl, 3-nitro-4-chlorophenyl, 3-nitrophenyl, 3-phenoxyphenyl, 3-pyridinyl, 3-thiophene-yl, 4-(3-dimethylaminopropoxy)phenyl, 4-(dimethylamino)phenyl, 4-hydroxymethylphenyl, 4-(methylthio)phenyl, 4-(trifluoromethyl)phenyl, 4-ethylaminophenyl, 4-methoxyphenyl, 4-biphenyl, 4-bromophenyl, 4-aminomethylphenyl, 4-fluorophenyl, 4-hydroxyphenyl, 4-isopropylphenyl, 4-methoxy-1-naphthyl, 4-methylphenyl, 3-hydroxy-4-nitrophenyl, 4-nitrophenyl, 4-phenoxyphenyl, 4-propoxyphenyl, 4-pyridinyl, 3-methoxy-4-hydroxy-5-bromophenyl, 5-methyl-2-thiophene-yl, 5-methyl-2-furyl, 8-hydroxyquinoline-2-yl, 9-ethyl-3-carbazole-yl, 9-formyl-8-hydroxyjulolidin-yl, pyrrole-2-yl, 3-hydroxy-4-methoxyphenyl, 4-methylsulphonylphenyl, 4-methoxy-3-(sulfonic acid, Na)phenyl and 5-bromo-2-furyl;

$R^3$, $R^4$, $R^5$, $R^6$ are, independently, a hydrogen atom;

X is cyclohexylamino; and

Y is $CH_2NH_2$.

10. The isoquinoline compound of claim 1, wherein:

$R^1$ is selected from the group consisting of methylene and a group of the formula:

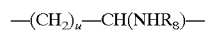

—$(CH_2)_u$—$CH(NHR_8)$— in either chiral form wherein u is selected from a number 1, 2 and 4 and $R^8$ is methyl;

$R^2$ is selected from the group consisting of 3-(3,4-dichlorophenoxy)phenyl, 1-methyl-2-pyrrolyl, 3-phenoxyphenyl, 4-phenoxyphenyl, 3-methoxy-4-hydroxy-5-bromophenyl and 9-ethyl-3-carbazolyl;

$R^3$, $R^4$, $R^5$, $R^6$ are, independently, a hydrogen atom;

X is 2-hydroxybenzyl; and

Y is $CH_2NH_2$.

11. The isoquinoline compound of claim 1, wherein:

$R^1$ is selected from the group consisting of methylene and a group of the formula:

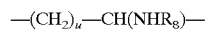

—$(CH_2)_u$—$CH(NHR_8)$— in either chiral form wherein u is selected from a number 1, 2 and 4 and $R^8$ is methyl;

$R^2$ is selected from the group consisting of 2,4-dichlorophenyl, 4-biphenyl and 4-ethylaminophenyl;

$R^3$, $R^4$, $R^5$, $R^6$ are, independently, a hydrogen atom;

X is selected from the group consisting of anilinyl, N-methylanilinyl, 2-chloroanilinyl, 2-methoxyanilinyl, 3-chloroanilinyl, 3-ethoxyanilinyl, 3-aminophenol, 4-chloroanilinyl, 4-methoxyanilinyl, benzylamino, N-benzylmethylamino, 2-chlorobenzylamino, 2-(trifluoromethyl)benzylamino, 2-hydroxybenzylamino, 3-methoxybenzylamino, 3-(trifluoromethyl)benzylamino, 4-chlorobenzylamino, 4-methoxybenzylamino, 4-(trifluoromethyl)benzylamino, phenethylamino, 2-chlorophenethylamino, 2-methoxyphenethylamino, 3-chlorophenethylamino, 4-methoxyphenthylamino, 3-phenyl-1-propylamino, cyclopentylamino, isopropylamino, cycloheptylamino, N-methylcyclohexylamino, cyclohexylmethylamino, piperidinyl, morpholinyl, 1-aminopiperidinyl, diethylamino, allylamino, isopropylamino, (2-aminoethyl)-trimethylammonium, ammonium and hydroxy; and Y is $CH_2NH_2$.

12. The isoquinoline compound of claim 1, wherein:
$R^1$ is of the formula:

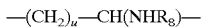
—$(CH_2)_u$—$CH(NHR_8)$— in either chiral form wherein u is selected from a number 1, 2 and 4 and $R^8$ is selected from the group consisting of a hydrogen atom, methyl, phenylethyl, 2-(N-methyl)aminoethyl and 2-aminoethyl;

$R^2$ is selected from the group consisting of 2,4-dichlorophenyl, 4-biphenyl and 4-ethylaminophenyl;

$R^3$, $R^4$, $R^5$, $R^6$ are, independently, a hydrogen atom;

X is selected from the group consisting of cyclohexylamino and 2-hydroxybenzylamino; and Y is $CH_2NH_2$.

13. The isoquinoline compound of claim 1, wherein:
$R^1$ is of the formula:

—$(CH_2)_u$—$CH(NHR_8)$— in the (s) chiral form wherein u is the number 4 and $R^8$ is methyl;

$R^2$ is selected from the group consisting of 4-propylaminophenyl, 4-butylaminophenyl, 4-cyclohexylmethylaminophenyl, 4-isobutylaminophenyl, 4-(2-methoxy)-ethylaminophenyl, 4-(4-methoxybenzyl)aminophenyl, 4-phenethylaminophenyl, 4-(4-methoxyphenethyl) aminophenyl, 2-(2-norboranyl)-ethylaminophenyl, 3,4-dichlorphenethylaminophenyl, 4-benzylaminophenyl and 4-p-chlorobenzylaminophenyl;

$R^3$, $R^4$, $R^5$, $R^6$ are, independently, a hydrogen atom;

X is selected from the group consisting of cyclohexylamino and 2-hydroxybenzylamino; and Y is $CH_2NH_2$.

14. The isoquinoline compound of claim 1, wherein:
$R^1$ is of the formula:

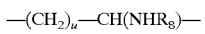
—$(CH_2)_u$—$CH(NHR_8)$— in the (s) chiral form wherein u is selected from the numbers 3 and 4 and $R^8$ is selected from the group consisting of a hydrogen atom, methyl, ethyl, phenylethyl, 2-(N-methyl)aminoethyl, 2-aminoethyl, 2-(N-methyl)propyl, hydroxyethyl, 2-(N-methyl) amino-2-phenethyl, a reduced form of succinic anhydride, methoxyethyl, butyl, cyclohexylmethyl, benzyl, 4-bromophenethyl, 4-methoxyphenethyl, 4-chlorobenzyl, 4-methoxybenzyl, 2-naphthylethyl and cyclohexylethyl;

$R^2$ is selected from the group consisting of 4-biphenyl, 4-ethylaminophenyl and 4-butylaminophenyl;

$R^3$, $R^4$, $R^5$, $R^6$ are, independently, a hydrogen atom;

X is selected from the group of cyclohexylamino, ammonia and phenethylamino; and Y is $CH_2NH_2$.

15. The isoquinoline compound of claim 1, wherein:
$R^1$ is of the formula:

—$(CH_2)_u$—$CH(NHR_8)$— in the (s) chiral form wherein u is selected from the numbers 3 and 4 and $R^8$ is selected from the group consisting of methyl, phenethyl and benzyl;

$R^2$ is selected from the group consisting of 4-pentylaminophenyl, 4-ethoxyphenyl, 4-propoxyphenyl, 4-butoxyphenyl and 4-amylphenyl;

$R^3$, $R^4$, $R^5$, $R^6$ are, independently, a hydrogen atom;

X is phenethylamino; and

Y is $CH_2NH_2$.

16. The isoquinoline compound of claim 1, wherein:
$R^1$ is of the formula:

—$(CH_2)_u$—$CH(NHR_8)$— in the (r) chiral form wherein u is selected from the numbers 3 and 4 and $R^8$ is selected from the group consisting of methyl, 2-(N-methyl)aminoethyl, 2-aminoethyl and phenethyl;

$R^2$ is selected from the group consisting of 4-biphenyl, 4-ethylaminophenyl and 4-nitrophenyl;

$R^3$, $R^4$, $R^5$, $R^6$ are, independently, a hydrogen atom;

X is selected from the group consisting of phenethyl, ammonia and cyclohexylamino; and Y is $CH_2NH_2$.

17. The isoquinoline compound of claim 1, wherein:
$R^1$ is of the formula:

—$(CH_2)_u$—$CH(NHR_8)$— in the (s) chiral form wherein u is 3 and $R^8$ is selected from the group consisting of a hydrogen atom, phenylethyl, benzyl and 4-isobutyl-α-methylphenylethyl;

$R^2$ is selected from the group consisting of 2,4-dichlorophenyl, 2-bromophenyl, 3,5-bis(trifluoromethyl)phenyl, 3-phenoxyphenyl, 4-phenoxyphenyl and 4-propoxyphenyl;

$R^3$, $R^4$, $R^5$, $R^6$ are, independently, a hydrogen atom;

X is selected from the group consisting of 2-(trifluoromethyl)benzylamino, 2-ethoxybenzylamino, 2-methoxyphenethylamino, 3-chlorophenethylamino, 3-methoxybenzylamino, 4-methoxybenzylamino, 4-methoxyphenethylamino, benzylamino, cycloheptylamino and cyclohexylamino; and Y is $CH_2NH_2$.

18. The isoquinoline compound of claim 1, wherein:
$R^1$ is of the formula:

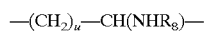
—$(CH_2)_u$—$CH(NHR_8)$— in the (s) chiral form wherein u is selected from the numbers 3 and 4 and $R^8$ is selected from the group consisting of ethyl and cyclohexylethyl;

$R^2$ is selected from the group consisting of 4-amylphenyl, 4-butoxyphenyl, 4-butylaminophenyl, 4-ethoxyphenyl, 4-ethylphenyl and 4-n-propoxyphenyl;

$R^3$, $R^4$, $R^5$, $R^6$ are, independently, a hydrogen atom;

X is selected from the group consisting of ammonia, hydroxy and phenethylamino; and Y is $CH_2NH_2$.

19. The isoquinoline compound of claim 1, wherein:
$R^1$ is of the formula:

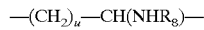
—$(CH_2)_u$—$CH(NHR_8)$— in the (s) chiral form wherein u is 3 and $R^8$ is selected from the group consisting of 4-(amino)-butyl, 4-(aminobenzyl)-butyl, 4-(diethylamino)-butyl, 4-(isopropylamino)-butyl, 4-(hydroxy)-butyl, 4-(phenethylamino)-butyl, 4-(piperidino)-butyl, 4-(t-butylamino)-butyl and 4-(aminophenyl)-butyl;

$R^2$ is 4-ethylaminophenyl;

$R^3$, $R^4$, $R^5$, $R^6$ are, independently, a hydrogen atom;

X is selected from the group consisting of ammonia and phenethylamino; and

Y is $CH_2NH_2$.

20. The isoquinoline compound of claim 1, wherein:
$R^1$ is of the formula:

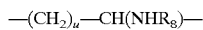
—(CH$_2$)$_u$—CH(NHR$_8$)— in the (s) chiral form wherein u is 3 and $R^8$ is selected from the group consisting of 4-(isopropylamino)-butyl, 4-(benzoamino)-butyl, 4-(diethylamino)-butyl, 4-(phenethylamino)-butyl, 5-(isopropylamino)-(3,4) cyclopropane-pentyl, 5-(benzoamino)-(3,4) cyclopropane-pentyl, 5-(diethylamino)-(3,4) cyclopropane-pentyl, 5-(phenethylamino)-(3,4) cyclopropane-pentyl, 2-amino-2-ethoxy-N-ethylisopropylamino-2-amino-2-ethoxy-N-ethylbenzyl, 2-amino-2-ethoxy-N-ethyldiethyl, 2-amino-2-ethoxy-N-ethylphenethyl, (2,3)benzyl-4-isopropylamino, (2,3)benzyl-4-benzylamino, (2,3)benzyl-4-diethylamino, (2,3)benzyl-4-phenethylamino, 3-(hydroxy)-5-(isopropylamino)-3-pentyl, 3-(hydroxy)-5-(benzylamino)-3-pentyl, 3-(hydroxy)-5-(diethylamino)-3-pentyl and 3-(hydroxy)-5-(phenethylamino)-3-pentyl;

$R^2$ is 4-ethylaminophenyl;

$R^3$, $R^4$, $R^5$, $R^6$ are, independently, a hydrogen atom;

X is selected from the group consisting of phenethylamino and ammonia; and

Y is $CH_2NH_2$.

21. The isoquinoline compound of claim 1, wherein:
$R^1$ is of the formula:

—(CH$_2$)$_u$—CH(NHR$_8$)— in the (s) chiral form wherein u is 4 and $R^8$ is selected from the group consisting of benzyl, p-methylbenzyl, p-bromobenzyl, p-methoxybenzyl and 4-phenylbenzyl;

$R^2$ is selected from the group consisting of 3,5-bis (trifluoromethyl)phenyl and 3-(trifluoromethyl)phenyl;

$R^3$, $R^4$, $R^5$, $R^6$ are, independently, a hydrogen atom;

X is selected from the group consisting of phenethylamino, tyramino, 2-(4-methoxyphenyl)ethylamino, 3,4-dimethoxyphenylethylamino, 4-ethoxyphenethylamino, 4-phenoxyphenethylamino, 2-(4-chlorophenyl)ethylamino and 2-(3-methoxyphenyl)ethylamino; and Y is $CH_2NH_2$.

22. The isoquinoline compound of claim 1, wherein:
$R^1$ is 5-(2-aminoethylamino)pentyl;

$R^2$ is p-(N-ethylamino)benzyl;

$R^3$, $R^4$, $R^5$, $R^6$ are, independently, a hydrogen atom;

X is selected from the group consisting of 2-methoxybenzylamino, 4-methoxybenzylamino, cyclohexylamino, phenethylamino and ammonia; and Y is $CH_2NH_2$.

23. The isoquinoline compound of claim 1, wherein:
$R^1$ is of the formula:

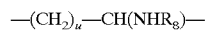
—(CH$_2$)$_u$—CH(NHR$_8$)— in the (s) chiral form wherein u is selected from the numbers 3 and 4 and $R^8$ is selected from the group consisting of pentyl, 4-phenoxybutyl and 4-hydroxypentyl;

$R^2$ is p-(N-ethylamino)benzyl;

$R^3$, $R^4$, $R^5$, $R^6$ are, independently, a hydrogen atom;

X is selected from the group consisting of phenethylamino and ammonia; and

Y is $CH_2NH_2$.

24. The isoquinoline compound of claim 1, wherein:
$R^1$ is of the formula:

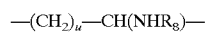
—(CH$_2$)$_u$—CH(NHR$_8$)— in the (s) chiral form wherein u is 4 and $R^8$ is selected from the group consisting of ($\alpha,\alpha,\alpha$-trifluoro-p-tolyl) ethyl, 3-(4-methoxyphenyl)propyl, 4-biphenylmethyl, 4-biphenylethyl, 4-chlorophenylethyl, 4-phenoxybutyl, butyl, glycolyl, a hydrogen atom, hydrocinnamylmethyl, isobutylmethyl, methyl, p-methoxybenzyl, 4-hydroxybutyl and 2-(trimethyl) ethyl;

$R^2$ is selected from the group consisting of 4-propoxyphenyl, 4-amylphenyl and 3,5-bistrifluoromethylphenyl;

$R^3$, $R^4$, $R^5$, $R^6$ are, independently, a hydrogen atom;

X is selected from the group consisting of ammonia and cycloheptylamino; and

Y is $CH_2NH_2$.

25. The isoquinoline compound of claim 1, wherein:
$R^1$ is of the formula:

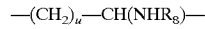
—(CH$_2$)$_u$—CH(NHR$_8$)— in the (s) chiral form wherein u is 4 and $R^8$ is selected from the group consisting of methyl and phenethyl;

$R^2$ is selected from the group consisting of 4-propoxyphenyl, 4-amylphenyl and 3,5-bistrifluoromethylphenyl;

$R^3$, $R^4$, $R^5$, $R^6$ are, independently, a hydrogen atom;

X is selected from the group consisting of 4-chlorobenzylamino, 4-methoxybenzylamino, 4-methoxyphenethylamino, phenylamino, benzylamino, cyclohexanemethylamino, cyclohexylamino, cyclooctylamino, cyclopentylamino, diethylamino, ethanolamino, isopropylamino, morpholino, n-methylanilino, n-methylcyclohexylamino, hydroxy, p-anisidino, phenethylamino, piperidino and t-butylamino; and Y is $CH_2NH_2$.

26. The isoquinoline compound of claim 1, wherein:
$R^1$ is of the formula:

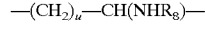
—(CH$_2$)$_u$—CH(NHR$_8$)— in the (s) chiral form wherein u is 4 and $R^8$ is selected from the group consisting of ($\alpha,\alpha,\alpha$-trifluoro-p-tolyl) ethyl, 1-adamantaneethyl, 3-(4-methoxyphenyl)propyl, 4-phenylbenzyl, 4-phenylphenethyl, 4-chlorophenethyl, 4-imidazolemethyl, 4-methoxyphenyethyl, 4-phenoxypentyl, α,α,α-trifluoro-p-toluylethyl, ethyl, benzyl, butyl, glycolyl, hydrocinnamylmethyl, isobutylmethyl, p-methoxybenzyl, phenethyl, 4-hydroxybutyl and 2-(trimethyl)ethyl;

$R^2$ is selected from the group consisting of 4-propoxyphenyl, 4-amylphenyl and 3,5-bistrifluoromethylphenyl;

$R^3$, $R^4$, $R^5$, $R^6$ are, independently, a hydrogen atom;

X is selected from the group consisting of ammonia and cycloheptylamino; and

Y is $CH_2NH_2$.

27. The isoquinoline compound of claim 1, wherein $R^1$ is —$(CH_2)_u$—$CH(NHR^8)$—; u is 4; and $R^8$ is methyl; $R^2$ is 2,4-dichlorophenyl; $R^3$, $R^4$, $R^5$, $R^6$ are, independently, a hydrogen atom; X is cyclohexylamino; and Y is $CH_2NH_2$.

28. The isoquinoline compound of claim 1, wherein $R^1$ is —$(CH_2)_u$—$CH(NHR^8)$—; u is 4; and $R_8$ is methyl; $R^2$ is 4-ethylaminophenyl; $R^3$, $R^4$, $R^5$, $R^6$ are, independently, a hydrogen atom; X is cyclohexylamino; and Y is $CH_2NH_2$.

29. The isoquinoline compound of claim 1, wherein $R^1$ is —$(CH_2)_u$—$CH(NHR^8)$—; u is 4; and $R^8$ is methyl; $R^2$ is 4-biphenyl; $R^3$, $R^4$, $R^5$, $R^6$ are, independently, a hydrogen atom; X is cyclohexylamino; and Y is $CH_2NH_2$.

30. The isoquinoline compound of claim 1, wherein $R^1$ is —$(CH_2)_u$—$CH(NHR^8)$—; u is 4; and $R^1$ is methyl; $R^2$ is 4-phenoxyphenyl; $R^3$, $R^4$, $R^5$, $R^6$ are, independently, a hydrogen atom; X is cyclohexylamino; and Y is $CH_2NH_2$.

31. The isoquinoline compound of claim 1, wherein $R^1$ is —$(CH_2)_u$—$CH(NHR^8)$—; u is 4; and $R^8$ is methyl; $R^2$ is 4-propoxyphenyl; $R^3$, $R^4$, $R^5$, $R^6$ are, independently, a hydrogen atom; X is cyclohexylamino; and Y is $CH_2NH_2$.

32. The isoquinoline compound of claim 1, wherein $R^1$ is —$(CH_2)_u$—$CH(NHR^8)$—; u is 4; and $R^8$ is methyl; $R^2$ is 4-ethylaminophenyl; $R^3$, $R^4$, $R^5$, $R^6$ are, independently, a hydrogen atom; X is cyclohexylamino; and Y is $CH_2NH_2$.

33. The isoquinoline compound of claim 1, wherein $R^1$ is —$(CH_2)_u$—$CH(NHR^8)$—; u is 3; and $R^8$ is 2-phenylethyl; $R^2$ is 4-ethylaminophenyl; $R^3$, $R^4$, $R^5$, $R^6$ are, independently, a hydrogen atom; X is 2-hydroxybenzylamino; and Y is $CH_2NH_2$.

34. The isoquinoline compound of claim 1, wherein $R^1$ is —$(CH_2)_u$—$CH(NHR^8)$—; u is 3; and $R^8$ is 2-phenylethyl; $R^2$ is 4-ethylaminophenyl; $R^3$, $R^4$, $R^5$, $R^6$ are, independently, a hydrogen atom; X is cyclohexylamino; and Y is $CH_2NH_2$.

35. The isoquinoline compound of claim 1, wherein $R^1$ is —$(CH_2)_u$—$CH(NHR^8)$—; u is 4; and $R^8$ is methyl; $R^2$ is 4-butylaminophenyl; $R^3$, $R^4$, $R^5$, $R^6$ are, independently, a hydrogen atom; X is 2-hydroxybenzylamino; and Y is $CH_2NH_2$.

36. The isoquinoline compound of claim 1, wherein $R^1$ is —$(CH_2)_u$—$CH(NHR^8)$—; u is 4; and $R^8$ is methyl; $R^2$ is 4-butylaminophenyl; $R^3$, $R^4$, $R^5$, $R^6$ are, independently, a hydrogen atom; X is cyclohexylamino; and Y is $CH_2NH_2$.

37. The isoquinoline compound of claim 1, wherein $R^1$ is —$(CH_2)_u$—$CH(NHR^8)$—; u is 4; and $R^8$ is 2-(N-methyl)ethyl; $R^2$ is 4-biphenyl; $R^3$, $R^4$, $R^5$, $R^6$ are, independently, a hydrogen atom; X is amino; and Y is $CH_2NH_2$.

38. The isoquinoline compound of claim 1, wherein $R^1$ is —$(CH_2)_u$—$CH(NHR^8)$—; u is 4; and $R^8$ is butyl; $R^2$ is 4-ethylaminophenyl; $R^3$, $R^4$, $R^5$, $R^6$ are, independently, a hydrogen atom; X is cyclohexylamino; and Y is $CH_2NH_2$.

39. The isoquinoline compound of claim 1, wherein $R^1$ is —$(CH_2)_u$—$CH(NHR^8)$—; u is 4; and $R^8$ is ethyl; $R^2$ is 4-ethylaminophenyl; $R^3$, $R^4$, $R^5$, $R^6$ are, independently, a hydrogen atom; X is amino; and Y is $CH_2NH_2$.

40. The isoquinoline compound of claim 1, wherein $R^1$ is —$(CH_2)_u$—$CH(NHR^8)$—; u is 4; and $R^8$ is 2-cyclohexylethyl; $R^2$ is 4-butylaminophenyl; $R^3$, $R^4$, $R^5$, $R^6$ are, independently, a hydrogen atom; X is amino; and Y is $CH_2NH_2$.

41. The isoquinoline compound of claim 1, wherein $R^1$ is —$(CH_2)_u$—$CH(NHR^8)$—; u is 3; and $R^8$ is 2-cyclohexylethyl; $R^2$ is 4-ethylaminophenyl; $R^3$, $R^4$, $R^5$, $R^6$ are, independently, a hydrogen atom; X is amino; and Y is $CH_2NH_2$.

42. The isoquinoline compound of claim 1, wherein $R^1$ is —$(CH_2)_u$—$CH(NHR^8)$—; u is 3; and $R^8$ is 4-hydroxybutyl; $R^2$ is 4-ethylaminophenyl; $R^3$, $R^4$, $R^5$, $R^6$ are, independently, a hydrogen atom; X is 2-phenethylamino; and Y is $CH_2NH_2$.

43. The isoquinoline compound of claim 1, wherein $R^1$ is —$(CH_2)_u$—$CH(NHR^8)$—; u is 4; and $R^8$ is 2-phenethyl; $R^2$ is 4-propoxyphenyl; $R^3$, $R^4$, $R^5$, $R^6$ are, independently, a hydrogen atom; X is cycloheptylamino; and Y is $CH_2NH_2$.

44. The isoquinoline compound of claim 1, wherein $R^1$ is —$(CH_2)_u$—$CH(NHR^8)$—; u is 4; and $R^8$ is ethyl; $R^2$ is 4-ethoxyphenyl; $R^3$, $R^4$, $R^5$, $R^6$ are, independently, a hydrogen atom; X is amino; and Y is $CH_2NH_2$.

45. The isoquinoline compound of claim 1, wherein $R^1$ is —$(CH_2)_u$—$CH(NHR^8)$—; u is 4; and $R^8$ is ethyl; $R^2$ is 4-propoxyphenyl; $R^3$, $R^4$, $R^5$, $R^6$ are, independently, a hydrogen atom; X is amino; and Y is $CH_2NH_2$.

46. The isoquinoline compound of claim 1, wherein $R^1$ is —$(CH_2)_u$—$CH(NHR^8)$—; u is 4; and $R^8$ is ethyl; $R^2$ is 4-n-butoxyphenyl; $R^3$, $R^4$, $R^5$, $R^6$ are, independently, a hydrogen atom; X is amino; and Y is $CH_2NH_2$.

47. The isoquinoline compound of claim 1, wherein $R^1$ is —$(CH_2)_u$—$CH(NHR^8)$—; u is 4; and $R^8$ is ethyl; $R^2$ is 4-n-pentylphenyl; $R^3$, $R^4$, $R^5$, $R^6$ are, independently, a hydrogen atom; X is amino; and Y is $CH_2NH_2$.

48. The isoquinoline compound of claim 1, wherein $R^1$ is —$(CH_2)_u$—$CH(NHR^8)$—; u is 3; and $R^8$ is 4-hydroxybutyl; $R^2$ is 4-ethylaminophenyl; $R^3$, $R^4$, $R^5$, $R^6$ are, independently, a hydrogen atom; X is amino; and Y is $CH_2NH_2$.

49. The isoquinoline compound of claim 1, wherein $R^1$ is —$(CH_2)_u$—$CH(NHR^8)$—; u is 3; and $R^8$ is pentyl; $R^2$ is 4-ethylaminophenyl; $R^3$, $R^4$, $R^5$, $R^6$ are, independently, a hydrogen atom; X is 2-phenethylamino; and Y is $CH_2NH_2$.

50. The isoquinoline compound of claim 1, wherein $R^1$ is —$(CH_2)_u$—$CH(NHR^8)$—; u is 4; and $R^8$ is 4-hydroxybutyl; $R^2$ is 4-pentylphenyl; $R^3$, $R^4$, $R^5$, $R^6$ are, independently, a hydrogen atom; X is amino; and Y is $CH_2NH_2$.

51. A method of altering the activity of a melanocortin receptor in a subject, comprising administering to the subject an effective amount of a melanocortin receptor ligand, wherein said melanocortin receptor ligand consists of the isoquinoline compound of claim 1.

52. The method of claim 51, wherein said melanocortin receptor activity regulates the activity of a cytokine.

53. The method of claim 52, wherein said melanocortin receptor ligand decreases said cytokine activity.

54. The method of claim 53, wherein said cytokine activity is tumor necrosis factor-α activity.

55. The method of claim 54, wherein said melanocortin receptor ligand consists of an isoquinoline compound of the formula:

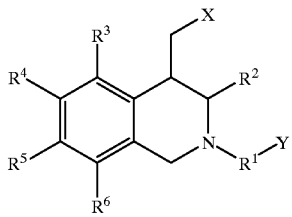

wherein:

$R^1$ is —$(CH_2)_u$—$CH(NHR^8)$—; u is 4; and $R^8$ is methyl; $R^2$ is selected from the group consisting of 2,4-dichlorophenyl, 4-biphenyl, 4-phenoxyphenyl, 4-propoxyphenyl and 4-ethylaminophenyl; $R^3$, $R^4$, $R^5$, $R^6$ are, independently, a hydrogen atom; X is cyclohexylamino; and Y is $CH_2NH_2$.

56. The method of claim 52, wherein said melanocortin receptor ligand enhances said cytokine activity.

57. The method of claim 56, wherein said cytokine activity is interleukin-10 activity.

58. The method of claim 57, wherein said melanocortin receptor ligand consists of an isoquinoline compound of the formula:

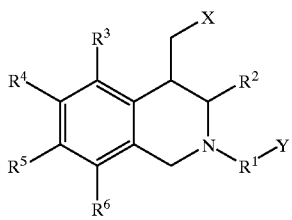

wherein:

$R^1$ is —$(CH_2)_u$—$CH(NHR^8)$—; u is 4; and $R^8$ is methyl; $R^2$ is selected from the group consisting of 2,4-dichlorophenyl, 4-biphenyl, 4-phenoxyphenyl, 4-propoxyphenyl and 4-ethylaminophenyl; $R^3$, $R^4$, $R^5$, $R^6$ are, independently, a hydrogen atom; X is cyclohexylamino; and Y is $CH_2NH_2$.

59. A method of decreasing inflammation in a subject, comprising administering to the subject an effective amount of a melanocortin receptor ligand, wherein said melanocortin receptor ligand consists of the isoquinoline compound of claim 1.

60. The method of claim 59, wherein said melanocortin receptor ligand consists of an isoquinoline compound of the formula:

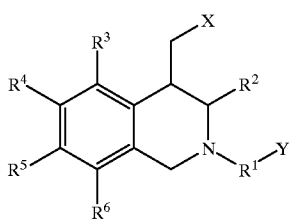

wherein:

$R^1$ is —$(CH_2)_u$—$CH(NHR^8)$—; u is 4; and $R^8$ is methyl; $R^2$ is selected from the group consisting of 2,4-dichlorophenyl, 4-biphenyl, 4-phenoxyphenyl, 4-propoxyphenyl and 4-butylaminophenyl; $R^3$, $R^4$, $R^5$, $R^6$ are, independently, a hydrogen atom; X selected from the group consisting of cyclohexylamino and 2-hydroxybenzylamino; and Y is $CH_2NH_2$.

61. A method of decreasing the body weight of a subject, comprising administering to the subject an effective amount of a melanocortin receptor ligand, wherein said melanocortin receptor ligand consists of the isoquinoline compound of claim 1.

62. The method of claim 61, wherein said melanocortin receptor ligand consists of an isoquinoline compound of the formula:

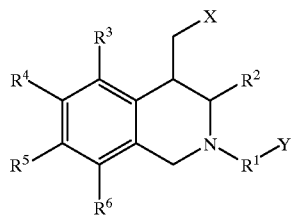

wherein:

$R^1$ is —$(CH_2)_u$—$CH(NHR^8)$—; u is 4; and $R^8$ is methyl; $R^2$ is selected from the group consisting of 2,4-dichlorophenyl, 4-biphenyl, 4-phenoxyphenyl and 4-propoxyphenyl; $R^3$, $R^4$, $R^5$, $R^6$ are, independently, a hydrogen atom; X is cyclohexylamino; and Y is $CH_2NH_2$.

63. A combinatorial library consisting of two or more isoquinoline compounds of the formula:

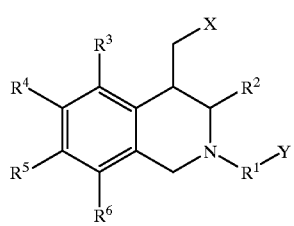

wherein:

$R^1$ is selected from the group consisting of $C_1$ to $C_9$ alkylene, $C_1$ to $C_9$ substituted alkylene, $C_2$ to $C_9$ alkenylene, $C_2$ to $C_9$ substituted alkenylene, $C_2$ to $C_9$ alkynylene, $C_2$ to $C_1$ substituted alkynylene, $C_7$ to $C_{12}$ phenylalkylene, $C_7$ to $C_{12}$ substituted phenylalkylene and a group of the formula:

—$(CH_2)_u$—$CH(NHR_8)$— wherein u is selected from a number 1 to 8; and $R^8$ is selected from the group consisting of a hydrogen atom, $C_1$ to $C_9$ alkyl, $C_1$ to $C_9$ substituted alkyl, $C_7$ to $C_{12}$ phenylalkyl and $C_7$ to $C_{12}$ substituted phenylalkyl;

$R^2$ is selected from the group consisting of phenyl, substituted phenyl, naphthyl, substituted naphthyl, $C_7$ to $C_{12}$ phenylalkyl, $C_7$ to $C_{12}$ substituted phenylalkyl, a heterocyclic ring and a substituted heterocyclic ring;

$R^3$, $R^4$, $R^5$ and $R^6$ are, independently, a hydrogen atom, halo, hydroxy, protected hydroxy, cyano, nitro, $C_1$ to $C_6$ alkyl, $C_2$ to $C_7$ alkenyl, $C_2$ to $C_7$ alkynyl, $C_1$ to $C_6$ substituted alkyl, $C_2$ to $C_7$ substituted alkenyl, $C_2$ to $C_7$ substituted alkynyl, $C_1$ to $C_7$ alkoxy, $C_1$ to $C_7$ acyloxy, $C_1$ to $C_7$ acyl, $C_3$ to $C_7$ cycloalkyl, $C_3$ to $C_7$ substituted cycloalkyl, $C_5$ to $C_7$ cycloalkenyl, $C_5$ to $C_7$ substituted cycloalkenyl, a heterocyclic ring, $C_7$ to $C_{12}$ phenylalkyl, $C_7$ to $C_{12}$ substituted phenylalkyl, phenyl, substituted phenyl, naphthyl, substituted naphthyl, cyclic $C_2$ to $C_7$ alkylene, substituted cyclic $C_2$ to $C_7$ alkylene, cyclic $C_2$ to $C_7$ heteroalkylene, substituted cyclic $C_2$ to $C_7$ heteroalkylene, carboxy, protected carboxy, hydroxymethyl, protected hydroxymethyl, amino, protected amino, (monosubstituted)amino, protected (monosubstituted) amino, (disubstituted) amino, carboxamide, protected carboxamide, $C_1$ to $C_4$ alkylthio, $C_1$ to $C_4$ alkylsulfonyl, $C_1$ to $C_4$ alkylsulfoxide, phenylthio, substituted phenylthio, phenylsulfoxide, substituted phenylsulfoxide, phenylsulfonyl and substituted phenylsulfonyl;

X is selected from the group consisting of hydroxy, amino, protected amino, (monosubstituted)amino, (disubstituted)amino, an amino acid, aniline, substituted aniline, a heterocyclic ring, an aminosubstituted heterocyclic ring, and a heterocyclic ring substituted with secondary or tertiary amine; and Y is selected from the group consisting of $CH_2NHR^7$ and $C(O)NHR^7$, wherein $R^7$ is a hydrogen atom, $C_1$ to $C_6$ alkyl and $C_1$ to $C_6$ substituted alkyl.

64. The combinatorial library of claim 63, wherein:

$R^1$ is selected from the group consisting of $C_1$ to $C_9$ alkylene, $C_1$ to $C_9$ substituted alkylene and a group of the formula:

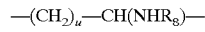

wherein u is selected from a number 1 to 8; and $R^8$ is selected from the group consisting of a hydrogen atom, $C_1$ to $C_9$ alkyl, $C_1$ to $C_9$ substituted alkyl, $C_7$ to $C_{12}$ phenylalkyl and $C_7$ to $C_{12}$ substituted phenylalkyl.

65. The combinatorial library of claim 63, wherein:

$R^2$ is selected from the group consisting of phenyl, substituted phenyl, a heterocyclic ring, amino substituted heterocyclic ring and a substituted heterocyclic ring.

66. The combinatorial library of claim 63, wherein:

$R^3$, $R^4$, $R^5$ and $R^6$ are, independently, a hydrogen atom.

67. The combinatorial library of claim 63, wherein:

X is selected from the group consisting of hydroxy, amino, protected amino, (monosubstituted)amino, (disubstituted)amino, aniline, substituted aniline, a heterocyclic ring, a substituted heterocyclic ring, an aminosubstituted heterocyclic ring, and a heterocyclic ring substituted with secondary or tertiary amine.

68. The combinatorial library of claim 63, wherein:

Y is $CH_2NHR^7$, wherein $R^7$ is selected from the group consisting of a hydrogen atom, $C_1$ to $C_6$ alkyl and $C_1$ to $C_6$ substituted alkyl.

69. The combinatorial library of claim 63, wherein:

$R^1$ is selected from the group consisting of $C_1$ to $C_9$ alkylene, $C_1$ to $C_9$ substituted alkylene and a group of the formula:

wherein u is selected from a number 1 to 8; and $R^8$ is selected from the group consisting of a hydrogen atom, $C_1$ to $C_9$ alkyl, $C_1$ to $C_9$ substituted alkyl, $C_7$ to $C_{12}$ phenylalkyl and $C_7$ to $C_{12}$ substituted phenylalkyl;

$R^2$ is selected from the group consisting of phenyl, substituted phenyl, a heterocyclic ring, amino substituted heterocyclic ring and a substituted heterocyclic ring;

$R^3$, $R^4$, $R^5$ and $R^6$ are, independently, a hydrogen atom;

X is selected from the group consisting of hydroxy, amino, protected amino, (monosubstituted)amino, (disubstituted)amino, aniline, substituted aniline, a heterocyclic ring, a substituted heterocyclic ring, an aminosubstituted heterocyclic ring, and a heterocyclic ring substituted with secondary or tertiary amine; and Y is $CH_2NHR^7$, wherein $R^7$ is selected from the group consisting of a hydrogen atom, $C_1$ to $C_6$ alkyl and $C_1$ to $C_6$ substituted alkyl.

* * * * *